US005834247A

United States Patent [19]
Comb et al.

[11] Patent Number: 5,834,247
[45] Date of Patent: Nov. 10, 1998

[54] MODIFIED PROTEINS COMPRISING CONTROLLABLE INTERVENING PROTEIN SEQUENCES OR THEIR ELEMENTS METHODS OF PRODUCING SAME AND METHODS FOR PURIFICATION OF A TARGET PROTEIN COMPRISED BY A MODIFIED PROTEIN

[75] Inventors: Donald G. Comb, Manchester; Francine B. Perler, Brookline; William E. Jack, Wenham; Ming-Qun Xu, Hamilton, all of Mass.; Robert A. Hodges, Norcross, Ga.; Christopher J. Noren, Boxford, Mass.; Shaorong S. C. Chong, Beverly, Mass.; Eric Adam, Beverly, Mass.; Maurice Southworth, Beverly, Mass.

[73] Assignee: New England Biolabs, Inc., Beverly, Mass.

[21] Appl. No.: 811,492

[22] Filed: Mar. 5, 1997

Related U.S. Application Data

[63] Continuation-in-part of Ser. No. 580,555, Dec. 29, 1995, abandoned, which is a continuation-in-part of Ser. No. 496,247, Jun. 28, 1995, abandoned, which is a continuation-in-part of Ser. No. 146,885, Nov. 3, 1993, abandoned, which is a continuation-in-part of Ser. No. 4,139, Dec. 9, 1992, Pat. No. 5,496,714.

[51] Int. Cl.⁶ .......................... C12N 15/62; C07K 19/00; C12P 21/00; C12P 21/04
[52] U.S. Cl. .................... 435/69.7; 435/69.1; 435/172.3; 435/252.3; 435/320.1; 530/350; 530/402; 530/412; 530/413; 536/23.4
[58] Field of Search .................................. 435/69.7, 69.1, 435/172.3, 252.3, 320.1; 550/350, 402, 412, 413; 536/23.4

[56] References Cited

U.S. PATENT DOCUMENTS

| | | | |
|---|---|---|---|
| 5,322,785 | 6/1994 | Comb et al. | 435/194 |
| 5,352,778 | 10/1994 | Comb et al. | 536/23.2 |
| 5,496,714 | 3/1996 | Comb et al. | 435/69.7 |
| 5,500,363 | 3/1996 | Comb et al. | 435/194 |

FOREIGN PATENT DOCUMENTS

| 2110938 | 6/1994 | Canada . |
|---|---|---|
| 0 602 899 | 6/1994 | European Pat. Off. . |

OTHER PUBLICATIONS

Davis, et al., Cell, 71:201–210 (1992).
Perler, et al., Proc. Natl. Acad. Sci. 89:5577–5581 (1992).
Hirata, et al., J. Biol. Chem., 265:6726–6733 (1990).
Kane, et al., Science, 250:651 (1990).
Davis, et al., J. Bact. 173:5653–5662 (1991).
Kong, et al., J. of Biol. Chem. 268:1965–1975 (1993).
Cooper, EMBO Journal, 12:7575–2583 (1993).
Xu, Cell, 75:1371–1377 (1993).
Hirata, et al., Biochemical and Biophysical Research Communications 188:40–47 (1992).
Bremer, et al., Nucl. Acids Research, 20:5458 (1992).
Watanabe, et al., Journal of Biological Chemistry, 264:15650–15665 (1990).

(List continued on next page.)

*Primary Examiner*—Robert A. Wax
*Assistant Examiner*—William W. Moore
*Attorney, Agent, or Firm*—Gregory D. Williams

[57] ABSTRACT

The present invention is directed to modified proteins and methods of their production. The modified proteins comprise a controllable intervening protein sequence (CIVPS) inserted into or adjacent a target protein, the CIVPS being capable of excision from or cleavage of the modified protein under predetermined conditions in cis or in trans, i.e., increase in temperature, exposure to light, unblocking of amino acid residues by dephosphorylation, treatment with chemical reagents or deglycosylation. If desired, the modified protein can be subjected to these conditions. The CIVPS may also be inserted into a region that substantially inactivates target protein activity. The CIVPS may be used in a number of applications including purification of the target protein in a one-step protocol.

103 Claims, 35 Drawing Sheets

OTHER PUBLICATIONS

Xu, et al., EMBO J., 13:5517–5522 (1994).
Pietrokovski, Protein Science, 3:2340–2350 (1994).
Shao, et al., Biochemistry, 34:10844–10850 (1995).
Cooper, et al., Trends in Biochemical Science, 20:351–358 (1995).
Clarke, PNAS, USA 91:11084–11088 (1994).
Dalgaard, J. of Biol. Chemistry, 269:28885–28892 (1994).
Davis, et al., Antonie van Leeuwenhoek, 67:131–137 (1994).
Southworth, J. of Cellular Biochemistry, Supplement 18D, Abstract S346 p. 161 (1994).
Gimble, et al., J. of Biol. Chemistry, 268:21844–21853 (1993).
Perler, et al., Nucl. Acids Res. 22:1125–1127 (1994).
Anraku, et al., J. of Biochem. 115:175–178 (1994).
Colston, et al., Molecular Microbiology, 12:359–363 (1994).
Hodges, et al., Nucl. Acids Res., 20:6153–6157 (1992).
Shub, et al., Cell, 71:183–186 (1992).
Wallace, Proteins Science, 2:697–705 (1993).
Cooper, et al., BioEssays, 15:667–674 (1993).
Perler, et al., J. of Cellular Biochemistry, Supplement 19B, Abstract B7–221, p. 245 (1995).
Xu, et al., Protein Engineering, vol. 8(Suppl.):96 (1995).
Koonin, Trends in Biochemical Science, 20:141–142 (1995).
Belfort, et al., J. of Bacteriology, 177:3897–3903 (1995).
Chong, et al., J. of Biol. Chem, 271:22159 (1996).
Cook, et al., Angew. Chem. Int. Ed. Engl. 34:1629–1630 (1995).
Gu, et al., J. Biol. Chem., 268:7372 (1993).
Comb, D. G., et al., NEB Transcript, Dec. 1995, "Protein splicing: Mechanism and possible use in molecular biology", pp. 10–13, 1995.
Pietrovski, S., Trends in Genetics, vol. 12, "A new intein in cyanobacteria and its significance for the spread of inteins", pp. 287–288, 1996.
Shao, Y., et al., Biochemistry, vol. 35, "Proteins splicing: Evidence for an N–O acyl rearrangement as teh initial step in the splicing process", pp. 3810–3815, 1996.
Kawasaki, M., et al., Biochemical and Biophysical Research Communications, vol. 222, "Folding–dependent in vitro protein splicing of the Saccharomyces cerevisiae VMA1 protozyme", pp. 827–832, 1996.

FIG. 1

I. Junction Similarities at upstream or 5' end of IVPSs:

```
                      5' EPS          5' IVPS
Pyrococcus sp. IVPS1:  I  K  I  L  A  N | S  I  L  P  E  E  W  V  P  L  I  K  N  G  K  V
T. litoralis IVPS1:    I  K  L  L  A  N | S  I  L  P  N  E  W  L  P  I  I  E  N  G  E  I
T. litoralis IVPS2:    K  V  L  Y  A  D | S  V  S  G  E  S  E  I  I  R  Q  N  G  K  I
Yeast TFP1:            A  I  L  Y  V  G | C  F  A  K  G  T  N  V  L  M  A  D  G  S  I  E
M. tuberculosis recA:  K  V  V  K  N  K | C  L  A  E  G  T  R  I  R  D  P  V  T  G  T  I
```

II. Junction Similarities at downstream or 3' end of IVPSs:

```
                              3' IVPS    3' EPS
Pyrococcus sp. IVPS1:  E  B  G  K  A  G  F  L  Y  A | H  N | S  Y  Y  G  Y  Y  G  Y  A
T. litoralis IVPS1:    E  N  F  L  V  G  F  G  L  L  Y  A | H  N | S  Y  Y  G  Y  M  G  Y  P
T. litoralis IVPS2:    E  T  H  R  F  F  A  N  N  I  L  V | H  N | T  D  G  F  Y  A  T  I  P
Yeast TFP1:            D  H  Q  F  L  L  A  N  Q  V  V  V | H  N | C  G  E  R  G  N  E  M  A
M. tuberculosis recA:  E  L  H  T  L  V  A  E  G  V  V  V | H  N | C  S  P  P  F  K  Q  A  E
```

IVPS = Intervening Protein Sequence

EPS = External Protein Sequence

- M (maltose-binding protein)
- Y (yeast intein)
- B (chitin-binding domain)

FIG. 25
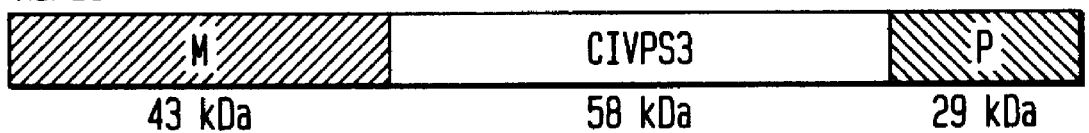
MIP21
M — 43 kDa | CIVPS3 — 58 kDa | P — 29 kDa
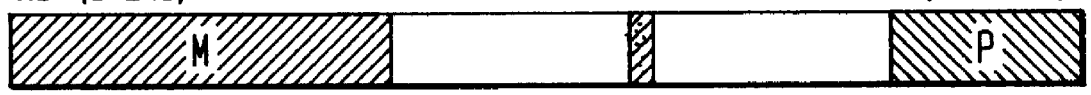
MI' (1-249)　　　　　　　　　　　　　　　I'P (250-537)
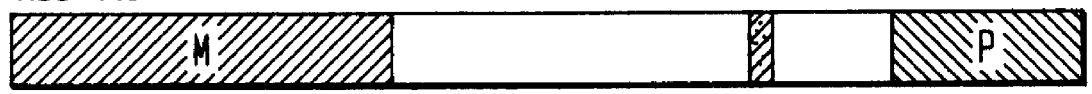
MI1-440　　　　　　　　　　　　　　　　I441-537P
MI441-537P
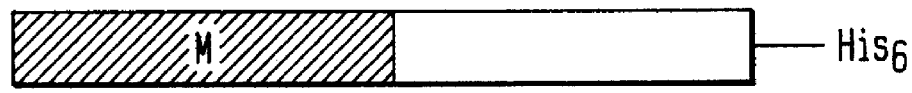
MI1-440His — His$_6$
```
▨ M = MBP
☐ CIVPS3
▧ P
▨ BREAKPOINT SEPARATING COMPLEMENTARY FRAGMENTS
```
NUMBERS REFER TO AMINO ACIDS FROM
CIVPS3 THAT ARE PRESENT IN EACH CONSTRUCT

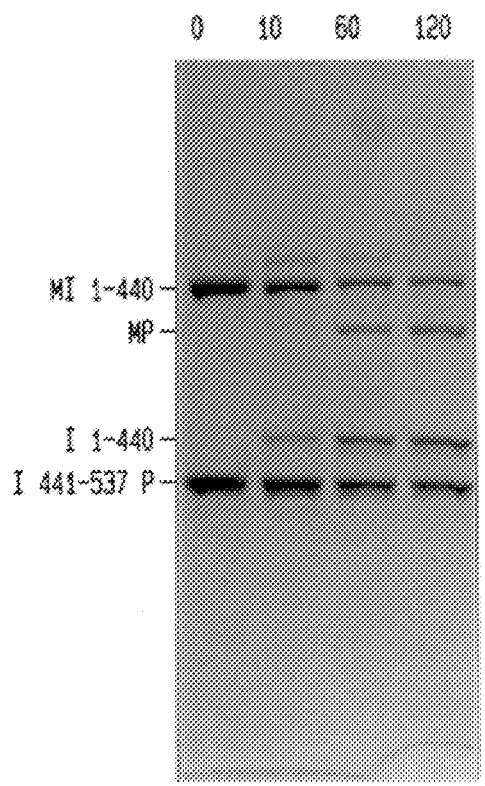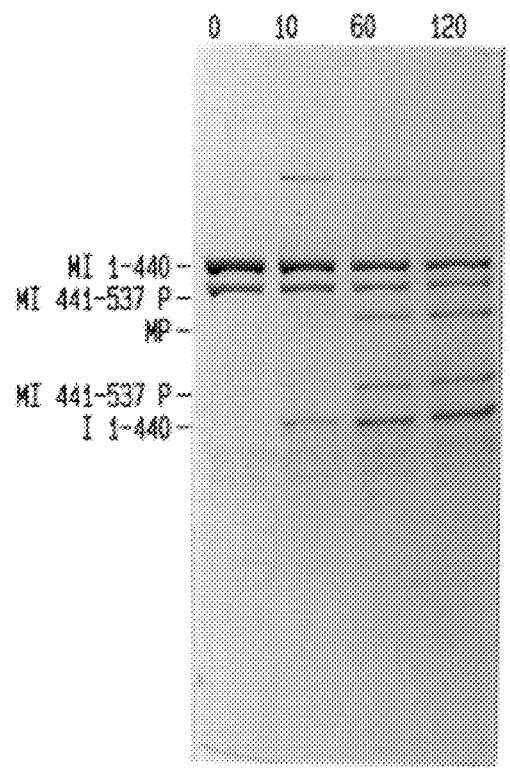

FIG. 36

ACID-ELUTED CLONES:

| | |
|---|---|
| (SEQ ID NO: 134) | H N F I K H R L P G H R |
| (SEQ ID NO: 135) | F H K H S P R S P I F I |
| (SEQ ID NO: 136) | H Y T R F H T H P K P L |
| (SEQ ID NO: 137) | M P R W H H H T P P A Y |
| (SEQ ID NO: 138) | W H K H Y P F K I P T Q |
| (SEQ ID NO: 139) | A A K Y H H H R W P L F |
| (SEQ ID NO: 140) | H V H R H H V R P H V H |
| (SEQ ID NO: 141) | A K L P W H H H G R P |
| (SEQ ID NO: 142) | K W F H P P R W H F P Y |
| (SEQ ID NO: 143) | Y H K H R P Y Y A T Q M |

MALTOSE-ELUTED CLONES:

| | |
|---|---|
| (SEQ ID NO: 144) | K H L Q H Y P R V K V A |
| (SEQ ID NO: 145) | F H K L P P R Y T P T V |
| (SEQ ID NO: 146) | I E Y V P S L A P L S P |
| (SEQ ID NO: 147) | F H K M P N L K P S K H |
| (SEQ ID NO: 148) | Y H W K P K D V S R M P |
| (SEQ ID NO: 149) | K H R L P T P P P S P A |
| (SEQ ID NO: 140) | H V H R H H V R P H V H |
| (SEQ ID NO: 150) | M L K L D Y S V L S Y G |
| (SEQ ID NO: 151) | H F K H N R Q P Y H L P |
| (SEQ ID NO: 152) | W H K Q W S Q M P S K L |

DTT-ELUTED CLONES:

| | |
|---|---|
| (SEQ ID NO: 153) | D Y A S T F T A V D A N |
| (SEQ ID NO: 154) | H P H M S P S T L A A G |
| (SEQ ID NO: 155) | A W D C P M L S C T S W |
| (SEQ ID NO: 155) | A W D C P M L S C T S W |
| (SEQ ID NO: 155) | A W D C P M L S C T S W |
| (SEQ ID NO: 155) | A W D C P M L S C T S W |
| (SEQ ID NO: 155) | A W D C P M L S C T S W |
| (SEQ ID NO: 155) | A W D C P M L S C T S W |
| (SEQ ID NO: 155) | A W D C P M L S C T S W |
| (SEQ ID NO: 155) | A W D C P M L S C T S W |

FIG. 38A

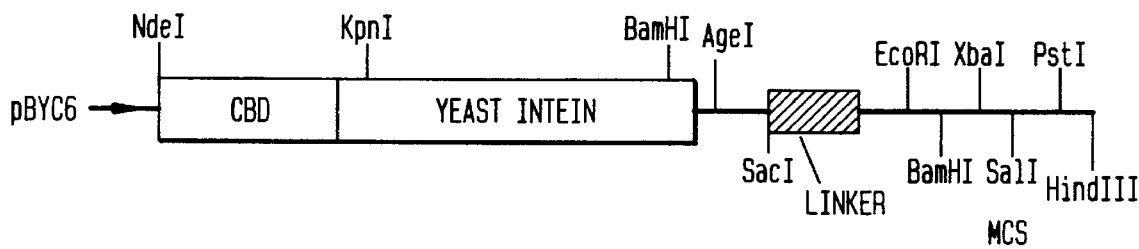

LINKER AND MCS SEQUENCE: 
```
                      SacI
GAGCTCGAACAACAACAACAATAACAATAACAACAAC
CTCGGGATCGAGGGAAGGATTTCAGAATTCGGATCCTCTAGAGTCGACCTGCAGGC
                         EcoRI   BamHI   XbaI    SalI  PstI
AAGCTTG... (SEQ ID NO.130)
HindIII
```

FIG. 38B

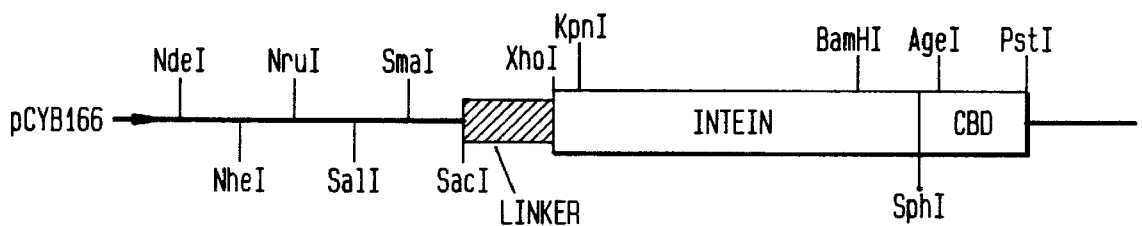

LINKER AND MCS SEQUENCE:
```
           NdeI    NheI    NruI     SalI    SmaI      SacI
CATATGGCTAGCTCGCGAGTCGACCCCGGGGGGAGCT
CCGAGCTCGAACAACAACAACAATAACAATAACAACAACCTCGGGATCGAGGGA
AGGGGTACGCTCGAGGGG.. (INTEIN)  (SEQ ID NO.133)
         XhoI
```

MODIFIED PROTEINS COMPRISING CONTROLLABLE INTERVENING PROTEIN SEQUENCES OR THEIR ELEMENTS METHODS OF PRODUCING SAME AND METHODS FOR PURIFICATION OF A TARGET PROTEIN COMPRISED BY A MODIFIED PROTEIN

CROSS-REFERENCE TO RELATED APPLICATION

This Application is a Continuation-In-Part Application of application Ser. No. 08/580,555, filed Dec. 29, 1995, and now abandoned which is a Continuation-In-Part Application of application Ser. No. 08/496,247, filed Jun. 28, 1995, and now abandoned which is a Continuation-In-Part Application of application Ser. No. 08/146,885, filed Nov. 3, 1993, and now abandoned which is a Continuation-In-Part of application Serial No. 08/004,139, filed Dec. 9, 1992, and issued as U.S. Pat. No. 5,496,714 on Mar. 5, 1996.

BACKGROUND OF THE INVENTION

The present invention is directed to modified proteins, methods of producing modified proteins, and methods of purifying target proteins or peptides. More specifically, the modified protein of the present invention comprises a target protein and a controllable intervening protein sequence (CIVPS), the CIVPS being capable of excision or cleavage under predetermined conditions.

Production of mature proteins involves the flow of information from DNA to RNA to protein. Precise excision of DNA and RNA elements which interrupt that information has been previously described (M. Belfort, Annu. Rev. Genet. 24:363 (1990); T. R. Cech, Annu. Rev. Biochem. 59:543 (1990); Hunter et al., Genes Dev. 3:2101 (1989)). More recently, evidence for the precise excision of intervening protein sequences has also been described for the TFPI allele from Saccharomyces cerevisiae (Hirata et al., J. Bio. Chem. 265:6726 (1990); Kane et al., Science 250:651 (1990)) and the rec A gene from Mycobacterium tuberculosis (Davis et al., J. Bact. 173:5653 (1991); Davis et al., Cell 71:1 (1992)). Each contains internal in-frame peptide segments which must be removed to produce the mature protein. Expression of Tfp1 and Rec A each results in two peptides: one representing the intervening protein sequence (IVPS) and the other the ligated product of the external protein sequences (EPS). This post-translational processing event has been termed "protein splicing". Similarly, the Vent® DNA polymerase gene from the hyperthermophilic archaea Thermococcus litoralis contains two in-frame IVPSs (Perler, et al., PNAS 89:5577 (1992)).

A major impediment to the development of methods of using IVPSs or protein splicing in other than research applications has been the inability to control the activity of the IVPS and thus the splicing event.

Thus, it would be desirable to have a method which provides a ready means to modify a target protein using an IVPS, particularly where the activity of the IVPS is controllable. It would also be desirable to have a method which can specifically modify target proteins such that their activity is substantially inactivated. It would be desirable to have a method which can be used to restore the activity of an inactivated modified protein. It would also be desirable to have a method for purifying target proteins based on the biological/biochemical properties of an IVPS or a modified IVPS.

SUMMARY OF THE INVENTION

The present invention relates to modified proteins comprising an IVPS and a target protein, the IVPS being capable of excision by protein splicing, or cleavage in the absence of splicing, under predetermined conditions in either cis or in trans. Such predetermined conditions depend on the IVPS used and can include, for example, increase in temperature, changes in pH conditions, exposure to light, dephosphorylation or deglycosylation of amino acid residues, exposure to chemical reagents which induce cleavage/splicing or exposure to a peptide (or derivative, analogic or mimetic thereof) which either activates or blocks protein splicing/cleavage. The development and application of methods for controlling splicing in vivo in accordance with the present invention will enable the study of protein function in living cells and organisms, e.g., controllable knockout mutations. One such method for the in vivo control of splicing employing inhibitor or activator peptides is described below.

The IVPS may be joined with the target protein either by inserting the IVPS into the target protein or fusing the IVPS with the target protein at either the amino or carboxy terminal end of the target protein. These IVPS, referred to as controllable intervening protein sequences (CIVPS), are therefore useful in controlling the splicing or cleavage reaction. The present invention further relates to methods for producing, selecting and testing CIVPSs as well as the methods for purifying a target protein which is expressed as part of a fusion system comprising the target protein, a CIVPS (or portion thereof) and a binding protein or binding domain.

In one preferred embodiment, a DNA sequence encoding a CIVPS is inserted into, or joined with, a DNA sequence encoding a target protein such that both coding sequences form a continuous open reading frame. Thereafter, expression of this fusion DNA is utilized to produce the modified target protein. In another embodiment, the modified protein so produced is subjected to predetermined conditions under which the CIVPS will be excised or cleaved. In certain embodiments, the CIVPS is inserted into a region of the target protein which renders the target protein substantially inactive and excision of the CIVPS restores the activity of the target protein.

Preferred CIVPSs include CIVPS1 and 2 obtainable from T. litoralis (also sometimes referred to as Vent® IVPS 1 and 2 or IVS1 and 2) and CIVPS 3 obtainable from Pyrococcus sp. (also sometimes referred to as Deep Vent® IVPS1 or IVS1). These CIVPSs are capable of excision, i.e., removal via protein splicing, from modified proteins upon an increase in temperature. Other preferred CIVPSs include those obtainable from yeast such as Saccharomyces cerevisiae.

In accordance with the present invention, it has also been found that certain CIVPS amino acid residues and at least the first downstream amino acid residue modulate the splicing reaction and that modification of these residues decreases or stops the splicing reaction. These residues have been shown to be conserved in other IVPSs. Modification of such residues can be used to convert a IVPS to a CIVPS.

In accordance with the present invention, it has been found that in certain situations, the complete splicing reaction is not necessary or desirable. In such situations, the CIVPS can be modified to allow cleavage in the absence of splicing, thus allowing for controlled separation or cleavage of the CIVPS from the target protein.

The potential uses for the modified proteins and CIVPSs of the present invention are manifold. These include, for example, control of a target protein's enzymatic activity, purification of modified proteins using antibodies specific to the CIVPS by affinity chromatography and production of proteins that are toxic to host cells.

The CIVPSs of the present invention may also be used in a method of protein purification in which a modified protein comprising a target protein fused to a CIVPS is produced. If desired, a three-part fusion can be produced in which the CIVPS is between the target protein and a protein having affinity for a substrate (binding protein), e.g., maltose binding protein or chitin binding protein. The modified protein is then contacted with a substrate to which the CIVPS or binding protein has specific affinity, e.g., using affinity chromatography. The highly purified target protein can be liberated from the column by subjecting the CIVPS to predetermined conditions under which cleavage, for example, between the CIVPS and the target protein is initiated. Alternatively, the fusion protein can be purified as above and then the target protein released from the fusion by subjecting the CIVPS to predetermined conditions.

The CIVPS of the present invention, and in particular, and the control of N-terminal cleavage with a thiol compound which results in a thioester bond at the carboxy terminus of the polypeptide N-terminal to the CIVPS, may also be utilized to generate polypeptide thioester intermediates for protein synthesis, tagging or modification. This would facilitate investigation of the target protein's biological function and structure.

In another emobodiment, certain regions of the intein, e.g., regions spanning conserved endonuclease motifs, (i.e., from endonuclease motif to another) may be deleted to reduce the overall size of the expressed molecule. This is particularly valuable where the IVPS or CIVPS is a component of a fusion system used in protein purification. Alternatively, the removed regions may be replaced with a desired peptide/protein, e.g., an affinity tag or binding domain.

In yet another embodiment, there is provided vectors for peptide library screening. These vectors contain a protein of interest, an intein and binding protein or binding domain which can be used to screen and/or study the interaction between the protein of interest and another polypeptide or ligand.

The CIVPS of the present invention is useful in overcoming problems associated with the release of phage-bound peptides in biopanning—a process for screening libraries of phage-bound peptides. Specifically, the CIVPS of the invention can be used in lieu of proteases which allow for separation of tightly bound peptides from their targets without reducing the viability of the phage displaying the peptide.

Finally, other uses for CIVPS include the synthesis of cyclic peptides using a modified CIVPS. Cyclic peptides are important as pharmacological agents and, in general, are more stable than linear peptides.

BRIEF DESCRIPTION OF THE DRAWINGS

FIG. 1 depicts the amino acid sequence (SEQ ID NO:30, SEQ ID NO:31, SEQ ID NO:32, SEQ ID NO:33, SEQ ID NO:34, SEQ ID NO:36, SEQ ID NO:37, SEQ ID NO:38 and SEQ ID NO:39) of proposed protein splice junctions. Amino-terminal (top) and carboxy-terminal (bottom) splice junctions are shown with splice sites indicated by arrows and conserved or similar amino acids boxed.

FIG. 13B represents the proposed structure of each band, including the branched molecule MIP*. The black boxes represent the MBP domain, the white boxes the IVPS doman and the gray boxes the paramyosin ΔSal domain. The pluses (+) indicate that the sample was heat treated at 37° C. for 120 min., minuses (−) indicate that the sample was not heat treated. Part A: Coomassie blue stained gel. Total, crude supernatants from MIP cultures. F.T., amylose resin flow through. Amylose eluate (−), amylose resin purified MIP preparations. Amylose eluate (+), the amylose eluate in lane 4 was treated at 37° C. for 120 min. to induce splicing. MonoQ, MonoQ purified sample. After chromatography on MonoQ, recovery of MBP-CIVPS3 (MI) was variable and generally low. Symbols are as follows: MIP*, 180 kDa apparent molecular mass branched molecule; MIP, 132 kDa precursor; single splice junction cleavage products (MI, MBP-CIVPS3; IP, CIVPS3-paramyosin ΔSal; M, MBP); and spliced products (MP, MBP-paramyosin ΔSal and I, CIVPS3=Pl-Pspl). Part B: Immunoblots. The MonoQ sample from Part A was heat treated as above and electrophoresed in triplicate. MIP-related proteins were identified by immune reactivity with anti-MBP sera, anti-paramyosin sera and anti-Pl-Pspl (anti-CIVPS3) sera.

FIG. 15A shows cleavage at the C-terminal splice junction from MIP23 fusion. Purified fusion protein samples were incubated at 4° C., 37° C., 50° C. or 65° C. for 1 hour. Products were analyzed by a 4/20% SDS-PAGE followed by Coomassie blue staining. Cleavage of the C-terminal splice junction of the MIP23 fusion protein (MIP) yielded MBP-CIVPS (MI) and paramyosin ΔSal (P).

FIG. 15B shows cleavage at the N-terminal splice junction from MIP28 fusion. Purified protein samples were incubated at 4° C., 42° C., 50° C. or 65° C. for 1 hour. Products were analyzed by a 4/20% SDS-PAGE followed by Coomassie blue staining. Cleavage of the N-terminal splice junction of the MIP28 fusion protein (MIP) yielded MBP (M) and CIVPS-paramyosin ΔSal (IP). Size standards (in kilodaltons) are shown on the left side.

FIG. 25 shows the trans-splicing constructs derived from MIP21. Both complementary pairs, Ml'1–249 and l'250–537P, and Mll–440 and l441–537P are shown along with the constructs with affinity tags at either the N-terminus of the C-terminal fragment (Ml441–537P) or the C-terminus of the N-terminal fragment (Mll–440His). Numbers refer to amino acids from CIVPS3 that are present in each construct.

FIG. 27 shows protein splicing in trans with (A) a new complementary pair, Mll–440 and l441–437P and (B) an affinity tag at the N-terminus of the C-terminal CIVPS3 fragment, Ml1–440 and Ml441–537P. The protein fragments were combined in 50% buffer A and incubated for 4 hours at 4° C. The reaction mixtures were diluted 10 fold into trans-splicing buffer and incubated at 37° C. to induce splicing. Time points were taken and examined on a 12% SDS-PAGE gel. (A) (Lanes 1–4): Ml1–440 and l441–537P; (B) (Lanes 5–8): Ml1–440 and Ml441–537P; lane 1,5:0 minute time point; lane 2,6: 10 minute time point; lane 3,7: 60 minute time point; lane 4,8: 120 minute time point. Ml1–440, l441–537P and Ml441–537P decrease, and MP (the spliced product), l1–440, and Ml155–537 increase.

FIG. 36 shows the sequences (SEQ ID NO:134 through SEQ ID NO:155) of peptides eluted after biopanning against MBP. The Ph.D.-12 library was panned against either MBP and eluted with either 0.2 M glycine (pH 2.2) or 0.1 mM maltose, or against MBP-intein-CBD and eluted with 10 mM DTT. The sequences of 10 clones eluted by each method after 3 rounds of biopanning are illustrated.

FIG. 38 illustrates the E. coli expression vectors pBYC6 and pCYB166.

FIG. 38A (SEQ ID NO:130) shows the pBYC6 contains the chitin-binding (CBD), the modified Sce VMA intein (with a His453 substitution), and multiple cloning sites (MCS) for cloning of the gene of interesrt. A linker sequence is inserted between the intein and the MCS. The sequence of the linker and MCS is shown under each diagram.

FIG. 38B (SEQ ID NO:133) shows pCYB166 contains the multiple cloning site, followed by the linker sequence, the modified Sce VMA intein (with a Asn454 Ala substitution) and chitin-binding domain.

DETAILED DESCRIPTION OF THE INVENTION

Figure 2:
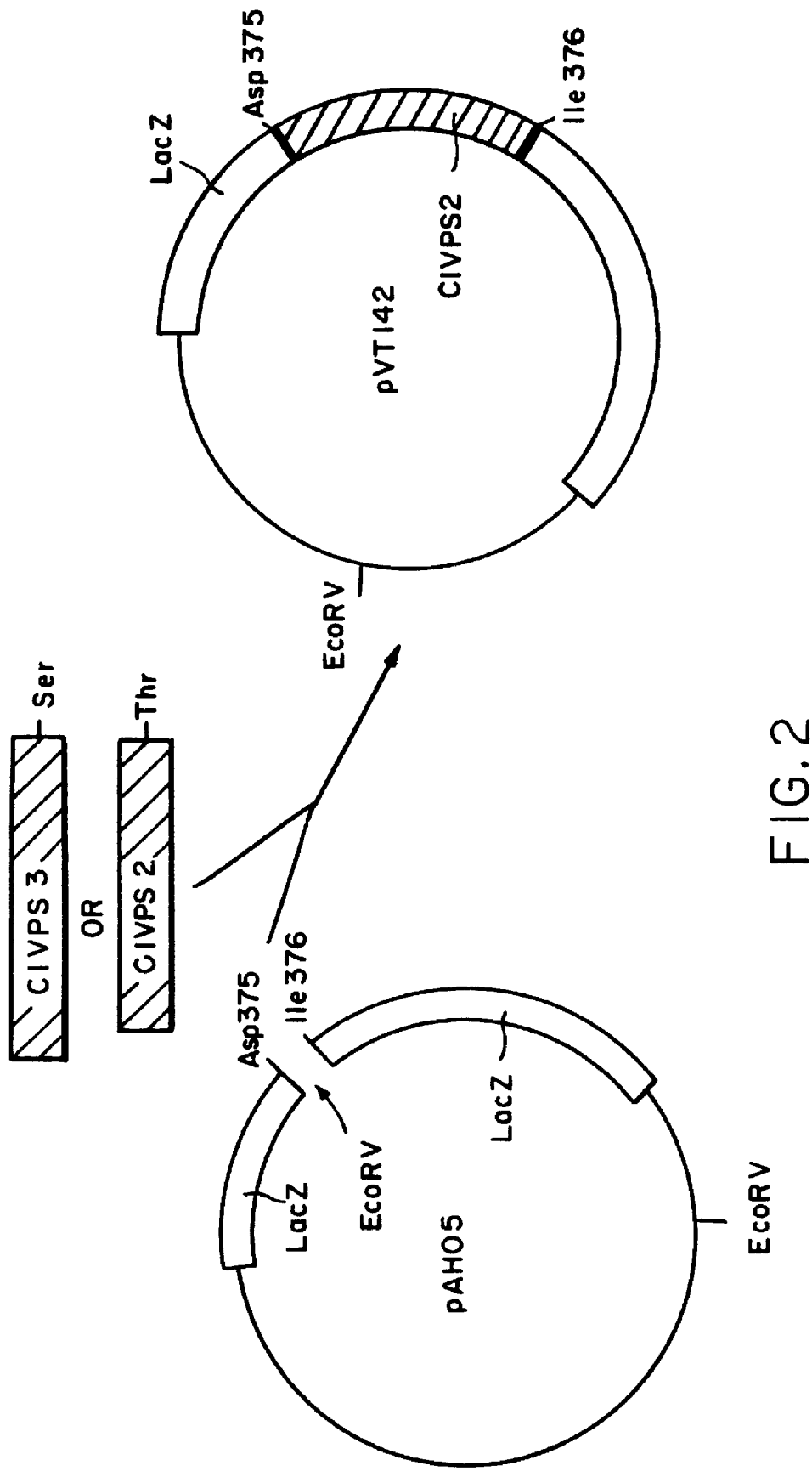
FIG. 2 illustrates insertion of IVPS into the EcoRV site of the β-galactasidase gene. PCR products of either Deep Vent® IVPS1 (CIVPS3) or Vent® IVPS2 (CIVPS2) are ligated to EcoRV digested pAHO5 between the Asp and Ile residues of β-galactosidase to produce a modified β-galactosidase product.

The present invention is directed to modified proteins and methods of their production. The modified proteins comprise a controllable intervening protein sequence (CIVPS) and a target protein, the CIVPS being capable of excision by protein splicing, or cleavage in the absence of splicing, under predetermined conditions, e.g., increase in temperature, changes in pH conditions, unblocking of amino acid residues by photolysis, dephosphorylation, deglycosylation, treatment with chemical reagents exposure to peptide activators or inhibitors which block or induce splicing or cleavage, or other means. If desired, the modified protein can be subjected to these conditions. The CIVPS may also be inserted into a region that substantially inactivates target protein activity.

Intervening protein sequences (IVPS) are internal in-frame peptide segments found within a precursor protein which are removed or excised via protein splicing to form the native protein. IVPSs have been described in the TFPI allele from *Saccharomyces cerevisiae* (Hirata et al., supra; Kane et al., supra) and rec A gene from *Mycobacterium tuberculosis* (Davis et al., supra (1991); Davis et al., supra (1992)). The disclosure of these references are herein incorporated by reference.

CIVPSs of the present invention include any intervening protein sequence in which excision or cleavage can be controlled, either by inherent properties of the native IVPS, such as an increase in temperature, or by modifications made to an IVPS that allow the reaction to be controlled.

The Vent® DNA polymerase gene from the hyperthermophilic archaea *Thermococcus litoralis* contains two in-frame IVPSs, IVPS1 (CIVPS1) and IVPS2 (CIVPS2), (Perler, et al. supra) that can be deleted at the DNA level without affecting the kinetic and biochemical properties of the expressed polymerase. Correct processing of the Vent® DNA polymerase gene containing both IVPSs occurs in the native archaea, T. litoralis. In addition, correct processing of expression constructs lacking IVPS1 has been observed in eubacterial *E. coli* (Perler, et al., supra), in eukaryotic baculovirus-infected insect cell and in vitro transcription/translation systems (Hodges, et al., *Nucleic Acids Research*, 20:6153 (1992)). Furthermore, rabbit reticulocyte and *E. coli* in vitro transcription/translation systems correctly remove IVPS2 sequences to produce the mature polymerase. While not wishing to be bound by theory, it is believed that the Vent® and Deep Vent® IVPSs are self splicing.

The nucleotide sequence for the Vent® DNA polymerase gene is set out in the Sequence Listing as SEQ ID NO:1. The nucleotide sequence for CIVPS1 is from nucleotide 1773 to 3386. The nucleotide sequence for CIVPS2 is from nucleotide 3534 to 4703. CIVPS1 and CIVPS2 can be obtained from phage NEB 619, which was deposited with the American Type Culture Collection (ATCC) on Apr. 24,1990 and received ATCC accession number 40795.

A third IVPS (CIVPS3 or DV IVPS1), has been found by the present inventors in the DNA polymerase gene of the thermophilic archaebacteria, *Pyrococcus* species (isolate GB-D). The *Pyrococcus* DNA polymerase is sometimes referred to as Deep Vent® DNA polymerase. The nucleotide sequence of the Deep Vent® DNA polymerase is set out in the Sequence Listing as SEQ ID NO: 2. The nucleotide sequence for CIVPS3 is from 1839 to 3449. CIVPS3 can be obtained from plasmid pNEB #720 which was deposited with the ATCC on Oct. 1, 1991 and received ATCC accession number 68723.

Other preferred CIVPs include those obtainable from *Saccharomyces* such as *Saccharomyces cerevisiae* (see Example 15 hereinbelow).

In accordance with one embodiment of the present invention, it has been found that the above CIVPS1, CIVPS2 and CIVPS3 are capable of excision from modified proteins upon an increase in temperature. For example, the CIVPSs are excised at reduced rates at temperatures from 370° C. and below, but undergo excision more efficiently at temperatures from about 42° C. to 80° C. Preferred excision temperatures are between about 42° C. and 60° C. Most preferably, predetermined excision conditions are experimentally determined taking into consideration temperatures at which the target protein will not denature or undergo thermal inactivation. The modified proteins can be subjected to the predetermined temperatures for a period of time ranging from less than one minute to several hours. In certain situations, depending on the thermal sensitivity of the target protein, it may be desirable to increase the incubation time period while decreasing the temperature.

Additionally, different modified proteins may exhibit differences in splicing efficiency at various temperatures. If necessary, the optimum temperatures for isolation and splicing of each modified protein can be experimentally determined. If the CIVPS splices at too low a temperature for a proposed purpose, the CIVPS can be modified, or its position in the target protein changed such that the optimum splicing temperature is increased. If the optimum splicing temperature for a particular modified protein is about 37° C., in order to insure that the modified protein does not splice in viva, and thus increase the yield of intact modified proteins, host cells can be grown and the modified protein purified at lower temperatures, e.g., 12° C.–30° C. This can also be accomplished by mutating the splicing element to shift the splicing temperature optimum from, for example, 30° C.–37° C. to 42° C.–50° C., and thus resulting in a reduced level of splicing at physiological temperature.

Other IVPSs can be isolated, for example, by identifying genes in which the coding capacity is significantly larger than the observed protein and that encodes a protein sequence not present in the mature protein. A protein containing an IVPS can be distinguished from a protein having a "pre-pro" precursor in that the mature protein will still have the N-terminal and C-terminal sequences of the IVPS containing precursor. Additionally, IVPSs can be detected by the absence of motifs that are conserved in certain protein families, e.g., DNA polymerases. The absence of such a motif may indicate that an IVPS is interrupting that motif (Perler et al., supra). Suspected IVPSs can be screened by inserting the suspected protein sequence into a marker protein, e.g., β-galactosidase, such that the insertion decreases marker protein activity. The resulting modified protein can then be evaluated at periodic intervals for an increase in marker protein activity. See, Example 1–3. Once identified, the DNA encoding the IVPS can be isolated and manipulated using standard DNA manipulation techniques.

Chemical activation of splicing or cleavage may be accomplished by reacting the CIVPS of interest with a chemical reagent which enhances or induces splicing or cleavage. In one preferred embodiment, splicing or cleavage is controlled by employing one or more chemical reagents in a two-step process which first inactivates cleavage or splicing by mutation of the CIVPS or any other means, and then activates cleavage or splicing by addition of a chemical reagent, such as hydroxylamine, β-mercaptoethanol or dithiothreitol, for example.

Control of cleavage or splicing by chemical reagents can be applied to both cis and trans CIVPS reactions.

The chemical reagent employed depends, in part, on whether cleavage is occurring at the N-terminus or the C-terminus. While not wishing to be bound by theory, N-terminal cleavage is believed to involve an ester or thioester formation between the N-terminal domain and the IVPS. Accordingly, any chemical reagent which facilitates cleavage of the ester or thioester such as hydroxylamine (Bruice and Benkovic, *Bioorganic Mechanisms*, W. A. Benjamin, Inc., New York, (1966)) β-mercaptoethanol or dithiothreitol may be used to induce N-terminal cleavage. C-terminal cleavage is believed to involve cyclization of the IVPS C-terminal conserved asparagine. Accordingly, any reagent which increases the rate of cyclization of asparagine could be used to facilitate C-terminal cleavage. In a process referred to as noncovalent chemical rescue, an enzyme can be mutated, resulting in an inactive form of the enzyme. The activity can then be restored by adding a chemical reagent to the reaction mixture. See, for example, Toney and Kirsch (*Science*, 243:1485–1488 (1989)). This process of noncovalent chemical rescue of cleavage activity in CIVPS3 is described in Example 14. Noncovalent chemical rescue of enzyme activity by a chemical reagent can be potentially applied to CIVPS cleavage or splicing mutants at the primary mutation or after introduction of a second mutation at many different possible amino acid residues in the CIVPS using the appropriate chemical reagents for each type of mutation (Toney and Kirsch, supra).

While not wishing to be bound by theory, C-terminal cleavage is believed to involve cyclization of the IVPS C-terminal conserved asparagine. Accordingly, any reagent which increases the rate of cyclization of asparagine could be used to facilitate C-terminal cleavage.

IVPSs may also be identified by a larger open reading frame than observed in the mature protein and the presence of a region which has some of the following properties: (1) similarity to HO endonuclease or other homing endonucleases, (2) the amino acid sequence (Ala/Val) His Asn (Ser/Cys/Thr) (SEQ ID NO:45).

CIVPSs of the present invention also include IVPSs which have been modified such that the splicing reaction can be controlled. As shown in FIG. 1 (SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, and SEQ ID NO:39), the aligned splice junctions of known protein splicing IVPSs reveal several similarities. In particular, —OH and —SH side chains are found on residues at the C-terminal side of both splice junctions, preceded by the dipeptide His-Asn at the downstream splice junction.

While not wishing to be bound by theory, it is believed that hydroxyl/sulfydryl groups participate in the splicing reaction and thus modification of these residues modulate the splicing reaction. Such modifications can be evaluated by inserting the modified CIVPS into a marker protein, e.g., β-galactosidase, such that the insertion decreases marker protein activity. The resulting modified protein can then be evaluated at periodic intervals and under controlled conditions for an increase in marker protein activity. See, Example 1–3. In addition, Western blot analysis can be used to evaluate splicing and cleavage products. See, Example 8. Once identified, the DNA encoding the CIVPS can be isolated and manipulated using standard DNA manipulation techniques.

In accordance with the present invention, it has been found that single amino acid changes at the serine 1082 of CIVPS2 slowed or blocked the protein splicing reaction. Specifically, the threonine substitution mutant displayed 10% of the polymerase activity of the wild-type enzyme, while the cysteine and alanine substitution mutants gave no detectable activity. However, a reaction product corresponding to cleavage at the altered splice junction was observed. This species accumulated in a mutant which replaced the serine at the splice junction with cysteine, but was unaltered when serine was replaced with either threonine or alanine. Wild-type CIVPS2 showed accumulation of a species of the size expected for cleavage at the carboxy terminal splice junction during the splicing reaction, although accumulation of this product decreased, but was still observed, when serine 1082 was changed to threonine, cysteine, or alanine. The S1 082A variant showed no evidence of protein splicing, but still produced this product.

Mutagenesis at the carboxy-terminal splice junction, namely amino acid substitutions for the threonine 1472 (T1472) residue with serine produced patterns of splicing identical to the wild-type. Replacement of T1472 with alanine, glycine, or isoleucine gave no detectable splicing. When asparagine 1471 was replaced with alanine, no splicing was observed, but evidence of cleavage at the amino splice junction was observed. Table 1, set forth below, summarizes the effects of amino acid substitutions on splicing and cleavage in CIVPS2.

Accordingly, cleavage at the CIVPS splice junctions can be accomplished in the absence of protein splicing, thus allowing for controlled separation of the CIVPS from the target protein. In certain situations, such activity is desired. In these situations, the CIVPSs of the present invention may also encompass autoproteolytic proteins, such as autoproteolytic proteases, for example, retroviral proteases such as the HIV-1 protease (Louis, et al., *Eur. J. Biochem.*, 199:361 (1991)) and Debouck, et al., *Proc. Natl. Acad. Sci. USA*, 84:8903–8906 (1987)). The skilled artisan is familiar with other such proteins. See, Kräusslich, et al., *Ann. Rev. Biochem.*, 701–754 (1988). Such proteins can be modified, in accordance with the disclosed methodology, such that the proteolytic activity is inducible under predetermined conditions.

TABLE 1

| | N-terminal cleavage ↓ | | C-terminal cleavage ↓ |
|---|---|---|---|
| WT aa residue | S | N | T |
| residue number | 1082 | 1471 | 1472 |
| splicing observed | T | | S |
| up/downstream junction cleavage | C | | C |
| upstream junction cleavage | | q,d,a | |
| downstream junction | a | | |
| no cleavage or splicing | | | I,a,G, stop |

The effect of single amino acid substitutions on protein splicing was evaluated using pulse-chase analysis of Vent ® DNA polymerase containing IVPS2 in an *E coli* expression system (Hodges, et al., supra (1992)). Arrows indicate the locations of the splice junctions. Small case letters indicate the effects are seen only after overnight incubation, as opposed to being seen within 2 hours for other samples. Where splicing is observed, cleavage products from both C- and N-terminal cleavage are also found.

Modification of the CIVPS amino acids, including splice junction amino acids, can be accomplished in a number of ways. For example, the sequence surrounding the amino acid residue to be modified may be altered to create a biological phosphorylation site allowing it to be a substrate for specific kinases and phosphatases. Examples of protein kinase include, for example, casein kinase II, cAMP-dependent protein kinase, cdc2, and pp60$^{c-src}$ (Pearson and Kemp, *Methods in Enzymology* 200:62 (1991)). Examples of phosphatases include, for example, protein phosphatase 2A, lambda phosphatase, and the yop phosphatase from Yersinia (Tonks, *Current Opinion in Cell Biology*, 2:1114 (1990)).

Using CIVPS2 as an example, as set forth in Example 6C, an arginine residue was placed at position 1079 to create a consensus Calmodulin-dependent protein kinase II site (XRXXS*; Pearson et al., supra) The protein splicing reaction may then be regulated by the degree of phosphorylation, using a kinase to create phosphoserine and block the splicing, and phosphatases to remove the phosphate, restoring the wild type serine and, consequently, protein splicing.

Figure 9:
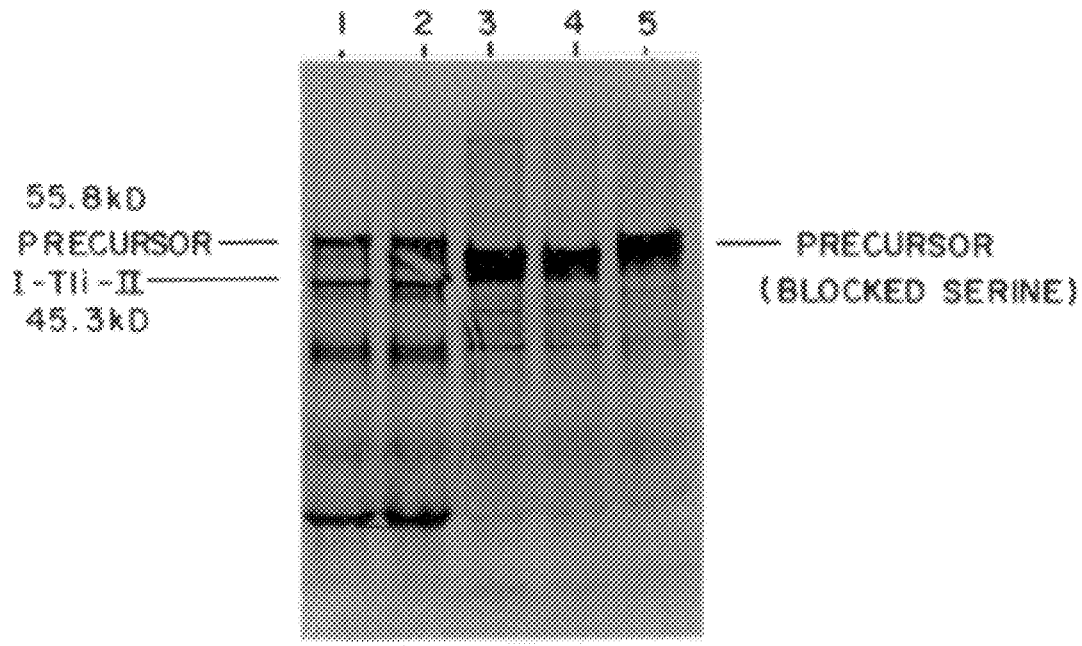
FIG. 9 is an autoradiogram of SDS-PAGE showing suppressor tRNA-mediated incorporation of a chemically blocked serine at the upstream junction of CIVPS2.
Figure 10:
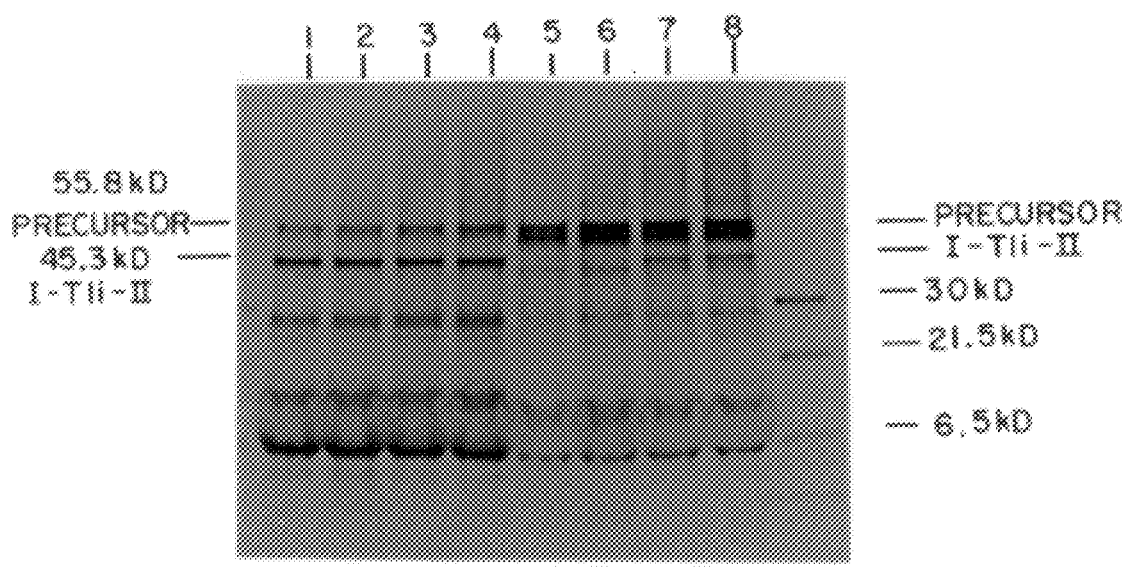
FIG. 10 is an autoradiogram of SDS-PAGE showing the splicing reaction of CIVPS2 initiated by visible light irradiation of a chemically blocked precursor protein.

Additionally, critical splice junction residues can be modified chemically such that the splicing reaction is blocked until the modification is reversed. This can be accomplished by using, for example, unnatural amino acid mutagenesis (Noren, et al., *Science* 244:182 (1989); Ellman, et al., *Methods in Enzymology* 202:301 (1991)). Using this method, one of the amino acids involved in the splicing reaction can be replaced, during translation, by a synthetic derivative in which the side chain functionality of the side chain is "masked" by a chemically or photolytically removable group. For example, as set forth in Example 7, serine 1082 of CIVPS2 was modified by this method as follows: An amber stop codon was introduced into the Vent® polymerase gene at the position corresponding to serine 1082 (see Example 6D). This gene was then added to an in vitro transcription/translation system (Ellman, et al., supra) that had previously been demonstrated to support protein splicing of the wild-type gene. In the absence of a tRNA to read through this codon, only truncated product was expected. When an amber suppressor tRNA that had been chemically aminoacylated with 0-(o-nitrobenzyl) serine was added to the system, translation was able to continue past this codon, resulting in site-specific incorporation of the modified serine. As expected, only full-length precursor was observed, indicating that the splicing reaction was blocked (FIG. 9). The o-nitrobenzyl group is removable by brief irradiation at 350 nm (Pillai, *Synthesis* 1 (1990)), so the blocked precursor would be expected to splice normally following irradiation. When the blocked precursor was exposed to visible light to free the serine and then incubated to allow the splicing reaction to occur, spliced product was clearly seen (FIG. 10).

This strategy could also be applied to threonine 1472, which is found at the downstream splice junction of CIVPS2, as well as any other residue in which either the chemical functionality of the side chain is required for splicing, or introduction of a bulky group at that position would interfere with splicing sterically. Blocking groups can be chosen not only on the basis of the chemistry of the side chain to be protected, but also on the desired method of deblocking (chemically or photolytically). For example, the cysteine groups present in other examples of protein splicing (FIG. 1) have thiol side chains that could be blocked using, for example, disulfide exchange (e.g., with dithiodipyridine) or complexation with transition metal ions (e.g., $Hg^{2+}$, 0 See, Corey and Schultz, *J. Biological Chemistry* 264:3666 (1989). The resulting blocked precursors could then be activated for splicing by mild reduction or addition of metal chelators, respectively.

It has been shown that IVPS1 and IVPS2 each encodes an endonuclease, 1-Tli-ll and 1-Tli-l, respectively. In addition, DV IVPS1 also encodes an endonuclease, 1-Pspl, which is inserted at the same position in the DV DNA polymerase gene as IVPS1 is in the Vent® DNA polymerase gene and is 62% identical to the Vent® IVPSI gene. It has been found that the IVPS open reading frames in Tfp1, *M. tuberculosis* rec A, Vent® and Deep Vent® DNA polymerase have protein sequence similarity to homing endonucleases, a class of intron-encoded proteins capable of cleaving alleles which lack the intron. (Hirata et al., supra, Kane et al., supra, Davis et al., supra, Perler et al., supra)

Certain host cells may not be able to tolerate the gene product of the CIVPS and thus, in some embodiments it may be preferable to inactivate the endonuclease function. In accordance with the present invention it has been shown that protein splicing can occur when the CIVPS endonuclease function has been inactivated. Such inactivation can be accomplished in a variety of ways, including for example, random mutagenesis, deletion or insertional inactivation, or site directed mutagenesis. Preferably, the endonuclease function is inactivated by site directed mutagenesis. l-Tli-l shares sequence similarity with other "homing endonucleases" in the pair of characteristic dodecapeptide motifs (Cummings et al., *Curr. Gent.* 16:381 (1989)). As shown in Example 6B, endonuclease activity was inactivated by oligonucleotide-directed mutagenesis of a single residue (aspartate 1236 to alanine) within one of these motifs. Substitution of alternative residues could also reduce or abolish endonuclease activity without affecting protein splicing. Inactivation of endonuclease function has been shown to increase the stability of constructs carrying the modified proteins.

Target proteins which can be used in accordance with the present invention include, for example, enzymes, toxins, cytokines, glycoproteins and growth factors. Many such proteins are well known to the skilled artisan. The amino acid and nucleotide sequence of such proteins are easily available through many computer data bases, for example, GenBank, EMBL and Swiss-Prot. Alternatively, the nucleotide or amino acid sequence of a target protein can be determined using routine procedures in the art.

If it is desirable to substantially inactivate target protein activity, the CIVPS is inserted into a region(s) that will inactivate such activity. Such regions are well known to the skilled artisan and include, for example, ) binding sites, enzyme active sites, the conserved motifs of proteins, e.g., DNA polymerases, and dimerization or multimerization sites.

Alternatively, the CIVPS may be inserted randomly and the activity of each modified protein measured until the desired level of activity is obtained. Preferably, such a modified protein has about a 50% reduced level of activity compared to the native protein. More preferably about 75%. Still more preferably greater than 99%.

The CIVPS may be inserted into the target gene by any number of means. Preferably, to assure proper protein splicing if the CIVPS is excised, it is important to insert the CIVPS immediately before a proper splice junction residue because excision of the CIVPS leaves that amino acid at the splice junction. This can be accomplished by either inserting the CIVPS immediately before the appropriate splice junction amino acid or by modifying the CIVPS such that it "brings" the appropriate amino acid with it.

For example, CIVPS1, 2 or 3 can be inserted immediately before the appropriate splice junction amino acids, for example, serine, threonine or cysteine residues, most preferably before serine or threonine. See, FIG. 1. Such sites are readily available in most target proteins.

In certain situations, such as when the target protein is a toxin, it may be desirable to further control protein splicing by adding a secondary control. This may be accomplished by inserting the CIVPS before a less optimal amino acid, for example, one that the CIVPS does not normally precede and thus may slow down the splicing reaction.

As set forth above, insertion can be at any site within the target protein if the CIVPS "brings" the appropriate downstream amino acid with it. This can be accomplished by creation of CIVPS DNA having a codon for the desired downstream amino acid. Methods for producing such DNA are set out in detail below. This DNA can then be inserted at any site within the target DNA. Upon protein splicing of the resulting modified protein, the extra residue brought by the CIVPS will be left behind. Thus, if activity of the final product is important, the skilled artisan must takes steps to assure that the extra residue will not be left in an area of the target protein that will adversely affect activity.

The CIVPS may be inserted into the target protein, or fused to the target protein, by chemically synthesizing the primary amino acid sequence of the target protein, including the CIVPS, inserted at any desired site, using standard methods (e.g., see Hunkapiller, et al., *Nature* 310:105 (1984)) and a commercially available protein synthesizer.

Alternatively, a DNA sequence encoding a CIVPS is inserted in, or fused to, a DNA sequence encoding for a target protein such that both coding sequences form a continuous reading frame. This can be accomplished using a variety of methods known to the skilled artisan, several of which are set out below.

For example, the CIVPS DNA is inserted into any restriction enzyme site that makes a blunt cut in the target gene and which is in frame. This can be accompanied by first, synthesizing an CIVPS DNA fragment with a threonine codon (for Vent® IVPS2) or a serine codon (for Deep Vent®

IVPS1 or Vent® IVPS 1) at its 3' end. This fragment is then ligated in-frame to a linear plasmid cut to blunt ends by the restriction endonuclease. Using the lacz DNA sequence, for example, an EcoRV site can be used to insert Vent® IVPS2 or Deep Vent® IVPS1 between residue 375 (aspartic acid) and 376 (isoleucine). See, FIG. 2. However, as discussed above, using this method, if the CIVPS is excised an extra residue is expected to remain at the splice junction and therefore depending on where the CIVPS is inserted, the resulting protein may not have the same function or structure as the native protein.

The CIVPS DNA could also be inserted by making silent mutations (preserving the amino acid residue) near one end or both ends of the CIVPS to create restriction sites compatible with the target gene. Using CIVPS2 as an example, a BspEl restriction site can be made near the 5' end and a Spel restriction site near its 3' end, by silent mutations. Using PCR primers overlapping the new restriction sites and continuing through the beginning of the lacZ target gene at either asp 594 or thr 595, one can generate a lacZ fragment with compatible BspE1 and Spel restriction sites. Then, the CIVPS is inserted between an aspartic acid codon (residue 594) and a threonine codon (residue 595) within the lacZ coding region. DNA fragment(s) can be synthesized from both the CIVPS and the target gene by PCR with their ends at the insertion site overlapping with the termini of the CIVPS, therefore, including the same restriction sites. After appropriate restriction endonuclease treatment, DNA fragments with compatible ends can then be ligated to create a fusion gene. Since no extra residue would be left after excision of the CIVPS, native polypeptide will form when splicing occurs. Preferably, the restriction site being created is unique within the CIVPS and within the target gene to avoid ligation of multiple fragments and thus, complicated screening procedures.

If the plasmid vector carrying the target gene sequence is relatively small, for example, less than about 5 Kb, a linear form of the plasmid can be generated using PCR, and then the linear plasmid can be ligated to the CIVPS gene. Using this method the CIVPS gene can be inserted at any location in the target gene as follows: First, plasmid DNA containing the target gene can be synthesized by PCR using a pair of primers O starting at the insertion site, for example, serine or threonine codons for CIVPS1, 2 and 3, or any codon if the CIVPS also brings the appropriate downstream amino acid. Next, the CIVPS gene (with or without serine or threonine) can be ligated to the linear plasmid DNA (without the serine or threonine codon). The required splice junction amino acids (serine or threonine) can be positioned on either the CIVPS fragment or on the target gene. The advantage of having the required amino acid on the CIVPS fragment when placing upstream of an endogenous serine or threonine is that the self-ligated vector DNA (without the CIVPS insert) may only express a deficient product of the target gene because of the deletion of the serine or threonine in the coding region. This may aid in phenotype selection for the fusion construct if the fusion protein can splice to produce a functional product.

The fusion DNA encoding the modified protein can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. For instance, when expressing a modified eukaryotic protein, it may be advantageous to use appropriate eukaryotic vectors and host cells. Expression of the fusion DNA results in the production of the modified proteins of the present invention.

Once obtained, the modified proteins can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis.

If desired, the modified proteins can be subjected to predetermined conditions under which the CIVPS is excised. Such conditions depend on the CIVPS used. For example, CIVPS 1, 2 and 3 are capable of excision by subjecting the modified protein to increased temperature, 42° C.–80° C., most preferably, 42° C.–60° C. This can be accomplished using any known means, for example a water bath or a heat generating laser. The time period for incubation can range from less than one minute to greater than several hours. As discussed above, in certain situations, depending on the thermal sensitivity of the target protein, it may be desirable to increase the incubation period while decreasing the temperature. In addition, if in vivo splicing is desired, temperatures compatible with the growth of the host organism are preferred.

The present invention may be used to produce proteins that are highly toxic to the host cells by using the CIVPS to modifying a toxic target protein such that the modified protein is non-toxic. This can be accomplished, for example, by inserting the CIVPS into a region(s) responsible for toxicity. After isolation, the non-toxic modified protein can then be subject to predetermined condition under which the CIVPS will excise and the resulting toxin can be isolated.

If a protein is extremely toxic to a host cell it may be desirable to produce that protein using a method referred to as "transplicing". Using this method the toxic protein is produced in two or more pieces in separate host cells, each piece being modified by insertion of a CIVPS. For example, a first modified protein can be produced comprising an amino portion of a target protein to which is inserted at its carboxy terminus an amino terminal fragment of a CIVPS, thereafter a second modified protein comprising the remaining portion of the target protein into which is inserted at its amino terminus the remaining fragment of CIVPSs. Alternatively, overlapping CIVPS fragments can be used. Each modified protein is then isolated from the host cells and incubated together under appropriate conditions for splicing of the CIVPS. This results in a ligated target protein. By dividing the target protein in two different hosts, there is no possibility that even a minute fraction will splice in vivo, adversely affecting the host. In addition, the entire CIVPS may be inserted on either side of the splice junction of the first modified protein and the remaining target protein fragment added to the splicing mixture.

Accordingly, trans-splicing may allow expression of highly toxic genes in *E. coli* by expressing only an inactive portion of the target protein in each of two different hosts. The two complementary fragments can then be purified in large amounts and ligated together by in vitro trans-splicing. By dividing the CIVPS into 2 parts, its splicing activity is effectively controlled until the two parts are brought together. Therefore, any IVPS becomes a CIVPS when divided into 2 parts which are purified from different hosts and kept separate until splicing is required.

The cleavage and reconstruction of protein splicing precursors via splicing in trans, opens up new avenues of protein engineering. Although the precursor contains a non-covalent linkage in the intein, after splicing the exteins are covalently linked with a native peptide bond. Splicing in trans can be used to label or modify only a portion of an intact protein. For example, a C-terminal fragment is isolated from an E. coli strain grown in normal media and an N-terminal fragment is isolated from E. coli grown in the presence of heavy atoms such as $^{13}C$ or $^{15}N$. After splicing, the intact protein is only labeled in the region of the N-extein. Such a partially labeled protein can possibly simplify structural determination by NMR analysis or allow the resolution of larger protein structures by NMR. Another use of splicing in trans would be the glycosylation, phosphorylation or dephosphorylation of only one of two sites in a protein to determine which post-translationally modified site is important for enzyme activity. Finally, splicing in trans provides absolute control of splicing since no single host contains the entire target protein and thus enables the synthesis of proteins which are toxic to the host in even minute amounts. As discussed above, formation of the toxic protein only occurs in vitro after purification of the protein fragments and the in vitro splicing reaction.

Trans-cleavage combines the properties of trans-splicing, CIVPS cleavage and the three part affinity-cleavage vector systems. In trans-cleavage, the CIVPS is separated into 2 fragments, which, when combined and activated, result in cleavage between the protein of interest and the CIVPS. In one envisioned application similar to that described for cis-cleavage in Example 9, trans-cleavage can be used for affinity purification of a protein of interest. In this application, one or both fragments of the CIVPS has an affinity tag for purification and a cloning site to make an in-frame fusion with the protein of interest. Each of the two constructs are grown and induced separately as described for trans-splicing. Protein from each of the two constructs is then purified either by standard chromatographic or affinity techniques. The two protein fragments are then combined under conditions which allow the two parts of the CIVPS to come together to form an active CIVPS. Cleavage is then induced by temperature, pH, chemical reagents or other means, releasing the purified protein of interest.

In one embodiment, the combination of the two parts of the CIVPS can occur while one part is bound to a solid matrix; in this case, after activation of cleavage, the protein of interest is released from the solid matrix while the CIVPS and any affinity tag remain on the solid matrix. Under some conditions, the two CIVPS fragments will remain associated after the cleavage reaction, allowing both to remain bound to the solid support even though only one fragment has an affinity tag. One might also have affinity tags on both fragments of the CIVPS to allow separation of the protein of interest from the CIVPS fragments after cleavage. As in the case of the 3 part fusion described in Example 9, the order of the binding domain, the CIVPS and the protein of interest can be varied. All variations described for CIVPS purification and cleavage schemes can be applied to trans-cleavage systems also.

By using the same information obtained for cis-cleavage on CIVPS fusions or by using new mutations, cleavage may be programmed to occur at either the N-terminal or the C-terninal of the CIVPS. The starting point for the CIVPS fragments are those described in Example 12. These CIVPS3 fragments were converted to trans-cleavage reagents by cassette replacement as described in Example 10. Some of the many possible mutations which we have shown result in transcleavage at the C-terminal of CIVPS3 are Ala535 of CIVPS3 to Lys, Ser1 of CIVPS3 to Ala and lle2 of CIVPS3 to Lys. Asn537 of CIVPS to Ala resulted in transcleavage at the N-terminal of CIVPS3.

The IVPSs of the present invention may be used in a "protein ligation" to add unnatural amino acid residues, structural probes, identifying epitopes or tags, or other determinants to a target protein. For example, the target protein can be fused to the amino terminus of the IVPS. A stop codon can be placed immediately following the carboxy terminus of the IVPS. The peptide to be fused can then be added to the mixture. If necessary, in order to more closely mimic the native splicing mechanism, the amino terminus of this peptide may be serine, threonine, or cysteine. The splicing reaction may then proceed, pushed by mass action towards splicing of the product.

The above reaction could also be adapted to occur with a starting material composed of the IVPS fused at the carboxy terminus to the amino terminus of the target protein. Initiation at a methionine engineered to precede the serine residue which begins in certain CIVPS would allow translation to occur which would likely be processed off in E. coli leaving an amino terminal serine residue. The peptide to be fused to the amino terminus of this target protein could then be added, and o splicing allowed to proceed. Such an approach may be favored since there is no known requirement for the carboxy terminal residue on the peptide being added. Additionally, current experimental evidence suggests that cleavage of the upstream splice junction precedes the ligation reaction, indicating this approach more closely approximates the native reaction mechanism. Targeting peptides could also be added to the peptide to facilitate translocation of the fusion protein.

The present invention can also be used to study the effect of a target protein during a specific part of the cell cycle or under specific conditions such as induction of another protein or differentiation. For example, the chromosomal copy of a gene encoding a particular protein can be replaced with a version containing a CIVPS. At a specific point in the cell cycle, differentiation or other desired point, the cells are heated causing the precursor to splice, and thus the active target protein is present only at this point.

The CIVPs of the present invention can also be used to isolate modified proteins by use of affinity chromatography with antibodies specific to the CIVPS. For example, monoclonal or polyclonal antibodies can be generated having binding affinity to a CIVPS using standard techniques. These antibodies can then be utilized in affinity chromatography purification procedures to isolate a modified protein. After purification, if desired, the modified proteins can be subjected to predetermined conditions under which the CIVPS will undergo excision.

As discussed above, cleavage at the CIVPS splice junction can be accomplished in the absence of protein splicing, thus allowing for controlled separation of the CIVPS from the target protein. Such CIVPSs can therefore be used in a fusion protein purification system.

Fusion protein purification systems are well known to the skilled artisan. See, EPO 0 286 239 and N. M. Sassenfeld, TIBTECH, 8:88–93 (1990). Typically, in such systems, a binding protein and a target protein are joined by a linker having a protease recognition site. The fusion is then purified by affinity chromatography on a substrate having affinity for the binding protein. The binding protein and the target protein are then separated by contact with a protease, e.g., factor Xa. In these systems, in order to obtain a highly purified target protein, the protease must be separated from the target protein, thus adding an additional purification step, as well as the potential for contamination. The method of the present invention, by using a CIVPS, instead of a protease, avoids these and other problems encountered in currently used protein fusion purification systems.

In accordance with another embodiment of the present invention, a modified protein comprising a fusion protein in which a CIVPS is between the target protein and a protein or peptide having affinity for a substrate (binding protein or binding domain) is formed. Techniques for forming such fusion proteins are well known to the skilled artisan. See, EPO 0 286 239 and J. Sambrook, et al., *Molecular Cloning: A Laboratory Manual* (1989), Cold Spring Harbor Laboratory Press, Cold Spring Harbor, N.Y. p. 17.29–17.33.

Binding proteins which may be employed in the method of the present invention include, for example, sugar binding proteins, such as maltose or arabinose binding protein, receptor binding proteins, amino acids binding proteins and metal binding proteins. One especially preferred binding protein is a chitin binding protein, or the chitin binding domain of a chitinase. Other binding proteins are well known to the skilled artisan. See, EPO 0 286 239 and N. M. Sassenfeld, *TIBTECH*, supra.

The modified protein is then contacted with a substrate to which the binding protein has specific affinity, e.g., using affinity chromatography.

The highly purified target protein can be liberated from the column by subjecting the CIVPS to predetermined conditions under which cleavage is initiated, for example, between the CIVPS and the target protein. Alternatively, the purified fusion protein can be eluted from the column and liberated as above.

Other preferred embodiments are described in more detail in the Examples hereinbelow. Accordingly, the present invention is further illustrated by the following Examples. These Examples are provided to aid in the understanding of the invention and are not construed as a limitation thereof.

All references cited above and below are herein incorporated by reference. All reagents are from New England Biolabs, Inc., Beverly, Mass. 01915 unless specified otherwise.

EXAMPLE 1

Synthesis Of IVPS Cassettes For Insertion Into Blunt Sites Between Target Gene Codons DNA fragments or cassettes for in-frame insertion of IVPSs into the lacZ coding region or any other target gene can be prepared by polymerase chain reaction (PCR) with or without the first downstream external protein sequence (EPS) codon. The native downstream residues are serine for Deep Vent® IVPS1 and Vent® IVPS1 or threonine for Vent® IVPS2. It has been found that IVPS2 can splice if it precedes a threonine or cysteine, although at reduced levels. Although not wishing to be bound by theory, it is believed that all the IVPSs can splice to some extent when preceding either serine, threonine or cysteine. Cassettes including the downstream serine or threonine can be inserted at any desired location in the target gene including preceding a serine or threonine. In the latter constructions, one may delete the serine or threonine from the target gene and substitute it with the incoming residue on the cassette. Cassettes lacking downstream serines, threonines or cysteines may be inserted prior to a serine, threonine or cysteine in the target gene.

The following protocol describes the production of cassettes for Deep Vent® IVPS1 (CIVP3) and Vent® IVPS2 (CIVPS2) (endo$^+$ and endo_versions), including the first downstream EPS codon.

The PCR mixture contains Vent® DNA polymerase buffer, supplemented with 2 mM Magnesium sulfate, 400 $\mu$M of each dNTP, 0.9 $\mu$M of each primer and 40 ng plasmid DNA and 2 units of Vent® DNA polymerase in 100 $\mu$l. Amplification was carried out by using a Perkin Elmer/Cetus (Emeryville, Calif.) thermal cycler at 94° C. for 30 sec, 48° C. for 30 sec and 72° C. for 2 min for 30 cycles. Deep Vent® IVPS1 was synthesized from pNEB #720 (ATCC No. 68723) which has a 4.8 Kb BamHl fragment containing the *Pyrococcus sp*. DNA polymerase gene inserted into the BamHI site of pUC19. Vent® IVPS2 was synthesized from pV153-2 which has a 1.9 kb EcoR1 fragment (2851–4766) of the Vent® DNA polymerase gene sequence in the vector Bluescribe SK-(Stratagene, LaJolla, Calif.). Alternatively, pNEB671 (ATCC No. 68447) can also be used for IVPS2. pAMQ29 is an endonuclease-deficient derivative of pVl53-2, carrying an amino acid substitution (aspartic acid 1236 to alanine) within the Vent® IVPS2 coding region. Primers 5'-AGTGTCT CCGGAGAAAGTGAGAT-3' (SEQ ID NO:3) (Vent® IVPS2 forward, 3534–3556, a substitution of A3542 to C) and 5'-AGTATTGTGTA CCAGGATGTTG-3' (SEQ ID NO:4) (Vent® IVPS2/Thr reverse, 4706–4706) were used to synthesize endo$^+$ or endo$^-$ Vent® IVPS2fragment (1173 bp) with a threonine codon at its 3' terminus. Primers 5'-AGCATT TTACCGGAAGAATGGGTT-3' (SEQ ID NO:5) (DV IVPS1 forward, 1839–1862) and 5'-GCTATTATGTGCATAGAGGAATCCA-3'(SEQ ID NO:6) (DV IVPS1/Ser reverse, 3428–3452) were used to synthesize the *Pyrococcus sp*. (or Deep Vent®) IVPS1 fragment (1614 bp) with a serine codon at its 3' end. Reverse primers lacking the final three nucleotides could be used to generate IVPS fragments lacking the C-terminal serine or threonine.

The PCR samples were extracted with phenol and chloroform, precipitated in 0.3 M NaAc and 70% ethanol at −20° C. for overnight, recovered by spinning at 10 K for 10 min in a microfuge, dried and each resuspended in 30 $\mu$l of distilled water, loaded on a 1 % agarose gel for electrophoresis at 60 volts for 15 hours. The gel slices that contain the PCR-amplified fragments were placed in a 1% low melting agarose gel for electrophoresis at 80 volts for 2 hours. DNA fragments were recovered from the low melting agarose gel by incubation in 0.5 ml of TE buffer (10 mM Tris-HCl/0.1 mM EDTA, pH8.0) at 65° C. for 30 min, extractions with phenol, phenol-chloroform (1:1 mixture) and chloroform, precipitation in 0.6 M NaAc (pH5.2) and 50% isopropanol at −20° C. for overnight. DNA was spun down, washed with 70% ethanol, dried and resuspended in 15.5 $\mu$l distilled water.

Phosphorylation of the IVPS DNA fragments was performed at 37° C. for 60 min with 2 $\mu$l of 10x polynucleotide kinase buffer, 15.5 $\mu$l of purified DNA, 2 $\mu$l 10 mM ATP, and 5 units of T4 Polynucleotide kinase in 20 $\mu$l. The samples were heated in a 65° C. water bath for 10 min. After addition of 80 $\mu$l of TE buffer (10 mM Tris-HCl/0.1 mM EDTA, pH8.0), the samples were sequentially extracted with phenol, phenol-chloroform (1:1 mixture) and chloroform. DNA was precipitated in 2.5 M NH₄Ac and 70% ethanol at −700° C. for 3.5 hours, pelleted by spinning at 10 K for 10 min in a microfuge, washed with cold 70% ethanol, dried and resuspended in distilled water (20 µl for Vent® IVPS2 or Deep Vent® IVPS1 DNA, 10 µl for Vent® IVPS endo⁻ DNA).

EXAMPLE 2

In-Frame Insertion of IVPS in a Restriction Enzyme Linearized Plasmid, Such as One Encoding β-Galactosidase In this example, we describe how the IVPS cassettes can be cloned into a target gene by inserting the cassette at a restriction enzyme site which makes a blunt cut in the target gene between 2 codons. The cassette can carry a C-terminal serine, cysteine or threonine if necessary. This protocol works best if the restriction enzyme cuts the target gene vector once or twice. As an example, we describe insertion into the EcoRV site of the lacZ gene (FIG. 2).

Preparation of EcoRV-Linearized PAHO5 pAHO5 carries the entire lacZ gene sequence on a 3.1 kb BamHl-DraI fragment from pRS415 (Simons, et al., *Gene* 53:85–96 (1987)) inserted between BamHI and SmaI sites in the polylinker of pAGR3 downstream of a tac promoter. The tac promoter is a transcription control element which can be repressed by the product of the ladI$^q$ gene and be induced by isopropyl β-D-thiogalactoside (IPTG). The 5.9 Kb vector pAHO5 also has a transcription terminator sequence upstream of the tac promoter and the polylinker, and the *E. coli* lacI$_q$ gene. pAHO5 contains two EcoRV recognition sequences. EcoRV leaves blunt ends at its cleavage site. One of the EcoRV cleavage sites cuts within the lacZ coding region between the 375th codon (aspartic acid) and the 376th codon (isoleucine) and is planned as the site for in-frame insertion of the IVPS fragments. The other site is located 3.2 Kb downstream within the *E. coli* lacI$^q$ gene. The plasmid is cut partially to produce some molecules in which only one of the EcoRV sites has been cleaved. These linear plasmids are purified. The IVPS cassettes will be randomly cloned into either EcoRV site. Therefore, the resultant recombinants must be screened for orientation and insertion into the proper EcoRV site. DNA was partially digested by incubation of 15 µg of pAHO5 DNA with 40 units of EcoRV in 100 µl of 1×NEB buffer 2 at 37° C. for 60 min. 20 µl agarose gel loading dye was added to the sample after the sample was heated to 65° C. for 10 min to inactivate EcoRV. DNA fragments were separated by electrophoresis on a 1% low melting agarose gel. Linearized pAHO5 plasmid DNA was recovered from the low melting agarose gel as described in example 1 and resuspended in 44.6 µl of distilled water.

Dephosphorylation of EcoRV-linearized pAHO5 was carried out in 50 µl of 1×NEB buffer 2 at 50° C. for 60 min. in the presence of 2 µg DNA and 4 units of Calf Intestinal Alkaline Phosphotase. The sample was heated in a 65° C. water bath for 30 min after addition of 0.5 µl of 0.5 M EDTA (pH8.0) and extracted with phenol, phenol-chloroform (1:1 mixture), and chloroform. DNA was precipitated in 0.75 M NH4Ac and 70% ethanol for 2 hours, recovered as described in Example 1, and resuspended in 20 µl of distilled water.

Construction of IVPS-lacZ Fusion Genes

Ligation of dephosphrylated pAHO5 DNA with phosphorylated IVPS fragments was carried out at 16° C. for 15 hours in 20 µl volume with addition of 8.6 µl distilled water, 2 µl of 10×T4 DNA ligase buffer, 4 µl of 0.1 µg/µl dephosphorylated pAHOS DNA, 5 µl IVPS DNA prepared as described above (0.25 µg of Vent® IVPS2, 0.4 µg Deep Vent® IVPS1 or 0.25 µg of Vent® IVPS2 endo⁻) and 160 units of T4 DNA ligase.

*E. coli* strain RR1 was transformed by mixing 100 µl of competent RR1 cells with 10 µl of ligation sample on ice for 30 min., heating at 42° C. for 2 min., chilling on ice for 5 min., adding 0.8 ml LB media (10 grams/liter tryptone, 5 grams/liter yeast extract, 10 grams/liter NaCl, 1 gram/liter Dextrose, 1 gram/liter MgCl₂·6H₂O pH7.2 at 25° C.) and incubating at 30° C. for 45 min. The samples were plated onto LB plates, supplemented with 100 µ/ml ampicillin. After incubation overnight at 30° C., about 150–300 colonies per plate were observed.

Colony hybridization was utilized to screen for clones that carry recombinant plasmids. The Vent® IVPS2 forward primer and the Deep Vent® IVPS1 forward primer, described in Example 1, were radio-labeled with T4 polynucleotide kinase and used as hybridization probes. Colonies were lifted onto nitrocellulose and treated for 5 min. in each of the following solutions: 10% SDS, 0.5 M NaOH/1.5 M NaCl, 0.5 M Tris-HCl (pH7.5)/0.5 M NaCl (twice) and 2XSSC (twice). The nitrocellulose filters were dried at room temperature for 1 hour, baked in vacuum at 80° C. for 2 hours, soaked in 6×SSC for 5 min and washed in a solution of 50 mM Tris-Cl (pH8.0), 1 M NaCl, 1 mM EDTA and 0.1% SDS at 42° C. for 2 hours. After treatment at 42° C. for 4 hours in 6×NET, 5× Denhardt's, 0.5% SDS and 25 µg/ml of denatured salmon sperm DNA, the filters were incubated with the radiolabeled oligomer probe under the same conditions for 16 hours and then washed in 6×SSC at room temperature three times for 15 min, twice at 42° C. for 2 min and twice at 50° C. for two min, followed by autoradiogram. 36 clones were found to hybridize to the corresponding oligomer probes.

The positive clones were further analyzed to determine insert location by PCR amplification of plasmid DNA extracted from these clones, using the Vent® IVPS2 forward primer (or the Deep Vent® IVPS1 forward primer) described in Example 1, and a lacZ reverse primer (5'-AGGGTCGACAGATTTGATCCAGCG-3' (SEQ ID NO:7)) complementary to the lacZ coding sequence (1417–1440, with a G:T mismatch at 1437) 392 nt downstream of the insertion site. PCR reactions from 14 clones produced the corresponding DNA fragments. Clones pVT133, 138, 139, 141, 142, and 144 contain the 1.4 Kb Vents IVPS2 insert, and pVTE 834, 836, 839 and 841 contain the Vent® IVPS2 (endo⁻) insert, all yielding DNA fragments of approximately 1.1 kb. Clones pDVS 712, 742, 745 and 746 carry the 1.6 Kb Deep Vent® IVPS1 insert, producing DNA fragments of about 2.0 Kb.

Expression of the IVPS-lacZ Fusion Genes

The clones were further examined by their ability to express fusion (modified) proteins with inducer IPTG.

The clones were cultured in LB medium supplemented with 100 µg/ml ampicillin at 30° C. until OD₆₀₀ nm reached 0.5. To prepare lysate from uninduced cells, 1.5 ml of culture was pelleted and resuspended in 100 µl of urea lysis buffer, followed by boiling for 10 min. After addition of IPTG to a final concentration of 0.3 mM, the cultures were grown at 30° C. for 4 additional hours. Cells from 1.5 ml culture were pelleted and then lysed with 250 µl of the urea lysis buffer after induction for 2 hours and 4 hours. Protein products were analyzed by Coomassie Blue stained gels. Three of the Vent® IVPS2-lacZ fusion constructs (pVT139, 142 and 144) and all four Vent® IVPS2 (endo⁻)-ladZ fusion constructs showed a major product of about 162–165 KDas, the expected size for a Vent® IVPS2-β-galactosidase fusion protein. All four Deep Vent® IVPS1 -lacZ fusion clones expressed a larger product of 173–178 KDa, the expected size for the Deep Vent® IVPS1-β-galactosidase fusion protein.

The identity of the Vent® IVPS2 fusion proteins from pVT142 and 144, and pVTE836 and 839 was further analyzed by western blots using antibody raised against l-Tli-l or β-galactosidase (Promega, Madison, Wis.). Samples were electrophoresed on 4–20% SDS gels (ISS, Daiichi, Tokyo, Japan) with prestained markers (BRL, Gaithersburg, Md.), transferred to nitrocellulose, probed with antisera (from mouse), and detected using alkaline phosphate-linked anti-mouse secondary antibody as described by the manufacturer (Promega, Madison, Wis.). A band of approximately 160 KDa from all four clones being examined reacts with both sera and migrates at the same location as the Coomassie Blue stained band. Deep Vent® IVPS1 fusions were also examined. Western blot analysis of pDVS712 and 742 using sera against β-galactosidase and l-Pspl (the protein product of Deep Vent® IVPS1) yielded the predicted major band at about 168–175 KDa, identical to the Coomassie Blue stained band.

EXAMPLE 3

Thermal Control of Protein Splicing in β-Galactosidase-IVPS Fusions

The constructs described above (IVPSs inserted into the lacZ EcoRV site) yield fusion (modified) proteins after induction. The IVPS protein can be excised from the fusion protein to generate a ligated target protein (active β-galactosidase) and free IVPS endonuclease by incubation at elevated temperatures.

Splicing is Controllable by Temperature Induction: β-Galactosidase Activity in Crude Extracts Increasesin Response to Temperature Shift Crude extracts were prepared from cultures of RR1 (the *E. coli* host) and RR1 containing pAHO5 (the non-fusion β-galactosidase parent plasmid described in Example 2) or the fusion constructs, pVT1 42 (Vent® IVPS2 or CIVPS2), pVTE836 (Vent® IVPS1 endo⁻) or pDVS712 (Deep Vent® IVPS1 or CIVPS 3) by the following steps. A single colony was inoculated in 10 ml LB medium supplemented with 100 μg/ml ampicillin, incubated at 30° C. overnight, subcultured in 1 liter LB medium (100 μg/ml ampicillin) at 30° C. to $OD_{600}$ nm about 0.5 and induced with IPTG at 0.3 mM at 30° C. for 2 hours. Cells were spun down and resuspended in 100 ml of LB, sonicated for 3 min at 4° C. and spun at 7000 rpm for 15 min. The supernatants were recovered and stored at –20 °C.

Figure 3A:
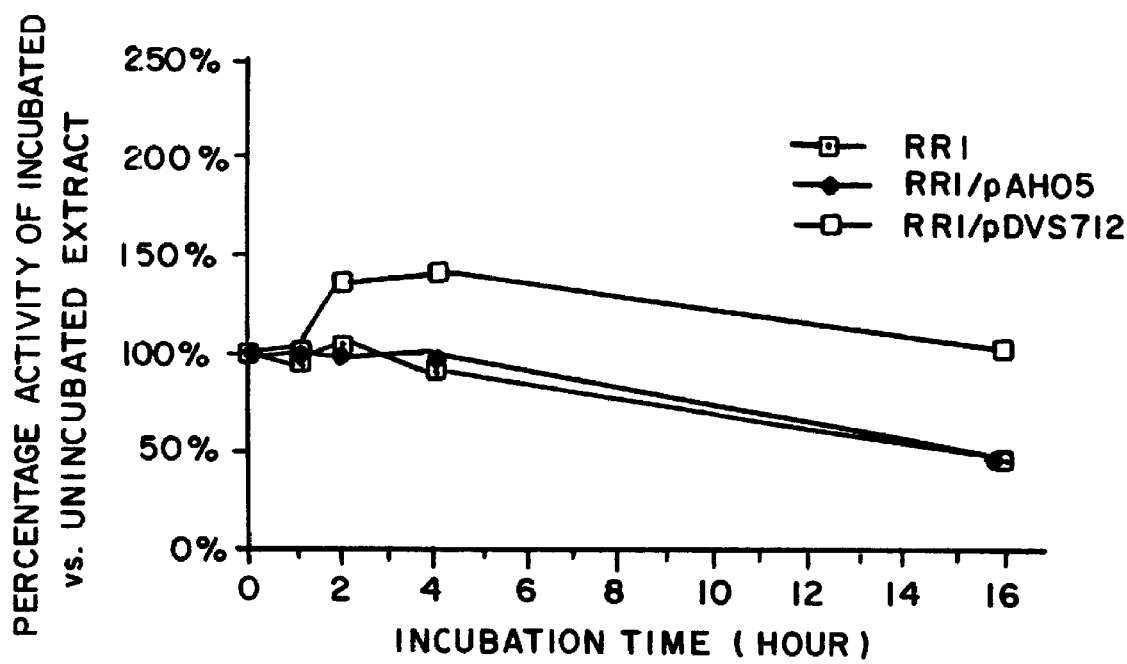
FIGS. 3A and 3B are graphs showing that splicing of modified βgalactosidase yields active β-galactosidase. Incubation of crude extracts from hosts expressing the indicated IVPS-β-galactosidase fusion proteins at 42° C. yields an increase in enzyme activity with time, whereas incubation at 42° C. with the host alone (RR1) or an unmodified β-galactosidase construct (pAHO5) shows no increase in enzyme activity.
Figure 3B:
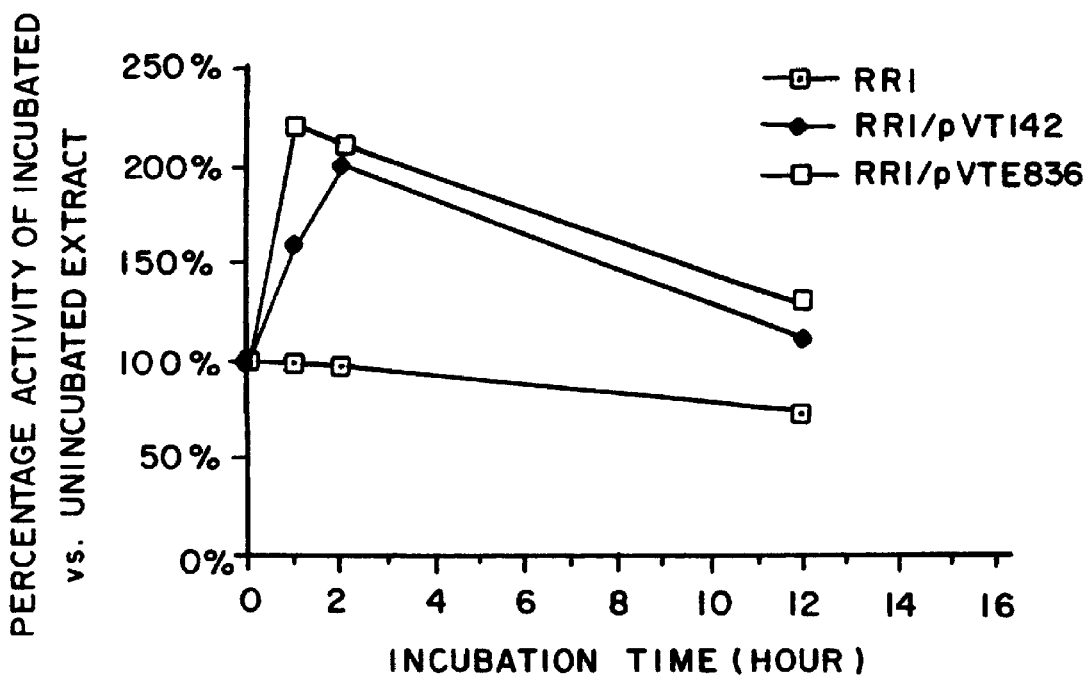

7.5 ml aliquots of crude extracts were incubated in 42° C. or 50° C. water baths; 1 ml aliquots were taken at 1, 2 and 12 hours for pVT142 and pVTE836 extracts or 0.5, 1, 2, 4 and 16 hours for pDVS712, pAHO5 or RR1 extract.

β-galactosidase activity was measured according to Miller et al. (*Experiments in Molecular Genetics* (1972), Cold Spring Harbor, N.Y. Cold Spring Harbor Laboratory). Assay buffer was prepared by mixing Z buffer with 2.7 μ/ml of 2-mercaptoethanol. Substrate o-nitrophenyl-β-D-galactopyranoside (ONPG) was dissolved in the assay buffer at 4 μg/ml. 0.1 ml of treated or untreated extract was transferred into a test tube containing 0.9 ml of assay buffer and 1 drop of 0.1%SDS and incubated for 5 min at 28° C. 0.1 ml LB medium was used for blank. 0.2 μl of 4 mg/ml ONPG was added to start an assay reaction. When adequate yellow color developed, the reaction was stopped by addition of 0.5 ml of 1 M $Na_2CO_3$ The incubation time was recorded and activity was measured on a spectrophotometer at $OD_{420}$ nm and $OD_{550}$ nm. The enzymatic activity from the heat-treated extract was calculated as follows. The activity after incubation was divided by the activity of the zero time point; the ratio was then multiplied by 100 to yield a percentage. Comparison of enzymatic activity indicated that while heat treatment had no effect on activity from RR1 or RR1/pAHO5 extract in the first two hours of incubation, all three IVPS-LacZ fusion constructs, pVT142, pVTE836 and pDVS712, exhibited an increase in enzymatic activity in response to the temperature shift to 42° C. from 143% to 221% of untreated samples (FIGS. 3A and 3B). This increase in β-galactosidase activity was due to excision of the IVPS and ligation of the two halves of β-galactosidase, forming more enzyme which was active. The splicing was confirmed by Western blot analysis. β-galactosidase activity in RR1 cells comes from expression of the chromosomal gene. The overnight incubation resulted in lower enzymatic activity from all samples, probably due to thermal inactivation of β-galactosidase (FIGS. 3A and 3B).

Splicing is Controllable by Temperature Induction: Analysis of Proteins by Coomassie Blue Staining and Western Blots Analysis of IVPS-lacZ fusion protein synthesis in RR1 cells is complicated by chromosomal expression of β-galactosidase. Therefore, for ease of analysis, all the constructs were transferred to an *E. coli* host which did not synthesize β-galactosidase.

Preparation of crude cell extracts from the IVPS-lacZ fusion clones and western blot analysis of heat-treated samples were performed as followings.

The fusion constructs and the lacZ expression vector pAOH5 were introduced into a lacZ-deletion *E. coli* strain ER2267 (New England Biolabs, Inc.) by the standard transformation procedure as previously described.

The cultures of ER2267 (50 ml), ER2267/pAHO5 (50 ml), pVT142 or pDVS712 plasmid (each in 1 liter) were grown at 30° C. in LB media, supplemented with ampicillin at 100 μ/ml for plasmid-containing cells. When $OD_{600}$ nm reached between 0.48 and 0.55, inducer IPTG was added into the cultures to 0.3 mM final concentration and the cultures were incubated at 23° C. for 3 additional hours. Cells were spun down, resuspended in 50 ml (for ER2267 or pAHO5-bearing ER2267) or 100 ml (for pVT142- or pDVS712-bearing ER2267) LB media, sonicated for 3 min at 4° C. and spun at 7000 rpm for 10 min. The supernatants were stored at –20° C. Three 5 ml aliquots of each extract were incubated and sampled at 23° C., 42° C. or 50° C. for 16 hours. Aliquots of 0.9 ml were transferred into 1.5 ml microfuge tubes after incubation for 1, 2, 3, 4, 6 hours. 5 μl of untreated or treated extract was mixed with 10 μl of water and 5 μl of 5x sample buffer (0.31 M Tris-Cl, pH6.8/ 10%SDS/25% 2-mercaptoethanol/50% glycerol/0.005% Bromophenol blue) and boiled for 10 min.

Figure 4:
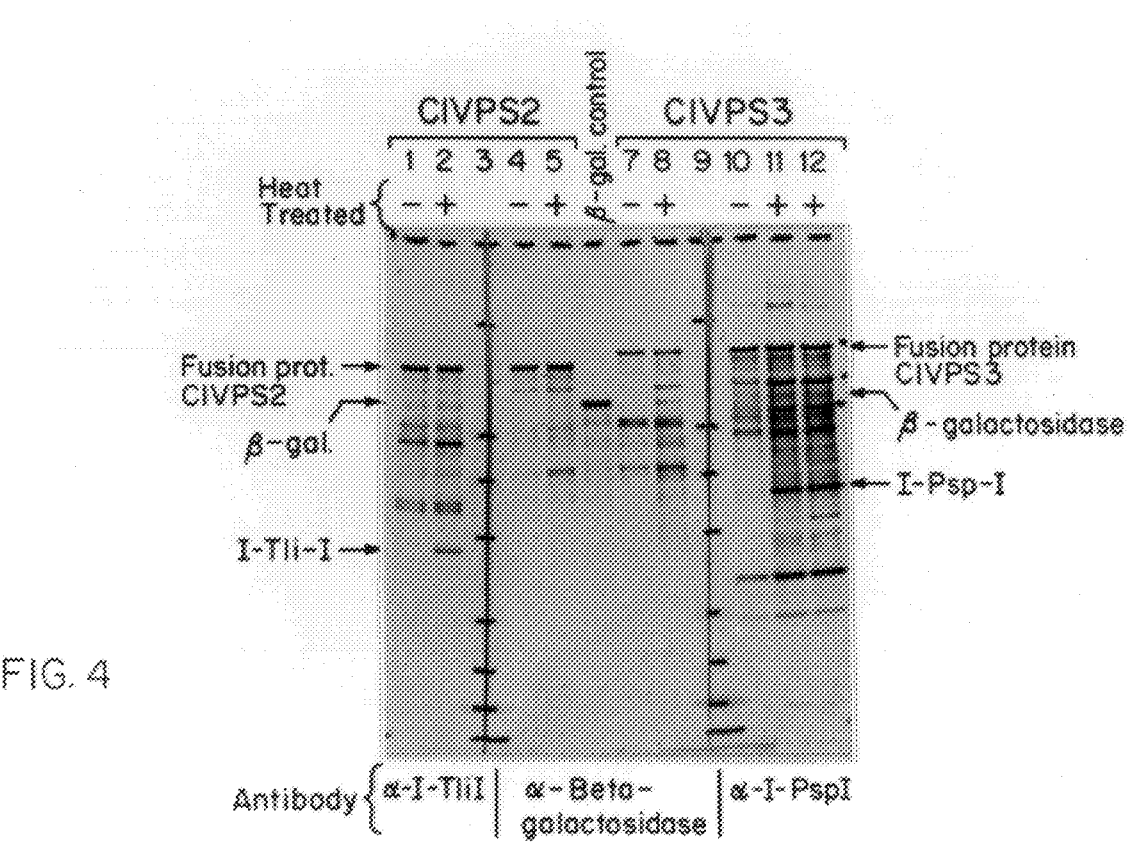
FIG. 4 is a western blot showing the results of temperature controlled protein splicing experiments. CIVPS2 and CIVPS3 were cloned into the EcoRV site of β-galactosidase. Western blot examination of cell extracts with sera directed against β-galactosidase or the CIVPS protein (l-Tlil and l-PspI, respectively) detects modified β-galactosidase fusion protein (Lanes 1,4,7,10). Treatment of extracts at 42° C. (Lanes 2,5,8,11) or 50° C. (Lane 12) for 6 hours results in splicing and the production of free CIVPS proteins and unmodified β-galactosidase (except for retained serine or threonine residue, see text example 2 & 3). Unmodified β-galactosidase from pAHO5 is in lane 6. Lanes 3 & 9 contain size markers.

5 μl of each sample was loaded on a 4/20% SDS polyacrylamide and electrophoresed at 100 volts for 3–4 hours. Western blots, using antibody raised against β-galactosidase (Promega, Madison, Wis.) and antibody raised against endonuclease l-Tli-l or l-Pspl, were carried out according to the procedure of Promega. The results showed barely trace amounts of endonuclease present in cells after IPTG induction at 23° C. from both pVT142 and pDVS712 constructs, indicating inefficient excision activity, if any. However, after shifting the ER2267/pVT142 extract to higher temperatures, 42° C. or 50° C., abundant IVPS2 product (l-Tli-l about 42 KDa), identical to the excised endonuclease from the Vent® DNA polymerase precursor, was accumulated (FIG. 4). A similar pattern was observed for pDVS712/ER2267 extract treated at 42° C. or 50° C. (FIG. 4), resulting in accumulation of a product of about 60 KDa, expected for the Deep Vent® IVPS1 product, l-Pspl.

Western blot analysis using antibody against β-galactosidase indicated that excision of the IVPS domains was coupled with ligation or rejoining of the N-domain and the C-domain of the interrupted β-galactosidase. The heat-treated samples of both fusion constructs contained a product of 114 KDa, identical in size to full-length β-galactosidase (FIG. 4). However, this product was only accumulated in small amount in the samples of pVT142, indicating that splicing from this fusion protein is inefficient under these conditions.

The fusion proteins were further tested for their ability to splice at higher temperatures, up to 80° C. The initial reaction rates at different temperatures were compared. The extracts were incubated in 300 μl aliquots in 1.5 ml-microfuge tubes at 42° C., 50° C., 65° C. or 80° C. 20 μl were taken from each heated extract sample at 15 and 30 min and 1, 2, and 4 hours, and mixed with 40 μl of water and 20 μl of 5 x sample buffer and boiled for 10 min. Western blot analysis showed that Deep Vent® IVPS-β-galactosidase fusion protein was able to splice at 65° C. and at 80° C., although splicing seems more efficient at 65° C. as measured by the accumulation of the 114 KD product. Excision of the Vent® IVPS2 was efficient at 65° C. but seems blocked at 80° C. Lack of accumulation may be due to thermal denaturation and precipitation of β-galactosidase at 80° C. with time.

EXAMPLE 4

In-Frame Insertion Of IVPS In A PCR Generated Linear Plasmid, Such As One Encoding β-Agarase I In Example 2, we described inserting the IVPS cassettes from Example 1 into a restriction enzyme linearized plasmid. This method is limited by the availability of appropriate restriction enzyme sites in a target gene. PCR amplification using opposing primers on a circular plasmid allows linearization of any plasmid at any position, limited only by the capacity of the PCR reaction. Once the target plasmid is linear, the process is essentially the same as described in Example 2 for restriction enzyme generated linear plasmids.

As described in Example 2, insertion of an IVPS cassette into a target gene can be accomplished by ligation of an IVPS fragment with linear plasmid. In this example, PCR primers are used to generate plasmids linearized just prior to a serine or threonine codon. Thus, when the IVPS is excised and the two halves of the target protein are ligated, no extra amino acid is left behind in the target protein. The serine or threonine at the insertion site can be positioned on either the IVPS fragment or on the target gene fragment. If the serine or threonine is present on the IVPS cassette, then the target gene PCR primer can be constructed with a deletion of the 3 nucleotides encoding the first residue of the downstream EPS. If the IVPS cassette lacks the serine or threonine codon, then PCR with opposing, abutting PCR primers is used to synthesize target plasmid linearized at the serine or threonine codons.

This example describes cloning two IVPS elements, Vent® IVPS2 and Deep Vent® IVPS1, into a gene encoding β-agarase I (Yaphe, W., Can. J. Microbiol. 3:987–993 (1957)) by the procedure described in Example 2. The Deep Vent® IVPS1 is inserted in front of a serine, the 108th codon, of the 290 amino acid β-agarase I gene, while the Vent® IVPS2 is inserted in front of a threonine, the 133th codon of the β-agarase I gene.

The IVPS DNA fragments, including the serine codon (for Deep Vent® IVPS1) or the threonine codon (for Vent® IVPS2) at the 3' end, were prepared as described in Example 1. pAG6a1, a 3.8 Kb recombinant plasmid containing the β-agarase I gene sequence in vector pUC18 in the orientation of lac promoter, was used as a PCR template to synthesize linear plasmid DNA fragments. Primers agaS108.rv (5'-GAGAACTTTGTTCGTACCTG-3' (SEQ ID NO:8)) and agaS108.fw (5'-GGTATTATTTCTTCTAAAGCA-3' (SEQ ID NO:9)) are compementary to DNA sequence 5' and 3' of the 108th codon, respectively. Primers agaT133.rv (5'-GTTGTTTGTTGGTTTTACCA-3' (SEQ ID NO:10)) and agaT133.fw (5'-ATGGCAAATGCTGTATGGAT-3' (SEQ ID NO:11)) are complementary to sequence 5' and 3' of the 133th codon, respectively. Each pair of the primers was used to synthesize linear plasmid DNA fragments, lacking the serine or threonine codon. The PCR mixture contained Vent® DNA polymerase buffer, supplemented with 2 mM Magnesium sulfate, 400 μM of each dNTP, 0.5 μM of each primer, 20 ng plasmid DNA and 2 units of Vent® DNA polymerase in 100 μl. Amplification was carried out using a Perkin-Elmer/Cetus (Emeryville, Calif.) thermal cycler at 94° C. for 30 sec, 45° C. for 30 sec and 72° C. for 5 min for 30 cycles. The PCR samples were extracted with phenol and chloroform, precipitated in 0.3M NaAcetate and 50% isopropanol, recovered by spinning at 10 Krpm for 10 min in a microfuge, dried and resuspended in 100 μl of distilled water. The DNA samples were then electrophoresed on a 1% low melting agarose gel and PCR-synthesized fragments were recovered as described in Example 1.

Ligation of PCR-synthesized fragment with phosphorylated IVPS fragment (Example 1) was carried out at 16° C. for 12 hours in 20 μl volume with addition of 9.5 μl distilled water, 2 μl of 10×T4 DNA ligase buffer, 4 μl of 0.01 μg/μl PCR-synthesized plasmid DNA, 4 μl IVPS DNA (0.20 μg of Vent® IVPS2 or 0.32 μg Deep Vent® IVPS1) and 0.5 μl of 400,000 M/ml of T4 DNA ligase. Transformation of E. coli strain RR1 with the ligation samples was performed as described in Example 2. Transformants were cultured in LB medium, supplemented with 100 μg/ml ampicillin, for extraction of plasmid DNA using alkaline lysis method (Sambrook et al., Molecular Cloning: A Laboratory Manual (1989), Cold Spring Harbor Laboratory press, Cold Spring Harbor, N.Y.). Plasmid DNAs were compared with pAG6a1 by electrophoresis on a 0.8% agarose gel followed by staining with ethidium bromide. Recombinant plasmid pAG108S18 contains the Deep Vent® IVPS1 insert while pAG133T22, 26, 31 and 35 all contain the Vent® IVPS2 insert.

Expression Of The IVPS-β-Agarase I Fusion Genes

Figure 5:
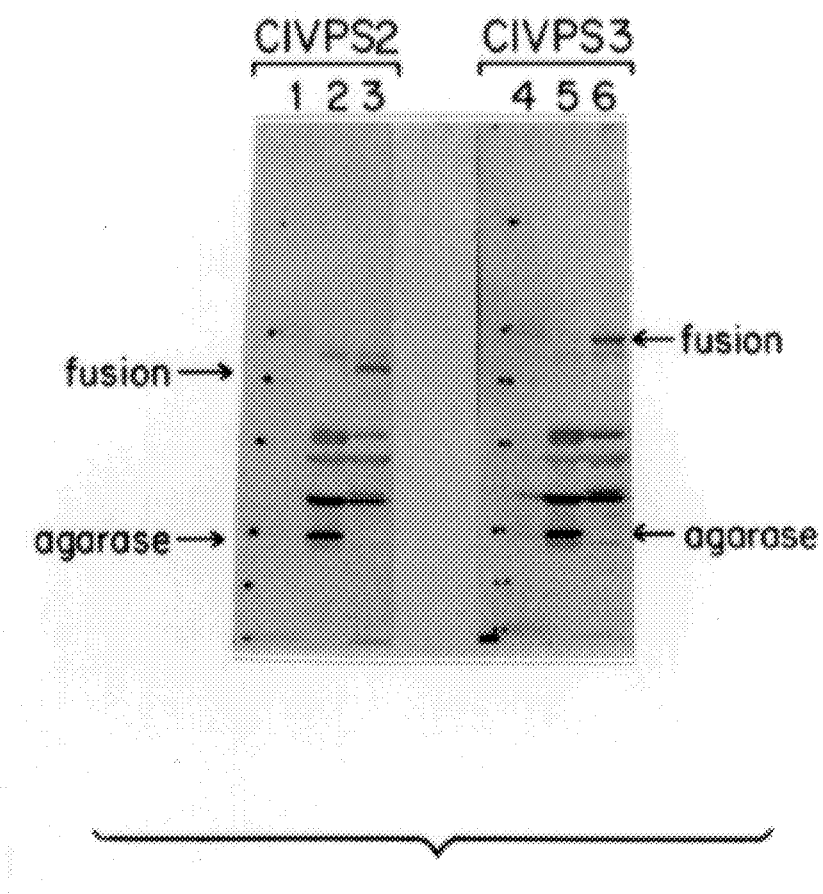
FIG. 5 shows by western blot examination of cell extracts with sera directed against β-agarase, the detection of modified β-agarase fusion protein. Lanes 1 & 4: size markers; Lanes 2 & 5: β-agarase standard; lane 3: CIVPS2-β-agarase fusion; lane 6: CIVPS3-β-agarase fusion.

The clones were further examined by their ability to express fusion proteins. RR1 cells carrying pAG108S18 or pAG133t35 were cultured in 1 liter of a modified LB medium, lacking dextrose, supplemented with 100 μg/ml ampicillin, at 30° C. until $OD_{600nm}$ reached about 0.5. After addition of inducer IPTG to a final concentration of 0.3 mM, the cultures were cooled down and grown at 25° C. for 4 additional hours. Cells were spun down and resuspended in 50 ml LB medium. Crude extracts were prepared as described in Example 3. Western blots using antibodies raised against l-Tli-l, l-Pspl and β-agarase I were performed to detect fusion (modified) proteins expressed from these clones. Samples were electrophoresed on 4–20% SDS gels (ISS, Daiichi, Tokyo, Japan) with prestained markers (BRL, Gaithersburg, Md.), transferred to nitrocellulose, probed with antisera (from mouse), and detected using alkaline phosphatase-linked anti-mouse secondary antibody as described by the manufacturer (Promega, Madison, Wis.). Both anti-l-Pspl sera and anti-β-agarase I sera reacted with a 90–95 KDa product expressed from pAG108S18/RR1, of the expected size for a Deep Vent® IVPS1 (approximately 60 KDa)-β-agarase I (approximately 30 KDa) fusion protein (FIG. 5). Both anti-l-Tli-l sera and anti-β-agarase I sera reacted with a 70–75 KDa product,from pAG108S18/RR1, approximately the size expected for a Vent® IVPS2 (42KDa)-β-agarase I fusion protein (FIG. 5).

EXAMPLE 5

Insertion Of IVPS Into Target Gene By Creation Of New Restriction Enzymes Sites Through Silent Substitutions In the previous examples, an IVPS cassette containing the entire IVPS sequence, with or without the first downstream EPS codon, was inserted into a blunt, linearized plasmid. It is also possible to create a restriction site by silent mutations (preserving the amino acid residue) near the ends of either the IVPS or the target gene.

Creation Of A Restriction Site Near The End Of The IVPS

It is possible to create a restriction site by silent mutations (preserving the amino acid residue) at both ends of an IVPS to facilitate insertion of the IVPS at any position within the target gene. After creation of the new restriction sites, the IVPS is cut with these enzymes.

Figure 6:
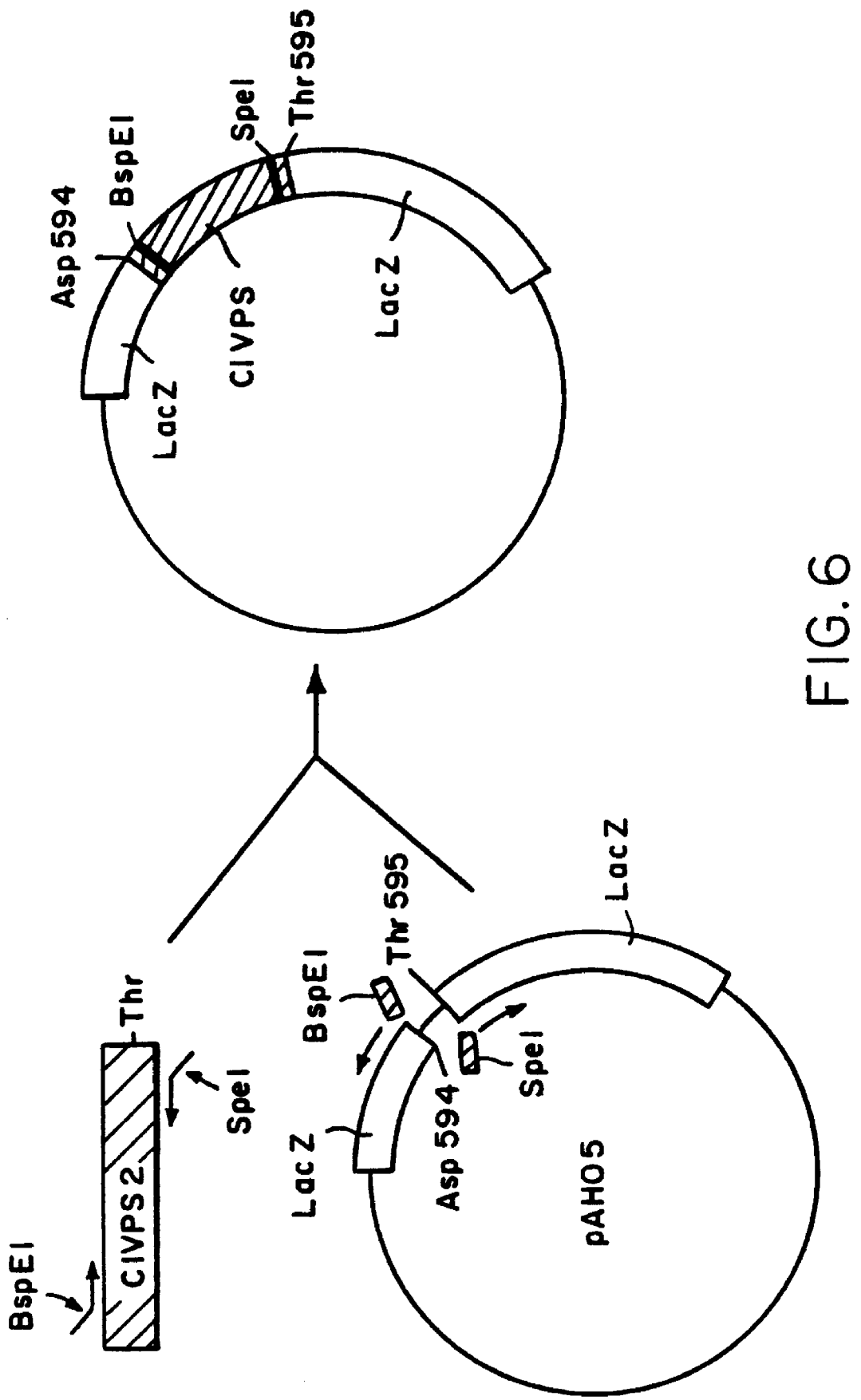
FIG. 6 illustrates insertion of IVPS2 (CIVPS2) into the β-galactasidase gene by creation of new restriction sites (BspEI and SpeI) within the IVPS by silent mutations.

The target gene plasmid is generated by PCR. Since the restriction sites are within the IVPS, one must include the missing IVPS sequences on the 5' end of the respective target gene PCR primers to complete the IVPS and to generate compatible cloning sites in the target gene (FIG. 6).

For example, silent mutations in Vent® IVPS2 can create a BspEl site at the 5' end using primer Vent® IVS2 Forward BspEl (5'-AGTGTCTCCGGAGAAAGTGAGAT-3' (SEQ ID NO:12)) and a Spel at its 3'end, by using primer, Vent IVS2 Reverse Spel (5'-ATTGTGTACTAGTATGTTGTTTGCAA-3' (SEQ ID NO:13)). It can then be inserted, for example, between an aspartic acid codon (residue 594) and a threonine codon (residue 595) within the lacZ coding region. A linear target gene plasmid can be generated by PCR as described in Example 4 with primers which include the BspEl and Spel sites, the remaining portion of the IVPS and a region with identity to lacZ using primer, lacz1BspE1 reverse (5'-GCCTCCGGAGACACTATCGCCAAAATCACCGCCG-TAA-3' (SEQ ID NO:14)) and primer, lacZ2Spel forward (5'-GCCACTAGTACACAATACGCCGAACGATCGCC-AGTTCT-3'(SEQ ID NO:15)). DNA fragments are synthesized from both the IVPS and the target gene by PCR. Both IVPS and target gene primers contain the new restriction sites. After cutting with the appropriate restriction endonucleases, DNA fragments with compatible ends can then be ligated to create a fusion gene. Since no extra residue would be left after excision of the IVPS, native β-galactosidase polypeptide would be expected to form if splicing occurs.

Insertion of IVPS At Restriction Sites Near The Insertion Site.

In another general approach (FIG. 7), a restriction site near the insertion site in the target gene (for example, a threonine or a serine codon), can be used to insert an IVPS with ends compatible to the target gene. Restriction site(s) can be created by silent nucleotide substitution at or near the insertion site or native restriction sites can be used. A linear target gene plasmid is made by PCR as described in Example 4, beginning at the restriction sites near the insertion site. The IVPS is synthesized with primers containing the compatible restriction sites and the remainder of the target gene sequence (the sequence between the restriction site and the insertion site). The IVPS DNA fragment, with the ends overlapping the sequence at the insertion site, can be synthesized, cut with the appropriate enzyme(s), and then ligated to the vector that is cut by the same enzyme(s).

Figure 7:
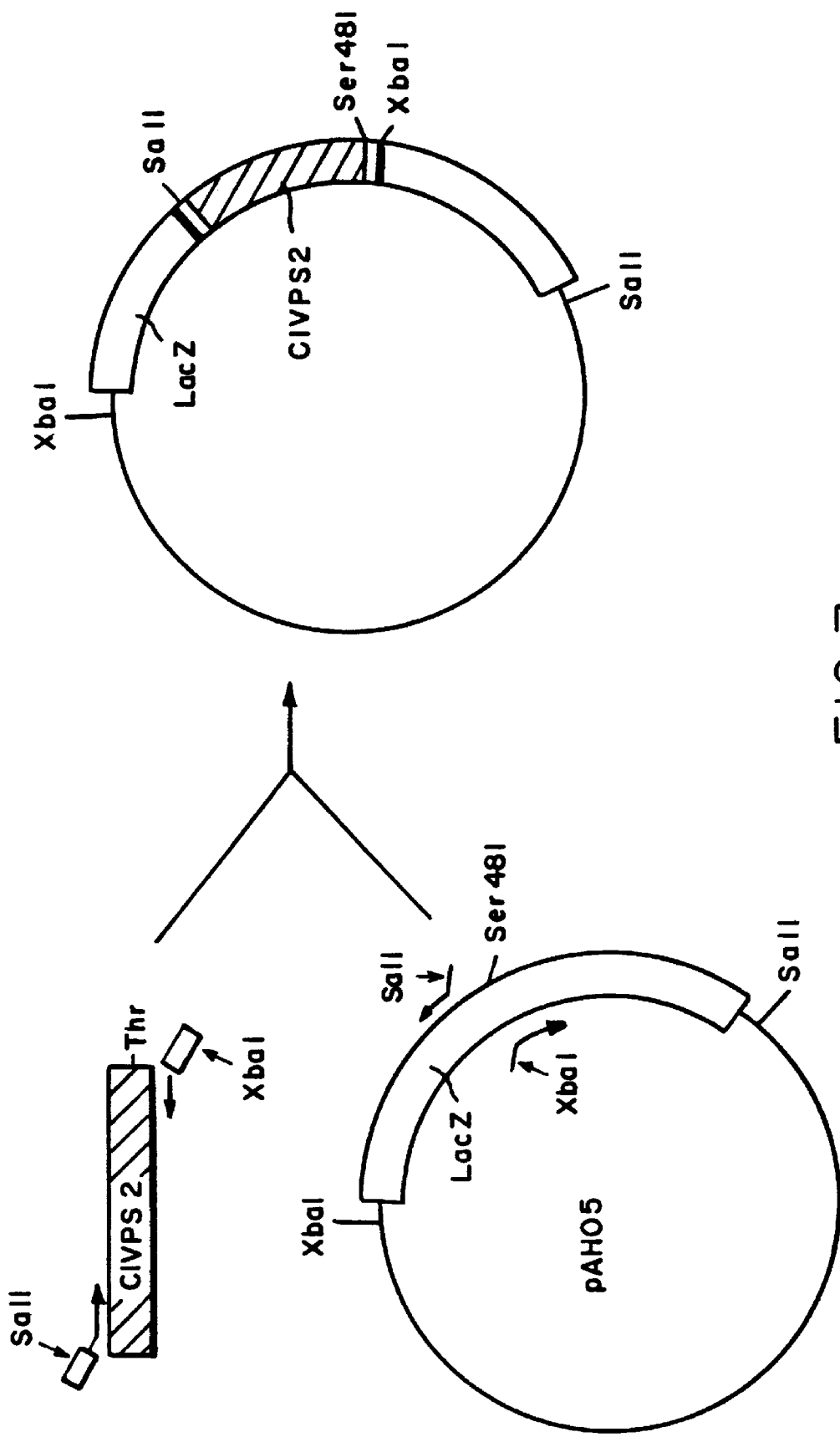
FIG. 7 illustrates insertion of either Deep Vent® IVPS1 (CIVPS3) or Vent® IVPS2 (CIVPS2) into the β-galactasidase gene by creation of new restriction sites (XbaI and SalI) by silent mutations within the target gene.

For example, IVPS elements can be inserted between residue 479 (aspartic acid) and 481 (serine) within the lacZ gene by creating a SalI site (residues 478–479) and a XbaI site (residues 481–482 serine-arginine) by silent mutations. This can be achieved by PCR of the target plasmid, pAHO5, described in Example 2, using primers, lacZ3 Sal reverse (5'-AGGGTCGACAGATTTGATCCAGCG-3' (SEQ ID NO:7)) and lacZ4 Xba forward (5'-CCTTCTAGACCGGTGCAGTATGAAGG-3' (SEQ ID NO:16)). Next the IVPS2 fragment is generated by PCR using primers, Vent® IVS2 Forward SalI (5'GCCGTCGACCCTAGTGTCTCAGGAGAAAGTGAG-ATC-3' (SEQ ID NO:17)) and Vent® IVS2 reverse XbaI (5'-GCCTCTAGAATTGTGTACCAGGATGTTG-TTTGC-3' (SEQ ID NO:18)). DNA fragments are synthesized from both the IVPS and the target gene by PCR. Both IVPS and target gene primers contain the new restriction sites. Unfortunately, this vector also contains single XbaI and Sal sites (FIG. 7). Therefore, the target gene vector PCR product must be cut under conditions which produce partial digestion. The required linear plasmid is then isolated from agarose gels. After cutting with the appropriate restriction endonucleases, DNA fragments with compatible ends can then be ligated to create a fusion gene. Since no extra residue would be left after excision of the IVPS, native β-galactosidase polypeptide would be expected to form if splicing occurs. Generally, it is important to select or create an unique site within the target gene and vector to facilitate the cloning process as described above.

EXAMPLE 6

Figure 8:
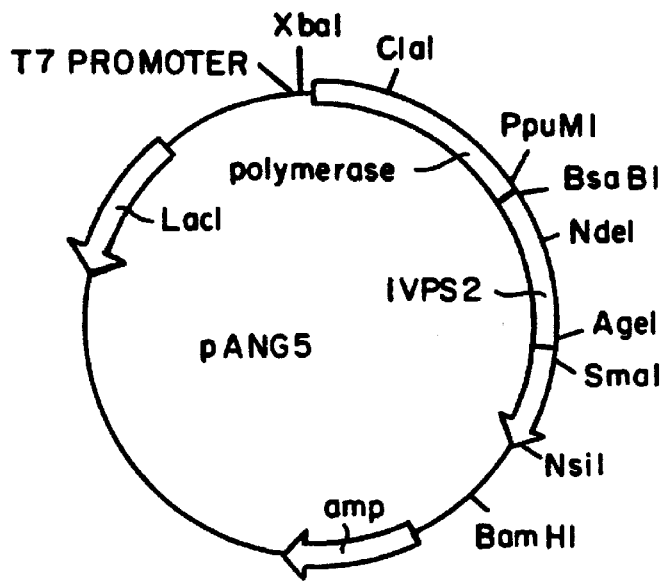
FIG. 8 is a plasmid map of pANG5.

A. To facilitate experimentation on the splicing of IVPS2 in Vent® DNA polymerase, a modified version of the T7 promoter construct pV174-1B1 was created. This modified version, pANG5 (FIG. 8), encodes a Vent® DNA polymerase precursor identical to that of pV174-1B1. Numerous silent mutations were introduced to simplify the generation of mutants as discussed in this application, particularly at the upstream and downstream splice junctions.

Changes included:

1. Destroying XmaI and PpuMI sites in the vector backbone. The XmaI site was removed first by cutting the T7 expression vector pAll17 with XmaI, repairing the cohesive ends with the Klenow fragment of DNA polymerase I, and then religating the blunt termini. Plasmids were screened for resistance to cleavage by XmaI. The PpuMI site was similarly removed from the resulting vector, screening this time for resistance to PpuMI cleavage. The final vector was named pAML1. This vector allowed the use of unique XmaI and PpuMI sites within the polymerase gene.

2. Introduction of silent base changes to create restriction sites. Changes were introduced using oligonucleotide-directed mutagenesis as described by Kunkel (T. A. Kunkel, J. D. Roberts and R. A. Zakour, *Methods in Enzymology* 154:367–382 (1987)). Single-strand templates were created in two Bluescript SK-phagemid derivatives by superinfection with the f1 helper phage IR1 (Enea, et al., *Virology* 122:22–226 (1982)). The first contained a BsaAI to BamHI fragment (representing nucleotides 3714–5837 of the Vent® DNA polymerase sequence) from pV174-1B1 ligated into BamHI/EcoRV cut Bluescript. The second fragment included a Clal to Sspl fragment (nucleotides 816–4408) ligated into Clal/EcoRV cut Bluescript.

The BsaAI/BamHI construct was mutagenized simultaneously with three oligonucleotides:

5'-GCAAAGAACCGGTGCGTCTCTTC-3' (SEQ ID NO:19) (AgeI nt 4669–4674)

5' -AGCAACAGAGTTACCTCTTG-3' (SEQ ID NO:20) (amber 1703ochre)

5'-CAGTTTCCAGCTCCTACAATGA GACCTACGAGC-3' (SEQ ID NO:21) (D1236A)

where modified bases are underlined, and changes are indicated in parenthesis. The oligonucleotide to create D1236A also included silent base changes to create a Bsal site to assist in screening. The resulting isolate was named pAMN2.

The Clal/Sspl construct was mutagenized simultaneously with four oligonucleotides:

5'-GTAGTGTCGACCCCATGCGG-3' (SEQ ID NO:22) (SalI nt 3863–3468)

5'-CGTTTTGCCTGATTATTATCTCACTTTC-3' (SEQ ID NO:23) (BsaBI nt 3554–3563))

5'-GTCCACCTTCGAAAAAAGATCC-3' (SEQ ID NO:24) (BstBI nt 5 3608–3613)

5'-CCGCATAAAGGACCTTAAAGC-3' (SEQ ID NO:25) (PpuMI nt 3517–3523)

where markings are as above. Screening was also as above, with the resulting construct was named pAMO22.

The BsaAI/BamHI construct was also mutagenized with the oligonucleotide:

5'-GAGGAAGAGATCATCATCATAGC-3' (SEQ ID NO:26) (BsaBI blocking nt 5641)

and screened for resistance to BsaBI cleavage due to the addition of a dam methylation site. The resulting construct was named pAMW3.

Finally, the NdeI site at the initiation codon of pV174-1B1 was inactivated by partial NdeI cleavage, repairing the termini with Klenow, and recircularizing using T4 DNA ligase. Plasmids were screened for the loss of the appropriate NdeI site. One such construct was named pAKC4.

The pANG5 construct was assembled from the above parts:

1. XbaI/Cal from pAKC4 (translation initiation and amino terminus of vent DNA polymerase)
2. ClaI/NdeI from pAMO22 (more amino terminal polymerase plus the amino terminal region of IVPS2)
3. NdeI/NsiI from pAMN2 (carboxyl terminal region of IVPS2, carboxyl terminal region of vent DNA polymerase)
4. NsiI/BamHI from pAMW3 (final 5 amino acids of the polymerase plus the downstream region)
5. BamHI/XbaI from pAML1 (T7 promoter, origin of replication, ampicillin resistance).

Comparisons between pANG5 and the parent pV174-1B1 show identical patterns of Vent® DNA polymerase and l-TliI production, with the exception of the greater viability of the pANG5 containing strains, as discussed below. This is as expected if splicing occurs at the protein level, as opposed to at the RNA or DNA level.

B. During work on the expression of the Vent® DNA polymerase gene in *E. coli* it was found that a large increase in expression and cell viability occurred after deletion of IVPS1 and IVPS2. This increase could either represent toxic effects of l-TliII and l-TliI, the gene products of IVPS1 and IVPS2, respectively, or toxic effects of the splicing reaction itself. It was reasoned that endonuclease and splicing activities could well be independent, allowing inactivation of the endonuclease without affecting splicing. A single amino acid substitution to A as described in the construction of pANG5 was made in a conserved residue within the amino-proximal dodecapeptide motif of l-TliI (changed residue D1236). Although these constructs expressed Vent® DNA polymerase, no l-TliI activity was detected. Unlike pV174-1B1, T7 expression strains such as BL21 (DE3) tolerated pANG5 well, even at 37° C. Analysis of protein splicing by western blot and pulse-chase analysis showed no discernible differences in protein splicing between pANG5 and pV174-1B1, namely production of a full-length precursor and subsequent formation of the mature polymerase and a protein corresponding in size to l-TliI.

C. A consensus calmodulin-dependent protein kinase II site (XRXXS*; Pearson et al., supra) was constructed, replacing tyrosine 1079 with arginine using cassette replacement mutagenesis. In short, pANG5 was cut at the unique sites BsaBI and PpuMI and the duplex (SEQ ID NO:27) listed below was inserted, introducing the desired change.

5'-GTCCTTCGTGCGGACAGTGTCTCAGGAGAAA-GTGAGATAA-3'

3'-GAAGCAGCCTGTCACAGAGTCCTCTTTCAC-TCTATT-5'

The correct construct was verified by DNA sequencing.

D. Introduction of an amber stop codon for adding a blocked amino acid was accomplished by cassette replacement mutagenesis in pANG5. For example, serine 1082 was replaced by an amber codon using the following duplex (SEQ ID NO:28) inserted into pANG5 cut with PpuMI and BsaBI:

5'- G T C C T T T A T G C G G A C TAGGTCTCAGGAGAAAGTGAGATAA-3'

3'- G A A A T A C G C C T G ATCCAGAGTCCTCTTTCACTCTATT-5'.

Similarly, tyrosine 1472 was replaced with an amber termination codon by placing the following duplex (SEQ ID NO:29) into pANG5 cut with AgeI and SmaI:

5'-CCGGTTCTTTGCAAACAACATCCTGGTACA-CAATTAA

3'-AAGAAACGTTTGTTGTAGGACCATGTGTTAA-TTCTGCCGGACGGCTTTTATGCCACAATACCC-3'AAAATACGGTGTTATGGG-5'

Finally, since the Vent® DNA polymerase gene ends in an amber codon (TAG), that termination codon will be changed to an ochre codon (TAA) by inserting an appropriate restriction fragment from pAMN2 (described above) into the corresponding site in pANG5.

EXAMPLE 7

Control Of Protein Splicing By Incorporation Of 0-(O-Nitrobenzyl) Serine At The Splice Junction Of CIVPS2

Two vectors were constructed using pV174.1B1 to demonstrate photoactivatable protein splicing. The first construct, pANY5 (also referred to as "wild-type"), can be described on the amino acid level as follows: pV174.1B1 Δ1–1063, Δ1544–1702, V1542M, V1541M, 1543opal (TGA). This construct is designed to give a 55.8 kDa precursor protein, which splices out the 45.3 kDa endonuclease (l-TliI) and yields a 10.5 kDa ligation product, when translated in an in vitro transcription/translation system. The second construct, pAOD1 (also referred to as the "amber mutant"), can be described on the amino acid level as follows: pV174.1B1 Δ1–1063, Δ1544–1702, V1542M, V1541M, 1543opal(TGA), S1082amber(TAG). This construct is designed to give a 2.2 kDa amber fragment under standard in vitro transcription/translation conditions, but will incorporate a photoactivatible serine when the in vitro reaction is supplemented with an amber suppressor tRNA that has been chemically aminocylated with o-nitrobenzylserine. With the serine at position 1082 "blocked", the precursor is unable to splice. When irradiated with intense 350 nm light, the o-nitrobenzyl group is released (Pillai, supra), the nuceophilic hydroxyl side chain of serine is freed, and the protein is able to splice.

The amber suppresssor tRNA (lacking the 3' terminal CA residues) was synthesized on milligram scale by in vitro runoff transcription of FokI-linearized pYPhe2 plasmid template with T7 RNA polymerase as described (Ellman, et al., supra; Noren, et al., *Nucleic Acids Res.* 18:83 (1990)). Serine derivatives protected at the a amine with functionalities like BPOC, CBZ, or BOC are available from commercial sources (Bachem, Sigma, Aldrich). N-blocked serine can be converted to N-blocked 0-(o-nitrobenzyl) serine by a standard alkyl halide substitution reaction with a reagent such as o-nitrobenzylbromide. The fully blocked serine was then coupled to 5'-phosphodeoxyribocytidylyl-(3'–5')-riboadenosine (pdCpA) as described (Ellman, et al., supra). The aminoacylated dimer was then ligated to the truncated suppressor tRNA with T4 RNA ligase(New England Biolabs, Inc.) to yield full-length aminoacylated suppressor tRNA.

In vitro transcription/translation of the "wild-type" construct was carried out by combining on ice: 3 μg cesium chloride-purified plasmid DNA, 3 μl 100 mM magnesium acetate, 1 μl 100 mM calcium acetate, 7.5 μl low molecular weight mix (Ellman, et al., supra) (no calcium or methionine), 1 μl ($^{35}$S)-methionine (10 μCi/μL, 1000 Ci/mmol), 1 μl 3 mg/ml rifampicin, and water to 30 μL. The reactions were incubated for 3 minutes at 37° C. while an aliquot of S-30 extract prepared from *E. coli* D10 (Ellman, et al. supra) was thawed. 8.5 μl of S-30 extract was added, followed by 1.5 μl of T7 RNA polymerase (300 U/μL, New England Biolabs, Inc.), and the reactions were incubated 60 min. at 37° C. Samples were electrophoresed on a 10–20% tricine SDS-PAGE gel (Novex, Encinitas, Calif.) and autoradiographed to visualize the proteins (FIG. 9).

In vitro transcription/translation of the "amber mutant" was carried out as described for the "wild-type" except that the reactions werre supplemented with 3.5 μl of chemically aminoaceylated o-nitrobenzylsserine-tRNA$_{amber}$ at a concentration of approx. 3 μg/μl. The suppressor tRNA was added to the reaction immediately before addition of the S-30 extract.

FIG. 9 shows a 10–20% tricine SDS-PAGE gel of in vitro transcription/translation reactions primed with either the "wild-type" (pANY5) or "amber mutant" (pAOD1) constructs. Lane 1 shows the 55.8 kDa precursor and excised 45.3 kDa l-TliI endonuclease expressed in vitro from the "wild-type" construct. Lane 2 shows the "wild-type" reaction supplemented with 13.5 μg of full length uncharged amber suppressor tRNA to demonstrate there is no inhibition of translation due to added tRNA. Lanes 3 and 4 show the result of in vitro expression of the "amber mutant" without and with full length unacylated supressor tRNA (10.5 μg) added. Neither of these reactions produce the full length precursor molecule, nor any splice products, as expected. This indicates that the suppressor tRNA is not aminoacylated by any of the endogenous aminoacyl-tRNA synthetases in the cell extract. The band of approximate molecular weight 52 kDa is apparently caused by a secondary translational initiation site just downstream from the amber mutation. Lane 5 shows the result of supplementing the "amber mutant" with the chemically aminoacylated 0-nitrobenzylserine-tRNA$_{amber}$. Precursor protein is produced in vitro, but no splice products (i.e., l-TliI) are visible.

Controlled splicing was achieved by photochemically removing the o-nitrobenzyl group from the serine which had been incorporated site-specifically at position 1082 of the precursor protein. A 6 μL aliquot of an in vitro reaction was treated with 0.5 μl of RNase A (10 μg/μl) to arrest translation, irradiated with intense (275 W) visible light from a GE model #RSK6B tanning lamp at 10 cm for 10 minutes, diluted with 4 μl of water, and then incubated at 37° C. for 60 minutes to allow splicing to occur. The resulting splice products were visualized by electrophoresis on a 10–20% tricine SDS-PAGE gel followed by autoradiography (FIG. 10).

FIG. 10 illustrates the results of exposing the chemically blocked precursor (Lane 5, FIG. 9) to 350 nm light. Lanes 1 through 4 are controls in which the "wild-type" reaction (Lane 1, FIG. 9) was treated as follows. Lane 1, incubated 60 min. at 37° C.; Lane 2 added 0.5 μl RNase (10 μg/μl) and incubated 60 min. at 37° C.; Lane 3, irradiated 10 minutes with 350 nm light and incubated 60 min. at 37° C.; Lane 4, treated with RNase as above, irradiated 10 min. with 350 nm light and incubated 60 min. at 37° C. Lanes 5–8 show the result of treating the "blocked" precursor (Lane 5, FIG. 9) in the same way as for Lanes 1–4, respectively. Irradiated of the "blocked" precursor results in the excision of the l-lil (45.3 kDa) endonuclease encoded by IVPS2 (cf. Lanes 7–8 with Lanes 5–6).

EXAMPLE 8

In-Frame Insertion Of Modified IVPS Into A Target Gene And Thermal Control Of Peptide Bond Cleavage In this example, we describe how an IVPS (CIVPS) cassette can be modified and inserted into a target gene. As an example, we describe modification of *Pyrococcus sp.* (or Deep Vent®) IVPS1 (CIVPS3) by substitution or deletion of the first native downstream residue (serine), and in-frame insertion of the modified cassettes into the EcoRV site of the *E. coli* lacz gene.

Modification Of IVPS Cassettes

In general, an IVPS cassette can be modified by substitution and deletion of residue(s) or addition of residue(s) to one or both ends of IVPS. The modified or fusion proteins using such modified IVPS cassettes may exhibit different catalytic activities, such as splicing (peptide ligation) or cleavage at a specific peptide bond.

As previously discussed, the first downstream residues at the carboxyl splice junction are serine for Deep Vent® IVPS1 (CIVPS3) and Vent® IVPS1 or threonine for Vent® IVPS2. The first IVPS residue at the amino splice junction of CIVPS1, CIVPS2 and CIVPS3 is serine. Cysteine residues have been found at the splice junctions of the yeast TFP1 and *M. tuberculosis* RecA (See, Hirata, et al., supra; Kane, et al., supra; Davis, et al., supra). It is believed that serine, threonine or cysteine residues at splice junctions are essential for protein splicing and cleavage. The previous examples have shown that an IVPS with the first downstream residue is sufficient to contain information for protein splicing. However, these residues may function differently in various IVPS contexts. Substitutions of the native residue, for example, a serine by threonine or cysteine in the Vent® IVPS2 (CIVPS2) resulted in reduced splicing and altered cleavage activity (see, Hodges, et al., supra).

Synthesis Of Modified IVPS Cassettes For In-Frame Insertion Into Blunt Sites Between Target Gene Codon IVPS cassettes for in-frame insertion into the lacZ coding region or any other target gene can be prepared by polymerase chain reaction (PCR). The following protocol describes the production of four Deep Vent® IVPS1 cassettes without or with an additional carboxyl terminal codon, serine, threonine or cysteine, referred as CIVPS3, CIVPS3/Ser, CIVPS3/Thr and CIVPS3/Cys, respectively.

Primer 5'-AGCATTTTACCGGAAGAATGGGTT-3' (SEQ ID NO:5) (DV IVPS1 forward, 1839–1862) and one of the four reverse primers described below were used to synthesize the cassettes from pNEB#720 (ATCC No. 68723). pNEB#720 used as template has a 4.8 Kb BamHI fragment containing Deep Vent® DNA polymerase gene inserted into the BamHI site of pUC19. Reverse primers 5'-GCAATTATGTGCATAGAGGAATCCA-3' (SEQ ID NO:40) and 0.9 $\mu$M of each primer and 40 ng plasmid DNA and 2 units of Vent® DNA polymerase in 100 $\mu$l. Amplification was carried out by using a Perkin-Elmer/Cetus (Emeryville, Calif.) thermal cycler at 94° C. for 30 sec., 48° C. for 30 sec. and 72° C. for 2 min for 20 cycles. Primer 5'-ATTATGTGCATAGAGGAATCCAAAG-3' (SEQ ID NO:42) (3425–3449) was used to synthesize CIVPS3 fragment (1611 bp) by PCR as described above except the amplification was carried out for 30 cycles. Primer 5'-GCTATTATGTGCATAGAGGAATCCA-3' (SEQ ID NO:6) (3428–3452) were used to synthesize IVPS1/Ser fragment (1614 bp) as previously described in Example 1.

The PCR samples were extracted with phenol and chloroform, and precipitated in 0.3 $\mu$M NaAc and 50% isopropanol at -20° C. for 6 hours, followed by spinning at 10 Krpm for 10 min. in a microfuge, dried and each resuspended in 20 $\mu$l of distilled water, loaded on a 1 % low melting agarose gel for electrophoresis at 80 volts for 6 hours. DNA fragments were recovered from the low melting agarose gel by incubation in 0.4 ml of TE buffer (10 mM Tris-HCl/0.1 mM EDTA, pH 8.0) at 65° C. for 30 min., extractions with phenol and chloroform, precipitation in 0.3 $\mu$M NaAc (pH5.2) and 50% isopropanol at -20° C. for overnight. DNA was spun down, washed with 70% ethanol, dried and resspended in 10 $\mu$l distilled water.

Phosphorylation of the IVPS1 DNA fragments was performed at 37° C. for 60 min. with 4 $\mu$l of 10 x polynucleotide kinase buffer, 31 $\mu$l of purified DNA, 4 $\mu$l 10 mM ATP, and 10 units of T4 polynucleotide kinase in 40 $\mu$l. The samples were heated in a 65° C. water bath for 10 min. After addition of 80 $\mu$l of TE bffer (10 mM Tris-HCl/0.1 mM EDTA, pH 8.0), the samples were sequentially extracted with phenol and chloroform. DNA was precipitated in 2.4 $\mu$M NH$_4$AC and 70% ethanol at -70° C. overnight, pelleted by spinning at 10 Krpm for 10 min. in a microfge, washed with cold 70% ethanol, dried and resuspended in 20 $\mu$l distilled water. Phosphorylation of the CIVPS3/Ser fragment was as described above.

In-Frame Insertion Of CIVPS3 Cassettes Into The Ecorv Sited Of The *E. Coli* lacZ Gene In Vector pAH05

PCR-synthesized CIVPS cassettes can be inserted into a target coding region by ligation with linearized vector bearing the target gene. Linear plasmid vector can be prepared by restriction enzyme or PCR synthesis as previously described. pAH05 carries the entire lacZ gene sequence on a 3.1 kb BamHI-Dral fragment from pRS415 (Simons, et al., *Gene*, 53:85–96 (1987)) inserted between BamHI and SmaI sites in the polylinker of pAGR3 downstream of a tac promoter. The tac promoter is a transcription control element which can be repressed by the product of the lacI$^q$ gene and be induced by isopropyl β-D-thiogalactoside (IPTG). pAH05 contains two EcoRV recognition seqences. EcoRV leaves blunt ends at its cleavage site. One of the EcoRV cleavage sites cuts within lacZ coding region between the 375th codon (aspartic acid) and the 376th codon (isoleucine).

DNA was partially digested by incubation of 15 $\mu$g of pAH05 DNA with 40 units of EcoRV in 100 $\mu$l of 1×NEB buffer 2 at 37° C. for 60 min. 20 $\mu$l agarose gel loading dye was added to the sample after the sample was heated to 65° C. for 10 min. to inactivate EcoRV. DNA fragments were separated by electrophoresis on a 1% low melting agarose gel. Linearized pAH05 plasmid DNA was recovered from the low melting agarose gel as described in Example 8 and resuspended in distilled water.

CONSTRUCTION OF CIVPS-lacZ FUSION GENES

Construction of CIVPS3/Ser-lacZ fsion was described in Example 2. CIVPS3-lacZ fusion was made by ligation of dephosphorylated pAH05 DNA to the phosphorylated IVPS1 fragment. The reaction was carried at 16° C. for 5 hours in 20 $\mu$l volume with 1X T4 DNA ligase buffer, 0.1 $\mu$g pAH05 DNA, 0.5 $\mu$g IVPS1 DNA and 160 units of T4 DNA ligase. *E. coli* strain RR1 was transformed by mixing 100 $\mu$l of competent RR1 cells with 10 $\mu$l of ligation sample on ice for 30 min., heating at 42° C. for 2 min., chilling on ice for 5 min., adding 0.8 ml LB media (10 grams/liter tryptone, 5 grams/liter yeast extract, 10 grams/liter NaCl, 1 gram/liter dextrose, 1 gram/liter MgCl$_2$6H$_2$O , pH 7.2 at 25° C.) and incubating at 30° C. for 45 min. The samples were plated onto LB plates, supplemented with 100 $\mu$g/ml ampicillin. After incubation overnight at 30° C, abot 150–300 colonies per plate were observed.

CIVPS3/Thr-lacZ and CIVPS3/Cys-lacZ fusions were made by ligation of 0.1 $\mu$g EcoRV-linearized pAHOS DNA with 0.7 g of CIVPS3/Thr or CIVPS3/Cys fragment. Transformation of *E. coli* strain ER2252 was carried out by the same protocol as described above.

Colony hybridization was utilized to screen for clones that carry recombinant plasmids. The Deep Vent® CIVPS3 forward primer, described above, was radio-labeled with T4 polynucleotide kinase and used as a hybridization probe. Colonies were lifted onto nitrocellulose and treated for 5 min. in each of the following soltions: 10% SDS, 0.5 M NaOH/1.5 M NaCl, 0.5 M Tris-HCl (pH 7.4)/0.5 M NaCl (twice) and 2XSSC (twice). The nitrocellulose filters were dried at room temperature for 1 hour, baked in vacuum at 80° C. for 2 hours, soaked in 6×SSC for 5 min. and washed in a solution of 50 mM Tris-HCl (pH 8.0), 1 M NaCl, 1 mM EDTA and 0.1% SDS at 42° C. for 2 hours. After treatment at 42° C. for 4 hors in 6×NET, 5×Denhardt's, and 0.5% SDS, the filters were incubated with the radiolabeled oligomer probe under the same conditions for overnight and then washed in 2×SSC for times at 42° C. for 15 min. and twice at 50° C. for two min., followed by autoradiography.

Figure 11:
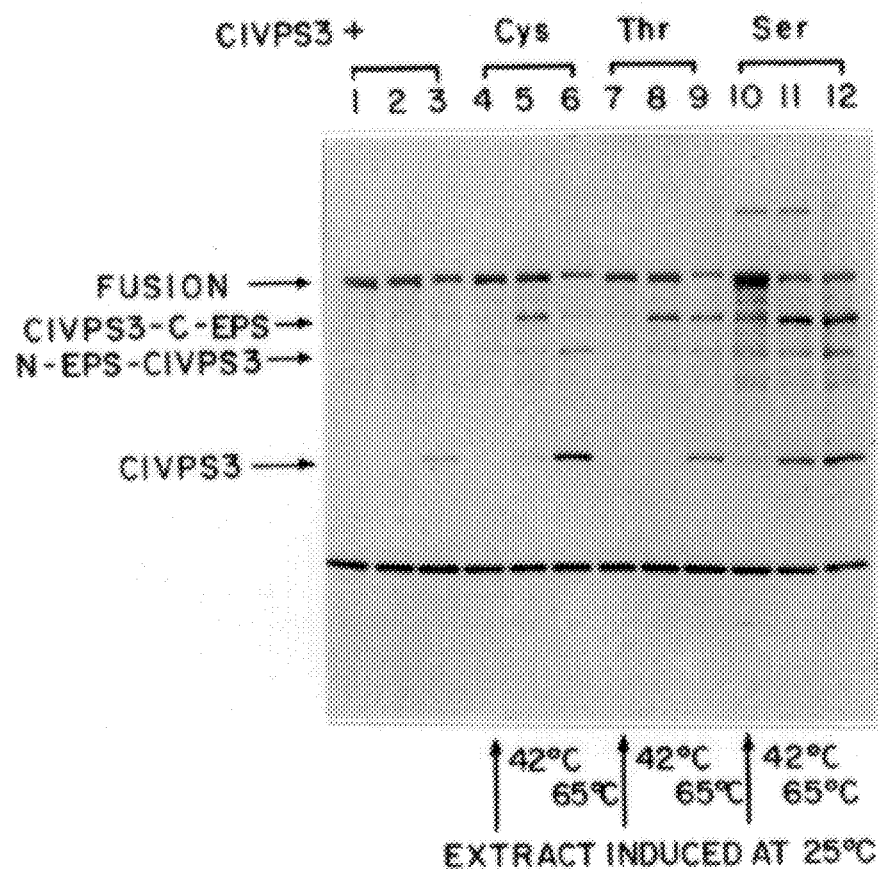
FIG. 11 is a gel showing temperature controlled protein splicing and cleavage. Deep Vent® IVPS1 (CIVPS3) cassettes were cloned into the EcoRV site of β-galactosidase. Western blot analysis was used to examine cell extracts of pDV7 (CVPS3 cassette, lanes 1–3), pDVC302 (CIVPS3/Cys cassette, lanes 4–6), pDVT321 (CIVPS3/Thr cassette, lanes 7–9) and pDVS712 (CIVPS3/Ser cassette, lanes 10–12). Antibody directed against the CIVPS3 protein (l-PspI) (NEB) detects fusion proteins and cleavage products including free CIVPS3, N-EPS-CIVPS3 and CIVPS3-C-EPS (from cleavage at one of the splice junctions). The untreated extracts were in lanes 1, 4, 7, and 10. Treatment of extracts at 42° C. (lanes 2, 5, 8, and 11) or 65° C. (lanes 3, 6, 9, and 12) for 2 hours results in increased splicing and/or cleavage activity at different efficiency.
Figure 12:
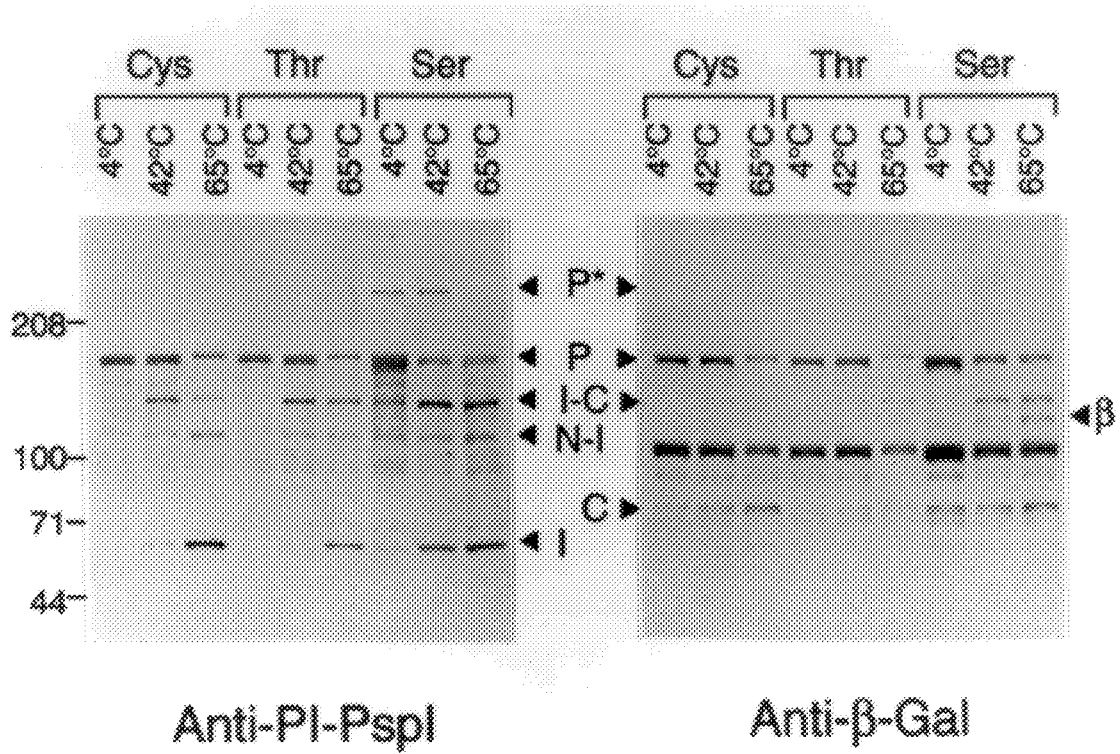
FIG. 12 is a Western blot showing temperature controlled protein splicing and cleavage. Western blot analysis using antibody directed against l-PspI and β-galactosidase (C-EPS domain) (Promega) were used to examine fusion constructs pDVC302 (lanes 1–3), pDVT321 (lanes 4–6) and pDVS712 (lanes 7–9). Treatment of extracts at 42° C. (lanes 2, 5, and 8) or 65° C. (lanes 3, 6, and 9) for 2 hours results in splicing (in pDVS712) or cleavage. Protein splicing in pDVS712 extract produced free CIVPS3 protein, l-PspI and unmodified β-galactosidase (except for retained serine). Lane 1 contains size markers.

The positive clones that hybridized to the oligomer probe were further examined by their ability to express fusion proteins with inducer IPTG. The clones were cultured in LB medium supplemented with 100 $\mu$g/ml ampicillin at 30° C. until OD$_{600}$ nm reached 0.5. After addition of IPTG to a final concentration of 0.3 mM, the cultures were grown at 30° C. for 4 additional hours. Crude lysates were prepared by boiling 0.1 ml of cells with 0.1 ml of the urea lysis buffer for 10 min. The identity of the fusion proteins from the positive clones described above was analyzed by Western blots using antibody raised against δ-galactosidase (Promega, Madison, Wis.) or I-PspI (the protein product of Deep Vent® CIVPS3). Samples were electrophoresed on 4–20% SDS gels (ISS, Daiichi, Tokyo, Japan) with prestained markers (BRL, Gaithersburg, Md.), transferred to nitrocellulose, probed with antisera (from mouse), and detected using alkaline phosphate-linked anti-mouse secondary antibody as described by the manufacturer (Promega, Madison, Wis.). Deep Vent® CIVPS3-lacZ fusion clones expressed a product, reacting with both antibodies, of 173–178 KDa, the expected size for the CIVPS3-β-galactosidase fusion proteins (FIG. 11). Clones pDV7 and pDV15 contain CIVPS3 insert. pDVC302, 306 and 307 carry the CIVPS3/Cys cassette while pDVT319, 321, 322 and 323 contain the CIVPS3/Thr cassette. pDVS712 and 742 containing the CIVPS3/Ser insert were previously described in Example 2. Thermal Control Of Specific Peptide Bond Cleavage In CIVPS3-β-Galactosidase Fusions Using Modified CIVPS3 Cassettes The DVIVPS1 (CIVPS3)-β-galactosidase fusions containing cassettes with a threonine or cysteine to substitute the serine at the carboxyl termini exhibit thermal-controllable cleavage at a specific peptide bond in the fusion proteins. The constructs described above (CIVPS3 cassettes inserted into the ladZ EcoRV site) yield fusion proteins after induction by IPTG. Cell extracts prepared from cells grown at 25° C. were treated at elevated temperatures (42° C. or 65° C.) and analyzed by Western blots using antibody against β-galactosidase (Promega) or I-Pspl (the product of Deep Vent® CIVPS3) (FIGS. 11 and 12). The IVPS1/Ser fusion protein can undergo protein splicing to generate a ligated protein and free IVPS endonuclease by incubation at elevated temperatures. While no ligation activity was observed, the fusion proteins with the CIVPS3/Thr or CIVPS3/Cys cassette cleave dominantly at the amino splice jnction at 42° C. and both fuuion proteins exhibit increased cleavage activity at the carboxyl splice jnction at 65° C.

Preparation of cell extracts from the CIVPS3-lacZ fusion clones were performed as follows. All the fusion constructs originally constructed in different *E. coli* hosts were introduced into a lacZ-deletion *E. coli* strain ER1991 (New England Biolabs, Inc.), which did not synthesize β-galactosidase, by the standard transformation procedure as described in Example 8. A single colony from pDV7, pDVC302, pDVT332 or pDVS712 clone was inoculated in 1.5 ml LB medium supplemented with 100 µg/ml ampicillin, incubated at 30° C. until $OD_{600}$ nm reached about 0.5 and induced with 0.3 mM IPTG by adding 1.5 ml of 0.6 mM IPTG, 00 µg ampicillin/ml LB at 25° C. for 5 hours. 3 ml of cells were spun down and resuspended in 0.5 ml of LB, sonicated for 1 min. at 4° C. and spun at 6,000 rpm for 5 min. at 4° C. The supernatants were recovered and stored at −20° C.

The cell extracts were heat-treated at 42° C or 650° C. after being quickly thawed at room temperature. The untreated control sample was prepared by mixing 48 µl of extract with 12 µl of 5 ×sample buffer (0.31 Tris-HCl, pH 6.8/10% SDS/25% 2-mercaptoethanol/50% glycerol/ 0.005% Bromophenol blue), followed by boiling for 10 min. Aliquots of 48 µl were transferred into 1.5 ml microfuge tubes and incubated for 30, 60, 120, or 240 min. in a 42° C. water bath, or 15, 30, 60 or 120 min. in a 65° C. water bath. Each was mixed with 12 µl of 5 x sample buffer and boiled for 10 min.

The treated samples were analyzed by Western blots using antibodies raised against I-Pspl (FIG. 11 and 12) or β-galactosidase (Promega, Madison, Wis.) (FIG. 12), 5 µl of each sample was loaded on 4/20% SDS polyacrylamide gels (ISS, Daiichi, Tokyo, Japan) and electrophoresed at 100 volts for 4 hours. Western blots were carried out according to the procedure of Promega.

The results show that fusion protein precursors were the dominant species and barely trace amounts of l-Pspl endonuclease were present in cells after IPTG induction at 25° C. from all for fusion constructs, indicating inefficient splicing and excision activity at low temperature. However, after shifting the pDVS712 (CIVPS3/Ser-β-galactosidase fusion) extract to higher temperatures, 42° C. or 65° C., abundant CIVPS3 product, l-Pspl, (of about 60 KDa) accumulated (FIGS. 11 and 12). Excision of the IVPS domains was coupled with ligation of the N-domain and the C-domain of the interrupted β-galactosidase, producing a product of 116 KDa, identical in size to full-length βgalactosidase (FIG. 12). Another major product (IVPS1-C-EPS) of about 130 KDa (corresponding to cleavage at the amino splice junction) was observed.

The fusion proteins of the other three variants (with CIVPS3, CIVPS3/Cys and CIVPS3/Thr cassettes) were more stable at low temperature. Very little l-Pspl or other products corresponding to cleavage at splice junctions were detected from the untreated extracts (FIG. 11). In contrast to the CIVPS3/Ser fusion, no ligated proteins were observed from the heat-treated samples of these three fusion constructs (FIG. 12). The pDV7 (CIVPS3-β-galactosidase fusion) sample produced only trace amounts of l-Pspl and products corresponding to cleavage at single splice junctions at 65° C., indicating poor excision at either splice junction (FIG. 11, lanes 1–3). pDVC302, containing CIVPS3/Cys cassette, showed accumulation of moderate amounts of l-Pspl and CIVPS3-C-EPS species at 42° C. (FIG. 11, lane 5). The yield in l-Pspl, C-EPS and a product (N-EPS-CIVPS3) of about 110 KDa, corresponding to cleavage at the carboxyl splice junction, was increased at 65° C. while CIVPS-C-EPS species is reduced (FIG. 11, lanes 4–6; FIG. 12). The results indicate that the peptide bond cleavage at the carboxyl splice junction from the fusion protein and/or CIVPS-C-EPS product was enhanced. pDVT321 (with CIVPS3/Thr cassette), when treated at 42° C., showed very little I-Pspl or C-EPS but a dominant product, CIVPS3-C-EPS (FIG. 11, lane 8; FIG. 12). The data indicates efficient cleavage of the peptide bond at the amino splice junction but not at the carboxyl splice junction at 42° C. The accumulation of small amount of l-Pspl at 65° C. indicated that cleavage at the carboxyl splice junction is enhanced (FIG. 11, lane 9).

In summary, the data has demonstrated that by substitution of a single native reside, serine, at the carboxyl splice junction of the Deep Vent® IVPS1 (CIVPS3), processing of the fusion proteins is altered and can be better controlled by temperature. The CIVPS3/Thr-β-galactosidase fusion protein (and CIVPS3/Cys fusion protein at a lesser extent) efficiently cleaved the specific peptide bond at the amino splice junction only at elevated temperatures.

EXAMPLE 9

Construction And Purification of MIP Purification Of CIVPS Fusions By Affinity Chromatography Cloning Of The Deep Vent IVPS1 Into An MBP Fusion Protein In one embodiment of the present invention a three-part fusion can be generated comprising a CIVPS; a segment which can be easily purified, e.g., a binding protein; and a protein or peptide of interest, i.e., a target protein. The order of these parts can be varied. The advantage of such a fusion is that it can be easily purified. Once the precursor protein is purified, the peptide of interest can be separated from the fusion by unidirectional protein cleavage induced by a modified CIVPS. In previous Examples, we have shown that if one of the CIVPS junctions is modified to reduce or prevent splicing or cleavage at that junction, then cleavage at the other junction will be favored over splicing (see Example 8). This allows for separation of the peptide of interest away from the fusion.

This Example demonstrates that such a 3-part fusion composed of a binding protein, maltose binding protein (MBP), CIVPS3 and a paramyosin peptide can be easily purified on an amylose resin as an unspliced precursor. The precursor can then be induced to splice, in this case by thermal activation. In this Example, no attempt has been made to limit cleavage to one side of the CIVPS so as to interfere with splicing to generate only cleavage products without ligation.

Synthesis Of Deep Vent IVPS1 Insert (CIVPS3)

A CIVPS3 cassette was synthesized by PCR as described in previous Examples, with the following modifications. The PCR mixture contained Vent® DNA polymerase buffer, 200M of each dNTP, 10 pmoles of each primer, 40ng of plasmid DNA and 2 units of Vent® DNA polymerase in 100l. Amplification was carried out using a Perken-Elmer thermal cycler at 94° C. for 30 sec, 50° C. for 30 sec and 72° C. for 2 min for 20 cycles. Deep Vent® IVPS1 was synthesized from PNEB #720.

The forward primer was, Primer 96-6, 5'-GGTACCCGTCGTGCTAGCATTTTACCGGAAGAA-TGGGTACCA-3'(SEQ ID NO:43), consisting of 26/27 bases at the 3' end which are identical to the 5' end of DV IVPS1, including 2 flanking Kpnl sites. The 3' Kpnl site includes a silent substitution which creates the restriction site without changing the amino acid residue. Deep Vent® IVPS1 reverse primer, Primer 96-7, 5'-CCCGCTATTATGTGCATAGAGGGATCC-3' (SEQ ID NO:44) has a BamHl site at the 3' end. 23/24 bases at the 3' end are homologous to the 3' end of DV IVPS1, with a single base substitution to create the BamHI site. Primers 96-6 and 96-7 were used to synthesize the Deep Vent® IVPS1 cassette (1.6kb).

The PCR sample was mixed 1:1 with chloroform and the top aqeous layer was loaded on a 1 % low melt agarose gel for electrophoresis. The 1.6 kb band was excised from the gel and incubated at 65° C. After the gel melted, 0.25 ml TE buffer (10 mM Tris-HCl/0.1 mM EDTA, pH7.5) at 65° C. was added and the sample was phenol-chloroform extracted (1:1 mixtre). The DNA was precipitated in 0.5M NaCl and 2 volumes isopropanol at –20° C. for 30 min. The DNA was spun down, dried and resuspended in 60 $\mu$l TE bffer.

Preparation Of pPR1002, A pMal-c2-Paramyosin ΔSal Plasmid pPR1002, a pMAL-c2-paramyosin ΔSal fusion plasmid, is a 7.2 kb vector that contains a tac promoter driven malE gene linked to an EcoRI-Sall fragment of the *D. immitis* Paramyosin gene, referred to as the paramyosin ΔSal deletion (Steel, et al., *J. Immnology,* 145:3917–3923 (1990)). Two samples of 4 $\mu$g each of pPR1002 were linearized with 6 units of Xmnl in 20 $\mu$l of 1X NEB buffer #2 containing 100 $\mu$g/ml BSA at 37° C. for 2 hours. The reactions were loaded onto a 1 % low melting agarose gel. The 7.2 kb band was excised and purified from the gel as above, and resuspended in 40 $\mu$l of TE buffer.

Construction Of pMIP17

Ligation of pPR1002 and Deep Vent® IVPS1 was carried out at 16° C. for 16 hours in a 25 $\mu$l volume with addition of 14.5$\mu$l distilled water, 2.5 $\mu$l of 10×T4 DNA ligase buffer, 1 $\mu$g/$\mu$g of cleaved pPR1002 DNA, 5 $\mu$l of 0.2 $\mu$g/$\mu$l Deep Vent® IVPS1 prepared as described above and 800 units of T4 DNA ligase.

*E. coli* strain ER2252 was transformed on ice for 5 min. by mixing 100 $\mu$l of competent ER2252 cells with 5 $\mu$l of ligation sample in 100 $\mu$l of a 1:2 mix of 0.1 MCaCl$_2$ and 1 XSSC (0.15 M NaCl, 15 mM NaCitrate), heating at 42° C. for 3 min., chilling in ice for 5 min, adding 0.1 ml LB media (10 grams/liter tryptone, 5 grams/liter yeast extract, 10 grams/liter NaCl, 1 gram/liter Dextrose, 1 gram/liter MgCl·6H$_2$O, pH7.2 at 25° C.) and incubating for 30 min. at 30° C. 300 $\mu$l of transformed cells were pelleted and resuspended in 100$\mu$l supernatant and plated onto an LB amp plate. After incubation overnight at 30° C., about 160 colonies were observed.

PCR amplification was utilized to screen for colonies that carried recombinant plasmids. Individual colonies were picked into 100 $\mu$l of distilled water in a 96 well microtitre dish, and boiled for 5 min to lyse the cells. The PCR mixture contained Vent® DNA polymerase buffer, 200 $\mu$M of each dNTP, 10 pmoles of each primer (same as above), 2.5 $\mu$l of cell lysate and 2 units of Vent® Exo⁻DNA polymerase in a 50$\mu$l reaction. Amplification was carried out by using a Perkin-Elmer (Emeryville, Calif) thermal cycler at 94° C. for 30 sec, 50° C. for 30 sec and 72° C. for 2 min for 30 cycles. 10 $\mu$l of each reaction was run on a 1 % agarose gel. The positive clones had bands corresponding to IVPS1 (1.6kb) and one positive plasmid was designated pMIP17.

Expression of MIP: The MBP-Deep Vent IVPS1-Paramyosin ΔSal Fusion

Positive clones containing pMIP17 were cultured in LB media supplemented with 100$\mu$g/ml ampicillin at 30° C. until OD$_{600}$ nm reached 0.5. To prepare a lysate from uninduced cells, 1.10 ml of culture was pelleted and resuspended in 50 $\mu$l Protein sample buffer (125 mM Tris, 700 mM B-mercaptoethanol, 2% SDS, 15% glycerol and 1 mg/ml Bromophenol Blue). Samples from induced cultures were prepared as follows. After addition of IPTG to a final concentration of 1 mM, the cultures were grown at 30° C. for 20 additional hours. Cells from 0.5 ml culture at 5 hours and 20 hours after induction were pelleted and then resuspended in 100 $\mu$l 5×protein sample buffer. The pre-induction and 5-hour samples were frozen at –20° C. for 16 hours and the 20-hour sample was frozen at –70° C. for 15 minutes. To improve precursor yield, cultures were induced at 12° C.–20° C. and amounts of precursor determined by Coomassie Blue stained gel. All the samples were boiled for 5 minutes and the protein products were analyzed by electrophoresis in SDS-PAGE followed by Coomassie Blue staining or Western blots using antibody raised against l-Pspl. The samples were electrophoresed on 4–20% SDS gels (ISS, Daiichi, Tokyo, Japan) with prestained markers (BRL, Gaithersburg, Md.), transferred to nitrocellulose, probed with antisera (mouse anti-l-Pspl), and detected using alkaline phosphate-linked anti-mouse secondary antibody as described by the manufacturer (Promega, Madison, Wis.). A predicted major band at about 132 kDa was observed in both the Coomassie Blue stained gels and Western blots (data not shown).

Figures 13A, 13B:
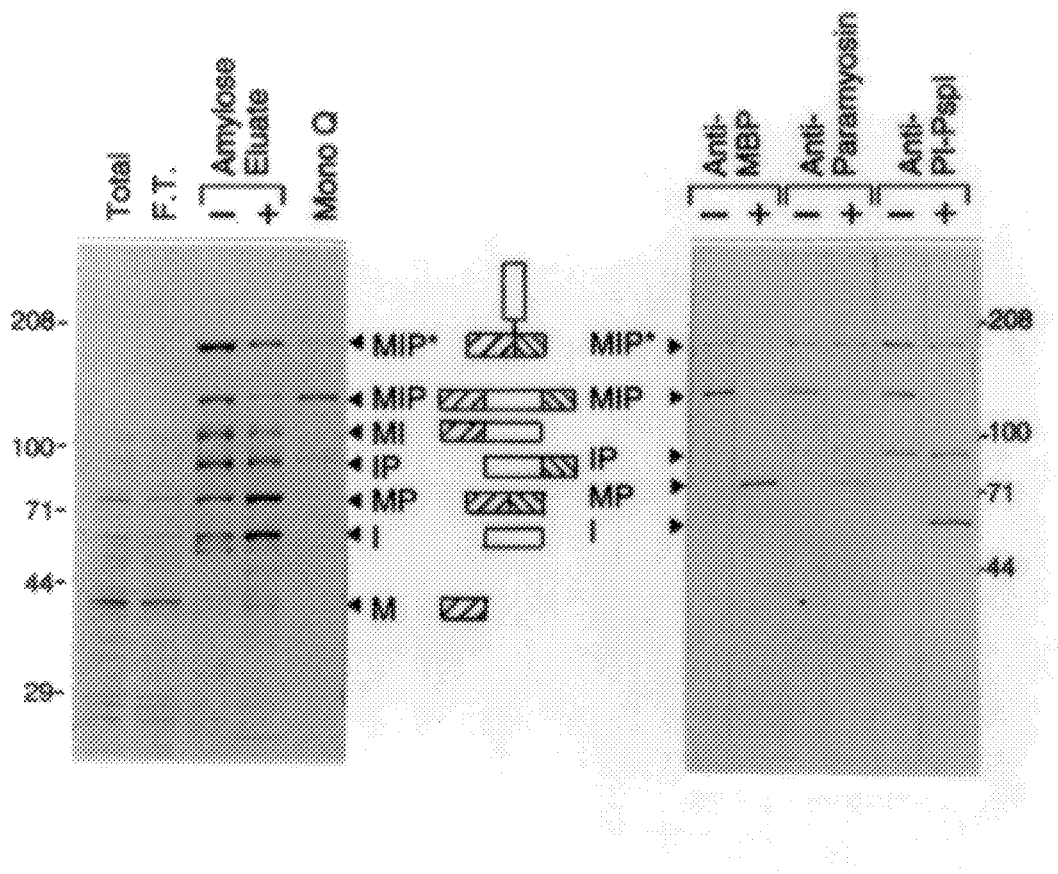
FIGS. 13A and 13B show the purification of MIP precursor on amylose and MonoQ columns examined by Coomassie blue staining and immunoblot. The diagram between FIG. 13A

Large Scale Purification Of The MBP-Deep Vent IVPS1 Paramyosin ΔSal Fusion On Amylose And MONOQ Columns Single colonies were used to inoculate 4×10 ml LB media supplemented with 100 $\mu$g/ml ampicillin and incubated at 30° C. until OD$_{600}$ nm reached 0.5. These cultures were used to inoculate 4×1 liter LB media supplemented with 100 μg/ml ampicillin and incubated at 30° C. until OD$_{600}$ nm reached 0.5. The cultures were then transferred to 12° C. and induced with 1 mM IPTG overnight. The cells were pelleted and resuspended in column buffer (20 mM NaPO$_4$ pH7.4, 200 mM NaCl and 1 mM EDTA), sonicated, spun down and the cleared culture lysate loaded over amylose resin (NEB Protein fusion and purification system). Fusion protein was eluted with maltose (as described by the manufacturer) and examined on an SDS-PAGE gel (FIGS. 13A and 13B). The amylose resin elute was further purified by chromatography on FPLC MonoQ anion exchange resin (Pharmacia, Piscataway, N.J.). The column was washed with 0.2 M NaCl, 10 mM Tris-HCl, pH8.5 and eluted with a linear gradient of NaCl from 0.2 to 1.0 M in 10 mM Tris-HCl, pH8.5. Protein eluted between 0.4–0.6 M NaCl.

Six protein bands were identified by Western blot with antibodies to MBP, I-PspI and paramyosin. Two bands of apparent molecular mass 180 kDa and 132 kDa reacted with all three antibodies. The full length precursor should be 132 kDa. The higher molecular weight band is thought to be a splicing intermediate and similar high molecular weight species have been seen with all CIVPS constructs. The excised I-PspI ran at 60 kDa and was only recognized by the I-PspI antibody, and the spliced product (MBP-Paramyosin ΔSal, 72 kDa) was only recognized by sera reactive with the MBP and Paramyosin antibodies. A band of approximately 103 kDa reacted with only the MBP and I-PspI antibodies and represents the product of a single cleavage at the C terminus of the IVPS. A band of approximately 89 kDa reacted with only the I-PspI and Paramyosin antisera and represents the product of a single cleavage at the N terminus of the IVPS (FIGS. 13A and 13B).

Excision And Ligation Of The MBP-Deep Vent IVPS1-Paramyosin ΔSal Fusion

Amylose resin and MonoQ preparations containing several MIP-related polypeptides, including precursor (132 kDa), slowly migrating species (180 kDa apparent molecular mass), products of cleavage at a single splice junction (103 kDa and 89 kDa), and small amounts of spliced and excised products (72 kDa and 60 kDa) were heat-treated at 37° C for 2 hours in 20 mM sodium phosphate (pH6.0) and 0.5 M NaCl.

The 132 kDa precursor and 180 kDa slowly migrating species decreased with time, while both the 72 kDa spliced product and the 60 kDa excised I-PspI increased (FIGS. 13A and 13B).

These results indicate that not only is it possible to purify 3-part CIVPS fusions, but that it is also possible to obtain single cleavage products. Further manipulation of the CIVPS junctions can favor cleavage at either splice junctions without ligation.

EXAMPLE 10

Modification Of CIVPS in MIP Fusions

Construction Of MIP With Replaceable Splice Junction Cassettes

In this Example, an MIP fusion (see Example 9) with replaceable cassettes at both splice junctions and modification of the CIVPS by cassette substitution was constructed. We also show in two cases that modified CIVPSs are capable of cleavage at predominantly a single splice junction in a thermal inducible manner.

In Example 9, we described a three part fusion, MIP, that can be generated with the following properties: a CIVPS, a binding domain which can be easily purified (MBP) and a gene of interest (Paramyosin ΔSal). Splicing of the purified fusion protein yielded two major products, the ligated protein domains, MBP-paramyosin ΔSal, and the excised CIVPS (or I-PspI). We reasoned that some modifications in the CIVPS may result in inhibition of the ligation reaction and enhancement of cleavage at one splice junction. This would result in separating the peptide of interest from the fusion protein by cleavage at a specific peptide bond catalyzed by a modified CIVPS. In Example 8, we have shown that cleavage at one splice junction can be enhanced by modification of CIVPS3 (substitution of the C-terminal Ser by Thr or Cys) and that these changes reduce or prevent splicing or cleavage at the other junction. In order to screen for modifications with favorable properties of controllable splicing or cleavage activity, it is necessary to introduce and analyze various mutations at the splice junctions. This could be accomplished by synthesis of the entire CIVPS cassette carrying each modification. However, this is likely to introduce extra mutations during PCR.

We have developed a strategy to facilitate the process by replacing only a short stretch of DNA around the splice junctions. In this Example, we describe how the original MIP fusion of Example 9 has been modified to contain two unique restriction sites flanking each splice junction. In a cassette replacement, following restriction digestion, the short stretch of DNA between the two unique restriction sites at one of the splice junctions can be replaced by another short DNA cassette. In this Example, we modified the pMIP17 fusion described in Example 9 to contain two unique restriction sites at each junction: a XhoI site and a KpnI site flanking the amino splice junction and a BamHI site and a StuI site flanking the carboxyl splice junction (see FIG. 14).

The MIP fusion with splice junction cassettes is constructed in two steps. First, the BamHI and StuI sites were introduced as follows. 4 μg of pMIP17 (Example 9) was digested in 1×EcoRI buffer with 0.5 units of EcoRI in 50 μl at 37° C. for 10 min. After electrophoretic separation in an 1% agarose gel, linearized pMIP17 plasmid DNA (8.8 Kb) was purified by using a GeneCleanII kit (BIO101). The purified pMIP17 DNA was digested in 1×BamHI buffer supplemented with 100 μg/ml BSA, 40 units of BamHI at 37° C. for 3 hours and then extracted with phenol and chloroform. DNA was precipitated in 0.3 M NaAcetate (pH5.2) and 50% 2-propanol at -20° C. for 2 hours. DNA was recovered by spinning for 10 min at 10,000 rpm in a microfuge, dried and resuspended in 20 μl sterile water.

Prior to ligation with the vector, two complementary oligomers, MIP301F (5'-GATCCCTCTATGCACATAATTCAGGCCTC-3'(SEQ ID NO:46)) and MIP302R (5'-AATTGAGGCCTGAATTATGTGCATAGAGG-3'(SEQ ID NO:47)) were allowed to anneal to form a double-stranded linker, MIP301F/MIP302R. 50 pmols of oligomers MIP301F and MIP302R were incubated in 1×T4 DNA ligase buffer at 68° C. for 15 min and slowly cooled to 20° C.–30° C. 1 μg of EcoRI-BamHI-digested pMIP17 DNA was ligated at 16° C. for 14 hours in 35 μl 1× T4 ligase buffer with 80 units of T4 DNA ligase and 25 pmols of the linker MIP301F/MIP302R.

Figure 14:
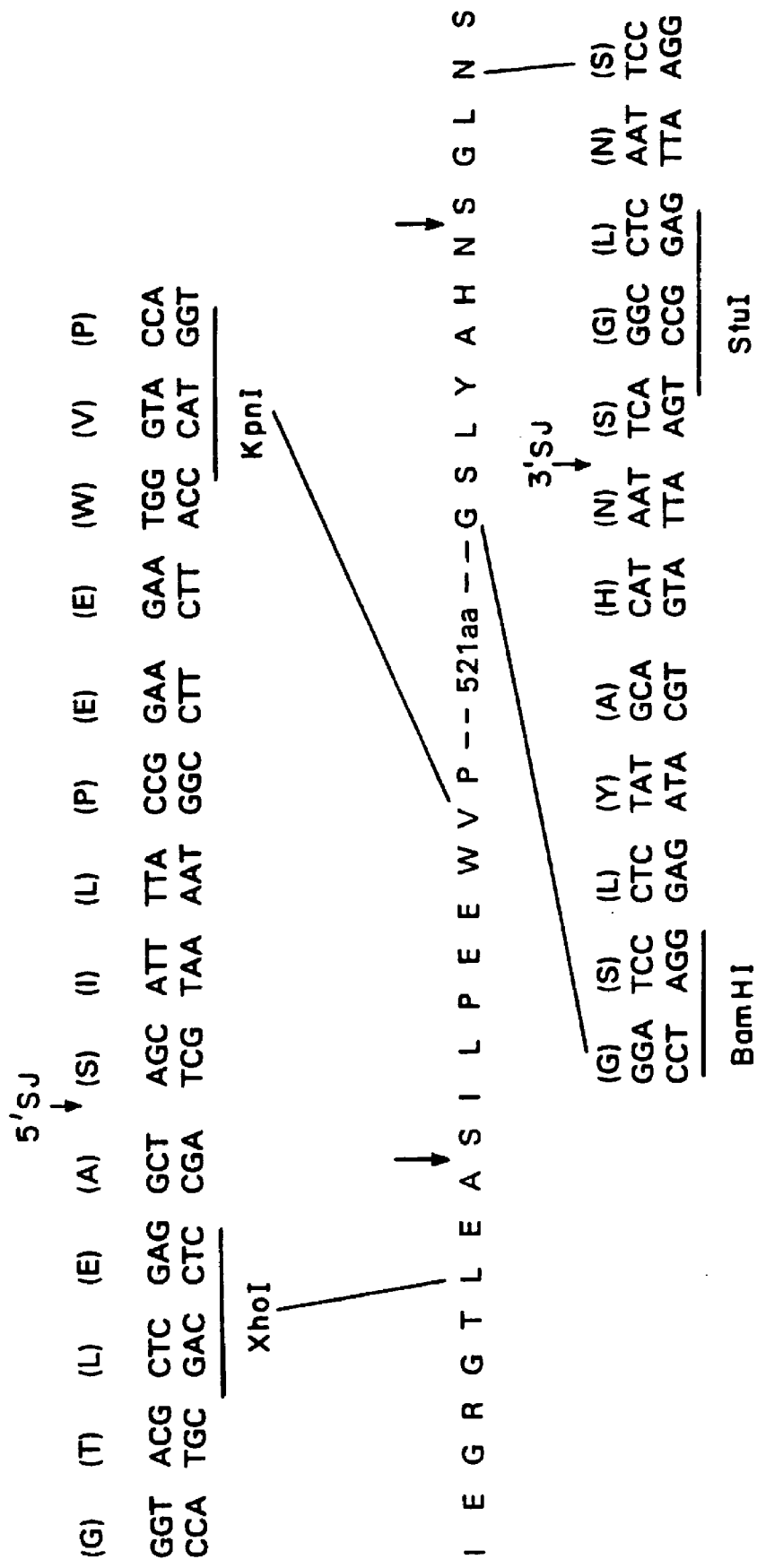
FIG. 14 illustrates the replaceable splice junction cassettes in MIP21 fusion. pMIP21 contains two unique restriction sites flanking each splice junction. Splice junctions are indicated by arrows. Amino acid residues around the splice junctions are shown. Splice junctions can be changed by replacing either the amino terminal XhoI-KpnI cassette or the carboxyl terminal BamHI-StuI cassette with another DNA cassette.

The resulting construct was termed pMIP18. The upstream XhoI and KpnI sites were introduced into pMIP18 as follows. 2 μg of pMIP18 was digested at 37° C. for 4 hours in 100 μl of 1×Buffer 2, 100 μg/ml BSA and 20 units of KpnI. Following electrophoretic separation, linear pMIP18 DNA was purified by using the GeneCleanII kit (BIO101). Prior to ligation with the vector, two complementary oligomers, MIP521 F (5'-GCTCGAGGCTAGCATTTTACCGGAAGAATGGGTAC-3'(SEQ ID NO:48)) and MIP522R (5'-CCATTCTTCCGGTAAAATGCTA GCCTCGAGCGTAC-3'(SEQ ID NO:49)) were allowed to anneal to form a double-stranded linker, MIP521F/MIPS22R. 50 pmols of oligomers MIP301F and MIP302R were incubated in 1x T4 DNA ligase buffer at 75° C. for 15 min and slowly cooled to 20° C.–30° C. 0.2 µg of digested pMIP18 was ligated at room temperature for 3 hours in 35 µl of 1x T4 DNA ligase buffer, 80 units of T4 DNA ligase and 25 pmols of the linker MIP521F/MIP522R. In each case, the ligated DNA samples were used to transform E. coli strain ER2252. The final construct, pMIP21, contains two unique restriction sites at each splice junction. There is a XhoI site and a KpnI site surrounding the N-terminal splice junction and a BamHI site and a StuI site surrounding the C-terminal splice junction (FIG. 14).

Western blot analysis was performed to examine expression of modified MIP21 fusion protein and splicing activity. ER2252 containing pMIP21 was cultured at 30° C. in LB medium supplemented by 100 µg/ml ampicillin until $OD_{600}$ nm reached 0.5. The culture was then induced by 1 mM IPTG at 30° C. for 3 hours. 4.5 ml of the culture was pelleted, resuspended in 0.5 ml LB medium and sonicated on ice. The cleared supernatant was electrophoresed on a 4/20% polyacrylamide gel at 100 volts for 4 hours. A Western blot was probed with anti-MBP sera. The results indicate that splicing activity from the modified MIP21 fusion was indistinguishable from that of MIP17.

Modification Of MIP21 By Splice Junction Cassette Replacement

In the modified MIP fusion construct, pMIP21, the amino splice junction cassette includes 8 amino acid residues between the XhoI and KpnI sites and the carboxyl splice junction cassette contains a sequence coding for 6 amino acid residues between the BamHI and StuI sites. Splice junctions can be changed by replacing either the N-terminal XhoI-KpnI cassette or the C-terminal BamHI-StuI cassette. In the case of the C-terminal cassette replacement, pMIP21 is first digested with BamHI and StuI. Complementary primers containing desired mutations are substituted for the original BamHI-StuI cassette. In this Example, two different junction cassettes were substituted for the MIP21 BamHI-StuI cassette.

In the following cassette replacement examples, we substituted $Ala_{535}$ by Lys or $His_{536}$ by Leu.

Complementary oligomers MIP303F (5'-GATCCCTCTATAAGCATAATTCAGG-3'(SEQ ID NO:50) and MIP304R (5'-CCTGAATTATGCTTATAGAGG-3' (SEQ ID NO:51)) were used to substitute residue $Ala_{535}$ by Lys. Complementary oligomers MIP311 F (5'-GATCCCTCTATGCACTGAATTCAGG-3'(SEQ ID NO:52)) and MIP312R (5'-CCTGAATTCAGTGCATAGAGG-3'(SEQ ID NO:53)) were used to substitute $His_{536}$ by Leu. These two pairs of complementary oligomers were treated as described above to form a double-stranded linker. Both linkers contain compatible termini to replace the carboxyl splice junction cassette following BamHI-StuI cleavage of pMIP21. 2 µg of pMIP21 DNA was digested with 40 units of BamHI in 1x BamHI buffer supplemented with 100 µg/ml BSA at 37° C. for 4 hours, extracted with chloroform and precipitated in 0.3 M NaAcetate (pH5.2) and 50% 2-propanol at –20° C. for 2 hours. DNA was recovered by spinning for 10 min at 10,000 rpm in a microfuge, dried and resuspended in 88 µl sterile water. The BamHI-digested pMIP21 DNA was then digested with 40 units of StuI in 100 µl 1x Buffer 2 at 37° C. for 3 hours, extracted with chloroform, precipitated in 0.3 M NaAcetate (pH5.2) and 50% 2-propanol at –20° C. for overnight. pMIP21 DNA was recovered by spinning for 10 min at 10,000 rpm in a microfuge, dried and resuspended in 30 µl sterile water. 0.1 µg BamHI-StuI digested DNA was ligated at 23° C. for 6 hours with 6 pmols of linker MIP303F/MIP304R or MIP311F/MIP312R in 10 µl of 1×T4 DNA ligase buffer in the presence of 40 units of T4 DNA ligase. The ligated DNA was used to transform E coli RR1. pMIP23 contains the $Ala_{535}$ to Lys substitution and pMIP28 contains the $His_{536}$ to Leu substitution. Expression of the modified MIP fusions, MIP23 and MIP28, was tested by western blot analysis with anti-MBP antibody as described above. The results indicated that splicing activity was blocked in both fusion constructs. However, each modification resulted in increased cleavage activity at only one of the splice junctions. The $Ala_{535}$ to Lys substitution in MIP23 drastically enhanced cleavage activity at the carboxyl splice junction and the $His_{536}$ to Leu substitution in MIP28 showed strong amino splice junction cleavage.

Purification Of Modified MIP Fusion Proteins And Thermal Inducible Cleavage Activity Expression of the fusion proteins was induced at low temperature and MIP fusion proteins were purified by amylose resin columns. RR1 harboring pMIP23 or pMIP28 were cultured in 1 liter of LB medium supplemented with 100 µg/ml anipicillin at 30° C. until $OD_{600}$ nm reached 0.5. After the cultures were cooled on ice to about 15° C., IPTG was added to a final concentration of 0.3 mM, and the cultures were grown at 12° C.–14° C. for 12 additional hours. Cells were pelleted, immediately frozen at –70° C. and stored at –20° C. The pellets were separately sonicated in column buffer (10 mM Tris pH8.5, 500 mM NaCl) and spun down. The cleared lysate from each MIP fusion was loaded over amylose resin (NEB Protein fusion and purification system), washed and eluted with maltose (as described in Example 9).

Figure 15A:
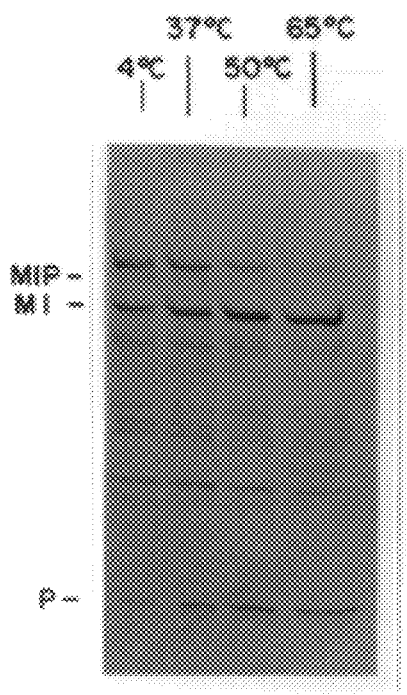
FIGS. 15A and 15B are gels showing thermal inducible cleavage at a single splice junction from modified MIP fusions. Fusion proteins were purified using amylose resin columns.

A purified sample of MIP23 was dialyzed in 20 mM $NaPO_4$ (pH6.0)/500 mM NaCl at 4° C. The sample was then incubated at 4° C., 37° C., 50° C., and 65° C. for one hour and then electrophoresed on a 4/20% SDS-PAGE gel followed by Coomassie Blue staining (FIG. 15A). The gel shows that with an increase in temperature MIP23 does not form the ligated product (MP) or the excised product (I), as the original construct does but instead accumulates the C-terminal cleavage products (MI, 103 kD and P, 29 kD).

Figure 15B:
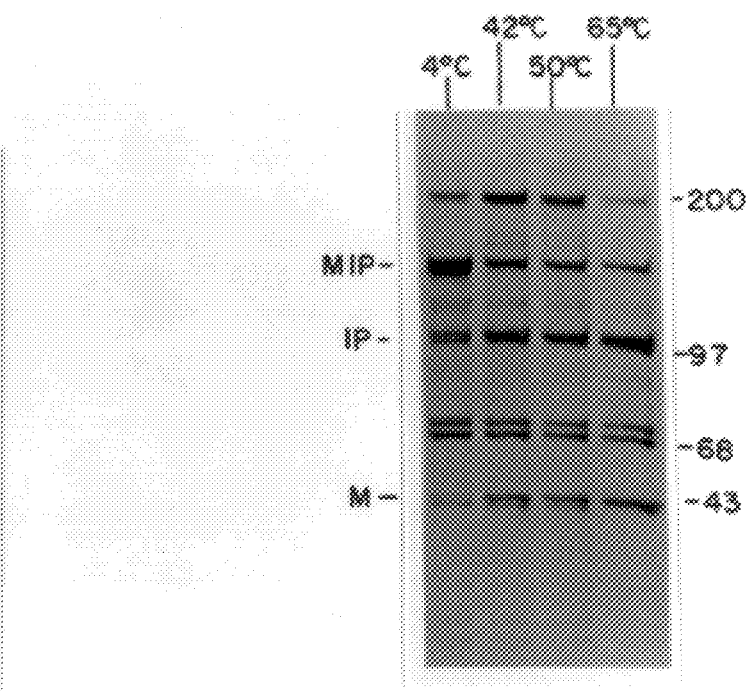

A purified MIP28 sample was dialyzed in 20 mM $NaPO_4$ (pH6.0)/500 mM NaCl at 4° C. for 1.5 hours. The sample was then incubated at 4° C., 42° C., 50° C., and 65° C. for one hour and mixed with ⅕volume of 5x Protein sample buffer (125 mM Tris,700 mM b-mercaptoethanol, 2% SDS, 15% glycerol and 1 mg/ml Bromophenol Blue). The protein products were analyzed by a 4/20% SDS-PAGE followed by Coomassie Blue staining (FIGS. 15A and 15B). The data indicated that splicing activity was completely blocked under these conditions. Cleavage activity at the amino splice junction was increased corresponding to the increase in temperature, yielding more MBP (M, 43 kD) and CIVPS3-paramyosin ΔSal (IP, 89 kD) at 65° C.

These results show that the splice junction cassette replacement method can be utilized to modify the splice junctions in a fusion construct and such modifications may result in drastic effects on splicing and cleavage activity. Furthermore, this data gives examples of constructs where cleavage at only one splice junction is observed in the absence of ligation and total excision of the CIVPS.

EXAMPLE 11

Construction And Purification Of MIC Replacement Of Foreign Gene In CIVPS Fusions A three-part fusion protein (MIP), composed of a binding domain for easy purification, a splicing domain (CIVPS3), and a target protein (paramyosin), was constructed as described in Example 9. This construct was purified and shown to be able to splice by thermal activation. To test the ability of this system to accept different target proteins, paramyosin in the MIP construct was replaced by the chitin binding domain (CBD) from the *Saccharomyces cerevisiae* chitinase gene (Kuranda and Robbins, *J. Biological Chem.*, 266(29):19758–19767 (1991)). The ability of this second protein fusion to splice and form both ligated and excised products shows that this fusion method can be employed with other foreign proteins. In addition, the chitin binding domain can be used as an alternate binding protein for protein purification.

Synthesis of Chitin Binding Domain (CBD)

A chitin binding domain was synthesized by PCR as described in the previous Examples, with the following modifications. The PCR mixture contained Vent® DNA polymerase buffer, 200 μM of each dNTP, 10 pmoles of each primer, 20 ng of plasmid DNA and 1 unit of Vent® DNA polymerase in 100 μl. Amplification was carried out using a Perkin-Elmer (Emeryville, Calif.) thermal cycler at 950° C. for 30 sec, 55° C. for 30 sec, and 72° C. for 30 sec for 20 cycles. The chitin binding domain was synthesized from pCT30, a plasmid containing the *Saccharomyces cerevisiae* chitinase gene (Kuranda and Robbins, *J. Biological Chem.*, 266(29):19758–19767 (1991)).

The forward primer, primer 99-02, 5'-GTCAGGCCTCTCAGACAGT ACAGCTCGTACAT-3' (SEQ ID NO:54) has a StuI site (AGGCCT (SEQ ID NO:55)) at the 5'end. 22 bases at the 3' end of the primer are identical to the 5' end of the chitin binding domain of the chitinase gene. The reverse primer, primer 99-03, 5'-CCCCTGCAGTTAAAAGTAATTGCTTTCCAAATAAG -3' (SEQ ID NO:56) has a PstI site (CTGCAG (SEQ ID NO:57)) at the 5' end. 26 bases at the 3' end of the primer are identical to the antisense strand at the 3' end of the chitin binding domain of the chitinase gene. Primers 99-02 and 99-03 were used to synthesize the chitin binding domain cassette (270 bp).

The PCR sample was extracted with phenol-chloroform (1:1 mixture) and the DNA was precipitated in 0.5 M NaCl and 2 volumes isopropanol at −20° C. for 30 min. The DNA was spun down, dried and resuspended in 40 μl TE buffer. (10 mM Tris-HCl, 0.1 mM EDTA, ph 7.5) A digest containing 20 μl of the resuspended DNA, 21 μl distilled water, 5 μl 10X NEB Buffer #2, 40 units PstI and 20 units StuI was then carried out at 37° C. for two hours in a 50 μl volume. The reaction was loaded on a 1.8% low melt agarose gel for electrophoresis. The 0.25 kb PstI/StuI digested product was excised from the gel and incubated at 65° C. until the gel melted. 0.25 ml TE buffer at 65° C. was added and the sample was phenol-chloroform extracted (1:1 mixture). The DNA was precipitated in 0.5 M NaCl and 2 volumes isopropanol at −20° C. for 30 min, spun down, dried and resuspended in 40 μl TE buffer.

Preparation Of PMIP21

A PstI/StuI double digest separates the paramyosin coding region from the remainder of the pMIP21, described in Example 10. Two samples of 5 μg each of pMIP21 were digested with 60 units PstI and 30 units StuI, 5 μl of NEB buffer #2, and 34 μl distilled water in a 50 μl volume at 37° C. for two hours. The reactions were loaded onto a 1% low melting agarose gel. The 8.1 kb band was excised and purified from the gel as above, and resuspended in 40 μl TE buffer.

Construction Of MBP-Deep Vent IVPS1CBD Fusions (MIC)

The chitin binding domain was substituted for paramyosin in MIP21 as follows to create MBP-Deep Vent® IVPS1-CBD constructs (MIC). 1 μl of 8.1 kb pMIP21 fragment, 10 μl of chitin binding domain (both prepared as described above) were combined with 9.5 μl distilled water, 2.5 μl of 10X T4 DNA ligase buffer, and 800 units of T4 DNA ligase and incubated at 16° C. for 4 hours in a 25 μl volume.

*E. coli* strain RR1 tonA was transformed by (1) mixing 100 μl of competent RR1 tonA cells with 5 μl of ligation sample and 100 μl of a 1:2 mix 0.1 MCaCl$_2$ and 1XSSC (0.15M NaCl, 15 mM NaCitrate) on ice for 5 min., (2) heating at 42° C. for 3 min., (3) chilling in ice for 5 min and (4) plating onto an LB amp plate. After incubation overnight at 30° C., about 200 colonies were observed.

Alkaline lysis mini-prep DNA (Sambrook, supra) was utilized to screen for clones that carry recombinant plasmids with the chitin binding domain. When digested with PstI and StuI, the positive clones had a band corresponding to chitin binding domain and a band corresponding to the vector. The restriction enzyme digests were carried out by mixing 10 μl miniprep DNA, 2.5 μl NEB buffer #2, 8.5 μl distilled water, 40 units PstI and 20 units StuI in a 25 μl volume at 37° C. for 2 hours.

Expression Of The MIC Fusions

To verify MIC constructs, small scale protein preparations were analyzed on Coomassie Blue stained gels and western blots. The positive clones were cultured in LB Media supplemented with 100 μg/ml ampicillin at 30° C. until OD$_{600}$ reached approximately 0.5. To prepare lysate from uninduced cells, 1.5ml of culture was pelleted and resuspended in 25 μl 5X Protein sample buffer (125 mM Tris, 700 mM b-Mercaptoethanol, 2% SDS, 15% glycerol and 1 mg/ml Bromophenol Blue). Protein samples from induced cultures were prepared as follows. After cooling the cultures to 12° C., IPTG was added to a final concentration of 1 mM and the cultures were grown at 12° C. for 5 additional hours. After 2 hours of induction, a 1.5 ml sample was taken and after 5 hours of induction a 3ml sample was taken. Samples were pelleted, resuspended in 50 μl 5X protein sample buffer, frozen at −20° C. for 16 hours, and then, thawed and boiled for 5 minutes. The protein products were analyzed by Coomassie Blue stained gels and Western blots using anti-MBP antibody. The samples were electrophoresed on 4–20%SDS gels (ISS, Daiichi, Tokyo, Japan) with prestained markers (BRL, Gaithersburg, Md.), transferred to nitrocellulose, probed with anti-MBP antibody, and detected using alkaline phosphate-linked anti-rabbit secondary antibody as described by the manufacturer (Promega, Madison, Wis.). A predicted major band at about 110 kDa for the MIC fusion protein was observed in both the Coomassie Blue stained gels and Western blots.

Large Scale Purification Of MIC On Amylose And MonoQ Columns

Single colonies were used to inoculate 3x10 ml LB media supplemented with 100 μg/ml ampicillin and incubated at 30° C. overnight. These cultures were used to inoculate 3x1 liter LB media supplemented with 100 μg/ml ampicillin and incubated at 30° C. until OD$_{600}$ reached 0.5. The cultures were then transferred to 12° C. and induced with 1 mM IPTG overnight. The cells were pelleted and resuspended in column buffer (110 mM Tris-HCl pH8.5, 500 mM NaCl), sonicated, spun down and the cleared culture lysate loaded over amylose resin (NEB Protein fusion and purification system). Fusion protein was eluted with maltose (as described by the manufacturer) and examined on an SDS-PAGE gel. The amylose resin eluate was further purified by chromatography on FPLC MonoQ anion exchange resin (Pharmacia, Piscataway, N.J.). The column was washed with 0.2 M NaCl, 10 Tris-HCl pH8.5 and eluted with a linear gradient of NaCl from 0.2 to 1.0 M NaCl in 10mM Tris-HCl,pH8.5. Protein eluted between 0.4–0.6M NaCl. The MIC and MIP protein fusion products purified similarity on both the amylose resin and the MonoO resin.

Excision And Ligation Of The MBP-Deep Vent IVPS1-CBD Fusion

Figure 16:
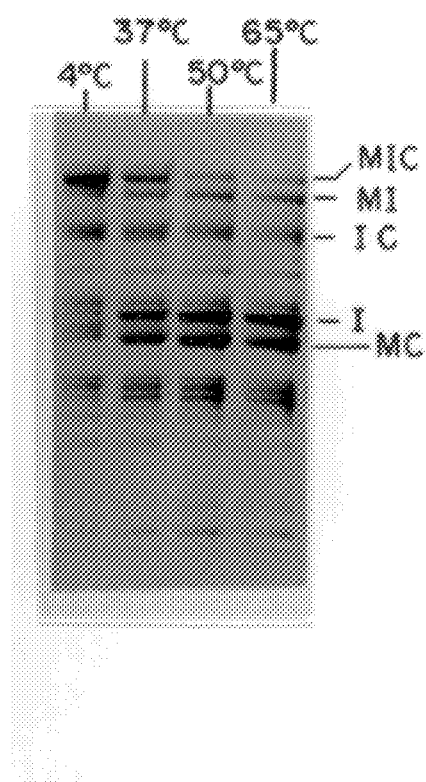
FIG. 16 is a gel showing thermal inducible cleavage of MIC fusion. Purified fusion protein samples were incubated at 4° C., 37° C., 50° C. or 65° C. for 1 hour. Products were analyzed by a 4/20% SDS-PAGE followed by Coomassie blue staining. Incubation of MIC fusion protein (MIC) yielded formation of ligated product, MBP-CBD(MC), and excised product, Deep-Vent IVPS1 (I=I-Psp I). Also, cleavage products, MBP-Deep-Vent IVPS1 (MI) and Deep-Vent IVPS1 -CBD(IC), are present in all samples and do not change with this heat treatment.

An amylose purified sample of MIC was dialyzed to 20 mM NaPO$_4$ pH6.0, 500 mM NaCl. The sample was then heat treated at 4° C., 37° C., 50° C., and 65° C. for one hour and then examined on an SDS-PAGE gel. (FIG. 16) The gel shows an abundance of MIC precursor, approximately 110 kDa, in the 4° C. sample which decreases after thermal induction. Along with the decrease in precursor, an accumulation of ligated product of approxiamtely 53 kDa in size, MBP-CBD(MC), and excised product of approxiamtely 60 kDa in size, Deep Vent® IVPS1 (l=l-Pspl), is observed with the increase in temperature. Also, the gel shows that bands of the same size as cleavage products, MBP-Deep Vent® IVPS1 (MI), approximately 103 kDa, and Deep Vent® IVPS1-CBD(IC), approximately 70 Da, are present.

EXAMPLE 12

Trans-splicing

This Example demonstrates that in vitro splicing can occur in trans between halves of a precursor protein. The position at which to split MIP (Example 9 and Xu et al., *Cell*, 75:1371–1377 (1993)) was chosen immediately upstream of a methionine residue in the native CIVPS3, although other sites might work equally well, including sites which result in gaps or overlapping CIVPS sequences. In this Example, one of the MIP half proteins was insoluble and splicing in trans was therefore performed in urea. Partial or full denaturation should not be construed as a requirement in general, since other separation points may result in solubility of both halves and since the insoluble half can be rendered soluble for trans-splicing experiments under non-denaturing conditions.

Construction Of MI'

A fusion of the malE gene (encoding MBP) with the first 249 amino acids of the CIVPS3 gene was synthesized by polymerase chain reaction (PCR) from pMIP21 (Example 10 and Xu et al., supra (1993) carrying a fusion between malE, CIVPS3 and *D. immitis paramyosin* ΔSal genes using the forward primer 5'-GGAATTC CATATGAAAATCGAAGAAGGT-3'(SEQ ID NO:58) (Nde I site underlined) and the reverse primer 5'-CG GGATCCCGTTATAGTGAGATAACGTCCCG-3'(SEQ ID NO:59) (BamHI site underlined). PCR reaction mixtures contained Vent® DNA polymerase buffer, 400 mM each dNTP, 0.84 mM primers, 5 mg/ml plasmid DNA, and 20 U/ml Vent® Exo$^+$DNA polymerase in 50 μl. Amplification was carried out using a Perkin-Elmer Cetus (Emeryville, Calif.) thermal cycler at 94° C. for 30 seconds (s), 52° C. for 30 s, and 72° C. for 135 s for 15 cycles. Restriction enzyme digests were performed as described by the manufacturer. Gel purified NdeI/BamHI digested PCR products were ligated directly into gel purified BamHI/NdeI digested pAll-17 T7 vector (Perler et al., *Proc. Natl. Acad. Sci. USA*, 89:5577–5581 (1992)) to create pMI/L249 (Sambrook, *Molecular Cloning: A Laboratory Manual,* 2nd Edition, (1989). Cold Spring Harbor Laboratory Press, Cold Spring Harbor, N.Y.)). *E. coli* ER2169 pLysS (BL21 (DE3) X P1 vir (ER1489)—>Tet$^R$)McrB-)) was transformed with pMI/L249 to create NEB941. The protein produced by NEB941 was called MI' for MBP (maltose binding protein)-CIVPS3 N-terminal domain (IVPS) fusion.

Construction Of I'P

Restriction enzyme digests were performed as described by the manufacturer. Gel purified XbaI/Bpu 1102I digested pET-21b fragments carrying the polylinker site and the 6 histidine tag sequence (Novagen; Madison, Wis.) were ligated directly into gel purified Bpu 1102I/XbaI digested pAll-17 T7 vector DNA (Sambrook, supra (1989)) to create the pPHT (Polylinker-HisTag)-T7 vector used for expression of I'P.

A fusion of the last 288 amino acids of the CIVPS3 gene with the *D. immitis paramyosin* ΔSal gene was synthesized by PCR from pMIP21 (Xu et al., supra (1993)) using the forward primer 5'-GGAATTC CATATGCCAGAGGAAGACTG-3'(SEQ ID NO:60) (Nde I site underlined) and the reverse primer 5'-ATAGTTTA GCGGCCGCTCACGACGTTGTAAAACG-3'(SEQ ID NO:61) (Not I site underlined). PCR mixtures were as described above, except in 100 μl. Amplification was carried out using a Perkin-Elmer Cetus thermal cycler at 94° C. for 30 s, 52° C. for 30 s, and 72° C. for 105 s for 10 cycles. Gel purified NdeI/NotI digested PCR products were ligated directly into gel purified NotI/NdeI digested pPHT-T7 vector to create pl/M250-PH (Sambrook, supra (1989). *Ecoli* ER2169 pLysS) was transformed with pl/M250-PH to create strain NEB942. The protein produced by NEB942 was called I'P for CIVPS3 C-terminal domain (IVPS)—*D. immitis* Paramyosin ΔSal-His Tag fusion. The C-terminal domain has no additional amino acids since it begins with a methionine present in CIVPS.

MI' Expression And Purification

NEB941 was grown at 30° C. in LB medium plus 100 μg/ml of ampicillin to an OD$_{600}$ of≈0.5. The culture was induced at 30° C. with 0.4 mM isopropyl β-D-thiogalactoside (IPTG) and immediately transferred to a 22° C. air shaker in a cold room overnight. The cells were harvested at 4° C. and stored at -200C. Frozen cells from a 1 liter culture were resuspended in 50 ml of amylose column buffer (0.01 M Tris-HCl pH 8.5, 0.2 M NaCl, 1.0 mM Na$_2$-EDTA) and broken by sonication. After centrifugation at 9,000 g for 30 min, the crude supernatant was passed through an amylose column (5 ml of resin), and the column was washed with 50 ml of the above buffer. Maltose, at a final concentration of 10 mM, was added to the column buffer and the elution continued until the MBP fusion was eluted.

I'P Expression And Purification

A HisTag was included in the construction of I'P to facilitate purification. When I'P protein was expressed in *E.coli*, approximately 90% was insoluble, which is common with many HisTag (6–10 histidines) fusion proteins. Therefore, I'P samples were solubilized in 6M urea for purification and chromatographed over a Ni$^{2+}$ affinity resin.

NEB942 was grown at 30° C. in LB medium plus 100 ρg/ml ampicillin to an OD$_{600}$ of≈0.5. The culture was induced at 30° C. with 0.4 mM IPTG overnight. The cells were harvested at 4° C. and stored at −20° C. Frozen cells from a 1 liter culture were thawed in 130 ml of amylose column buffer (0.2 M NaCl, 0.01 M Tris-HCl pH 8.5, 1.0 mM Na$_2$-EDTA) and broken by sonication. After centrifugation at 20,000 g for 30 min, the pellet containing insoluble material, including the l'P protein, was resuspended in 130 ml of column buffer and centrifuged as before. The washed pellet was resuspended a second time in 130 ml of column buffer and spun as before. The twice washed pellet was finally resuspended in 130 ml of $Ni^{2+}$ binding buffer (20 mM Tris-HCl pH 7.9, 500 mM NaCl, 16 mM Imidazole) complemented with 6 M urea. The solubilized pellet was stirred overnight at 4° C., then centrifuged a last time at 31,000 g for 1 hour. The supernatant was filtered through a 0.45 mM membrane (Millex, Millipore; Bedford, Mass.), passed through a $Ni^{2+}$ charged column (Novagen; Madison, Wis., 2.5 ml of resin), and the column was washed with 10 volumes of binding buffer. Imidazole at a final concentration of 60 mM was added to the binding buffer and elution of contaminant proteins was continued until undetectable by Bradford assay (BioRad; Hercules, Calif.). The l'P fusion protein was eluted with 180 mM of imidazole in the binding buffer and elution continued until the fusion had eluted completely as shown by the above assay.

Trans-splicing Experiments

Two complementary halves of MIP were constructed as described above. The product of the N-terminal half of MIP, containing all of MBP and the N-terminal domain of CIVPS3 (amino acids 1–249) was termed MI' and the product of the C-terminal half of MIP, containing the C-terminal domain of CIVPS3 (amino acids 250–537) and all of Paramyosin ΔSal was termed I'P. Unfortunately, I'P was insoluble, and needed to be solubilized and purified in 6 M urea. The denaturation and renaturation of enzymes with recovery of enzymatic activity has been reported in the literature (Burbaum and Schimmel, *Biochemistry*, 30:319–324 (1991); Hattori, et al, *J. Biol. Chem.*, 268:22414–22419 (1993); Sancho and Fersht, *J. Mol. Biol.*, 224:741–747 (1992), among others). However, each protocol differs. The initial protocol chosen for this study involved mixing both halves of MIP in urea, incubating at 4° C., rapidly diluting the proteins and then allowing the diluted proteins to refold. This was followed by a standard in vitro splicing protocol (Xu et al., *EMBO J.*, 13:5517–5522 (1994); Xu et al., supra (1993)) after concentration of the diluted proteins, although this concentration step is not necessary. Variation of the different parameters including initial concentration, urea concentration (or other denaturants), dilution factor, length of incubation and protein ratio, allows the optimization of refolding and trans-splicing efficiencies.

Figures 17A, 17B:
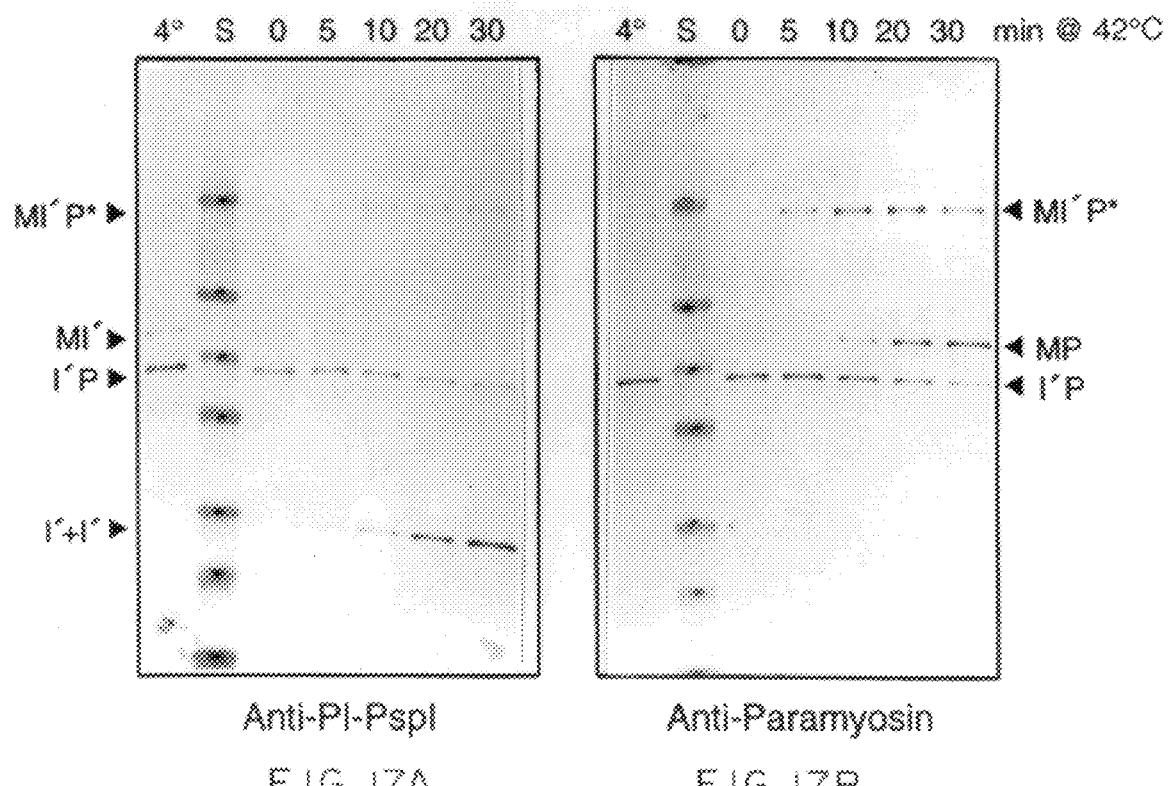
FIGS. 17A and 17B show the Western blot of a trans-splicing reaction with Ml' and l'P. l'P and Ml' were treated as described in the text to induce trans-splicing as observed by the accumulation of MP and l' products. Western blots with either anti-CIVPS3 (Anti-Pi-Pspl) sera or anti-Paramyosin sera were performed as described in the text. Lanes marked '4°' contain control l'P and Ml' samples incubated at 4° C. Lanes 3–7 contain cleavage reaction samples after incubation for 0, 5, 10, 20, and 30 minutes at 42° C., respectively. Lane S contains size markers (NEB broad range prestained protein markers).

Purified MI' and l'P fusion proteins were exchanged with buffer A (50 mM Tris-HCl pH 7.5, 5% acetic acid, 0.1 mM EDTA, 1 mM DTT and 140 mM β-mercaptoethanol) supplemented with 7.2 M urea and equilibrated at pH 7.5 prior to use. Macrosep (15 ml) and Microsep (3.5 ml) concentrator devices (Filtron Technology Corp.; Northborough, Mass.) were used in every step that required a buffer exchange or a protein concentration as described by the manufacturer. The two fusions were then mixed together at a final concentration of 2.3 mg/ml and incubated overnight at 4° C. The mixture was diluted 50-fold in buffer B (Tris-HCl pH 6,500 mM NaCl) and renaturation was allowed to occur during the 2 hour concentration step to 0.5–2 mg/ml at 4° C. The mixture was heated in a Perkin-Elmer Cetus (Emeryville, Calif.) thermal cycler at 42° C. for 1 hour to induce splicing. To follow the splicing reaction, samples were collected at time-points and Western blots (Sambrook, supra(1989)) were performed in duplicate with either mouse sera raised against CIVPS3 (anti-PI-Pspl) or paramyosin ΔSal (Steel et al., *J. Immunology*, 145:3917–3923 (1990)). In later experiments, the concentration step after mixing was found to be unnecessary. Unfortunately, Western blots are necessary to follow splicing because both the substrate, MI', and the product, MP, have similar molecular masses (approximately 72 kDa). The anti-paramyosin antibody is diagnostic, since it shows the decay of the l'P substrate (approximately 60 kDa) and the formation of the MP product (~72 kDa). On the other hand, anti-MBP sera which reacts with the similarly sized MI' and MP, is not diagnostic since as MI' decreases, MP increases at the same position in the gel. As a result, the anti-MBP sera detects a relatively constant band at 72 kDa. The Western blot with the mouse anti-CIVPS3 sera demonstrates the decay of the substrates (MI' and l'P) and the formation of the I' products (which are often inseparable during electrophoresis because of their similar molecular masses). Western blots using anti-Paramyosin antibodies show that there is no cross-reactivity, since anti-Paramyosin sera fails to react with MI' (FIGS. 17A and 17B). Anti-CIVPS3 (anti-Pl-Pspl) antibody was shown to react with both MI' and l'P (FIGS. 17A and 17B).

Protein splicing of MIP, in cis, is more efficient at high temperatures (up to 65° C.) and low pH (6.0) (Xu et al., supra(1994); Xu et al., supra(1993) and Example 11. After a few assays, the splicing reaction for trans-splicing was set at 42° C., pH 6.0, although other temperatures and pH's also work. A time course of trans-splicing is shown in FIGS. 17A and 17B. The trans-splicing reaction is best monitored by the accumulation of the 72 kDa MP as shown on Western blots using anti-Paramyosin sera and the decrease in Ml'and l'P and the formation of I' using anti-CIVPS3 sera (anti-Pl-Pspl, FIGS. 17A and 17B). In this experiment, both MI' and l'P were exchanged into 7.2 M urea in buffer A using a Microsep concentrator (Filtron Technology Corp.; Northborough, Mass.) and mixed at a final concentration of 1 mg/ml each protein. The mixtures were incubated overnight at 4° C. and then diluted 50-fold into buffer B. Diluted samples were immediately placed at 42° C. or 4° C. Samples were taken after 5, 10, 20, and 30 minutes of incubation and placed on ice. A zero time point was taken prior to placing the tube at 42° C. 5 μl of each time point was electrophoresed in duplicate 5–20% SDS-PAGE gels (Daiichi, Tokyo, Japan) and Western blots were performed (Perler et al., supra(1 992); Sambrook, surpa(1 989)) with either anti-CIVPS3 (anti-PI-Pspl) or anti-Paramyosin sera. No trans-splicing was observed in the samples incubated at 4° C. Within 5 minutes at 42° C., the branched intermediate (Ml'P*) was observed and by 10 minutes, spliced products (MP and both I') were observed (FIGS. 17A and 17B).

Re-establishment of l-PSP I Activity

Figure 18:
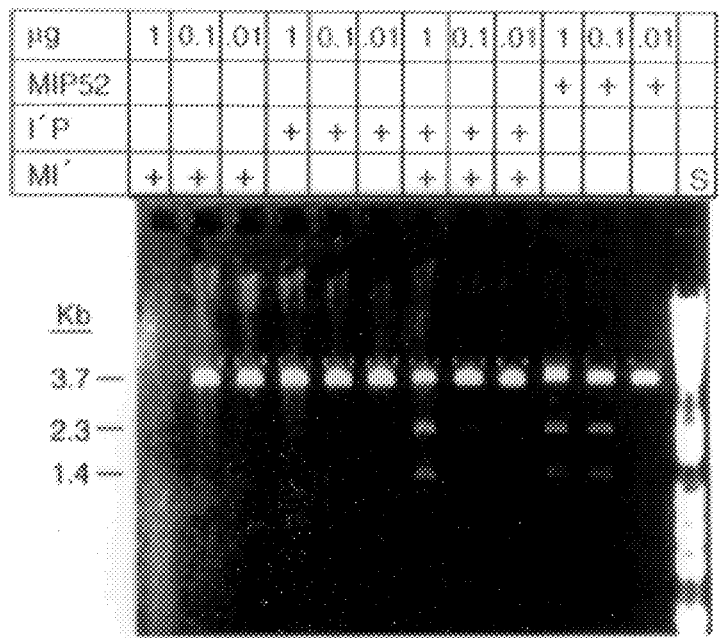
FIG. 18 shows that trans-splicing re-establishes l-Pspl endonuclease activity. XmnI linearized pAKR7 DNA was digested with 0.01, 0.1 or 1 µg of either Ml', l'P, the trans-splicing reaction products (indicated by a plus in both the l'P and Ml' rows) or cis-spliced MlP52. l-Pspl activity was only present in MIP52 and the trans-spliced mixture. Lane S contains size markers (a mixture of lambda DNA digested with HindIII and PhiX174 DNA digested with HaeIII).

After trans-splicing, the protein mixture was tested for l-Psp I activity (l-Pspl or Pl-Pspl is the same as CIVPS3 or I in this example). The substrate DNA used for I-Pspl digestion is pAKR7, which was generated by subcloning a 714 bp EcoRI fragment from pAKK4 (Perler et al., supra (1992)) into the EcoRI site of Bluescript SK-. This 714 bp fragment contains the coding region surrounding the sites where IVPS1 and IVPS2 were found in the wild type Vent® DNA polymerase clone. Cleavage with Xmnl and l-Pspl should give fragments of about 2327 and 1351 bp. Test substrate DNA, pAKR7, was reacted with either MI', l'P, the trans-splicing reaction products or cis-spliced MIP52 (FIG. 18). pAKR7 was cut with Xmnl to linearize the plasmid at a point near the l-Pspl restriction site. 5μg of pAKR7 DNA was digested with 6 Units Xmnl in NEB buffer 2 for 100 min at 37° C. One microgram of linearized pAKR7 DNA was mixed with 0.01, 0.1 or 1 μg of either MI', I'P or the trans-splicing reaction products in a final volume of 55 μl I-Pspl buffer and incubated at 50° C. for 1 hour. In an identical reaction, MIP52 protein was used as a control. MIP52 is a mutant form of MIP containing an insert of MILVA prior to Ser1 of CIVPS3 and this insertion has no effect on splicing or endonuclease activity. MIP52 was used rather than I-Psp I because the cis-spliced mixture more closely mimicked the trans-spliced mixture. The MIP52 control sample contained precursor MIP and cis-spliced MP and I products. Endonuclease activity was only present in the MIP52 enzyme and the trans-spliced mixture, indicating that the above trans-splicing protocol not only re-establishes the ability to splice, but also re-establishes endonuclease activity in CIVPS3. As another control, MI' and I'P were added separately to a digestion mixture as above; no digestion was observed (FIG. 18), indicating that both protein fragments are required to restore endonuclease activity.

EXAMPLE 13

Trans-Cleavage

In this Example, we describe cleavage at the C-terminal of CIVPS3 in trans using the MIP fragments described in Example 12 as a starting point.

Construction Of MI'22 Containing A ILE2LYS Mutation In CIVPS3

In Example 12, we described the construction of MI' and I'P, which were used for trans-splicing. In this example we replaced the splice junction cassette in pMI/L249 (which encodes MI') with a duplex oligomer which replaces Ile2 of CIVPS3 with Lys. The techniques used are as described in Examples 10 and 12. Briefly, prior to ligation with the vector, pMI/L249, two complementary oligomers, DVMIP525FW (5'-TCGAGGCTAGCAAATTACCGGAAGAATGGGTAC-3' (SEQ ID NO:62)) and DVMIP526RV (5'-CCATTCTTCCGGTAATTTGCTAGCC-3'(SEQ ID NO:63)) were allowed to anneal to form a double-stranded linker, DVMIP525FW/DVMIP526RV. 100 pmol of each oligomer was incubated in 50 µl of 1 ×T4 DNA ligase buffer at 68° C. for 15 min and slowly cooled to 20°–30° C. pMI/L249 DNA was digested with XhoI-KpnI as described by the manufacturer and the linear plasmid was purified after electrophoretic separation using the GenecleanII kit (BIO101; Vista, Calif). 0.1 µg of XhoI-KpnI-digested pMI/L249 DNA was ligated overnight at 16° C. in 10 µl 1×T4 ligase buffer with 80 units of T4 DNA ligase and 15.5 pmol of the linker DVMIP525FW/DVMIP526RV. The resulting construct was termed pMI'22 and the protein produced by this clone was called MI'22.

Purification Of MI'22 AND I'P

I'P was purified as described in Example 12. MI'22 was purified as described for MI' in Example 12. *E.coli* strain ER2497 (NEB975) was transformed with pMI'22 and grown at 30° C. in LB medium plus 100 µg/ml of ampicillin to an $OD_{600}$ of ≈0.5. The culture was induced overnight at 30° C. with 0.4 mM isopropyl β-D-thiogalactoside (IPTG). The cells were harvested at 4° C. and stored at −20° C. Frozen cells from a 1 liter culture were resuspended in 60 ml of amylose column buffer (20 mM Sodium phosphate, pH 8.5, 0.5 M NaCl, 1.0 mM $Na_2$-EDTA) and broken by sonication. After centrifugation at 9,000 g for 20 min, the crude supernatant was diluted two-fold in column buffer and passed through an amylose column (12.5 ml of resin), and the column was washed with 60 ml of the above buffer followed by 60 ml of amylose column buffer adjusted to pH 6. Maltose, at a final concentration of 10 mM, was added to the pH 6 column buffer and the elution continued until the MBP fusion was eluted.

Trans-cleavage

Two complementary halves of MIP were constructed as described above. The product of the N-terminal half of MIP, containing all of MBP and the N-terminal domain of CIVPS3 including the Ile2Lys substitution (amino acids 1–249) was termed MI'22 and the product of the C-terminal half of MIP, containing the C-terminal domain of CIVPS3 (amino acids 250–537) and all of Paramyosin ΔSal was termed I'P. The products of the trans-splicing reaction are the unchanged MI'22 and the cleaved I'P which forms the I' fragment and the P fragment, both of which are approximately 30 kDa. Unfortunately, I'P was insoluble, and needed to be solubilized and purified in 6 M urea. The initial protocol chosen for this study was as described in Example 12, involved mixing both halves of MIP in urea, incubating at 4° C., rapidly diluting the proteins and then allowing the diluted proteins to refold. This was followed by a standard in vitro splicing protocol (Xu, M., et al., supra (1994); Xu, M., et al., supra (1993)). Variation of the different parameters including initial concentration, urea concentration (or other denaturants), dilution factor, length of incubation and protein ratio, allows the optimization of refolding and trans-cleaving efficiencies.

Figure 19:
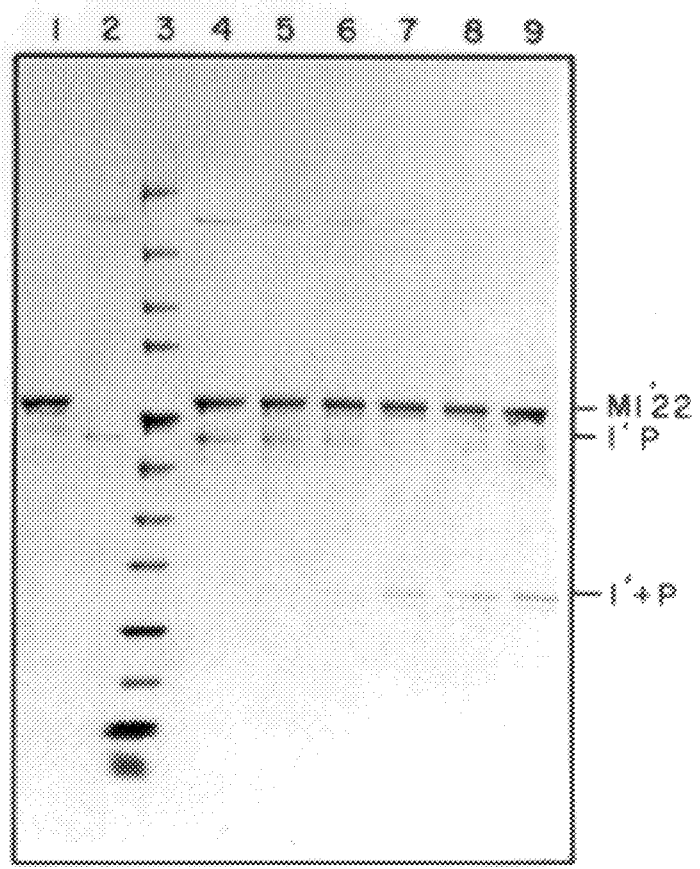
FIG. 19 shows the trans-cleavage of l'P by Ml'22. l'P and Ml'22 were treated as described in the text to induce trans-cleavage. Lanes 1 and 2 contain the starting samples Ml'22 and l'P, respectively. Lane 3 contains size markers (NEB broad range protein markers). Lanes 4–9 contain cleavage reaction samples from 0, 5, 10, 20, 40 and 90 minutes at 42° C., respectively.

Approximately 10 µg each of purified MI'22 and I'P fusion protein were mixed in 24 µl total volume of Novagen His Tag column binding buffer (20 mM Tris, HCl, pH 7.9, 0.5 M NaCl, 5 mM imidazole) adjusted to 6M urea and incubated on ice for 90 minutes. The sample was diluted 25-fold in 20 mM sodium phosphate buffer, pH6, 0.5 M NaCl and 1 mM EDTA and incubated at 42° C. Samples were taken and placed on ice at 0, 5, 10, 20,40 and 90 minutes. Samples were boiled in SDS-PAGE sample buffer (Sambrook et al., supra (1989)), electrophoresed on 4–20% gradient SDS-PAGE (Daiichi, Tokyo, Japan) and stained with Coomassie blue. As seen in FIG. 19, I'P (~60 kDa) disappears with time and I' and P appear at approximately the same position in the gel (~30kDa). Control samples which are not shown include incubating the mixture of MI'22 plus I'P at 4° C. or incubating each protein fragment separately at 42° C.; none of these control experiments showed any cleavage activity.

EXAMPLE 14

Chemical Control Of IVPS Activity

In previous Examples, we have demonstrated that splicing and cleavage activities of IVPSs can be controlled by amino acid substitution, temperature and pH. In this Example, we demonstrate that chemical treatment may also be used to activate or inhibit IVPS activity. Thus, an IVPS can become a CIVPS when its activity can be controlled by chemical treatment. In Example 10, we described modification of CIVPS3 in the MIP fusion by cassette replacement which resulted in cleavage at one of the splice junctions instead of splicing. pMIP21 contains two unique restriction sites at each splice junction: an XhoI site and a KpnI site flanking the N-terminal splice junction and a BamHI site and a StuI site flanking the C-terminal splice junction (FIG. 14, Example 10). The N-terminal splice junction residue(s) can be changed by replacing the XhoI-KpnI cassette, while the C-terminal splice junction residue(s) can be altered by substituting the BamHI-StuI cassette. In the case of the N-terminal cassette replacement, pMIP21 is first digested with XhoI and KpnI. A cassette carrying desired mutations, formed by annealing two complementary primers, is substituted for the original XhoI-KpnI cassette. Some modifications in the CIVPS may allow activation of cleavage or splicing activity by chemical treatment. In this specific example, we show that substitution of Ser1 by Cys in CIVPS3 results in a chemical-inducible CIVPS in the Ml (a truncated form of MIP) context, which, upon chemical activation with hydroxylamine, results in cleavage of the bond between MBP and cysteine in the modified CIVPS3.

Modification Of CIVPS3 By Replacing Ser1 With CYS

In this Example, we first modified pMIP21 (Example 10) by substituting a serine with a cysteine at the N-terminal splice junction of CIVPS3 (Ser1 Cys) by cassette replacement to yield pMIP47. 2 μg of pMIP21 was digested at 37° C. for 4 hours in 100 μl of 1 ×Buffer 1, 100 μg/ml BSA and 20 units of Xhol and 20 units of Kpnl. Following electrophoretic separation on an 1% agarose gel, pMIP21 DNA was purified by using the Geneclean II kit (BIO101; Vista, Calif.). Two complementary oligomers, MIP535FW (5'-TCGAGGCTTGCATTTTACCGGAAGAATGGGTAC -3' (SEQ ID NO:64)) and MIP536RV (5'-CCATTCTTCCGGTAAAATGCAAGCC-3'(SEQ ID NO:65)) were allowed to anneal to form a double-stranded linker, MIP535FW/MIP536RV. 100 pmol of each of oligomers MIP535FW and MIP536RV were incubated in 50 μl of 1 ×T4 DNA ligase buffer at 65° C. for 15 min and slowly cooled to 20–30° C. Approximately 0.1 μg of the Xhol-Kpnl digested pMIP21 DNA was ligated at 16° C. overnight in 10 μl of 1 x T4 DNA ligase buffer, 80 units of T4 DNA ligase and 15.6 pmol of the linker MIP535FW/MIP536RV, to yield pMIP47. The ligated DNA sample was used to transform E.coli strain ER2426 (NEB974).

Construction Of pMI84 Encoding Ml pMI84 was constructed in two steps by the following cassette replacement experiments. pMIP21 was first modified by replacing the C-terminal splice junction cassette with linker MIP353FW/MIP354RV to yield pMIP66. The linker MIP353FW/MIP354RV, containing a Sphl recognition sequence, was formed by annealing two complementary oligomers, MIP353FW (5'-GATCCCTCTATAAGCATAATATTGGCATGCAGTA-3' (SEQ ID NO:66)) and MIP354RV (5'-TACTGCATGCCAATATTATGCTTATAGAGG-3' (SEQ ID NO:67)) as described above. pMIP21 DNA was digested with BamHI and StuI as described in Example 10. 0.1 μg BamHI/StuI digested pMIP21 DNA was ligated at 16° C. overnight with 16.6 pmol of linker MIP353FW/MIP354RV in 10 μl of 1 ×T4 DNA ligase buffer in the presence of 40 units of T4 DNA ligase. After addition of 1 μl of 10× buffer 2 and 0.5 μl (10 units) of StuI, the ligated DNA sample was incubated at 37° C. for 3 hours before E.coli ER2426 (NEB974) was transformed.

pMIP66 contains unique BamHI and Sphl sites flanking the C-terminal splice junction, allowing linker replacement following BamHI and Sphl digestion. A stop codon was then inserted after the CIVPS C-terminus to create the Ml truncated fusion. Ser538 was mutated to a translational stop codon (TAA) by replacing the BamHI-Sphl cassette with the linker MIP385FW/MIP386RV. The linker was formed as described above by annealing two complementary oligomers, MIP385FW (5'-GATCCCTCTATGCACATAATTAAGGCATG-3' (SEQ ID NO:68)) and MIP386RV (5'-CCTTAATTATGTGCATAGAGG-3'(SEQ ID NO:69)). This mutagenesis cassette contains compatible termini to replace the C-terminal splice junction cassette following BamHI-Sphl cleavage of pMIP66. Approximately 1 μg of pMIP66 was digested at 37° C. for 4 hours in 30 μl of 1x BamHI Buffer, 20 units of BamHI and 20 units of Sphl. Following electrophoretic separation on 1% agarose gel, pMIP66 DNA was purified by the Geneclean II kit (BIO101; Vista, Calif.) in 20 μl of 10 mM Tris-HCl (pH 8.0)/0.1 mM EDTA. Approximately 0.05 μg of the BamHI-Sphl digested pMIP66 DNA was ligated at 16° C. overnight in 10 ml of 1×T4 DNA ligase buffer, 80 units of T4 DNA ligase and 16.6 pmol of the linker MIP535FW/MIP536RV, to yield pMI84. The ligated DNA samples were used to transform E.coli strain ER2426 (NEB974).

Construction Of pMI94 (Ml With The Ser1 CYS Mutation

The translational stop codon (TAA) introduced at the C-terminal splice junction in pMI84 was transferred into pMIP47 to yield pMI94 by ligation of a 6.6 Kb Kpnl-Pstl fragment of pMIP47 and a 2.3 Kb Kpnl-Pstl fragment of pMI84. 1 μg of each pMIP47 and pMI84 DNA was incubated at 37° C. for 4 hours in 30 μl of 1×Buffer 1, 10 units of Kpnl and 10 units of Pstl. Following electrophoretic separation on 1% agarose gel, the 6.6 Kb Kpnl-Pstl fragment from the pMIP47 sample and the 2.3 Kb Kpnl-Pstl fragment from the pMI84 sample were purified by the Geneclean II kit (BIO101), each in 20 μl of 10 mM Tris-HCl (pH 8.0)/0.1 mM EDTA. pMI94 was formed by incubation at 16° C. overnight of 1 μl of the purified 6.6 Kb pMIP47 DNA and 7.8 μl of the purified 2.3 Kb pMI84 DNA, 1 μl of 10x T4 DNA ligase buffer, 0.2 μl of 400,000 units/ml of T4 DNA ligase. The ligated DNA sample were used to transform E.coli strain ER2426 (NEB974). pMI94 encodes the Ml fusion protein with the Ser1Cys substitution which is present in pMI47 in the full MIP fusion context.

Purification of MI94 Followed By Chemical Inducible Cleavage Activity

The pMI94 construct expresses the MBP-CIVPS3 fusion protein, termed M194, containing a cysteine residue instead of the native serine residue at the N-terminal of CIVPS3. In order to conduct in vitro study of cleavage activity, expression of the M194 fusion protein was induced at low temperature (12° C.) and purified by amylose resin columns. ER2426 (NEB974) harboring pMI94 was cultured in 2 liters of LB medium supplemented with 100 μg/ml ampicillin and induced as described in Example 10. Cells were pelleted, sonicated in 100 ml of pH 8.5 column buffer (20 mM $NaPO_4$, pH 8.5, 500 mM NaCl) and spun down. The cleared lysate was loaded over a 15 ml amylose resin column. The column was washed with 100 ml of pH 8.5 column buffer and subsequently with 100 ml pH 6 column buffer (20 mM NaPO4, pH 6.0, 500 mM NaCl). MI94 was eluted with 10 mM maltose in pH 6 column buffer (as the procedure described in Example 9).

Figure 20:
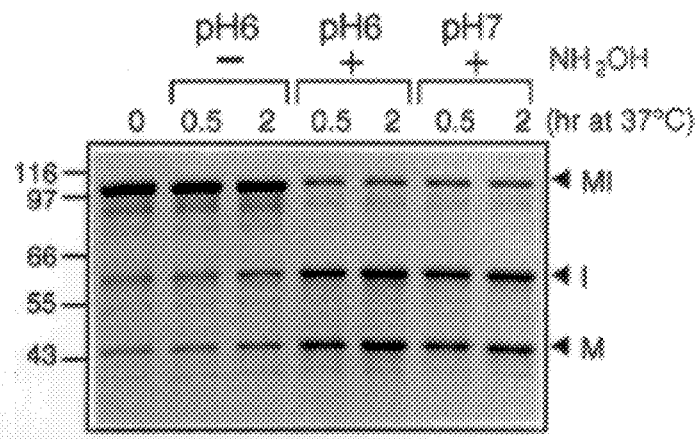
FIG. 20 illustrates the chemical activation of cleavage at the N-terminal splice junction from the Ml94 fusion containing the Ser1Cys substitution. Purified protein samples were incubated at 37° C with (+) or without (−) 0.25 M hydroxylamine. Products were analyzed by a 4–12% SDS-PAGE followed by Coomassie blue staining. Cleavage at the N-terminal splice junction of the Ml94 fusion protein (Ml) yielded MBP (M) and CIVPS3 (l). Size standards (in kilodaltons) are shown on the left side.

Hydroxylamine ($NH_2OH$) was used to activate cleavage activity at the N-terminal splice junction. The M194 protein sample (0.6 mg/ml) was treated with 0.25 M $NH_2OH$ at pH 6 and pH 7.75 μl of the purified MI94 sample was mixed with 25 μl of 0.4 M Bis-Tris-Propane, 0.5 M NaCl and 1 M $NH_2OH$—HCl (Sigma) adjusted to pH 6 with 6 N H Cl or with 25 μl of 0.4 M Bis-Tris-Propane, 0.5 M NaCl and 1 M $NH_2OH$—HCl (Sigma, St. Louis, Mo.) adjusted to pH 7 with 6 N NaOH. In a control experiment, 100 μl of the MI94 sample was mixed with 33 μl of 0.4 M Bis-Tris-Propane, 0.5 M NaCl adjusted to pH 6 with 6 N HCl. 40 μl of the control sample was mixed with 20 μl of 3X Protein Sample Buffer and stored on ice. Two 40 μl aliquots of each mixture were incubated at 37° C. for 0.5 and 2 hours, respectively. Each sample was mixed with 20 μl of 3× Protein Sample Buffer and boiled for 5 min. 5 μl of each sample was electrophoresed on a 4–12% SDS-Polyacrylamide gel (Novex, Encinitas, Calif.) followed by Coomassie Blue staining (FIG. 20). The data indicate that in comparison with the control experiment (minus $NH_2OH$), hydroxylamine treatment drastically increased cleavage activity at the N-terminal splice junction.

At both pH 6 and pH 7, Ml fusion protein was activated by hydroxylamine and efficiently cleaved, yielding more MBP (M, 43 kDa) and CIVPS3 (I, 60 kDa).

In this Example we demonstrate that modifications of an IVPS may result in drastic effects on splicing and cleavage activity after chemical treatment. Furthermore, this data gives another example of constructs where cleavage at N-terminal splice junction is observed in the absence of ligation and carboxyl junction cleavage activities of the CIVPS.

EXAMPLE 15

Chemical Control Of Cleavage Activity of IVPS From *Saccharomyces Cerevisiae*

Protein splicing activity of IVPS (yeast intein) from *Saccharomyces cerevisiae* has been described by Hirata et al, supra and Kane et al, supra. In this Example, we described the construction of a yeast intein fusion system similar to MIP fusion of Example 9. The yeast intein fusion system is a 3-part fusion composed of a maltose binding protein (MBP), a genetically engineered yeast intein (Y), a chitin binding domain (B). This yeast intein fusion system, named MYB fusion, can be induced to cleave at the N-terminal splicing juntion (Cys1) between the maltose binding protein and the yeast intein. MBP can be replaced by the target protein in the MYB protein purification system.

Construction Of Wild-Type MYP

Splice junction amino acid residues of the yeast IVPS are shown in FIG. 1. Yeast IVPS (Gimble, et al., *J. BioL Chem.*, 268(29) 21844–21853 (1993)) was amplified by PCR from the plasmid of pT7VDE and inserted into MIP21 (described in Example 10 ) between the Xhol site and the Stul site to replace the CIVPS3 (or the Pyroccocus IVPS). Primer pairs 5'-GCGCTCGAGGGGTGCTTTGCCAAGGGTACCAAT-3'(SEQ ID NO:70) and 5'-CCTCCGCAATTATGGACGACAACCTGGT-3'(SEQ ID NO:71) were used to to synthesize the IVPS fragment by PCR. pT7VDE plasmid DNA containing the yeast IVPS gene sequence in the orientation of T7 promoter, was used as template. The PCR mixture contains Vent® 400 uM of each dNTP, 1 uM of each primer, 50 ng pT7VDE DNA and 0.5 units of Vent® DNA polymerase in 50 ul. Amplification was carried out by using a Perkin-Elmer/Cetus (Emeryville, Calif.) thermal cycler at 94° C. for 30 sec, 50° C. for 30 sec and 72° C. for 5 min for 20 cycles. The samples were electrophoresed on an 1 % agarose gel and approximately 2 ug of PCR-synthesized 1.3 Kb fragment were recovered in 20 ul of distilled water by Geneclean II kit (BIO101; Vista, Calif.). The purified DNA was subjected to digestion in a 100 μl 1 ×NEB buffer 2 with 40 units of Xhol. The digested DNA was extracted with phenol and choroform and precipitated in 0.3 M NaAcetate pH5.2 and 70% ethanol at −20° C. overnight. DNA was spun down, dried and resuspended in 40 ul distilled water. 0.5 μg of MIP21 DNA was digested by Xhol and Stul and the 7.2 Kb vector DNA was purified from 1% agarose gel by Geneclean II (BIO101; Vista, Calif.) at 0.5 μg/20μl.

MYP1 was created by ligation of Xhol-digested IVPS fragment to the 7.2 Kb Xhol-Stul MIP21 fragment. The reaction was carried out at 22° C. for 5 hours in 10 ul volume with addition of 2 ul of 10X T4 DNA ligase buffer, 0.4 ug IVPS DNA, 0.025 ug MIP21 fragment. and 200 units of T4 DNA ligase. Transformation of *E. coli* strain RR1 with the ligation samples was performed as described in Example 2. Transfomants were cultured in LB medium, supplemented with 100 ug/ml ampicillin, for extraction of plasmid DNA using Qiagen spin column (Qiagen, Inc.; Study City, Calif.). The clones were further examined by their ability to splice to form MP species (71 KDa). Nine clones carrying MYP1–9 were cultured in LB medium supplemented with 100 μg/ml ampicillin, at 30° C. until $OD_{600}$ nm reached about 0.5. Expression of the MYP fusion gene was induced by addition of IPTG to a final concentration of 1 mM at 30° C. for 3 additional hours. Cells were spun down and resuspended in 0.5 ml LB medium. Crude extracts were prepared as described in Example 3. Western blots using antibodies raised against MBP were performed to detect fusion protein and splicing products expressed from these clones. Samples were electophoresed on 4–12% Tris-Glycine gels (Novex; Encinitas, Calif.) with prestained markers (Gibco BRL; Gaithersburg, Md.), transferred to nitrocellulose, probed with anti-MBP antibody (prepared from rabbit), and detected using alkaline phosphate-linked anti-rabbit secondary antibody as described by the manufacturer (Promega Corp.; Madison, Wis.). Western blot analysis showed that except in MYP2 clone, all the other 8 isolates yielded a major product of 71 kDa, indicating that wild-type MYP fusion protein are capable of efficient splicing in vivo.

Modification Of Wild-Type Intein

The first modificaiton of yeast intein was to create two unique restriction sites (BamHI and EcoRI) on the either side of the C-terminal splicing junction. This would facilitate further cassette mutagenesis. 1 μg of pMYP1 and 1 μg LITMUS 29 (NEB) were digested separately in a 15 μl reaction mixture containing 1x buffer 2, 0.5unit Xhol, and 0.5 unit Pstl at 37° C. for 2hr. After electrophoretic separation on a 1% low melting agarose gel (FMC Corp.; Rockland, Me.), the Xho-Pst fragment containing the yeast intein and the digested LITMUS 29 were excised from the gel. The gel slices were mixed and melt at 65° C. for 10 min. The mixture was then incubated at 42° C. for 10 min before 1 unit of β-agarase was added. After further 1 hr incubation, the mixture was ready for DNA ligation reaction. The ligation was conducted in 1 x T4 DNA ligase buffer containing 0.5 unit of T4 DNA ligase at 150C overnight. 15 μL of the ligation mixture was used to transform *E. coli* strain ER2267. The resulting construct was named pLit-YP, a LITMUS vector containing the yeast intein.

pLit-YP was used for the synthesis of the single-stranded DNA and the subsequent Kunkel mutagenesis (Kunkel, T. A., PNAS (1985), 82:488). pLit-YP was first transformed into the competent *E. Coli* strain CJ236. A single colony was picked to innoculate 50 ml rich LB medium. The cells were allowed to grow at 37° C. for 2–3 hr under vigorous aeration. 50 μL of M13K07 helper phage was then added to the culture. After another one hour culture, kanamycin was added to the final concentration of 70 μg per mL culture. After overnight culture, the cells were spun down. 10 mL of 20% PEG containing 2.5 M NaCl was added into the supernatant. The phage which contained the single-stranded Lit-YP DNA (ss pLit-YP) was allowed to precipitated on ice for 1 hr. The supernatant was then centrifuged at 8000 rpm for 10 min. The phage pellet was resuspended in 1.6 mL TE buffer (20 mM Tris, pH 8.0, 1 mM EDTA). 400 μl of of 20% PEG containing 2.5 M NaCl was then added to re-precipitate the phage for 5 min at 25° C. The phage pellet was spun down again and resuspended in 600 μl TE buffer. After three times phenol extraction and one time chloroform extraction, the single-stranded DNA was precipitated in 60% ethanol containing 0.2 M NaOAc. The DNA pellet was then dried and resuspended in 30 μl TE buffer.

Two mutagenic primers, MYP(EcoR) (5'-GAATGCGGAATTCAGGCCTCCGCA-3'(SEQ ID

NO:72)), and MYP (Bam) (5'-ATGGACGACAACCTGGGATCCAAGCAAAAACTG-ATGATC-3'(SEQ ID NO:73)) were first 5' phosphorylated. The mutagenic primers (20 pmol each) were added to a 20 µL reaction mixture containing 1 ×T4 polynucleotide kinase buffer, 1 mM ATP, and 1 unit of T4 polynucleotide kinase . The reaction was conducted at 37° C. for 30 min followed by a 10-min heat inactivation of the T4 polynucleotide kinase at 65° C. 10 pmol of the phosphorylated mutagenic primers were added to a 10 µL reaction mixture containing 0.1 µg of the single-stranded pLit-YP template, 1×annealing buffer. The reaction mixture was heated to 94° C. for 4 min and slowly cooled to 25° C. to allow the primers to anneal to the template. The next elongation reaction was conducted at 37° C. for 2 hrs in a 50 µL mixture containing 1 ×T7 polymerase buffer, 0.5 µg BSA, 300 mM dNTPs, 1 mM ATP, the annealed template, 1 unit of T7 DNA polymerase and 1 unit of T4 DNA ligase. 15 µL of the elongation mixture was used to transform the E. coli strain ER 2267. The resulting plasmid, pLit-YP', contained two unique restriction sites, BamH1 and EcoR1, on the either side of the yeast intein C-terminal splicing junction. The Gly447 and S448 of the intein were mutated into Ala and Asn, respectively.

1 µg of pMYP and 1 µg pLit-YP' were digested separately in a 15 µl reaction mixture containing 1×buffer 2, 0.5 unit Xhol, and 0.5 unit Pstl at 37° C. for 2hr. After electrophoretic separation on a 1% low melting agarose gel (FMC Corp.; Rockland, Me.), the Xho-Pst fragment from pLit-YP' and the digested pMYP were excised from the gel. The gel slices were mixed and melt at 65° C. for 10 min. The mixture was then incubated at 42° C. for 10 min before 1 unit of β-agarase was added. After further 1 hr incubation, the mixture was ready for DNA ligation reaction. The ligation was conducted in 1 ×T4 DNA ligase buffer containing 0.5 unit of T4 DNA ligase at 15° C. overnight. 15 µL of the ligation mixture was used to transform E. coli strain ER2267 (NEB#746). The resulting construct was named pMYP'.

The second modification was to replace Asn454 with Ala. This was achieved by cassette mutagenesis. 1 µg of pMYP' was digested at 37° C. for 2 hours in 15 µL of 1 × Buffer 1, 100 µg/ml BSA and 1 unit of Xhol and 1 unit of Kpnl. After electrophoretic separation on a 1 % low melting agarose gel (FMC Corp.; Rockland, Me.), the digested pMYP' plasmid DNA was excised from the gel. The gel slices were melt at 65° C. for 10 min and then incubated at 42° C. for 10 min before 1 unit of β-agarase was added. After further 1 hr incubation, the purified pMYP' digest was ready for DNA ligation reaction. Two complementary oligomers, MYP'(N454A) FW (5'GATCC CAGGTTGTCGTCCATGCATGCGGAGGCCTG-3' (SEQ ID NO:74)) and MYP'(N454A)RV (5'AATT-CAGGCCTCCGCATGCATGGACGACAACCTGG-3' (SEQ ID NO:75)) were allowed to anneal to form a double-stranded linker, MYP'(N454A)FW/RV. 100 pmol of each of the oligomers MYP'(N454A)FW and MYP' (N454A)RV were incubated in 20 µL of 1 × annealing buffer at 90° C. for 4 min and slowly cooled to 37° C. Approximately 0.1 µg of the Xhol-Kpnl digested pMYP' DNA was ligated with 20 pmol of the annealed linker MYP'(N454A)FW/RV at 16° C. overnight in a 20 µl reaction mixture containing 1×T4 DNA ligase buffer, 80 units of T4 DNA ligase. The ligated DNA sample was used to transform E.coli strain ER2267. The resulting plasmid was named pMYP'(N454A).

Construction Of the Yeast Intein Purification Vector pMYB 129

The yeast intein purification vector employed the chitin-binding domain as the affinity tag for affinity purification. Since pMIC (Example 11) contains the chitin-binding domain and compatible restriction sites for direct cloning, the Xhol-BamHI fragment from pMYP'(N454A) was first transfered into pMIC, replacing the original Xhol-BamHI sequence. On the next step, a BamHI-Agel linker insertion was conducted to restore the yeast intein C-terminal splicing junction sequence. 1 µg of pMYP' (N454A) and 1 µg pMIC were digested separately in a 15 µl reaction mixture containing 1×BamHI buffer, 0.5 unit Xhol, and 0.5 unit BamHI at 37° C. for 2hr. After electrophoretic separation on a 1% low melting agarose gel (FMC Corp.; Rockland, Me.), the Xhol-BamHI fragment from pMYP(N454A) and the digested pMIC were excised from the gel. The gel slices were mixed and melt at 65° C. for 10 min. The mixture was then incubated at 42° C. for 10 min before 1 unit of β-agarase was added. After further 1 hr incubation, the mixture was ready for DNA ligation reaction. The ligation was conducted in 1×ligase buffer containing 0.5 unit of T4 DNA ligase at 15° C. overnight. 15 µl of the ligation mixture was used to transform E. coli strain ER2267. The resulting construct was pMY-IC. 1 µg of pMY-IC was digested at 37° C. for 2 hours in 15 µL of 1×BamHI buffer, 1 unit of BamHI and 1 unit of Agel. After electrophoretic separation on a 1% low melting agarose gel (FMC Corp.; Rockland, Me.), the digested pMY-IC plasmid DNA was excised from the gel. The gel slices were melt at 65° C. for 10 min and then incubated at 42° C. for 10 min before 1 unit of β-agarase was added. After further 1 hr incubation, the purified pMY-IC digest was ready for DNA ligation reaction. Two complementary oligomers, MYB(Bam-Age)FW ( 5 ' G A T C C C A G G T T G T CGTCCATGCATGCGGTGGCCTGA-3'(SEQ ID NO:76)) and MYB (Bam-Age)RV (5'-CCGG-TCAGGCCTCCGCATGCATGGACGACAACCTGG-3' (SEQ ID NO:77)) were allowed to anneal to form a double-stranded linker, MYB(Bam-Age)FW/RV. 100 pmol of each of the oligomers MYB(Bam-Age)FW and MYB(Bam-Age) RV were incubated in 20 µL of 1× annealing buffer at 90° C. for 4 min and slowly cooled to 37° C. Approximately 0.1 µg of the BamHI-Agel digested pMY-IC DNA was ligated with 20 pmol annealed linkers at 16° C. overnight in a 20 µl reaction mixture containing 1 ×T4 DNA ligase buffer, 80 units of T4 DNA ligase. The ligated DNA sample was used to transform E.coli strain ER2267. The resulting plasmid was named pMYB129 (FIG. 21), a sample of which has been deposited under the terms and conditions of the Budapest Treaty with the American Type Culture Collection on Dec. 28, 1995 and received ATCC Accession Number 97398.

One Step Purification Of The Target Protein By The Chemical Inducible Cleavage Activity Of The Modified IVPS From *Saccharomyces Cerevisiae*

The pMYB129 construct was used to illustrate the one step purification of a target protein. Here the maltose binding protein is the target protein. The E. Coli strain ER2267 harboring pMYB129 was cultured at 37° C. in 1 liter of LB medium supplemented with 100 µg/mL ampicillin. The culture was allowed to grow until the OD at 600 nm reached 0.7. The induction was conducted by adding IPTG to the final concentration of 0.4 mM. The induced culture was grown at 30° C. for 3 hr before the cells was harvested by centrifugation at 4000 rpm for 25 min. The cell pellet was resuspended in 50 mL of the column buffer (20 mM HEPES, pH 7.6, 0.5 M NaCl). The cell suspension was sonicated for 6 min and then centrifuged at 13,000 rpm for 30 min to give the clear lysate (around 50 mL).

Figure 22A:
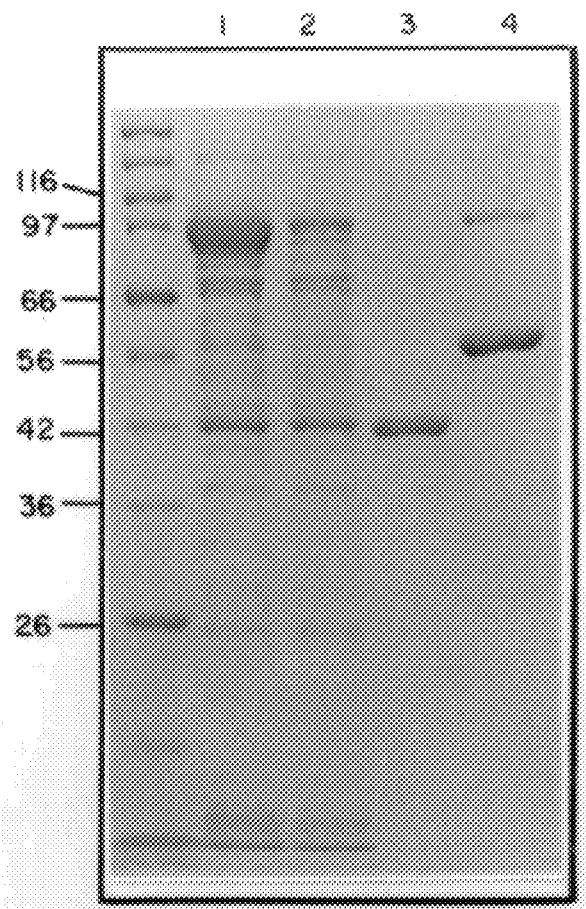
FIG. 22A and 22B illustrate one-step purification of the target protein (MBP) by chitin. Cleavage is induced by 30 mM DTT at pH 7.6 at 4° C. at 16 hours. Size markers (NEB) (on the left); lane 1: cell lysate; lane 2: flow-through lysate; lane 3: DTT-induced cleavage product, MBP (M); lane 4: 6 M guanidine wash.
Figure 22B:
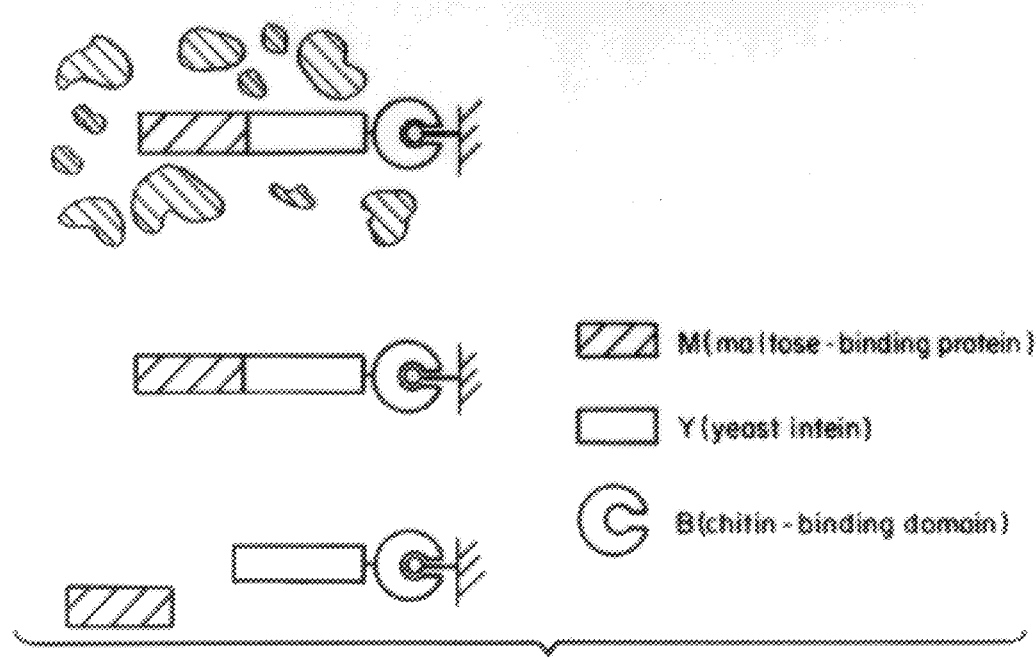

The lysate was directly loaded onto a chitin column (Sigma; St. Louis, Mo.) and binding was allowed at 4° C. for 30 min. (Other preferred chitin resins which can be employed are described hereinbelow.) The chitin was then washed with 10 volumes of column buffer (20 mM HEPES, pH 7.6, 0.5 M NaCl). The column buffer containing 30 mM dithiothreitol (DTT) was used to elute the MBP protein (FIGS. 22A and 22B). The elution was conducted at 4° C. for 16 hr. Only the maltose binding protein was eluted from the chitin under these conditions (FIGS. 22A and 22B).

Figure 23A:
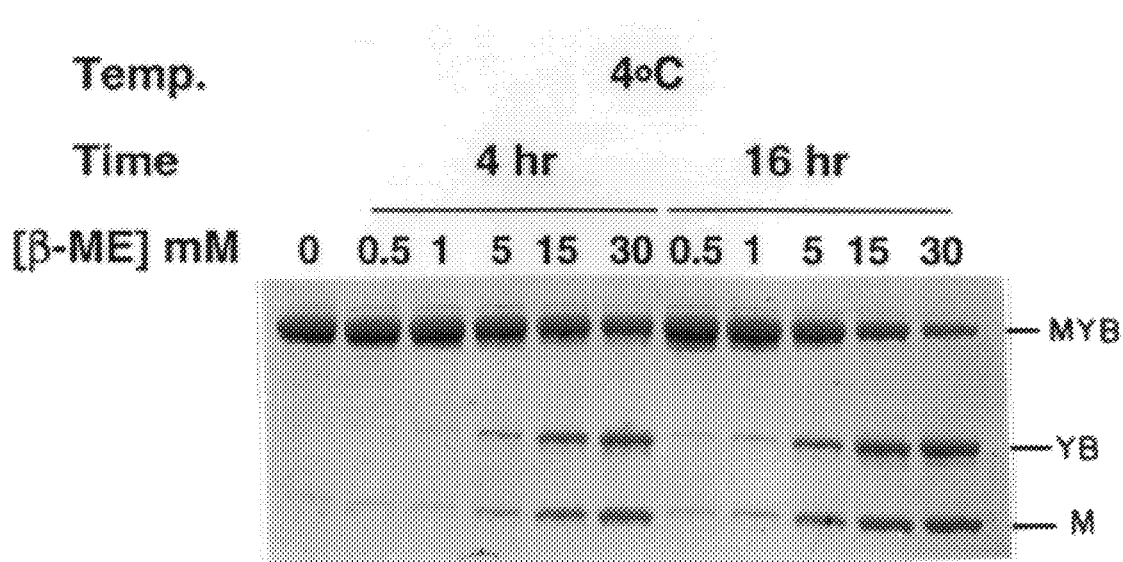
FIGS. 23A and 23B shows activation of cleavage of MYB fusion protein by β-mercaptoethanol (β-ME) (FIG. 23A) and DTT (FIG. 23B).
Figure 23B:
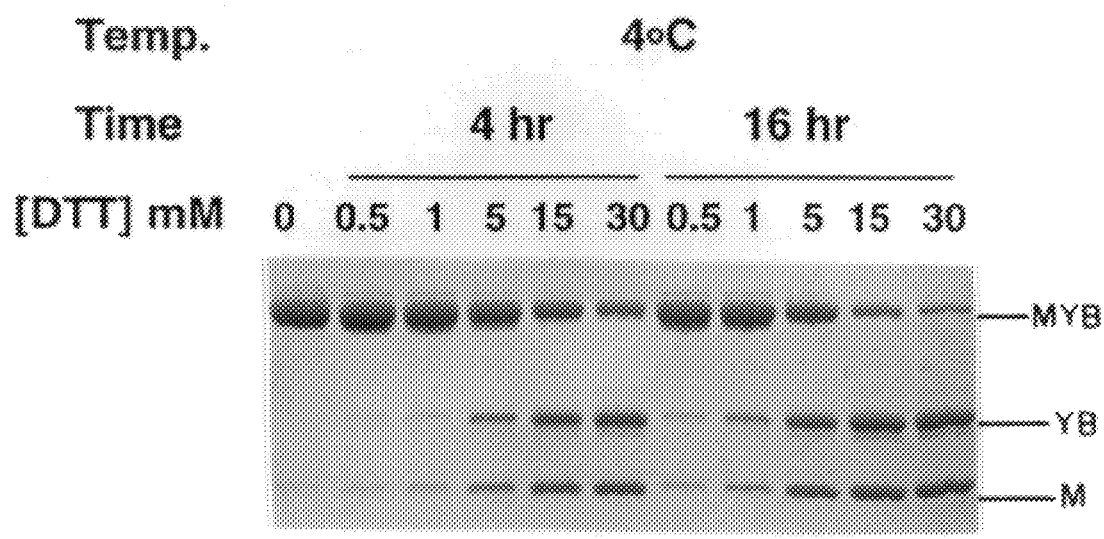

MYT fusion protein was purified on a amylose resin (NEB Protein fusion and purification system) as described in Example 9. In vitro cleavage experiments have shown that 30 mM βmercaptoethanol (β-ME) and 30 mM DTT result in approximately 70% and 90% cleavage of MYB, respectively (FIGS. 23A and 23B).

Preparation Of Chitin Bound To Sepharose 4B

One liter settled bed volume Sepharose 4B (Pharmacia; Piscataway, N.J.) (prewashed with 5 volume of water) is suspended in 1 liter of 0.3 M NaOH, 1 liter of 1,4-Butanediol diglycidoxy ether and 2 grams of sodium borohydride. The suspension is gently rocked in a closed container at room temperature for 4 hours. The epoxy activated Sepharose 4B beads are washed in a buchner funnel (placed on a side arm flask equipped with vacuum or aspirator) with 3 liters of 0.3 M NaOH aqueous solution followed by 6 volumes of deionized water until the effluent pH is neutral. After washing, the epoxy activated Sepharose 4B beads are suspended in 1 liter of aqueous solution containing 40 grams of Sodium meta-periodate. The suspension is shaken in a closed container at room temperature for 90 minutes. The resulting spacer linked aldehyde Sepharose 4B beads are washed with 3 liter of water in a buchner funnel (vacuum assisted or aspirator). The bead paste is added to 1.2 liter of 4% (v/v) aqueous acetic acid solution containing 45 grams of chitosan (Pfanstiehl Laboratories; Wauken, Ill.) and 4 grams of sodium cyanoborohydride. (the chitosan solution is prepared by autoclaving the carbohydrate polymer in the 4% (v/v) aqueous acetic acid in an autoclave for one hour). The suspension of aldehyde sepharose 4B beads in the chitosan solution is gently rocked in a closed container for 18 hours at room temperature. The resulting chitosan coupled sepharose 4B is washed in a buchner funnel (vacuum assisted or aspirator) with 10 liters of water. The beads are then washed with 1 liter of methanol. The methanol bead paste is suspended into 750 ml of acetic anhdride and gently rocked in a sealed polyethylene container for 18 hours a room temperature. The resulting chitin bound bead suspension is transferred to buchner funnel. After removal of acetic anhydride by filtration (vacuum assisted or aspirator). The beads are washed with 3 liters of methanol followed by 6 liters of deionized water. Test for completion of acetylation is accomplished by using a glucosamine standard and the TNBS: perchloric acid assay (Wilkie, S. Landry, D. BioChromatography, 3(5): 205–214 (1988)). If amine is detected the beads are reacetylated as already described. Finally the beads are washed in a buchner funnel with 1 liter of 0.3M NaOH. The chitin beads are suspended in 1 liter of 0.3 M NaOH containing 0.5 grams of sodium borohydride and gently rocked in a sealed container for 18 hours at room temperature. The beads are washed in a buchner funnel with 6 liters of deionized water until the pH of the effluent is neutral. The chitin bound sepharose beads are stored suspended in 30% methanol/$H_2O$ (v/v).

Preparation Of Chitin Beads

The beaded form of chitin is prepared by the solidification (precipitation) of chitosan in aqueous solution while the aqueous solution is shaped into beaded droplets. Beaded droplets of the aqueous solution are created by a stirring the aqueous solution with an organic water insoluble layer (pentanol) forming an emulsion which is stabilized by adding a surfactant or stabiliser (Tween 80). The beads of chitosan are formed as the pH is increased and are crosslinked in the reaction with the addition of 1,4 butanediol diglycidyl ether. The bead quality such as size and shape is directly affected by concentration and length of chitosan, volumes and densities of water and oil layer, shapes and relative dimensions of stirrer and reaction vessel, the amount and chemical type of stabiliser and temperature.

Figure 24:
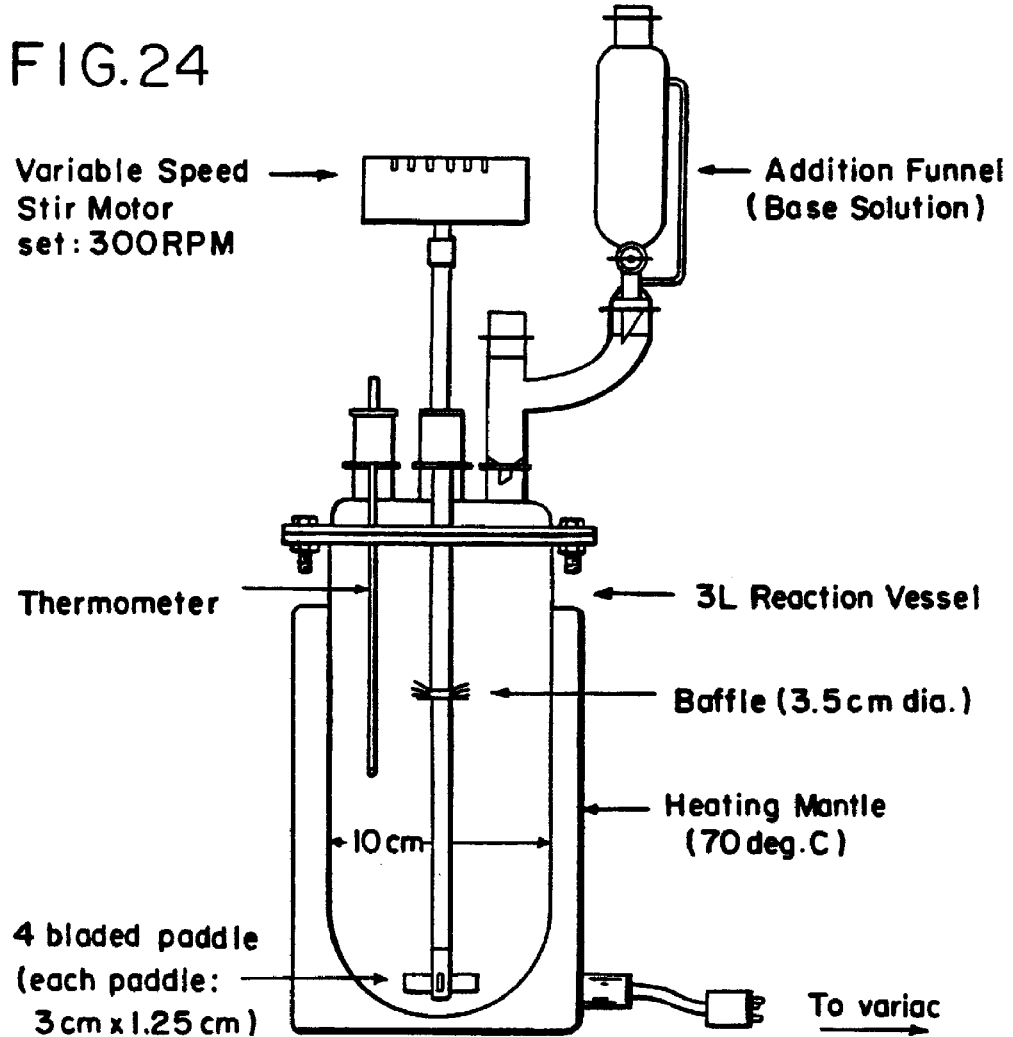
FIG. 24 illustrates the reaction vessel dimensions and set up used in the preparation of chitin beads.

The apparatus with dimensions shown in FIG. 24 is set up. To the reaction vessel is added 1 liter pentanol, 50 ml polyoxy-ethylenesorbitan monooleate (Tween 80; Sigma Chemical Co., St. Louis, Mo.), and 50 ml 1,4 butanediol diglycidyl ether. The stirring solution is equilibrated to 70° C. The stirring shaft is maintained at 300 rpm. A filtered solution of 7.5 chitosan (MW=70,000; Fluka Chemical Co., Ronkonkoma, N.Y.) in 1 liter of 5% acetic acid in water (v:v; preheated to 70° C.) is added to the stirring solution of pentanol, detergent and crosslinker. The emulsion is maintained at 70° C. and 100 ml of 10 M NaOH is added dropwise over a period of 12 minutes. The emulsion is allowed to stir at 300 rpm at 70° C. for one hour. The stirring and heating is stopped after one hour and the pentanol layer (top) is allowed to separate from the aqueous bead suspension. The top alcohol layer is siphoned off from the bottom aqueous layer by an aspirator.

The aqueous chitosan bead suspension is transferred to a buchner funnel equipped with an aspirator pump and washed with 5 liters of water followed by 1.5 liters of methanol. The methanol bead paste is transferred to a polyethylene container and suspended in 200 ml of acetic anhydride. The beads are acetylated in the sealed container at room temperature with gentle rocking for 18 hours. The resulting chitin beads are transferred to a buchner funnel and washed with 2 liters of methanol followed by 4 liters of water. Finally the beads are washed with 1 liter of 0.3 M NaOH.

The alkaline beads paste is transferred to a polyethylene container and suspended in 1 liter of 0.3 M NaOH containing 0.5 grams of sodium borohydride. The chitin bead suspension is gently rocked in the sealed polyethylene container for 18 hours at room temperature. The chitin bead suspension is transferred to a buchner funnel and washed with 4 liters deionized water or until the pH of the effluent as neutral. The beads are stored in 500 ml of 30% methanol water (v/v).

EXAMPLE 16

Protein Splicing In Trans With A Second Fragmentation Point, With Overlapping Fragments And With Tags Added To The Ends Of CIVPS3

Introduction

Examples 12 and 13 defined and demonstrated splicing and cleavage, respectively, of CIVPS3 fragments in trans. In these previous examples, a naturally occurring methionine residue (M250) was chosen as the start of the C-terminal CIVPS fragment. In this example, we demonstrate that in vitro protein splicing can occur in trans with overlapping CIVPS sequences. We next describe a second successful breakpoint for fragmenting CIVPS3 (between R440 and K441). An initiating methionine residue, required for translation initiation, was introduced in front of K441 in this C-terminal fragment of CIVPS3. Finally, we demonstrate that purification tags can be added to either or both CIVPS fragments to facilitate purification. FIG. 25 depicts the different constructs used in these experiments.

The present state of knowledge concerning the best positions to fragment proteins so as to allow them to subsequently be combined to regenerate the native protein structure (with a nick in the peptide backbone) is rudimentary. However, our approach to this problem has suggested that the best positions to fragment a protein or IVPS may be a surface location, a surface loop or an inter-domain region. In the absence of structural information, the process is even harder. One can use computer programs for predicting structure and surface location. We have found that a simpler approach is to scan the IVPS for protease sensitive sites with the assumption that the most sensitive protease site is easily accessible and therefore not buried within the protein. Purified IVPS protein, alone or as part of a fusion protein, is treated with various dilutions of one or more commonly available proteases, such as trypsin, chymotrypsin, etc., using standard procedures known in the field. Examination of cleavage fragments produced with increasing protease treatment identifies the most accessible protease sites. These protein fragments are then sequenced by any standard method to determine the exact location of the most accessible proteolytic cleavage sites. In the case of CIVPS3, such a site after amino acid 442 yielded a complementary pair (fragmented between residue 440 and 441) that spliced very efficiently in trans.

Several clones containing CIVPS fragments derived from MIP (Example 9 and Xu et al., *Cell,* 75:1371–1377 (1993)) were constructed so that there was an overlap in the CIVPS protein or to generate a complementary pair splitting CIVPS3 between amino acid 440 and 441. Any site in which complementary pairs or overlaps are produced might work equally as well as the examples described below. In these Examples, proteins were purified over amylose resin or Nickel resin. The protein fragments were combined in urea as described in Example 12 to demonstrate protein trans-splicing. Mutations described previously in this patent (Example 10) and in Xu et. al. (*EMBO J* ,15:5146–5153 (1996)) which result in cleavage instead of splicing, can also be introduced into the clones described in this example to achieve cleavage instead of splicing in trans.

This Example also demonstrates that the overlapping region may contain a binding domain. The Maltose Binding Protein at the N-terminus of the C-terminal fragment or a His tag at the C-terminus of the N-terminal fragment. This not only allows easier purification, but may also help to convert an insoluble C-terminal protein fragment (such as I440–537P) into a soluble protein (MI440–537P). This example also demonstrates that the two protein fragments containing a binding domain can splice after being combined in urea as efficiently as homologous fragments lacking the binding domain.

Construction And Expression Of Clones Containing Fragments Of CIVPS3

Construction Of The N-Terminal Fragment, Ml1–440

In Example 12, a fusion of the malE gene (encoding MBP) with the first 249 amino acids of the CIVPS3 gene was described (Ml'). In this Ml' clone, the CIVPS3 gene is flanked at its 5' end by an XhoI site that is 3 codons (Leu, Glu and Ala) 5' to the beginning of CIVPS3; this Xho site is also present in pMIP21 (Example 9). At the 3' end of the Ml' gene, there is a stop codon immediately after Leu 249, followed by a BamHI site (which is unrelated to the BamHI site in MIP). Different N-terminal fragments were generated by polymerase chain reaction (PCR) using pMIP21 as the template, a forward primer from the MBP gene 5' to the XhoI site in pMIP21 and novel reverse primers containing a BamHI site, a stop codon, and sequences complementary to specific regions of CIVPS3. Next, the XhoI/BamHI fragment of Ml' was deleted and replaced with Xho/BamHI digested CIVPS3 PCR fragments containing different lengths of CIVPS3 sequences (see below).

In Ml1–440 (FIG. 25), the CIVPS3 region of Ml' was replaced with a CIVPS3 region containing the first 440 codons of the CIVPS3 gene. A DNA fragment encoding the 3' end of the malE gene and the first 440 codons of the CIVPS3 gene was synthesized by PCR from pMIP21 using the forward malE primer 5'-GGTCGTCAGACTGTCGATGAAGCC-3' (SEQ ID NO:78) (NEB catalog number 1237) and the reverse primer 5'-ATTGGAT CCTTATCTGTATTCCGTAAACTTA-3' (SEQ ID NO:79) (BamHI site and stop codon underlined). PCR reaction mixtures contained Vent® DNA polymerase buffer, 0.2 mM each dNTP, 0.4 μM primers, 100 ng pMIP21 DNA and 1 U Vent® DNA polymerase in a 0.1 ml reaction. Amplification was carried out using a Perkin-Elmer/Cetus (Emeryville, Calif.) thermal cycler at 94° C. for 30 seconds, 52° C. for 30 seconds and 72° C. for 120 seconds for 17 cycles. The amplified DNA fragment was digested with the restriction enzymes XhoI and BamHI as described by the manufacturer. The XhoI site is present in the pMIP template 3 codons (Leu, Glu and Ala) 5' to the beginning of CIVPS3 and the BamHI site is present in the reverse primer. The plasmid, pMl', containing MBP fused to the first 249 amino acids of CIVPS3 (construction described in Example 12) was digested with XhoI/BamHl to remove the fragment containing amino acids 1–249 of CIVPS3. Gel purified XhoI/BamHI digested PCR products (from above) were ligated directly with the gel purified XhoI/BamHI digested vector backbone of Ml', to create pMl1–440. This resulted in the substitution of the CIVPS3 fragment in Ml' with the larger 440 amino acid CIVPS3 fragment in pMl1–440. Ligations were performed as described by Sambrook et. al. (*Molecular Cloning: A Laboratory Manual,* 2nd edition. (1989). Cold Spring Harbor laboratory Press, Cold Spring Harbor, N.Y.).

Construction Of The C-Terminal Fragment, I441-537P

In Example 12, a fusion of the last 288 codons of the CIVPS3 gene with the *D. immitis* paramyosin ΔSal gene previously fused to a His tag was described (l'P). In l'P, the CIVPS3 gene is flanked by an NdeI site (at its 5' end, encoding the initiating Met) and a BamHI site (codons 531 and 532 of CIVPS3). A new C-terminal fragment of CIVPS3 was generated by PCR (FIG. 25), containing an NdeI site at its 5' end and the BamHI site (codons 531 and 532 of CIVPS3). This new Nde/BamHI fragment was then used to replace the NdeI/BamHI fragment in l'P encoding amino acids 250–532 of CIVPS3 (see below).

Amino acids 250–532 of CIVPS3 in l'P were replaced with the last 97 amino acids of CIVPS3 to generate pI441–537P. A DNA fragment encoding amino acids 441–532 of the CIVPS3 gene was synthesized by PCR from pMIP21 using the forward primer, 5'-GAA CATATGAAGAAAAAGAATGTATATCACTCTC-3' (SEQ ID NO:80 (NdeI site underlined) and the reverse primer RPCT (5'-GGGG GATCCAAAGCCAGCAAGGAAATTCTC-3' (SEQ ID NO:81), BamHI site underlined). PCR reaction mixtures were as described above. The amplified fragment was digested with the restriction enzymes NdeI/BamHI as described by the manufacturer to give a DNA fragment encoding amino acids 441–532 of the CIVPS3 gene including the NdeI and BamHI sites.

The plasmid, l'P, (renamed I250–537P in this Example) containing the last 287 amino acids of CIVPS3 (construction described in Example 12) was digested with NdeI/BamHI to remove the CIVPS3 coding fragment. Gel purified NdeI/

BamHI digested PCR product was ligated directly with the gel purified NdeI/BamHI digested vector backbone of I'P, to create pI441–537P (FIG. 25). This resulted in the substitution of the CIVPS3 fragment in I'P with the smaller 97 amino acid CIVPS3 fragment in pI441–537P. Ligations were performed as described by Sambrook et. al supra.

Addition Of A N-Terminal MBP Tag To I441–537P

The Maltose Binding protein (M or MBP) was placed in front of the CIVPS3 fragment in I441–537P to generate pMI441–537P (FIG. 25). pMAL-c2 contains the malE gene encoding MBP followed by a polylinker sequence including an EcoRI site and a PstI site. pI441–537P contains a NdeI site at the N-terminus of the CIVPS3 fragment and a Pst site after the C-terminus of the paramyosin gene fragment. The EcoRI site of pMAL-c2 and the NdeI site of pI441–537P were blunted prior to ligation. The NdeI/PstI fragment from pI441–537P (encoding the CIVPS3-paramyosin gene fusion) was cloned into the EcoRI/PstI sites of pMAL-c2 as described below to form an in-frame fusion of MBP with I441–537P. 1 µg pMAL-c2 DNA was digested with EcoRI (20 units) and 1x EcoRI buffer in a 20 µl reaction volume; 1 µg pI441–537P DNA was digested with 20 units NdeI and 1 ×Buffer 4 in a 20 µl reaction volume. Both reactions were incubated at 37° C. for 1 hour followed by 65° C. for 10 minutes. The restriction sites in both plasmids were filled in by addition of 1 µg 2 mM dNTP and 1 µl T4 DNA polymerase (3 units/µl) and incubated at 11° C. for 20 minutes and 70° C. for 15 minutes. Both reactions were then separately digested with 1 µl PstI (20 units/µl) at 37° C. for 1 hour.

The pMAL-c2 vector fragment and the CIVPS3 fragment were gel purified and the products ligated to yield pMI441–537P. Methods are as described by Sambrook et. al. supra Expression And Purification Of MI1–440, And I 441–537P pMI1–440 was transformed into ER2504plysS (*E. coli* B fhuA2 [lon] ompT gal sulA11=90 Δ(mcrC-mrr)114::IS10 R(mcr-73::miniTn10; TetS)2 (lamdaDE3) endA1) and grown at 37° C. in LB medium supplemented with 0.1 mg/ml ampicillin to an OD$_{600}$ of~0.5. The culture was then induced with 0.4 mM isopropyl β-D-thiogalactoside (IPTG) and transferred to a 30° C. air shaker overnight. The cells were harvested by centrifugation at 4° C. and stored at −20° C. MI1–440 protein was purified over amylose resin as described for Ml' in Example 12.

pI441–537P was transformed into ER2417 (*E. coli* K12 thi-1 supE44 mcr-67 Δ(mcrC-mrr)114::IS10 (lambdaDE3) endA1 tonA) and grown at 30° C. in LB medium supplemented with 0.1 mg/ml ampicillin to an OD$_{600}$ of~0.5. The culture was then induced with 0.4 mM IPTG and transferred to a 30° C. air shaker overnight. The cells were harvested at 4° C. and stored at −20° C. Frozen cells from a 2 liter culture were resuspended in 50 ml of 1x Binding Buffer (Novagen; Madison, Wis.) and broken by sonication. After centrifugation at 10,000 g for 30 minutes, the pellet from pI441–537P was resuspended in Ni$^{2+}$ charged column buffer containing 6 M urea and passed through a Ni$^{2+}$ charged column (Novagen; Madison, Wis., 15 ml of resin). The column was washed and the protein eluted as described by the manufacturer. The purified protein, I441–537P was stored at −20° C.

Expression And Purification Of MI441–537P pMI441–537P was transformed into *E. coli* strain ER2267 and grown at 30° C. in LB medium supplemented with 0.1 mg/ml ampicillin to an OD$_{600}$ of ~0.6. The culture was then induced with 0.4 mM IPTG and transferred to a 30° C. air shaker for 3 hours. The cells were harvested at 4° C. and stored at −20° C. Frozen cells from a 1 liter culture were resuspended in 60 ml of Amylose column buffer (20 mM NaPO$_4$, pH 8, 0.5 M NaCl, 1 mM EDTA) and broken by sonication. After centrifugation at 20,000 g for 25 minutes, the crude supernatant was passed over amylose resin (20 ml of resin). The column was then washed and the protein eluted as described by the manufacturer. The purified protein, MI441–537P was stored at −20° C.

When pI441–537P was induced, the resultant I441–537P protein product was found in the insoluble fraction (see above). Addition of MBP to the N-terminus of I441–537P resulted in production of a soluble protein although I441–537P alone was insoluble.

Trans-Splicing With Overlapping Fragments

In this experiment, splicing in trans was performed with MI14 440 (CIVPS3 residues 1–440) and I250–537P (see Example 12 for purification, CIVPS3 residues 250–537) (FIG. 25). These two CIVPS3 fragments overlap by 190 amino acids. Expected spliced products are MP and the excised intein fragments I1–440 and I250–537.

I250–537P was in buffer A (Example 12, 50 mM Tris HCl, pH 7.5, 5% acetic acid, 0.1 mM EDTA, 1 m M DTT, 140 mM β-mercaptoethanol and 7.2 M urea) to a final concentration of 1.6 mg/ml as determined by the Bradford method (Bio-Rad Laboratories, Hercules, Calif.).

MI1–440 was in amylose elution buffer (20 mM NaPO$_4$, pH 8, 0.5 M NaCl, 1 mM EDTA, and 10 mM Maltose) at a concentration of 1 mg/ml as determined by the Bradford method (Bio-Rad Laboratories, Hercules, Calif.).

The two protein fragments were combined in a reaction containing 15 µl MI1–440, 10 µl I250–537P and 5 µl buffer A, and incubated overnight at 4° C. The reaction mixture was then diluted 10-fold to 300 µl in trans-splicing buffer (20 mM NaPO$_4$, pH 6, 0.5 M NaCl) and immediately incubated at 42° C. to induce splicing. To follow the splicing reaction, samples were collected at time points of 5, 10, 25 and 40 minutes, and immediately added to ⅕ volume of 5x protein gel sample buffer (Sambrook et. al., supra). 25 µl of each time point sample was loaded onto a 4–20% SDS-PAGE gel (Daiichi, Tokyo, Japan) and electrophoresed at 60 mA for 2 hours. The gel was then stained with Coomassie blue and subsequently destained (Sambrook et. al. supra).

Figure 26:
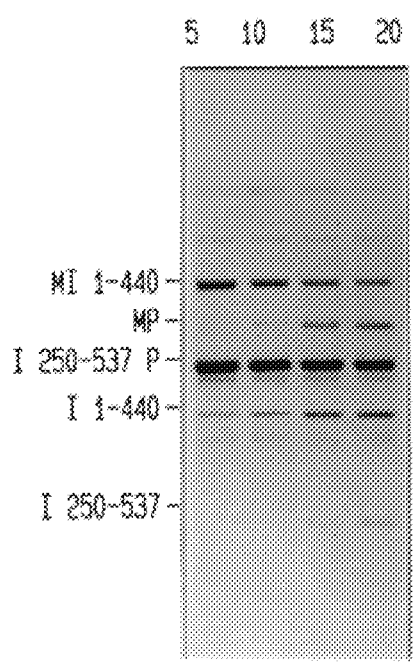
FIG. 26 shows protein splicing in trans with a 190 amino acid overlap in the CIVPS3 sequence. Mll–440 and l'P were combined in 50% buffer A and incubated overnight at 4° C. The reaction mixture was diluted 10 fold into trans-splicing buffer and incubated at 42° C. to induce splicing. Time points were taken and examined on a 4–20% SDS-PAGE gel. Lane 1: 5 minute time point; lane 2: 10 minute time point; lane 3: 25 minute time point; lane 4: 40 minute time point. Both Mll- 440 and l250–537P decrease, and MP (the spliced product), ll–440 and l250–437 increase.

The time course clearly demonstrated the decay of both substrates (MI1–440 and I250–537P) and the formation of the splicing products, MP (72 kDa), I1–440 (51 kDa) and I250–537 (30 kDa), see FIG. 26.

Splicing In Trans Of A Second Complementary Pair Of CIVPS3 Fragments, MI1–440 And I441–537P In this experiment, the N-terminal CIVPS containing fragment (MI1–440) was mixed with its complement, I441–537P (FIG. 25). Splicing of this new pair of complementary CIVPS3 fragments occurred efficiently (FIG. 27).

Because of solubility problems, I441–537P was stored in Buffer A (50 mM Tris, HCl pH 7.5, 5% acetic acid, 0.1 mM EDTA, 1 mM DTT, 140 mM β-mercaptoethanol and 7.2 M urea). I441–537P (at 2.1 mg/ml) in buffer A and MI1–440 (at 3.4 mg/ml) in amylose elution buffer (20 mM NaPO$_4$, pH 8, 0.5 M NaCl, 1 mM EDTA and 10 mM Maltose) were combined in a reaction containing 4.5 µl MI1–440, 7 µl I441–537P, 10.5 µl amylose elution buffer and 8 µl buffer A.

The reaction mixture was pretreated on ice for 4 hours and diluted 10-fold with 270 µl trans-splicing buffer (20 mM NaPO$_4$, pH 6, 0.5 M NaCl). The diluted reaction mixture was immediately incubated at 37° C. to induce splicing and samples collected at time points of 0, 10, 60 and 120 minutes, followed by addition of ⅕ volume of 5× protein sample buffer, as above. 25 µl of each time point sample was loaded onto a 12% SDS-PAGE gel (Novex, San Diego, Calif.), and electrophoresed at 60 mA for 2 hours. The gel was stained with Coomassie blue and subsequently destained.

The time course clearly demonstrated the decay of the substrates (Ml1–440 and l441–537P) and the formation of the spliced product, MP (72 kDa), and the CIVPS fragments, l1–440 (51 kDa) (FIG. 27). The l441–537 (11 kDa) fragment was not visible on the gel as it runs with the dye front on a 12% SDS-PAGE gel.

Protein Splicing In Trans With An Affinity Tag At The N-Terminus Of The C-Terminal CIVPS3 Fragment An experiment was carried out to demonstrate that splicing in trans can be obtained when non-CIVPS sequences are added to the fragmentation site such that the unrelated protein sequence is placed immediately after the C-terminus of the N-terminal CIVPS fragment or immediately prior to the N-terminus of the C-terminal CIVPS fragment. Instead of the two CIVPS fragments having a complementary junction, there is now an unrelated sequence at the end of one or both CIVPS fragments. This is conceptually similar to the above Example with overlapping CIVPS fragments. In this example, we demonstrate that the CIVPS fragments are still able to reassociate and splice, despite the presence of this unrelated protein sequence.

In this experiment, the N-terminal CIVPS containing fragment (MI1–440) was mixed with MI441–537P, containing the MBP protein in front of a CIVPS3 fragment containing residues 441–537 (FIG. 25) When equivalent splicing reactions were performed, the splicing of MI1–440 was equally efficient with its complementary partner lacking the MBP tag, I441–537P, or its complementary partner containing the MBP tag, MI441–537P (FIG. 27). MI441–537P (at 1.9 mg/ml) and MI1–440 (at 3.4 mg/ml) in amylose elution buffer were combined in a reaction containing 4.5 µl MI1–440, 8 µl MI441–537P, 2.5 µl amylose elution buffer and 15 µl buffer A.

The reaction mixture was pretreated on ice for 4 hours and diluted 10-fold with 270 µl trans-splicing buffer (20 mM NaPO$_4$, pH 6, 0.5 M NaCl). The diluted reaction mixture was immediately incubated at 37° C. to induce splicing and samples collected at time points of 0, 10, 60 and 120 minutes, followed by addition of ⅕ volume of 5×protein sample buffer, as above. 25 µl of each time point sample was loaded onto a 12% SDS-PAGE gel (Novex, San Diego, Calif.), and electrophoresed at 60 mA for 2 hours. The gel was stained with Coomassie blue and subsequently destained.

The time course clearly demonstrated the decay of both substrates (MI1–440 and MI441–537P) and the formation of the spliced product, MP (72 kDa), and the excised CIVPS fragments, I1–440 (51 kDa) and MI441–537 (56 kDa) (FIG. 27).

Protein Splicing In Trans With An Affinity Tag At The C-Terminus Of the N-Terminal CIVPS3 Fragment To demonstrate that we can add an affinity tag to the C-terminus of CIVPS3 and still see trans-splicing, a clone was constructed that contained 6 His residues at the C-terminus of a CIVPS3 fragment. These 6 His residues constitute a functional His tag. In the experiment described below, 6 histidine residues were placed after the CIVPS3 fragment encoding CIVPS3 residues 1–440, initially in clone pLI1–440 and then in clone pMI1–440. This Example demonstrates that the fusion was easy to purify and still spliced in trans when an unrelated affinity tag was placed at the C-terminus of the N-terminal CIVPS fragment.

Construction Of LI1–440His

We described above the construction of MI1–440. The malE portion of this clone is flanked by Ndel and Kpnl sites and can be replaced by fragments of other genes of interest. One such clone, LI1–440, containing a fragment of the Lck Tyrosine Kinase gene encoding amino acids 42–120 (L) linked to CIVPS3 residues 1–440 was constructed (Roger Kautz, Boston University, Boston, Mass.). To this was added 6 Histidine residues to generate clone LI1–440His.

The 3' end of the l1–440 CIVPS3 gene fragment contains the following DNA and amino acid sequences (SEQ ID NO:823), with two unique restriction sites (underlined):

```
        AflII                              BamHI
5' CTT AAG TTT ACG GAA TAC AGA TAA GGA TCC 3'

3' GAA TTC AAA TGC CTT ATG TCT ATT CCT AGG 5'
    L   K   F   T   E   Y   R  STOP
```

This sequence can be removed by digesting any Ml 1–440 derivative such as LI1–440 or MI1–440 with AfIII and BamHI restriction enzymes. The sequence can then be replaced with a cassette encoding

```
5'-TT    AAG TTT ACG GAA TAC AGA CAC CAC CAC CAC CAC CAC TAA G-3'

3'-      C AAA TGC CTT ATG TCT GTG GTG GTG GTG GTG GTG ATT CGA TC-5'
         F   T   E   Y   R   H   H   H   H   H   H  STOP
(SEQ ID NO: 83)
```

(SEQ ID NO:83)

The above double-stranded oligonucleotide was generated by annealing each of the above single-stranded oligonucleotides (5'-TTAAGTTTACGGAATACAGACACCAC-CACCACCACCACTAAG -3'(SEQ ID NO:84), and 5'-CTAGCTTAGTGGTGGTGGTGGTGGTGTCTGTATTCC GTAAAC -3'(SEQ ID NO:85)). The two oligonucleotides were annealed in a reaction containing 10 µl of each oligonucleotide (10 µM/µl each oligonucleotide ), 5 µl 10×T4 DNA ligase buffer and 25 µl dH$_2$O. The mixture was heated to 85° C. for 10 minutes, then cooled slowly at room temperature for 2 hours.

The plasmid LI1–440 (1 µg) was digested with AfIII (10 units) and BamHI (20 units) in 1 ×Buffer 2 and 100 µg/ml BSA in a 20 µl reaction for 2 hours at 37° C. The vector DNA was then gel purified to remove the AfIII/BamHI fragment described above.

The annealed AfIII/BamHI cassette containing the His tag was ligated to the gel purified AfIII/BamHI digested vector backbone of LI1–440, to create LI1–440His. This resulted in the addition of 6 His residues to the C-terminus of the CIVPS3 fragment in LI1–440. Gel purification and ligations were performed as described by Sambrook et. al., supra.

Construction Of MI1–440 His

The I1–440His portion of clone LI1–440His is flanked by a Kpnl site at the 5' end of the CIVPS3 sequence and a BamHI site at the 3' end of the CIVPS3 sequence just after the stop codon. This fragment was cloned into MI' (see Example 12, M' contains MBP fused to the first 250 amino acids of the CIVPS3 gene) to yield MI1–440His (FIG. 25).

The plasmids LI1–440His (1 µg) and MI' (1µg) were digested with 20 units Kpnl and 20 units BamHI in 1×Buffer 1 and 100 μg/ml BSA in a 20 μl reaction and incubated at 37° C. for 2 hours. The I1–440His fragment from Ll1–440His and the vector backbone of MI' were gel purified and ligated together to yield MI1–440His, as described by Sambrook et. al. supra.

Expression And Purification Of MI1–440His

Mi1–440His was transformed into ER2504 (*E. coli* B fhuA2 [lon] ompT gal sulA 11=90 Δ(mcrC-mrr)114::IS10 R(mcr-73::miniTn10; TetS)2 (lamdaDE3) endA 1) and grown at 30° C. in 2×1 liter of LB medium supplemented with 0.1 mg/ml ampicillin to an $OD_{600}$ of~0.5. The culture was induced with 0.4 mM IPTG and incubated at 30° C. for 2 hours. The cells were harvested by centrifugation at 4° C. and resuspended in 75 ml of 1× Binding Buffer (Novagen; Madison, Wis.) and broken by sonication. After centrifugation at 20,000 g for 30 minutes, the crude supernatant was passed through a $Ni^{2+}$ charged column (Novagen; Madison, Wis., 10 ml of resin). The column was washed with lx Binding buffer, followed by 1x Wash buffer (Novagen; Madison, Wis.) and the protein eluted with 1x Elute buffer (Novagen; Madison, Wis.). The majority of the MI1–440His fusion protein (21 mg) eluted in the 1 x Wash buffer and not in the Elute buffer. The purified MI1–440His was stored at −20° C.

Trans-splicing Reaction l441–537P (at 1.8 mg/ml) in buffer A (50 mM Tris, HCl pH 7.5, 5% acetic acid, 0.1 mM EDTA, 1 mM DTT, 140 mM β-mercaptoethanol and 7.2 M urea) and Ml1–440His (at 5 mg/ml) in Wash buffer (20 mM Tris-HCl, pH 7.9, 0.5 M NaCl and 60 mM Imidazole) were combined in a reaction containing 3 μl Ml1–440His, 9 μl I441–537P, 12 μl amylose elution buffer and 6 μl buffer A. The reaction mixture was incubated on ice for 4 hours, and diluted 10-fold with 270 μl trans-splicing buffer (20 mM $NaPO_4$, pH 6, 0.5 M NaCl). The diluted reaction mixture was immediately incubated at 37° C. to induce splicing and samples collected at time points of 0, 10, 60 and 120 minutes, followed by addition of ⅕ volume of 5x protein sample buffer. 25 μl of each time point sample was loaded onto a 12% SDS-PAGE gel, and electrophoresed at 60 mA for 2 hours. The gel was stained with Coomassie blue and subsequently destained.

The time course demonstrated the decay of both substrates (Ml1–440His and l441–537P) and the formation of the spliced product, MP (72 kDa), and the CIVPS fragment, l1–440His (51 kDa). The l441–537 fragment was not visible on the gel as it runs with the dye front on a 12% SDS-PAGE gel.

EXAMPLE 17

In Vivo Control Of Protein Splicing Mediated By A Blocking Or An Activating Peptide Introduction In previous examples, we have described the insertion of a CIVPS into a foreign gene. In these cases, protein splicing can be controlled by temperature, mutation, pH, photo-activated blocking groups or phosphorylation. In this Example we describe how an CIVPS can be controlled by addition of a specific peptide which inhibits protein splicing. We also describe how splicing of a modified, inactive CIVPS can be subsequently activated by interaction with a specific activating peptide. We further describe a way in which specific activating or inhibiting peptides can be isolated after genetic selection. Genetic selection or screening is used to identify CIVPSs which can either splice or fail to splice, depending on the context of the experiment. Although the pheS genetic selection system is described in this Example, any genetic selection system can also be used to isolate peptide sequences which activate or inhibit CIVPSs. Although we describe the specific use of the Sce VMA CIVPS (Gimble and Thorner, *Nature*, 357:301–306 (1992), this strategy is equally applicable to any IVPS (also know as an intein (Perler et al., *Nucleic Acids Research*, 22:1125–1127(1994)) present in its native protein context or in a foreign protein context. Furthermore, once a peptide activator or inhibitor is identified, it can then be used as a lead compound to develop analogs (e.g., peptidomimetics, (Francis, et al., *EMBO J.* 13:306–317 (1994), James, et al., *Science*, 260:1937–1942 (1993) and Bianchi, et al., *J. Mol. Biol*, 247:154–160 (1995)), derivatives (e.g., cyclic peptides), and drugs such IVPS inhibitors or activators would be especially useful in combating diseases such as leprosy or tuberculosis, where the causitive agents (Mycobacterium) have essential genes which naturally contain IVPS or inteins (e.g., recA in *M. leprae* and *M. tuberculosis* and gyrA in *M. leprae*) (Davis, et al., *EMBO J.*, 13:699–703 (1994)).

We propose to use a combinatorial peptide library for selection of the required peptides. Although several types of combinatorial peptide libraries can be used, in this example we chose to describe a combinatorial peptide library that is inserted in a larger protein and expressed in vivo. This Example demonstrates the generation of combinatorial peptide library in the EF hand of chicken α-spectrin. However, any suitable protein can be used as a scaffold for presentation of the peptide to the CIVPS and other methods of generating inhibiting or activating peptides can be used, including rationale peptide design if the structure of the CIVPS is known. Finally, the same strategy can be used for screening any type of CIVPS activator or inhibitor that can be introduced into a living cell or be detected in an in vitro assay.

We will first describe how the phes genetic selection system works and how we have inserted an IVPS into the pheS gene. We will then describe how one would construct an in vivo combinatorial library in chicken α-spectrin and screen such a library for peptides that block splicing. We will then describe how one would generate splicing deficient CIVPSs and how they could then be activated by a suitable peptide.

Finally, activation or inhibition of splicing in native or foreign protein contexts by peptides or other reagents identified in the proposed selection protocols and their derivatives (e.g., cyclic peptides, peptidomimetics, etc.) is equally applicable to splicing in trans and in cis (as described in this Example) or for cleavage at one or both splice junctions either in cis or in trans, rather than splicing.

PheS, A Double Positive Selection System

Background And Construction Of A PheS/CIVPS Fusion

In general, a double positive selection system consists of a gene that can be both essential and detrimental to the host organism depending on the growth media or the host strain genetic background (Burns and Beacham, *Gene*, 27:323–325(1984). Thus, the expression of active gene product can be selected for under conditions where the gene product is essential for cell growth. Inactive proteins would not enable cell growth. Under different growth or host strain genetic backgrounds, the same gene product can be lethal for the cell, killing the host unless the gene product is inactivated. In the context of a protein splicing genetic selection system, the double positive selection system is defined as a system that allows for selection for or against the splicing of a CIVPS cassette inserted in-frame into a host gene. If splicing occurs in the protein product of the host gene, the host protein will be active; if splicing is blocked the host protein will be inactive. As our selected example, pheS is an essential *E. coli* gene which is part of a two gene operon consisting of pheS and pheT. PheS encodes the α subunit of the PheRS multi-subunit enzyme (2 α subunits plus 2 β subunits) responsible for phenylalanyl-tRNA synthetase activity (Mechulam et al., *J. Bacteriol* 163:787–791 (1985). In this application, we will refer to the protein product of the pheS gene as 'PheS' and not as the 'α subunit of PheRS'.

The following protocol describes the cloning of the Sce VMA CIVPS (Gimble and Thorner, supra (1992)) cassette into the *E. coli* pheS gene. The chosen insertion site should be a splicing favorable site because it shares sequence identity with the native Sce VMA CIVPS extein regions. Exteins are defined as the protein sequences flanking the CIVPS. The CIVPS insertion site was chosen immediately upstream of the unique pheS Cys272:
V269L270 G271c f a—v h n C272G273.
Amino acid numbers refer to the position of the amino acid in *E. coli* PheS. The underlined amino acids (single letter amino acid code) are the amino acids identical in both PheS and the Sce VMA exteins. The lower case letters represent Sce VMA CIVPS amino acids. The dashes are positioned in places where the remainder of the residues of the protein are not listed.

First, the pheS gene was cloned by PCR using *E. coli* K12 genomic DNA under the following experimental conditions. A forward primer 5'-GTA CCGAGCTCATGTCA-CATCTCGCAGAACTGGTTGCC AGT-3'(SEQ ID NO:86) and reverse primer 5'-ACATGCATGCTTATTT AAACTGTTTGAGGAAACGCAGATC-3'(SEQ ID NO:87) were used in a PCR mixture containing 20 U/ml Vent® Exo+ DNA polymerase, 400 μM of each dNTP, 4 nM each primer and 100 ng of *E. coli* K12 highly pure genomic DNA. The *E. coli* DNA was prepared using the QIAamp tissue kit (Qiagen, Studio City, Calif.). Amplification was carried out in a Perkin-Elmer/Cetus (Emeryville, Calif.) thermal cycler 480 for 5 min at 94° C. as a hot start after which the polymerase was added and thie mixture cycled at 55° C., 30 sec; 72° C., 1 min; 94° C., 30 sec for 20 cycles. The PCR products of 10 tubes of 50 μl reaction volume were pooled, concentrated and purified using the QIAEX II beads (Qiagen, Studio City, Calif.). 500 ng of plasmid pMBL18 (Nakano et al., *Gene* 162:157–158 (1995) and 500 ng of PCR products were digested in NEB buffer 1 using 500 U/ml of SacI and 375 U/ml of SphI in the presence of 100 μg/ml of BSA. The digestion was performed at 37° C. for 2 hours. pMBL18 vector DNA (2.7 kb) and digested PCR product (984 bp) were separated by electrophoresis on a 0.7% low melting agarose gel and the excised bands further purified with the QIAEX II beads (Qiagen, Studio City, Calif.). Ligation was carried out at 20° C. for 1 hour using a 1:3 ratio of vector to insert. 7.5 μg/ml of plasmid DNA was combined with 7.5 μg/ml of PCR products and the reaction started upon addition of 40 000 U/ml of T4 ligase. 40 μl of *E. coli* strain ER2502 competent cells were transformed using 19 ng of ligation products incubated on ice for 30 min, followed by a 45 sec heat shock at 42° C. and recovery in 960 μl of LB media for 1 hour at 37° C. Plating of 100 μl of cells on ampicillin plates (100 μg/ml) gave rise to an average of 279 colonies per plate with less than 5.6% vector alone background. Plasmid DNA from 6 randomly picked transformants was checked by PstI digestion which linearize the correct clones by a single cut within the insert. 6 out of 6 clones were positive, giving the correct digestion pattern. The resultant plasmid containing the *E. coli* pheS gene was named pEA200. The sequence of the pheS insert was checked by DNA sequencing of pEA200.

Second, a 126 bp DNA cassette with flanking PstI/AflIII restriction enzymes sites was designed to be cloned into the unique pEA200 pheS PstI/AflIII sites. This cassette also encodes for the exact pheS-Sce VMA CIVPS in-frame protein fusion as described below (single letter amino acid code):

[AEVDVMGKNGKWLEVLG (271) cfakgtnvlnqvvvhnC (272) GMVHPNV]
PstI------------------------KpnI---SexAI------------AflIII
(SEQ ID NO: 88)

(SEQ ID NO:88)
This cassette also contains the unique KpnI/SexAI sites that are present within the Sce VMA CIVPS cassette close to the splice junctions. The 126 bp cassette was synthesized by re-annealing of 6 oligonucleotides : 5'-GAAGTGGACGTCATGGGTAAAAACGGTAAATG GCTGGAAGTGCTGGGC-3'(SEQ ID NO:89), 5'P-TGCTTTGCC -3', 5'P-TAATTGCGGGATGGTGCATCCGAA-3'(SEQ ID NO:90), 5'-CACGTTCGGATGCACCATCCCGCAATT-ATGGACGACAACCTGG-3'(SEQ ID NO:91), 5'P-TTTAAAACATTGGTACCCTTGGCAAAGCAGCCCA-GCACTTCCAGCC-3' (SEQ ID NO:92), 5'P-ATTTACCGTTTTTACCCATGACGTCCACTTCTGCA-3' (SEQ ID NO:93). 5 nM of each oligonucleotides were combined in T4 ligase buffer, heated up to 80° C. for 5 min and cooled down at room temperature. 500 ng of pEA200 was digested with PstI and AflIII in NEB buffer 3 using 100 U/ml AflIII and 200 U/ml PstI supplemented with 100 μg/ml BSA. After a 90 min incubation at 37° C. the digestion products were separated on a 0.7% low melting agarose gel. The vector band was excised and purified using QIAEX II beads (Qiagen, Studio City, Calif.). Ligation with the 126 bp synthetic cassette was carried out at 20° C. for 1 hour using a 1:2 ratio of vector to insert. 7.5 μg/ml of plasmid DNA was combined with 0.65 μg/ml of the 126 bp re-annealed DNA cassette and the reaction started upon addition of 40 000 U/ml of T4 ligase. 40 μl of *E. coli* strain ER2267 competent cells were transformed using 12.5 ng of ligation products, 30 min incubation on ice, 45 sec heat shock at 42° C. and recovery in 960 μl of LB media for 1 hour at 37° C. Plasmid DNA from 10 randomly picked transformants was checked by KpnI digestion which linearizes the correct clones by a single cut within the insert. 8 out of 10 clones were positive. The resultant plasmid was named pEA201.

Third, the 1010 bp EcoRI/HindIII insert (the pheS/126 bp cassette) from plasmid pEA201 was transferred to pKK223-3 (Pharmacia, Piscataway, N.J.). 200 ng of pKK223-3 and 2 μg of pEA201 were digested in NEB EcoRI buffer using 500 U/ml of EcoRI and 500 U/ml of HindIII. The digestion was performed at 37° C. for 2 hours. Vector (4.6 kb) and pEA201 insert (1010 bp) DNAs were separated by electrophoresis on a 0.7% low melting agarose gel and the excised bands further purified by QIAEX II beads (Qiagen, Studio City, Calif.). Ligation was carried out at 16° C. overnight using a 1:4 ratio of vector to insert. 3 μg/ml of plasmid DNA was combined with 2.6 μg/ml of pEA201 insert and the reaction started upon addition of 40 000 U/ml of T4 ligase. 40 μl of *E. coli* strain ER2267 competent cells were transformed as above using 15 ng of ligation products.

Plasmid DNA from 6 randomly picked transformants was checked by KpnI digestion which linearizes the correct clones by a single cut within the insert. 6 out of 6 clones were positives. The resultant plasmid was named pEA202.

Fourth, the Sce VMA CIVPS gene was cloned by PCR using *Saccharomyces cerevisiae* FY1679 genomic DNA (Pr. P. Philippsen, Biozentrum der Universitat Basel) under the following experimental conditions. Forward primer 5'-GGAATTCTGCTTTGCCAAGGGTACCAATG-3' (SEQ ID NO:94) and reverse primer 5'-ATTGGTTCTGCAGATTATGGACGACAACCTGG-TTGGC-3'(SEQ ID NO:95) were used in a PCR mixture containing 20 U/ml Vent® Exo+ DNA polymerase, 400 µM of each dNTP, 4 nM each primer and 1 ng of Sce FY1679 pure genomic DNA. Amplification was carried out in a Perkin Elmer/Cetus (Emeryville, Calif.) thermal cycler 480 for 2 min at 94° C. as a hot start after which the DNA polymerase was added and the mixture cycled at 55° C., 30 sec; 72° C., 80 sec; 94° C., 30 sec for 26 cycles. The PCR products of 10 tubes of 50 µl reaction volume were pooled, concentrated and purified using the QIAEX II beads (Qiagen, Studio City, Calif.). 500 ng of plasmid pUC19 and 500 ng of PCR products were digested in NEB EcoRI buffer using 500 U/ml of EcoRI and 500 U/ml of PstI. The digestion was performed at 370° C. for 4 hours. Vector DNA (2.7 kb) and digested PCR products (1350 bp) were separated by electrophoresis on a 0.7% low melting agarose gel and the excised bands further purified by QIAEX II beads. Ligation was carried out at 19° C. for 6 hours using a 1:3 ratio of vector to insert. 7.5 µg/ml of plasmid DNA was combined with 11.2 µg/ml of PCR products and the reaction started upon addition of 40 000 U/ml of T4 ligase. 40 µl of *E. coli* strain ER2504 (dcm-) competent cells were transformed using 19 ng of ligation products, as described above. Plasmid DNA from 5 transformants was checked by EcoRI/PstI digestion which removes the Sce VMA CIVPS insert from the correct clones. 2 out of 5 clones were positive. The resultant plasmid was named pEA400 and the sequence of the insert was checked.

Finally, the Sce VMA CIVPS cassette present in pEA400 was transferred to plasmid pEA202. 2 µg of pEA400 and 1 µg of pEA202 were digested in NEB buffer 1 using 400 U/ml of KpnI and 200 U/ml of SexAI. The digestion was performed at 37° C. for 1 hour. Vector DNA (5.6 kb) and pEA400 insert DNA (1350 bp) were separated by electrophoresis on a 0.7% low melting agarose gel and the excised bands further purified by QIAEX II beads. Ligation was carried out at 20° C. for 30 min using a 1:4 vector to insert ratio. 15 µg/ml of plasmid DNA was combined with 15 µg/ml of pEA400 insert and the reaction started upon addition of 40 000 U/ml of T4 ligase. 40 µl of *E. coli* strain ER2267 was transformed using 75 ng of ligation products, as described above. Clones were checked by digestion with KpnI. The resultant plasmid was named pEA213.

PHES As A Positive Selection For Splicing Deficient CIVPS Cassettes

A single pheS alanine294 to glycine mutation, in the catalytic pocket of the PheRS α subunit, allows incorporation of para-Chloro-phenylalanine (p-Cl-phenylalanine) into host proteins. Incorporation of this phenylalanine substrate analog into host proteins leads to cell death. This mutation is dominant in a mero-diploid cell due to the similar incorporation rates of the suicide (p-Cl-phenylalanine) and unmodified phenylalanine substrates by the mutant PheRS enzyme, irrespective of the presence of the native PheRS enzyme synthesized from the host gene. Therefore, transformation of any host strain with a CIVPS cassette that disrupts the pheS A294G mutated gene provides a positive selection for splicing deficient clones since inactivation of the mutant PheRS protein would prevent incorporation of the suicide p-Chloro-phenylalanine analog (Hennecke et al., *Gene*, 19:231–234 (1982); Kast and Hennecke, *J. Mol. Bio.* 222:99–124 (1991). Splicing competent CIVPSs would result in the production of active mutant PheRS which would allow the incorporation of the suicide analog and lead to cell death.

The A294G amino acid substitution was performied using the Quick Change™ Site-Directed Mutagenesis Kit (Stratagene, LaJolla, Calif.) according to the manufacturer's instructions. Forward primer 5'-CTCTGGTTTCGGCTTCGGGATGGGG-3'(SEQ ID NO:96) and complementary reverse primer 5'-CCCCATCCCGAAGCCGAAACCAGAG-3' (SEQ ID NO:97) were HPLC purified and used in a PCR mixture containing 50 U/ml Pfu DNA polymerase, 50 µM of each dNTP, 288 nM of forward primer, 294 nM of reverse primer and 200 ng/ml of pEA213 plasmid DNA. Amplification was carried out in a Perkin Elmer/Cetus (Emeryville, Calif.) thermal cycler 480 for 30 sec at 95° C. as a hot start after which the DNA polymerase was added and the mixture cycled at 55° C., 1 min; 68° C., 16 min; 95° C., 30 sec for 16 cycles. The PCR reaction products were then digested with 200 U/ml of DpnI for 1 hour at 37° C. 1 µl of the DpnI-treated DNA was transferred to 50 µl of *Epicurean Coli* XL1 -Blue Supercompetent Cells, incubated on ice for 30 min, heat pulsed for 45 sec at 42° C. and then place on ice again for 2 min. 500 µl of 42° C. pre-heated SOC medium was added to the cells and transformants were incubated for 1 hour at 37° C. 100 µl of cells were platted on ampicillin (100 µg/ml) agar and 1 randomly picked transformant was checked by DNA sequencing. The resultant plasmid was named pEA214.

PheS As A Positive Selection System For Splicing Efficient CIVPS Cassettes

The pheS thermosensitive *E. coli* strain, NP37 (*E. coli* Genome Center, strain CGSC #4913, (Kast et al., *J. Bacteriol.* 174:1686–1689 (1992)) can grow at 30° C. where its PheS protein is active as part of the PheRS hetero-tetramer, but not at 40° C. where it is inactive. However, the inability of NP37 to grow at 40° C. can be overcome by expression of a non-thermosensitive pheS allele present on a plasmid. NP37 transformants containing plasmid pEA213 will be viable under non-permissive conditions at 40° C. only if the Sce VMA CIVPS cassette is able to splice out of the PheS subunit to restore its PheS function in vivo. Therefore, this system selects for CIVPSs which are capable of splicing.

As a control, we demonstrated that a splicing proficient CIVPS/pheS fusion was able to grow at 40° C. in NP37. We have constructed the splicing deficient CIVPS/pheS fusion, as described below, but have not as yet tested it in this system. Theoretically, this mutant should not complement the NP37 pheS mutant at 40° C.

A splicing deficient Sce VMA CIVPS cassette containing mutations in 2 of the 3 catalytic residues (Cys1 to Ala and Asn454 to Ala) was generated in pEA213 using the Quick Change™ Site-Directed Mutagenesis Kit (Stratagene. LaJolla, Calif.) as described by the manufacturer, using the forward C1A primer 5'-GGCTGGAAGTG-CTGGGCgcgTTTGCCAAGGGTACCAATGTTTTAA-3' (SEQ ID NO:98), the reverse C1A primer 5'-GGTACCCTTGGCAAAcgcGCCCAGCACTTCCAG-CC-3' (SEQ ID NO:99), the forward N454A primer 5'-GGTTGTCGTCCATgcgTGCGGGATGGTGC-3' (SEQ ID NO:100) and the reverse N454A primer 5'-GCACCATCCCGCAcgcATGGACGACAACC-3'(SEQ ID NO:101). The mutated nucleotides are in lower case. The pheS C1A/N454A double mutation plasmid was named pEA215 and should express an inactive pheS gene product when transformed in NP37 under non-permissive conditions (40° C.).

Design Of An In Vivo Peptide Library Using The Chicken α-Spectrin EF-Hand Loop

In vivo expression of peptides may be hampered by the host's efficient proteolytic degradation systems. Therefore, it is thought to be better to express peptides in vivo in the context of larger proteins, especially in surface loop regions of larger proteins. In vivo expression of peptides fused to larger proteins has been achieved for example, in the catalytic loop of thioredoxin (Colas et al., Nature 380:548–550 (1996)) and it is possible to express peptides fused within many different proteins. Peptides expressed in-frame in highly soluble, well expressed, thermostable, solvent-exposed loops of a protein are less subject to in vivo proteolysis or degradation and such fusions enhance the functional expression of peptides in a cell.

This theoretical example describes the synthesis of a combinatorial peptide library in a fragment of chicken α-spectrin, but is equally applicable to any protein of choice. The EF hand region of chicken alpha-spectrin was chosen for because its structure is known, its EF hand domain forms a small protein with a stable structure, and it has a flexible surface loop. The structure of the chicken alpha-spectrin EF hand domain was elucidated by NMR analysis (Trave et al., EMBO J 14:4922–4931 (1995); Trave et al., Eur. J. Biochem. 227:35–42 (1995)). The term EF hand describes a type of protein tertiary structural motif consisting of a helix, a turn (loop) and a second helix. The EF hand domain of chicken α-spectrin is located at the amino terminus of chicken α-spectrin. Its 84 amino acid structure is arranged in two EF hand helix-turn-helix motifs separated by a 14 amino acid long flexible linker. The protein is extremely soluble without any detectable precipitation or aggregation even at concentrations of up to 10 mM. The linker loop is mainly unstructured in solution and mutagenesis data show that minor deletions or insertions in the loop do not disturb the stabilizing hydrophobic interactions between the 2 EF-hand.

We are taking advantage of this last property which allows the insertion of random peptides in the linker region between the chicken α-spectrin EF hands. Peptide libraries of various sizes can be investigated. Generation of combinatorial oligonucleotides encoding combinatorial peptide libraries is well documented and any of the available techniques for generating these combinatorial libraries can be used. We propose to modify the α-spectrin EF hand domain such that the region encoding the flexible loop can be replaced by 2 unique restriction enzyme sites separated by a small stuffer DNA sequence. This modified α-spectrin EF hand domain may then be cloned into pEA213 or pEA214, depending on the selection strategy adopted as described below. The modified α-spectrin EF hand domain can be operably linked to a constitutive or inducible promoter, as desired. Finally, the stuffer DNA in the α-spectrin gene may be removed by digestion with the 2 unique restriction enzymes and replaced with a combinatorial oligonucleotide library encoding the combinatorial peptide library in-frame with the α-spectrin gene.

Selection Of Blocking Peptides That Inactivate Protein Splicing Of Splicing Efficient CIVPSs Plasmid pEA214 encodes the A294G mutated pheS gene interrupted by the Sce VMA CIVPS cassette upstream of C272 in PheS. As stated above, the A294G mutated pheS gene product can incorporate p-Cl-phenylalanine and kill its host cell. If splicing of pEA214 is inhibited or blocked, then pEA214 will be able to grow in the presence of p-Cl-phenylalanine. The α-spectrin peptide library encoding unit will be transferred to pEA214 as described above. Transformation of any highly competent host strain (e.g. electrocompetent DH10B E. coli cells rated at 1–5×10$^{10}$ pUC19 transformants/μg, GIBCO-BRL, (Gaithersburg, Md.) followed by plating on p-Cl-phenylalanine provides a positive selection for splicing deficient clones. Since there is no mutation step in the CIVPS, splicing will only be blocked if one or more of the peptides encoded by the α-spectrin combinatorial library can interact with the CIVPS in such a way as to inhibit splicing. Surviving clones will be isolated and the plasmids sequenced to determine the peptide sequence responsible for the splicing deficient phenotype. Once a lead peptide has been obtained, reiterative rounds of selection of related sequences can be performed to identify blocking peptides with higher affinities or other desirable properties. Highly competent cells are required because it is envisioned that a very large number of peptides will have to be screened to find the ones that block splicing. However, if the structure of the CIVPS is known, rational design of blocking peptides can be used and lead peptides defined and improved in this same genetic selection system.

Selection Of Activating Peptides That Restore Protein Splicing Of Mutated Splicing Deficient CIVPs In this theoretical embodiment, the CIVPS must first be mutated so that it will no longer splice. Several types of mutations can be attempted, ranging from random mutagenesis to specific mutagenesis of active site residues. There are several potential conserved CIVPS (also known as intein) residues which are required for splicing (Chong et al., J. Biol. Chem. 271:22159–22168 (1996); Xu and Perler, EMBO J. 15:5146–5153 (1996)), such as the amino acid following each splice junction, the CIVPS C-terminal amino acid and preceding His, and the conserved His in intein (CIVPS) block B which is usually around 100 amino acids from the CIVPS N-terminus (Pietrokovski, Protein Sci., 3735:2340–2350 (1994). In this Example, we are looking for peptides which can then complement the mutationally induced splicing deficiency in a manner similar to the chemical assisted splicing activity described in Example 14. Randomly mutated Sce VMA CIVPS cassettes can be generated by numerous protocols, including PCR with a DNA polymerase such as Taq DNA polymerase that doesn't contain a proofreading exonuclease or by using modified dNTP ratios (Cadwell and Joyce, PCR AMethods Appl. 3:S13614 S140 (1994). Such mutated cassettes will be cloned into pEA214 upstream of the PheS cysteine 272, to replace the wild type Sce VMA CIVPS cassette or constructed using protocols similar to the construction of pEA214. Transformants will be plated as above on plates containing ampicillin and p-Cl-phenylalanine. Only mutated CIVPSs which fail to generate active PheS by splicing will grow, since, as stated above, incorporation of p-Cl-phenylalanine by the mutated, but active PheS present on this plasmid will kill the cells. Randomly picked surviving clones will be sequenced to determine all the mutations present in the CIVPS gene and checked for the presence or accumulation of unresolved precursor by SDS-PAGE after staining with Coomassie blue or by western blot analysis of cytoplasmic proteins using anti-Sce VMA CIVPS serum.

Each of these individual splicing deficient clones will then be sequentially tested for a gain of splicing activity using the alpha-spectrin EF hand in vivo peptide library described above. The mutated Sce VMA CIVPS and the α-spectrin EF hands will be cloned into pEA213 (wild type pheS gene) and transformed in NP37. Since the host chromosomal copy of the pheS gene in strain NP37 is thermosensitive, growth will only occur at 40° C. if the plasmid contributes an active, thermostable PheS protein. Growth at 40° C. would result in the positive selection of clones which express a peptide capable of restoring the splicing potential of the mutated splicing deficient CIVPS. Such a peptide is called an Activating peptide. Once an activating peptide is identified, the clone encoding it will be sequenced. If several activating peptides are identified, their deduced amino acid sequences will be compared to attempt to determine commonalties. Reiterative rounds of selection based on modification of the lead activating peptide will be performed until a highly efficient activating peptide is generated.

Uses Of In Vivo Controlled CIVPS Elements

Once activating or inhibiting peptides are identified, they will be tested with CIVPSs cloned in different genes. If the peptides bind to the CIVPS, then they should block or activate splicing in any context in which the CIVPS is placed. The control of splicing by peptides or by other reagents has many advantages. It allows very tight control of splicing and doesn't require the temperature shifts presently employed in controlling some CIVPSs.

Inhibiting peptides or reagents and their derivatives (e.g., cyclic peptides, peptidomimetics) can be used to block splicing of toxic proteins in vivo, followed by removal of the blocking agent and in vitro splicing to synthesize the toxic protein. The protocols described in this example can be used to design drugs against pathogenic organisms that naturally have essential genes interrupted by IVPSs. Control of IVPSs by trans-acting inhibitors or activators which function within a living cell can be used to study gene function in any type of cell, tissue and organism or to generate controllable knockout mutations.

Approximately 36 IVPSs have been identified and sequenced and are available from public databases. Sequencing projects of small prokaryotic genomes (e.g. Mycobacterium tuberculosis and Methanococcus jannaschii) already account for the majority of published CIVPS cassettes. Host genes of these CIVPS cassettes are often involved in essential cellular functions as DNA replication, DNA expression or in metabolic genes. We expect to be able to take advantage of these naturally occurring IVPSs to block essential functions in pathogens using in vivo blocking peptides and their derivatives designed for the IVPS present in an essential pathogen gene. This may result in a potential effect on growth rate or may even be lethal to the pathogen. The emerging problem of acquired multiple resistance to existing drugs against Mycobacterium species can also be addressed in our system (Davis et al., EMBO J. supra; Zhang and Young, J. Antimicrob. Chemother. 34:313–319 (1994); Fsihi, et al., PNAS USA, 93: 3410–3415 (1996A)).

EXAMPLE 18

Cloning Of the Bacillus circulans WL-12 Chitinase A1 Chitin-Binding Domain

In this Example, the E. coli maltose-binding protein (MBP or M) in MIP fusion gene (see Example 10) was replaced with the chitin binding domain (CBD or B) of Bacillus circulans WL-12 Chitinase A1. The chitin binding domain (CBD) can be used as a fusion partner for affinity purification on a chitin matrix of a CBD-CIVPS-target protein fusion (see Example 20) or target protein-CIVPS-CBD fusion (see Example 15).

Designing A Synthetic Gene For The Chitin Binding Domain

The chitin binding domain (CBD) of Bacillus circulans WL-12 Chitinase A1 was synthetically constructed. The following eight oligonucleotides were ordered from organic synthesis division, New England Biolabs, Inc., Beverly, Mass. They comprise both strands of the CBD and overlap by 12 base pairs. The internal 6 oligonucleotides contain a phosphate group at the 5' end to allow ligation at the internal overlaps while the outer oligonucleotides were left without the phosphate group to stop concatamerization. Also, an Nde I overhang is present at the 5' end of the CBD and a Sac I overhang is present at the 3'end of the CBD for cloning purposes.

(1) 5'-TATGACGACAAATCCTGGTGTATCCGC-TTGGCAGGTC-3'
(SEQ ID NO:102)

(2) 5'-pATAAGCTGTGTT GACCTGCCAA-GCGGATACACCAGGATTTGTCGTCA-3'
(SEQ ID NO:103)

(3) 5'-pAACACAGCTTATACTGCGGGACAA-TTGGTCACATATAACGGC-3'
(SEQ ID NO:104)

(4) 5'-pTTTATACGTCTTGCCGTTATATGTGACC-AATTGTCCCGCAGT-3'
(SEQ ID NO:105)

(5) 5'-pAAGACGTATAAATGTTTGCAGCCCCAC-ACCTCCTTG GCA GGA-3'
(SEQ ID NO:106)

(6) 5'-pGGATGGTTCCCATCCTGCCAAGGAGG-TGTGGGGCTGCAAA CA- 3'
(SEQ ID NO:107)

(7) 5'-pTGGGAACCATCCAACGTTCCTGCCTT-GTGGCAGCTTCAATCG AGCT-3'
(SEQ ID NO:108)

(8) 5'-CGATTGAAGCTGCCACAAGGCAGGAA-CGTT-3'
(SEQ ID NO:109)

Annealing Reaction

These eight oligonucleotides were each resuspended to a final concentration of 10 picomoles/µl. Then, 200 picomoles of each oligonucleotide were mixed in 1 X Ligase buffer in a final volume of 200 µl. This oligonucleotide mix was incubated at 80° C. for 5 minutes to fully denature all the oligonucleotides. The mixture was then allowed to cool to room temperature in a room temperature water bath for 20 minutes.

Vector Preparation pHIP22/23 is a derivative of pMIP21 (see Example 9) that contains a six histidine affinity tag in place of M, the E. coli maltose-binding protein, upstream of the CIVPS, I-Pspl. The first residue serine-1 in the 1-Pspl CIVPS was substituted with alanine and residue alanine-535 was replaced by lysine residue. pHIP22/23 also has an unique Nde I site in front of the six histidine and an unique Sacl site following the six histidine residues. The DNA sequence encoding for the Bacillus circulans chitin binding domain (CBD) was inserted between the NdeI and SadI sites in place of the six histidine tag. 10 µl of pHIP22/23 were digested with 30U Nde I and 40U Sac l in 1 X NEB#4 supplemented with 0.1 mg/ml BSA in a final volume of 50 µl and incubated at 37° C. for 2 hours. 5 µl of 10X stop dye (25% Glycerol, 0. 15% bromphenol blue, 100 mM Tris pH8, 100 mM EDTA) were added and the reaction was loaded onto a 1 % agarose gel. The large vector band was cut from the gel and the agarose piece was melted at 65° C. for 10 minutes. Then, 10 µl 10X β-agarase buffer were added and the 100 μl mixture was moved to 40° C. After 10 minutes, 4 of β-agarase were added and the reaction was allowed to proceed for 2 hours at 40° C. This process removed the six histidines from the vector backbone and left an Nde I and a Sac I overhang.

Ligation, Transformation, And Screening

5 μl of annealed oligonucleotide mixture and 1 μl of gel purified vector were ligated in 1X T4 DNA Ligase buffer with 900 U T4 DNA Ligase in a final volume of 25 μl for 1 hour at room temperature. E.coli strain ER2420 was transformed by mixing 12.5 μl of the ligation mix with 50 μl competent ER2420 cells, chilling on ice for 10 minutes, heating at 42° C. for 3 minutes, and chilling on ice for 5 minutes. The cells were then plated on LB ampicillin plates and after overnight incubation at 37° C., 14 colonies were observed.

PCR amplification was utilized to screen for clones that carry the recombinant plasmid pBIP22/23. Individual colonies were picked into 100 μl of distilled water and boiled for 5 minutes to lyse the cell. The PCR mixture contains 1X Vent® DNA polymerase buffer, 200 mM of each dNTP, 10 picomoles of primer NEB#1224 and NEB#1233, 2.5 μl of cell lysate and 2 units of Vent® Exo⁻ DNA polymerase in a final volume of 50 μl. Amplification was carried out at 94° C. for 30 seconds, 65° C. for 30 seconds and 72° C. for 30 seconds for 30 cycles. 20 μl of each reaction was run out 0.7% agarose gel. The positive clones had bands corresponding to the three-part-fusion. (2.7 Kb)

Expression Of The CBD-I-PspI-ΔSal Paramyosin Fusion, BIP22/23

The clones were cultured in LB Media supplemented with 100 mg/ml ampicillin at 30° until OD$_{600}$ nm reached 0.5. To prepare lysate from uninduced cells, 1.0 ml of culture was pelleted and resuspended in 50 μl lysis buffer (2.5X Reducing SDS Sample Buffer and 4 M Urea). After addition of IPTG to a final concentration of 1 mM, the cultures were grown at 30° C. for 20 additional hours. 0.5 ml of induced culture was pelleted and resuspended in 50 ml lysis buffer. The pre-induction sample was frozen at −20° C. for 16 hours and the 20 hour sample was frozen at −70° C. for 15 minutes. All the samples were boiled for 5 minutes and 10 μl of each sample was electrophoresed on 4–20%SDS gels (ISS, Daiichi, Tokyo, Japan) with protein markers. A predicted band at about 98.5 kDa was observed in the Coomassie Blue stained gels for the induced samples that was not apparent in the uninduced sample.

EXAMPLE 19

Production Of Recombinant Polypeptides Containing C-Terminal Thioesters For Peptide Ligation One of the methods used in protein synthesis involves the in vitro ligation of two polypeptide chains to form a single polypeptide chain such that polypeptide with a thioester at its carboxyl terminus can form a native peptide bond with a second polypeptide with a N-terminal cysteine residue (Dawson et al, Science, 266:776–779 (1994)). The second peptide, in unmodified or modified form, can be obtained by chemical synthesis or purified from a recombinant source.

Figure 29:
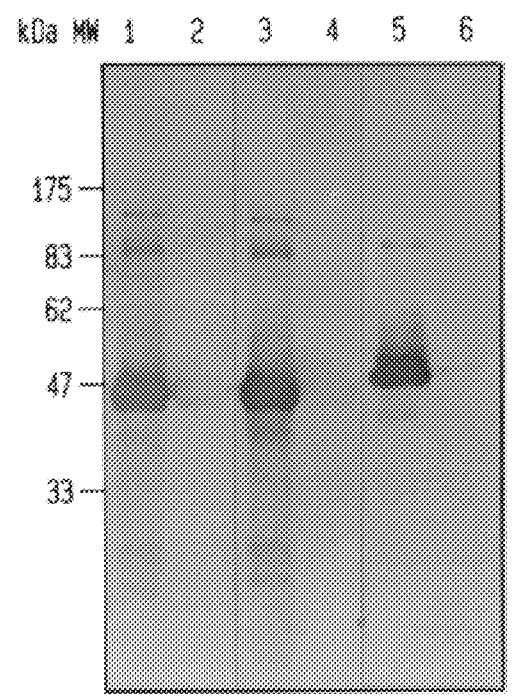
FIG. 29 shows the detection of ligation products by Western blot analysis. MYB fusion protein expressed from pMYBl 29 vector was immobilized onto chitin beads. MBP released from chitin beads after DTT-induced cleavage of MYB fusion protein was incubated with various peptides. Lane 1: [Arg8]-Vasopressin (AVP); Lane 2: Biotinyl-AVP; lane 3, Oxytocin; Lane 4, no peptide; Lane 5: CysGly-Elk1-2; and lane 6, Elk1-2-Cys. Rabbit antiserum to [Arg8]-Vasopressin (AVP) was used to probe the nitrocellulose membrane slice with lane 1 and 2; Rabbit antiserum to GP Oxytocin was used to probe the membrane slice with lane 3 and 4; and Rabbit antiserum to residues 350–360 of human p44 MAP kinase was used to probe the membrane slice with lane 5 and 6 to detect the presence of the amino acid sequence of Elk1-2. Prestained protein markers (M) (NEB) were shown on the left.
Figure 28:
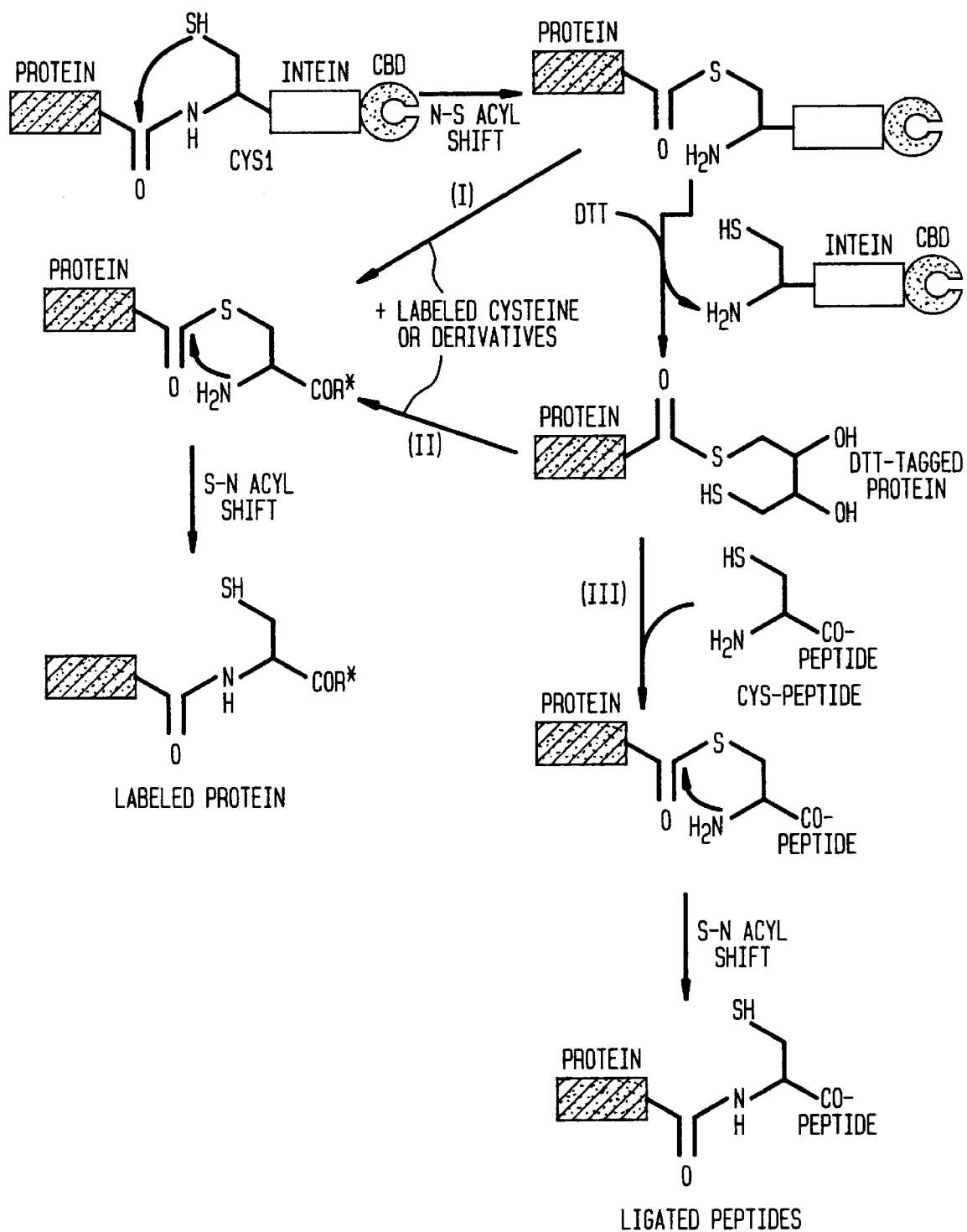
FIG. 28 shows the utilization of the intein-mediated reaction to generate a polypeptide with a thioester at its carboxyl terminus for protein synthesis. The DNA sequence encoding for a N-terminal portion (the target protein sequence) of a desired protein product is cloned into a expression vector containing the intein-CBD as described in Example 15. The target protein sequence is fused to the N-terminus of the intein which is in turn fused to the CBD. The target protein-intein-CBD fusion protein from the crude cell extract is purified by adsorption to a chitin affinity column. The intein is induced to undergo on-column self-cleavage (arrow) by a thiol compound such as 1,4 dithiothreitol (DTT). The target protein is released from the column and eluted as a pure protein with a thioester at its C-terminus. (I) A labeled cysteine or derivative can be used to induce the cleavage reaction resulting in the attachment of the labeled molecule to the C-terminus of the target protein. (II) Alternatively, the labeled cysteine can be used following a thiol-induced cleavage. (III) The initial nucleophilic attack on the thioester linkage by the sulfhydryl group of a cysteine at N-terminus of a second polypeptide generates a thioester bond between the two peptides. A spontaneous rearrangement (S-N shift) results in a native peptide bond between the two peptides, yielding the desired protein product.

As described by Chong et al. J. Biol. Chem., 271(36):22159–22168 (1996) and in Example 15, induction of cleavage activity at the N-terminal splice junction of a modified CIVPS such as the ("Sce VMA") intein from Saccharomyces cerevisiae with a thiol compound such as 1,4 dithiothreitol (DTT) results in a thioester bond at the carboxyl terminus of the polypeptide N-terminal to the CIVPS (FIG. 28). The utilization of an intein-mediated reaction to generate polypeptide thioester intermediates for protein synthesis would provide novel approaches for production of proteins and facilitate investigation of their biological functions. In this Example, we describe the use of the modified Sce VMA intein to generate a polypeptide, the E. coli maltose-binding protein (MBP) with a thioester at its carboxyl terminus, which can be used to ligate to a second polypeptide with a cysteine at its N-terminus (FIG. 28). We demonstrate the effectiveness of the ligation reaction using polypeptides with an unprotected N-terminal cysteine (FIG. 29).

Production Of The Maltose-binding Protein By Thiol-induced Cleavage

As described in Example 15, pMYB129 expresses a fusion protein MYB containing the E. coli maltose-binding protein (MBP or M), the modified Sce VMA intein (Y) and chitin-binding protein (B). Expression of the MYB fusion protein was induced as described in Example 15. 10 grams of cells were sonicated at 4° C. in 75 ml of column buffer (20 mM HEPES, pH8.0, 0.5 M NaCl, 0.1 mM EDTA) and the clarified cell extract was obtained by centrifugation at 12,000 rpm for 30 minutes. The fusion protein was immobilized onto chitin beads by passing the clarified extract through a column packed with 20 ml of chitin beads. Cleavage at the N-terminus of the intein was induced by incubation of the immobilized MYB protein with 30 mM DTT in column buffer for 16 hr at 4° C. The eluate was collected in 5 ml fractions and the protein concentration was determined by the Bradford assay.

Ligation Reactions

40 μl of the fraction 2 sample containing 5.5 mM of free MBP (42 kDa) was immediately incubated with each of the 5 peptides listed below at 270 μM final concentration in 80 μl final volume in 1X column buffer for 48 hrs at 4° C. As a control, a 40 μl aliquot of the fraction 2 sample was also mixed with 40 μl column buffer and incubated at 4° C for 48 hrs in the absence of peptide sample. All reactions were stopped by mixing the protein samples with ½ volume (40 μl) of 3X Protein Sample Buffer and boiling for 5 min.

List of peptides used in the ligation reactions described above:

(1) [Arg8]-Vasopressin or AVP (Catalog No. 8103, Peninsula Laboratories, Inc. Belmont, Calif.)

H$_2$N-CysTyrPheGlyAsnCysProArgGly—COOH
(SEQ ID NO:1 10)

(2) Biotinyl-AVP (Catalog No. 8126, Peninsula Laboratories, Inc.)

Biotin-CysTyrPheGlyAsnCysProArgGly—COOH)
(SEQ ID NO:111)

(3) Oxytocin (Catalog No. 8152, Peninsula Laboratories, Inc. Belmont, Calif.)

H$_2$N-CysTyrIleGlnAsnCysProLeuGly—COOH
(SEQ ID NO:1 12)

(4) CysGly-Elk1-2 (Organic Synthesis Division, New England Biolabs, Inc.)

H$_2$N-CysGlyMetGluLeuAsp AspLeuProLysLysArgLeuArgLys —COOH)
(SEQ ID NO:113)

(5) Elk1-2-Cys (Organic Synthesis Division, New England Biolabs, Inc.)

H$_2$N-MetGluLeuAspAspLeuProLysLysArgLeuArg LysCys—COOH)
(SEQ ID NO:1 14)

Western Blot Analysis

The ligation reactions were examined by Western blot analysis using antiserum specific for each of the peptides (FIG. 29). 2 ml of each sample were loaded on a 12% Tris-Glycine PAGE (Novex, Encinitas, Calif.) with prestained protein markers and the gel was electrophoresed at 100 Volts for 2 hours. The running buffer was 25 mM Tris, pH8.3, 190 mM glycine, 0.1% SDS. Proteins were transferred onto nitrocellulose membrane in transfer buffer (pH 9.5, 20 mM glycine, 20%methanol, 6 ml ethanolamine/4 liter). The nitrocellulose membrane was sliced into 3 pieces. The blots were probed by the rabbit antiserum (as described below) diluted 1000 fold in 1X TBSTT buffer (20 mM Tris, pH7.5, 150 mM NaCl, 0.2% Tween, 0.05% Triton-X 100) and detected using alkaline phophatase-linked anti-rabbit secondary antibody as described by the manufacturer (Promega, Madison, Wis.). Rabbit antiserum to [Arg8]-Vasopressin (or AVP) (IHC 8103, Peninsula Laboratories, Inc. Belmont, Calif.) was used to probe the membrane slice with lane 1 and 2; Rabbit antiserum to GP Oxytocin (IHC 8152, Peninsula Laboratories, Inc. Belmont, Calif.) was used to probe the second membrane slice with lane 3 and 4; and Rabbit antiserum to residues 350–360 of human p44 MAP kinase was used to probe the membrane slice with lane 5 and 6 to detect the presence of the amino acid sequence of Elk1-2.

As shown in FIG. 29, when [Arg8]-Vasopressin (AVP) (lane 1), Oxytocin (lane 3) or CysGly-Elk1-2 (lane 3) were incubated with MBP samples generated by the DTT induced cleavage reaction, antiserum specific to each of the peptides reacted strongly to protein species of approximately 44 kDa expected for the MBP-peptide ligation products. As expected, antiserum to GP Oxytocin showed very weak reactivity to the MBP control sample which was incubated with no peptide (lane 4). This control reaction indicates the background reactivity of the MBP to the antibody. In contrast to the reactions with unprotected N-terminal cysteine, when Biotinyl-AVP (with a N-terminal cysteine with the primary amino group protected by biotinylation) (lane 2), or Elk1-2-Cys (with a cysteine at its carboxyl terminus) (lane 6) were used in the reactions with MBP, the antisera detected only very weak reactivity (similar to the background in the control sample) to protein species of about 44 kDa, the expected size for the putative MBP-peptide ligation products. The data suggest that the Biotinyl-AVP and Elk1-2-Cys cannot be ligated to the MBP produced by the DTT-induced cleavage reaction.

These results indicate that a modified CIVPS such as the Sce VMA intein, can produce a polypeptide intermediate with a thioester at its carboxyl terminus and that peptides with unprotected N-terminal cysteine can become ligated to the polypeptide released from a CIVPS-mediated reaction as described above. This method can be utilized to synthesize as functional proteins such as enzymes that are toxic to the host cells. The cysteine-peptides may contain a specific label, non- peptide bond or unnatural amino acids. This method also provides a new tool to label the C-terminus of a target protein. A labeled cysteine or cysteine derivative can be used to induce a CIVPS-mediated cleavage reaction or added to a protein sample following a thiol-induced cleavage reaction. The labeled cysteine can become covalently attached to the C-terminus of the target protein (FIG. 28).

EXAMPLE 20

Chemical Control Of C-Terminal Cleavage Activity Of IVPS From *Saccharomyces Cerevisiae*

Figure 21:
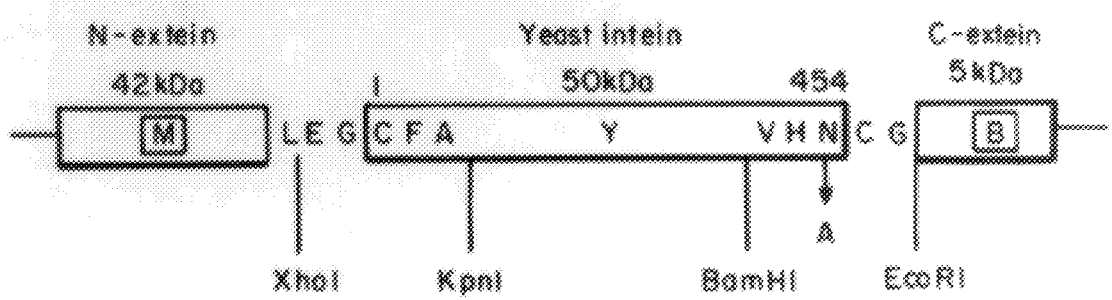
FIG. 21 illustrates pMYB129 fusion construct carrying N454A substitution.

In the MYB protein purification system described in Example 15, the yeast intein was modified so that the N-terminal splice junction of the intein can be induced to cleave by thiols. Therefore, using the MYB system for purification, the target protein is fused to the N-terminus (Cys1) of the intein (FIG. 21). This results in two potential disadvantages for production of recombinant proteins. First, the expression of the fusion protein varies with different target proteins, thus low level of the expression of the fusion protein could occur due to the inherent low expression of the target protein itself. Second, the target protein will always have a N-terminal methionine residue. As an alternative to the MYB system, we describe in this Example a protein purification system in which the target protein is fused to the C-terminus of the yeast intein and purified by inducing the C-terminal cleavage activity of the intein. A fusion protein, named BYT4 fusion, was expressed in which the chitin-binding domain (B) was fused to the N-terminus of the intein (Y) whose C-terminus is in turn fused to a target protein (T4 ligase was used as a example). The translation of the BYT4 fusion initiated with a sequence from the first 10 amino acid residues of *E. coli* maltose-binding domain, a known highly expressed protein in *E. Coli*, followed by the CBD sequence. The intein was modified by amino acid substitution so that the C-terminal cleavage reaction could be induced by the thiol-induced N-terminal cleavage reaction.

Construction Of The BYT4 Fusion

The first step was to modify the yeast intein so that it could be induced to undergo C-terminal cleavage. This was achieved by cassette mutagenesis of pMYB129 (Example 15).

1 μg of pMYB1 29 was digested at 37° C. for 2 hours in 15 μl of 1x BamHI buffer, and 1 unit of BamHI and 1 unit of AgeI. After electrophoretic separation on a 1% low melting agarose gel (FMC Corp., Rockland, Me.), the digested pMYB129 plasmid DNA was excised from the gel. The gel slices were melted at 65° C. for 10 min and then incubated at 42° C. for 10 min before 1 unit of β-agarase was added. After further 1 hr incubation, the purified pMYB129 digest was ready for DNA ligation reaction. Two complementary oligomers, MYB (N454Q/C455A) FW (5' GATCCCAGGTTGTCGTCCATGCATGCGGAGGCC-TG-3' (SEQ ID NO:1 15)) and MYB (N454Q/C455A)RV (5'AATTCAGGCCTCCGCATGCATGGACGACAACC-TGG-3' (SEQ ID NO:1 16)) were allowed to anneal to form a double-stranded linker as follows: 100 pmol of each of the oligomers were incubated in 20 μl of 1X annealing buffer at 90° C. for 4 min and slowly cooled to 37° C. Approximately 0.1 μg of the pMYB129 digest was ligated with 20 pmol of the annealed linker at 16° C. overnight in a 20 μl reaction mixture containing 1×T4 DNA ligase buffer, 80 units of T4 DNA ligase. The ligated DNA sample was used to transform *E.coli* strain ER2267. The resulting plasmid was named pMYB(Q/A). pMYB(Q/A) was double-digested with XhoI and PstI and the excised XhoI-PstI fragment containing the modified intein and CBD was then ligated with XhoI-PstI digested pCYB vector (the DNA pCYB vector was derived from the MYB fusion vector (Example 15) by replacing the maltose-binding protein sequence with multiple cloning site including NdeI, XhoI), replacing the original intein-CBD fragment to yield pCYB(Q/A).

The second step was to replace the CBD sequence in pCYB(Q/A) with the T4 DNA ligase gene, and placedthe CBD sequence at the N-terminus of the intein.

The gene for T4 DNA ligase was amplified by PCR and inserted into pCYB (Q/A) between the AgeI site and the PstI site to replace the CBD (B). Primer pairs 5'-GGTGGTACCGGTATTCTTAAAATTCTGAACGM-ATAGCA-3' (SEQ ID NO:1 17) and 5'-GGTGGTC- TGCAGTCATAGACCAGTTACCTCATGAAAATCA-
CC-3' (SEQ ID NO:118) were used in the PCR mixture
containing Vent® DNA polymerase buffer, supplemented
with 7 mM magnesium sulfate, 300 uM of each dNTP, 1 uM
of each primer, 20 µl T4 phage and 0.5 units of Vent® DNA
polymerase in 100 ul. Amplification was carried out by using
a Perkin-Elmer/Cetus (Emeryville, Calif.) thermal cycler at
95° C. for 1 min, 50° C. for 1 min and 72° C. for 2 min for
30 cycles.

The gene for CBD was amplified by PCR from pMYB129
(Example 15) in order to introduce NdeI and XhoI sites, and
the N-terminal 10 amino acid sequence of MBP in the
primers and to facilitate insertion of the amplified CBD gene
into the same sites of pCYB (Q/A). Primer pairs
5'-GGTGGTCATATGAAAATCGAAGAAGGTAAACT-
GACAAATCCTGGTGTATCCGCTTGG -3' (SEQ ID
NO:119) and 5'-GTGGTCTCGAG-
ACCGTTGTTACCGTTGTTTTGAAGCTGCCACAA-
GGCAGGAAC-3' (SEQ ID NO:120) were used in the PCR
mixture containing Vent® DNA polymerase buffer, supple-
mented with 7 mM magnesium sulfate, 300 uM of each
dNTP, 1 uM of each primer, 100 ng pMYB129 and 0.5 units
of Vent® DNA polymerase in 100 ul. Amplification was
carried out by using a Perkin-Elmer/Cetus (Emeryville,
Calif.) thermal cycler at 95° C. for 1 min, 50° C. for 1 min
and 72° C. for 1 min for 22 cycles.

Figure 30:
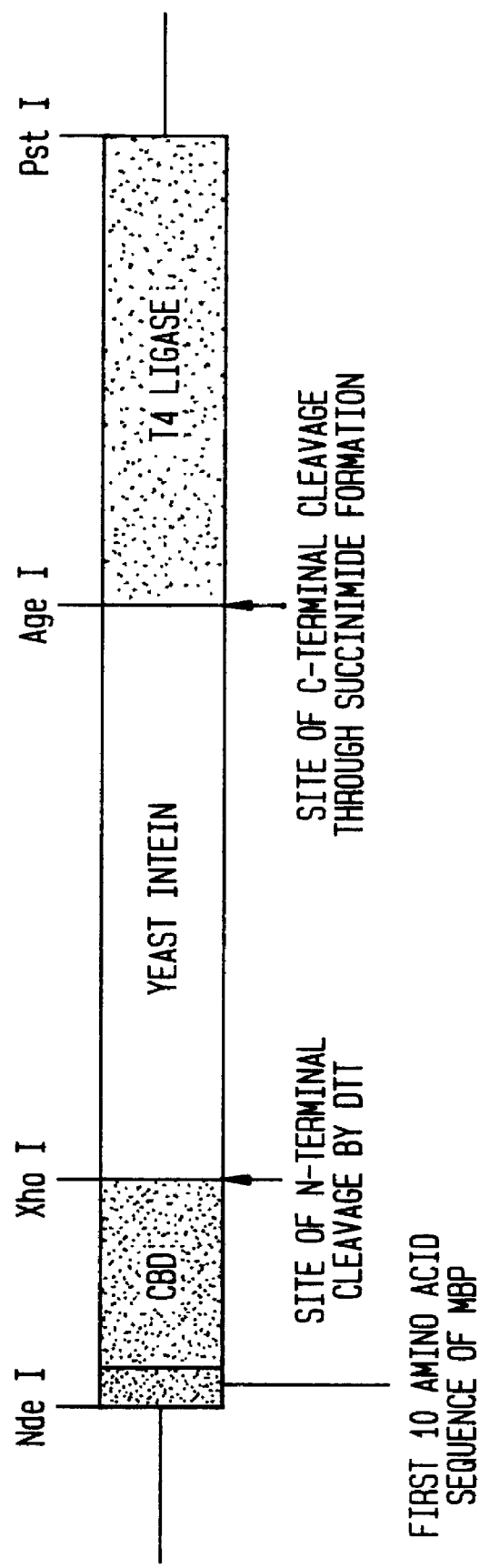
FIG. 30 is a schematic representation of the BYT4 fusion.

The PCR-amplified T4 DNA ligase gene described above
was double-digested with AgeI and PstI. The digested frag-
ment was electrophoretically separated on a 1% low melting
agarose gel (FMC Corp., Rockland, Me.) and ligated with
AgeI-PstI double-digested pOYB (Q/A) replacing the CBD
to yield pCYT4 in which the T4 ligase gene was linked to
the C-terminus of the intein. In the next step, the PCR-
amplified CBD gene described above was double-digested
with NdeI and XhoI. The digested fragment was electro-
phoretically separated on a 1% low melting agarose gel
(FMC Corp., Rockland, Me.) and ligated with NdeI-XhoI
double-digested pCYT4 vector to yield pBYT4 in which the
CBD gene was fused to the N-terminus of the intein. pBYT4
expressed a fusion protein, named BYT4 fusion protein
(FIG. 30).

Purification Of The Target Protein (T4 DNA Ligase) By The
Inducible C-Terminal Cleavage Activity Of The Modified
IVPS From *Saccharomyces cervevisiae*

The pBYT4 construct was used to illustrate the purifica-
tion of a target protein (T4 DNA ligase) using the inducible
C-terminal cleavage activity of the yeast intein. The *E. coli*
strain ER2267 harboring pBYT4 was cultured at 37° C. in
1 liter of LB medium supplemented with 100 µg/mL ampi-
cillin. The culture was allowed to grow until the OD at 600
nm reached 0.7. The induction was conducted by adding
IPTG to a final concentration of 0.4 mM. The induced
culture was grown at 20°C. for 16 hr before the cells was
harvested by centrifugation at 4000 rpm for 25 min. The cell
pellet was resuspended in 50 mL of the column buffer (20
mM HEPES, pH 8.0, 0.5 M NaCl). The cell suspension was
sonicated for 6 min and then centrifuged at 13,000 rpm for
30 min to give the clear lysate (around 50 µl).

The lysate was directly loaded onto 20 mL chitin beads
and the binding was allowed at 4° C. for 30 min. The beads
were then washed with 10 volumes of column buffer (20
mM HEPES, pH 8.0, 0.5 M NaCl). The column buffer (50
mL) containing 50 mM dithiothreitol (DTT) was then
quickly passed through the chitin beads to initiate the
on-column cleavage reaction. The flow was stopped and the
reaction continued at 4° C. for 16 hr. After incubation, the
protein sample was directly eluted from the column. The
fractions were combined and dialyzed in column buffer at
40° C. for 16 hr.

Figure 31:
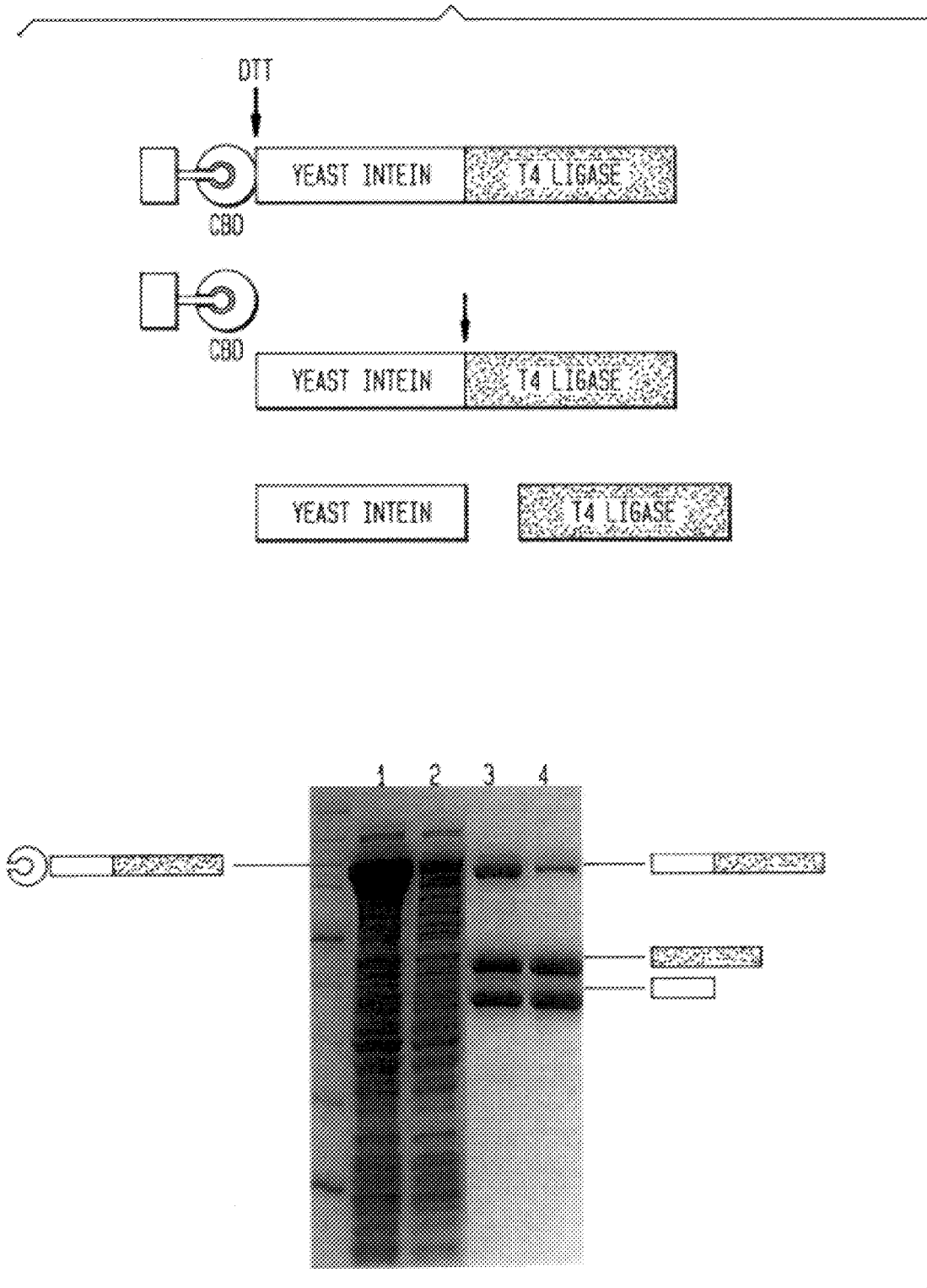
FIG. 31 shows the chemical control of the C-terminal cleavage of the yeast intein. The N-terminal cleavage of the yeast intein was induced by DTT (Example 15) which initiated the C-terminal cleavage reaction through succinimide formation by Asn454 thereby separating T4 ligase from the yeast intein. Lane 1: crude cell extract; lane 2: flow-through; lane 3: elution from chitin beads after 16 hr. incubation with DTT; lane 4: fractions from lane 3 after 16 hr. dialysis.

As shown on SDS-PAGE (FIG. 31), the on-column cleav-
age reaction resulted in elution of the N-terminal cleavage
product, i.e., the intein-T4 ligase fusion, a significant
amount of which also underwent the intein C-terminal
cleavage reaction (i.e., through succinimide formation by
Asn454 (Chong, et al.,*J. Biol. Chem.,* 271(36):22159
(1996)) yielding the intein and T4 DNA ligase (FIG. 31, lane
3). After 16 hr dialysis, the remaining intein-T4 ligase fusion
underwent further cleavage to yield the intein and T4 ligase
(FIG. 31, lane 4).

It is apparent that the method described above did not
result in complete purification of T4 ligase by one chro-
matographic step. Nevertheless, it did simplify the purifica-
tion of T4 ligase from crude cell lysate into mere separation
of the intein from T4 ligase.

Figure 32:
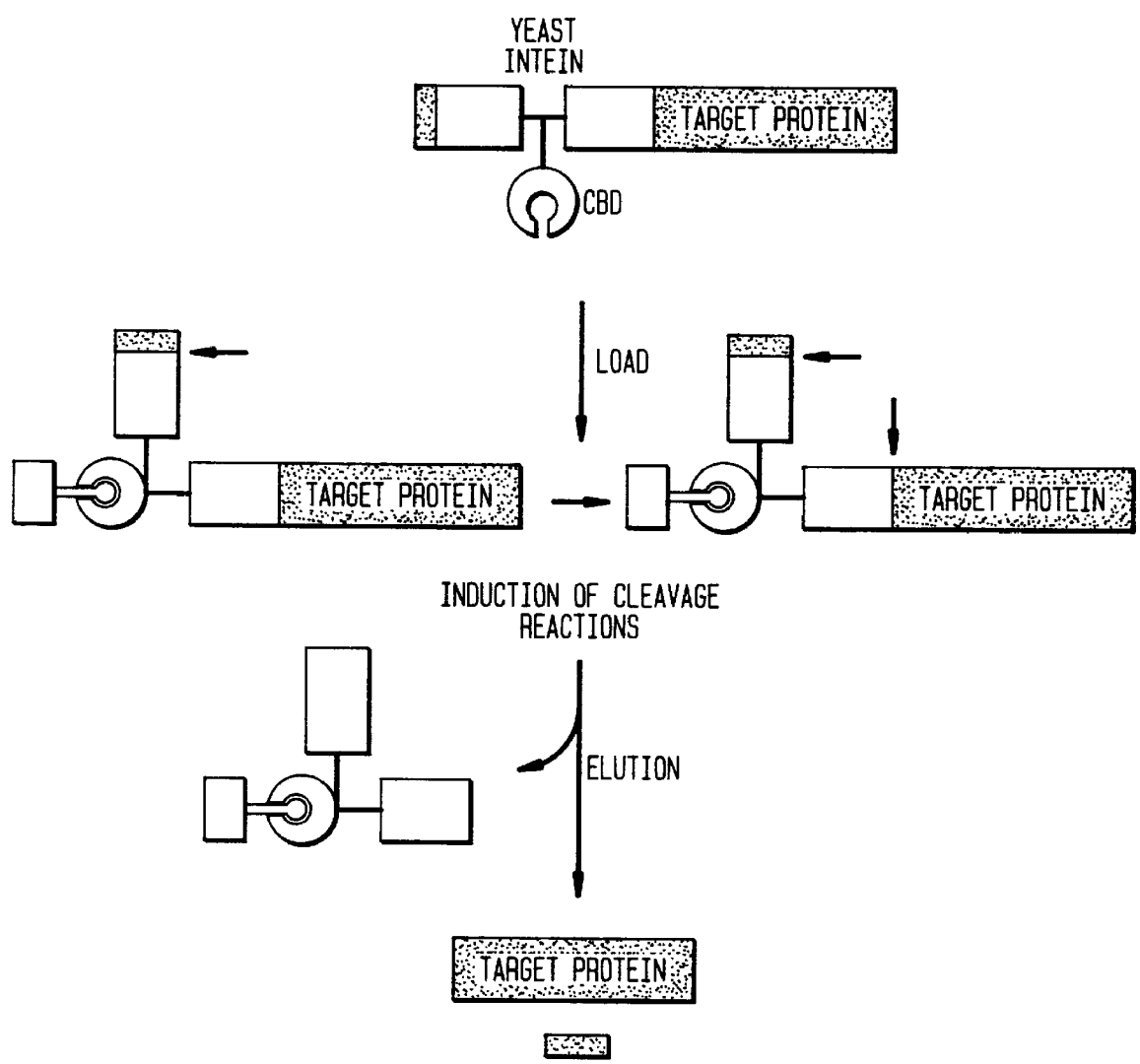
FIG. 32 is a scheme showing by inserting an affinity domain in the yeast intein and inducing cleavage reactions on-column, a target protein can be purified in one or two chromatographic steps.

In order to further improve the separation and purification
of the target proteins, an affinity tag can be inserted into the
modified yeast intein and both N- and C-terminal cleavage
reactions can be induced while the fusion protein is immo-
bilized on the column (FIG. 32) . It is therefore possible that
by utilizing the N- and C-terminal cleavage activities of the
modified yeast intein, a target protein can be purified in a
single chromatographic step, or at most, by two affinity
columns (FIG. 32).

EXAMPLE 21

Deletion Of The Central Region Including The
Endonuclease Motif Of IVPS From *Saccharomyses
cervisiae*

Figure 33:
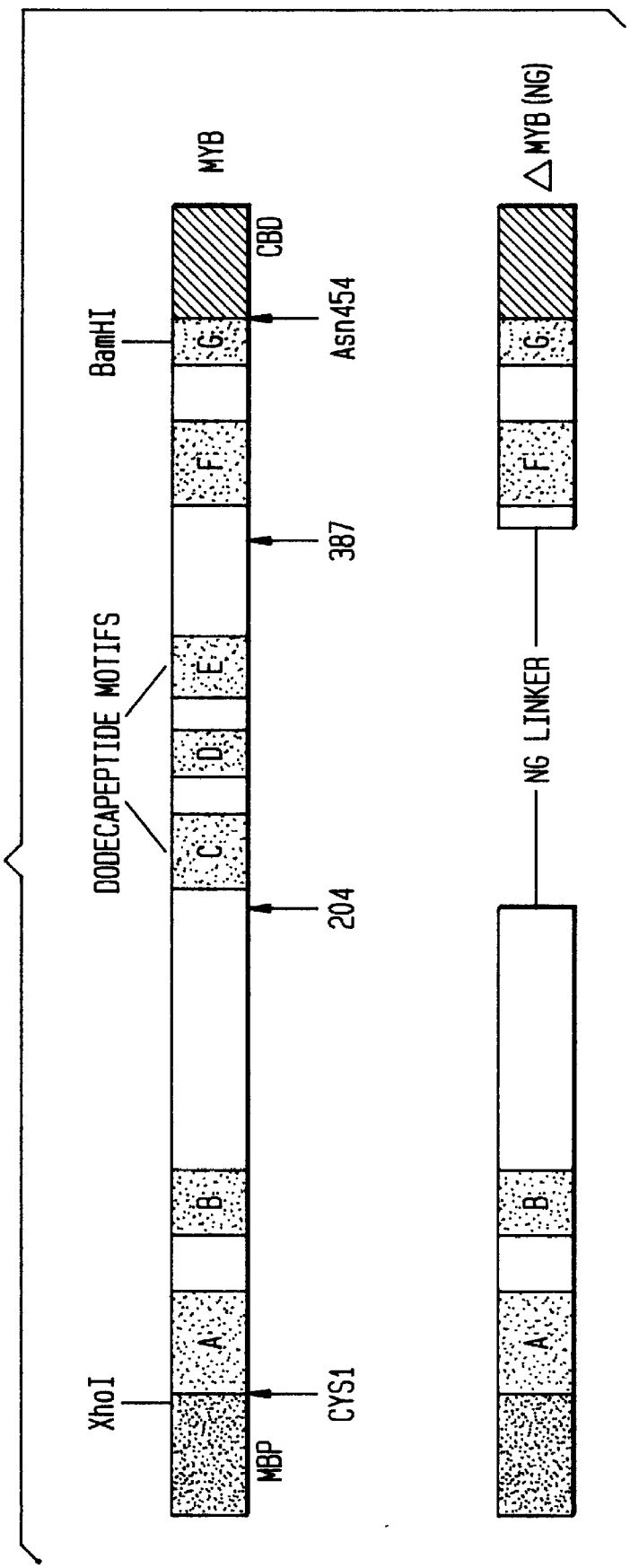
FIG. 33 illustrates the conserved motifs of the yeast intein and the positions of the deletion.

Many IVPS elements (inteins) contain endonuclease
motifs at the central region of their sequences. Sequence
alignment reveals that the yeast intein contains 7 conserved
motifs, A through G, with motifs A and G being the splice
junction motifs containing Cys-1 and Asn-455, and motifs C
and E being the endonuclease motifs (FIG. 33)
(Pietrokovsky, *Protein Science,* 3:2340 (1994)). In this
Example, we demonstrate that a large portion of the central
region including the endonuclease motifs of the yeast intein
may be deleted with the remaining intein sequence still
being capable of catalyzing efficient protein splicing reac-
tions.

Construction Of pMYB pMYB was derived from pMYT1 (Example 15). The *E.
coli* thioredoxin sequence in pMYT1 was replaced with a
chitin-binding domain (B) from *Bacillus circulans* yielding
pMYB 129 (Example 15). pMYB1 29 was digested with
BamHI and AgeI and ligated with complementary oligmers,
5'-GATCCCAGGTTGTTGTACACAACTGTGGTGG-
CCTGA-3' (SEQ ID NO:121) and
5'-CCGGTCAGGCCACCACAGTTGTGACAACAACC-
TGG-3' (SEQ ID NO:1 22) to yield pMYB, in which the
Asn454Ala mutation in the C-terminal splice junction of
pMYB129 was changed back to the wild-type asparagine
residue.

Construction Of pΔMYB

Figure 34:
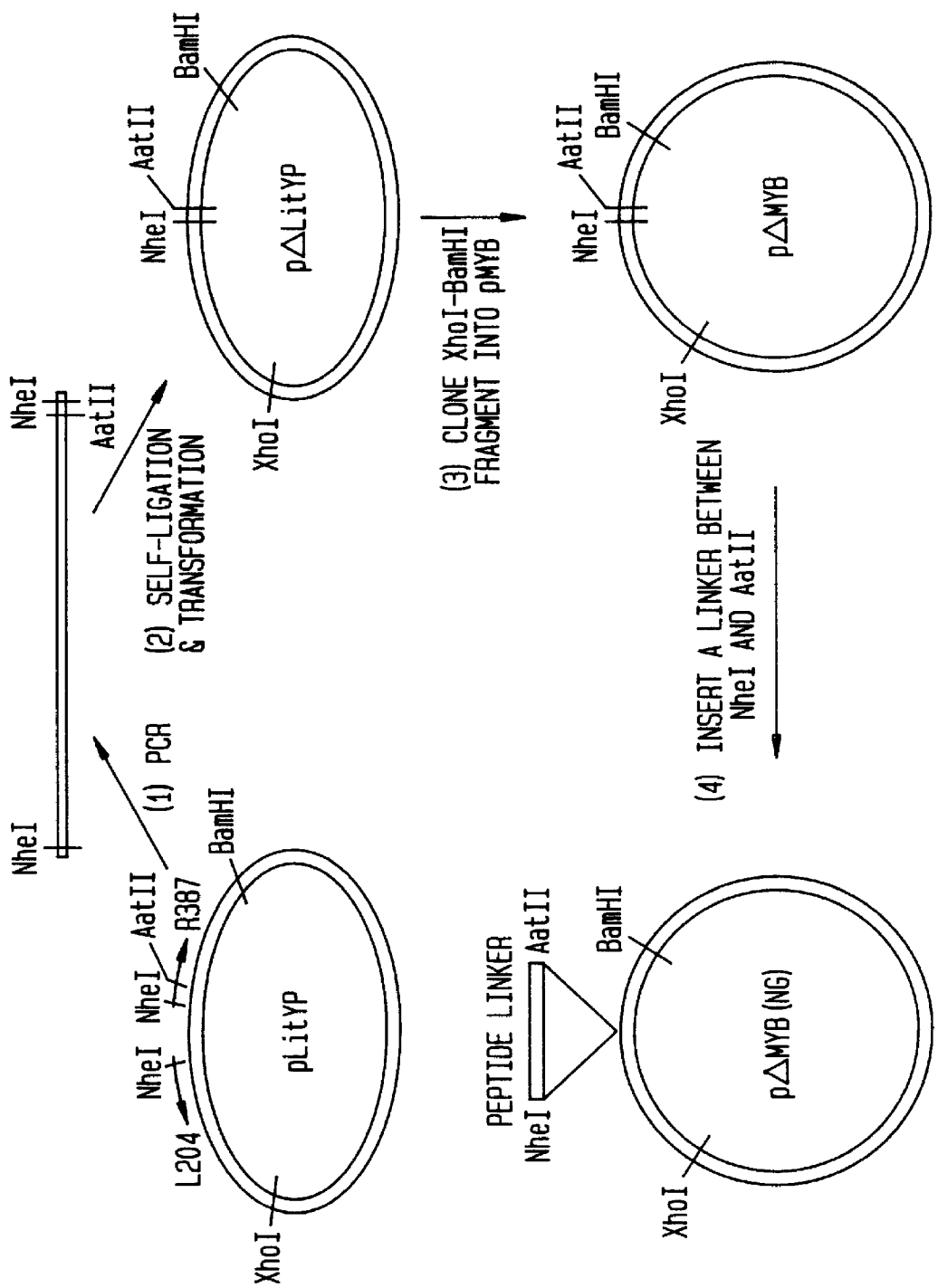
FIG. 34 illustrates the construction of p ΔMYB.

Deletions were made by the polymerase chain reaction
(PCR) using pLitYP containing an engineered BamHI site in
the intein sequence (Example 15) as a template. The
mutagenesis scheme is shown in FIG. 34. The primer
sequences are: L204, 5'-GGTGG- TGCTAGCACCT-
TCAATGGTGAGATGAAACTT (SEQ ID NO:123); R387,
5'-GTTGTTGCTAGCGGTGGTGACGTCGGTGGAGA-
TGTTTTGCTTAACGTT-3' (SEQ ID NO:124). Polymerase
chain reaction mixtures (100 µl) contained Vent® DNA polymerase buffer, 3 mM MgSO$_4$, 300 μM each of the 4 dNTPs, 10 μM of each primer, 50 ng of pLitYP and 0.5 units of Vent® DNA polymerase. Amplification was carried out for 20 cycles using a Perkin-Elmer/Cetus (Emeryville, Calif.) thermal cycler at 94° C. for 1 min, 50° C. for 1 min, and 72° C. for 4 min (FIG. 24, step (1)). The product was digested with NheI and then self-ligated by T4 ligase to form a circular plasmid pΔLitYP which was subsequently amplified by transforming into E. coli ER2267 (FIG. 34, step (2)). The XhoI and BamHI fragments from pΔLitYP were ligated with pMYB digested with XhoI and BamHI to replace the wild-type sequence, yielding pΔMYB (FIG. 34, step (3)).

pΔMYB was digested with NheI and AatII and ligated with the complementary oligomers, 5'-CTAGCAACAACGGTAACGGCCGTAACGGTGGC- AACAACGGTGGCAACAACGACGT-3' (SEQ ID NO:125), and 5'-CGTTGTTGCCACCGTTGTTG- CCACCGTTACGGCCGTTACCGTTGTTG-3' (SEQ ID NO:126), to yield pDMYB(NG) in which a peptide linker sequence encoding Ala-Ser-Asn-Asn-Gly-Asn-Gly-Arg-Asn-Gly-Gly-Asn-Asn-Gly-Gly-Asn-Asn-Asp-Val (SEQ ID NO:127) (NG linker) was inserted into the intein deletion site (FIG. 34, step (4)).

Splicing of pΔMYB

The procedures for protein expression and purification were the same as described in Example 15 except that the E. coli strain ER2426 (Elisabeth Raleigh, New England Biolabs, Inc.) was used instead. The crude cell extracts (FIG. 35, lane 4) and amylose-purified proteins (FIG. 35, lane 5) were analyzed by SDS-PAGE, followed by Coomassie blue staining.

Figure 35:
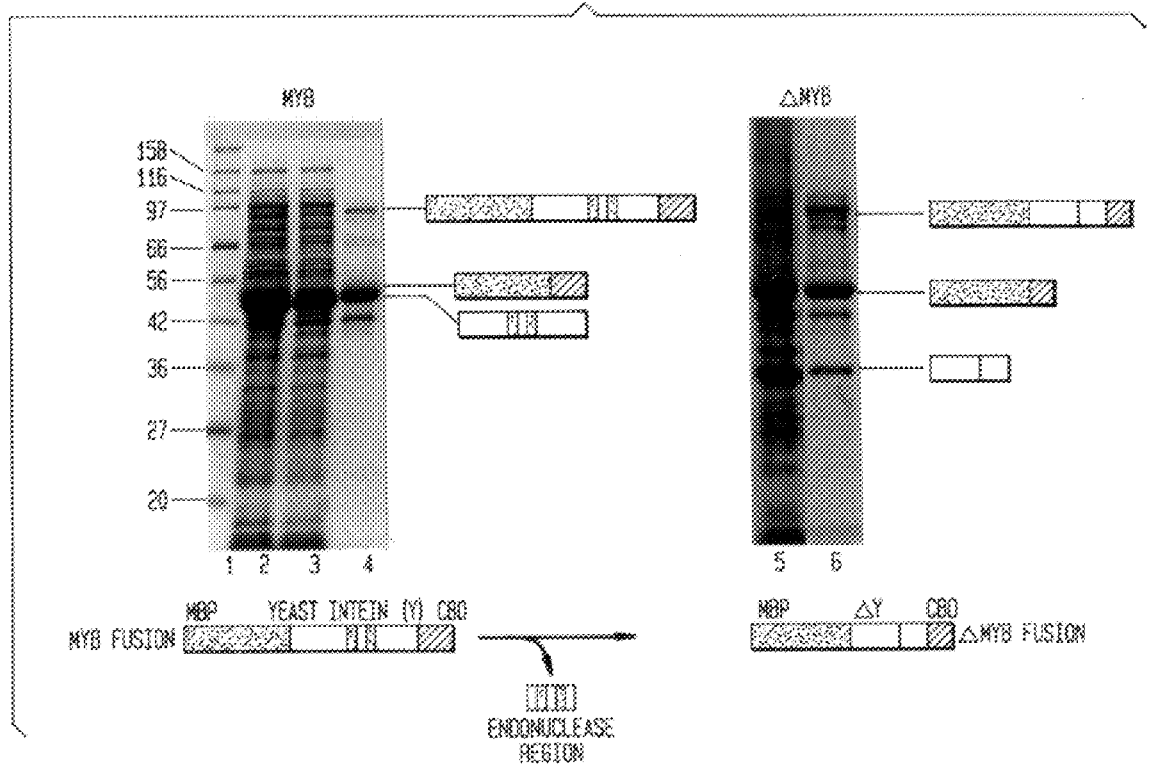
FIG. 35 illustrates in vivo splicing of the full-length yeast intein in MYB fusion and the deletion mutant in AMYB fusion. Lane 1: NEB broad-range molecular weight marker (kDa); lane 2 & 5: crude cell extract; lane 3: flow-through; lane 4 & 6: amylose-purified proteins.

As shown in FIG. 35, in the crude extract of the full-length yeast intein in MYB (lane 2), splicing proceeded completely yielding the ligated exteins (MBP-CBD fusion, 51 kDa) and excised yeast intein (Y, 50 kDa), amylose-purified proteins showed predominantly MBP-CBD fusion (lane 4). In the crude extract of the intein deletion mutant in ΔMYB (lane 5), splicing proceeded efficiently but not completely, yielding the ligated exteins (MBP-CBD fusion, 51 kDa) and excised intein mutant (ΔY, ~33 kDa), amylose-purified proteins (lane 6) showed predominantly MBP-CBD fusion and some unspliced precursors (ΔMYB).

In this Example, it is demonstrated that the N- and C-terminal regions of the yeast intein including motifs A, B, F and G contain sufficient structural and catalytic elements for splicing whereas the central region of the intein including the dodecapeptide motifs C and E and motif D are not essential for protein splicing. While this result may apply to other IVPS elements with endonuclease motifs, it also has significant importance for intein-related applications. For instance, when utilizing the N- and C-terminal cleavage activities to purify recombinant proteins, a low expression level of the fusion protein could sometimes occur. One of the reasons might be that the yeast intein has a relatively large molecular weight (50 kDa). Use of the splicing-proficient intein mutant described in this Example may help to improve the protein expression. Another possible application is that one may replace the intein endonuclease domain with other functional domains such as an affinity domain or ligand recognition domain so that the modified intein will obtain new functions such as binding to affinity resin in addition to protein splicing.

EXAMPLE 22

Use Of Self-cleaving Intein Mutants To Elute Peptide-linked Bacteriophages From Their Targets During Phage Display The display of short peptides on the surface of bacteriophage Ml 3 has been previously described (Cortese, Curr. Opin. Biotechnol, 6:73–80 (1995)). Screening libraries of phage-bound peptides by a process called biopanning allows the rapid identification of peptide ligands for a variety of target molecules such as antibodies, enzymes and cell-surface receptors. One problem with current protocols, however, is that high affinity peptide ligands are difficult to elute from their targets and therefore are not easily identified. One attempt to overcome this obstacle involves inserting a protease cleavage site between the target and its solid support and then eluting the phage by treatment with the corresponding protease (Wrighton, Science, 273:458–463 (1996)). One disadvantage of this method, however, is the phage itself could be sensitive to the protease used for elution.

In accordance with the present invention, the use of a self-cleaving intein replaces a protease cleavage site and resolves this problem. In this Example, we describe how inteins can be used to elute phage displayed peptides from their targets during biopanning. This method allows the separation of even extremely tightly bound peptides from their targets without reducing the viability of the bacteriophage displaying the peptide.

As an example of this method, a biopanning target of E.coli maltose binding protein (MBP) fused N-terminally to an intein self-cleaving element and a chitin binding domain (MBP-intein-CBD) was used to optimize conditions for binding to phage-displayed peptides, as well as conditions for subsequent elution of the bound peptides from its target by 1,4-dithiothreitol (DTT)-induced autocleavage of the intein.

Escherichia coli strain ER2272 harboring a plasrnid expressing the MBP-intein-CBD fusion plasmid (pMYB129, see Example 15) was grown at 37° C. to mid log and expression of the fusion protein induced with 1 mM IPTG for 2.5 hours. Cells were lysed by sonication in column buffer [20 mM Tris-HCl (pH 8.0), 500 mM NaCl, 0.1 mM EDTA, 0.1% (v/v) Triton X-100] and the cell debris removed by centrifugation. Chitin beads (0.2 ml) were then added to 1 ml of supernatant and incubated at 4° C. for 45 min. Beads were washed with 1 ml cold column buffer 5 times to remove unbound proteins and then resuspended in 1 ml TBST [50 mM Tris-HCl (pH 7.5), 150 mM NaCl, 0.1% (v/v) Tween-20]. 10 μl (1 ×10$^{11}$ phage) of Ph.D.-12 Phage Display Peptide Library were added and the mix was incubated with shaking at room temperature for one hour. Unbound phage were then removed by 10 washes with 1 ml TBST and the beads resuspended in 0.5 ml cleavage buffer [20 mM Tris-HCl (pH 8.0), 50 mM NaCl, 0.1 mM EDTA] containing 10 mM DTT. After a 2 hour incubation at room temperature, the chitin beads were removed from the eluted phage by centrifugation (1000 rpm for 2 min. at 4° C.) and washed once with 0.5 ml cleavage buffer to extract any remaining eluted phage.

Pooled phage was then titered to determine elution efficiency (Table 2), amplified in ER2537 and subjected to 2 more rounds of biopanning. Conditions for biopanning in these subsequent rounds were identical to the first except that the Tween-20 concentration in TBST was raised to 0.5% (v/v). Control experiments in which MBP was directly coated onto polystyrene plates and eluted non-specifically with 0.2 M glycine-HCl (pH 2.2) or specifically with 0.1 mM maltose, were also carried out.

TABLE 2

Efficiency of phage elution during successive rounds of biopanning.

| | Percentage of Input Phage Eluted[1] |
|---|---|
| Intein Elution (DTT) | |
| Round 1 | .007 |
| Round 2 | .03 |
| Round 3 | .21 |
| Glycine Elution | |
| Round 1 | .004 |
| Round 2 | .21 |
| Round 3 | 4.3 |
| Maltose Elution | |
| Round 1 | .001 |
| Round 2 | .02 |
| Round 3 | .92 |

[1](Number of plaque forming units eluted)/(number of phage particles added) × 100.

After 3 rounds of biopanning, 10 clones isolated by each of the three elution methods were sequenced (FIG. 36). Although most the peptides eluted by 0.2 M glycine (pH 2.2) or by maltose contain a high percentage of histidines and prolines, no clear consensus sequence is observed. A fourth round of biopanning might be necessary to further elucidate a strong mimitope for maltose binding protein. The clones eluted from MBP-intein-CBD by DTT, however, show a very clear consensus sequence. 8 out of 10 clones all contain the identical sequence which contains a 4 amino acid disulfide-constrained loop. This result suggests that a consensus sequence for MBP binding has been isolated by this elution method. It is interesting to note that this consensus sequence was never found in the clones eluted by the other 2 methods. Therefore, it is possible that by eluting the peptide-displaying phage from its target by intein cleavage, we have isolated a high affinity sequence which was not elutable by common methodologies. Further analysis of the isolated clones will be done to prove that this peptide sequence binds to MBP rather than the intein-CBD portion of the fusion protein as well as to characterize the binding affinity of the peptide.

EXAMPLE 23

Construction Of E. coli Vectors pBYC6 And pCYB166 To Facilitate Studying The Interactions Of The Target Protein With Other Peptides In this Example, we describe the construction of two E.coli expression vectors containing the intein (Y)- chitin binding domain (CBD or B) fusion for the purpose of screening or studying the interaction between a protein of interest and another polypeptide or ligand. (FIG. 38A and FIG. 38B). A polylinker sequence (MCS or C) was added for cloning of the protein of interest. pBYC6 is for expression of a CBD-intein-target protein fusion, and pCYB166 is for expression of a target protein-intein-CBD fusion. For consistent performance, a linker sequence, which was destined for controllable cleavage regardless of the sequence of the target protein, was engineered between the intein cleavage site and the target protein.

Construction Of the C-Terminal Fusion Vector pBYC6 pBYT4 is a 8.0 Kb vector that expresses a CBD-intein-T4 DNA ligase fusion protein (Example 20). Forward Primer 5'CCGGTTCCGGGAGCTCGTAACTGCA-3' (SEQ ID NO:128) and reverse primer 5'-GTTACGAGCTCCCGGAA-3' (SEQ ID NO:129) were used to form a linker to introduce a SacI site into pBYT4, replacing the T4 DNA Ligase gene (T4). The 50 ul annealing mixture contained 1X T4 DNA Ligase Buffer and 100 pmols of each primer. The reaction mixture was incubated at 65° C. for 15 minutes, and then slowly cooled to room temperature. 1 ug of pBYT4 DNA was digested with 2 units of AgeI in 30 ul of 1X NEB buffer 4 at 25° C. for 60 minutes. 20 units of PstI were then added to the sample and incubated at 37° C. for 60 minutes. 3 ul of agarose gel loading dye was added to the sample and the DNA fragments were separated by electrophoresis on a 1 % low melting agarose gel. Digested pBYT4 DNA was recovered from the low melting agarose gel by incubation at 65° C. for 10 minutes, 42° C. for 10 minutes, and the addition of 1 unit of β-agarase to the 100 ul volume of melted agarose gel at 42° C. for 60 minutes. Ligation of 0.5 μg of the digested pBYT4 DNA with 42 pmols of the linker was carried out at 16° C. for 4 hours in 50 ul volume with addition of 5 ul 10X T4 DNA ligase buffer and 3 ul T4 DNA Ligase. E.coli strain ER2504 was transformed by mixing 150 ul of competent cells with 15 ul of ligation sample on ice for 10 minutes, heating at 42° C. for 2 minutes, adding 1 ml of LB media (10 grams/liter tryptone, 5 grams/liter yeast extract, 10 grams/liter NaCl, 1 gram/liter Dextrose, 1 gram/liter $MgCl_2 \times 6H_2O$ pH7.2 at 25° C.) and incubating at 37° C. for 60 minutes. The samples were plated onto LB plates, supplemented with 100 ug/ml ampicillin, and incubated overnight at 37° C. Transformants were cultured in LB medium, supplemented with 100 ug/ml ampicillin, for extraction of plasmid DNA using the Qiaprep250 kit (Qiagen, Studio City, Calif.) Positive clones were determined by restriction digest analysis: 1 ug of extracted DNA, 20 units NdeI, 20 units SacI in 30 ul of 1X NEB buffer 4 at 37° C. for 120 minutes. 3 ul of agarose gel loading dye was added to the sample and the DNA fragments were separated by electrophoresis on a 1% low melting agarose gel. The positive clones had 2 Kb bands corresponding to the digestion of the SacI site, which was introduced by the cassette, and the NdeI site downstream of the chitin binding domain. One positive clone was designated pBYC5.

The linker sequence which was added between the C-terminus of the intein and the multiple cloning site was obtained from the pMAL-c2 vector. 5'-GAGCTCGAACAACAACAACAaTAACAATAAC-AACAACCTCGGGATCGAGGGAAG-GATTTCAGAATTCGGATCCTCTAGAGTC-GACCTGCAGGCAAGCTTG . . . lac Z-3' (SEQ ID NO:130). 1 ug of pMAL-c2 DNA was digested with 20 units of SacI and 20 units of EcoRV in 30 ul of 1X NEB buffer 1, supplemented with 100 ug/ml of BSA at 37° C. for 120 minutes. 1 ug of pBYC5 DNA was digested with 20 units of SacI and 20 units of EcoRV in 30 ul of 1X NEB buffer 1, supplemented with 100 ug/ml of BSA at 37° C. for 120 minutes. 3 ul of agarose gel loading dye was added to each sample and the DNA fragments were separated by electrophoresis on a 1 % low melting agarose gel. Digested 2 Kb pBYC5 fragment DNA and the 4.9 Kb pMAL-c2 vector DNA fragment was recovered from the low melting agarose gel by incubation at 65° C. for 10 minutes, 42° C. for 10 minutes, and the addition of 1 unit of β-agarase to the 100 ul volume of melted agarose gel at 42° C. for 60 minutes. Ligation of 0.5 μg digested pBYC5 fragment DNA with 0.1 μg of pMAL-c2 vector DNA was carried out at 16° C. for 4 hours in 35 ul volume with the addition of 3.5 ul 10X T4 DNA ligase buffer and 1.5 ul T4 DNA Ligase. E. coli strain ER2504 was transformed by mixing 150 ul of competent cells with 15 ul of ligation sample on ice for 10 minutes, heating at 42° C. for 2 minutes, adding 1 ml of LB media (10 grams/liter tryptone, 5 grams/liter yeast extract, 10 grams/liter NaCl, 1 gram/liter Dextrose, 1 gram/liter MgCl$_2$ ×6H$_2$O pH7.2 at 25° C.) and incubating at 37° C. for 60 minutes. The samples were plated onto LB plates, supplemented with 100 ug/ml ampicillin, and incubated overnight at 37° C. Transformants were cultured in LB medium, supplemented with 100 ug/ml ampicillin, for extraction of plasmid DNA using the Qiaprep250 Kit (Qiagen, Studio City, Calif.) Positive clones were determined by restriction digest analysis: 1 ug of extracted DNA, 20 units SacI, 20 units *EcoRV* in a 30 ul of 1X NEB buffer 4 supplemented with 100 ug/ml of BSA at 37° C. for 120 minutes. 3 ul of agarose gel loading dye was added to the samples and the DNA fragments were separated by electrophoresis on a 1% low melting agarose gel. The positive clones had bands corresponding to the size of the fragment removed from the pBYC5 vector (2 Kb) and from the pMAL-c2 vector (4.9 Kb) One positive clone was designated pBYC6, see FIG. 38(A). Both the linker and the polylinker (C) regions in the pBYC constructs were sequenced.

Construction Of N-Terminal Fusion Vector pCYB166

The construction of the N-terminal fusion vectors was similar to that of the C-terminal vectors, in that a SacI site was added prior to insertion of a linker from pMAL-c2. pCYB1 is a 6.8 Kb *E. coli* expression vector that is designed for insertion of a target gene into the polylinker (MCS) in-frame with the N-terminus of a modified Sce VMA intein (Y) linked to the chitin-binding domain (B). The modified Sce VMA intein contains a Seu 454 Ala substitution (Example 15). Forward Primer 5'-TCGACCCCGGGGGGAGCTCCC-3'(SEQ ID NO:131) and reverse primer 5'-TCGAGGGAGCTCCCCCCGGGG-3' (SEQ ID NO:132) were used to form a linker cassette to introduce a SacI site into pCYB1 between the polylinker (MCS) and the intein (Y). The 50 ul annealing mixture contained 1X T4 DNA Ligase Buffer and 100 pmols of each primer. The reaction mixture was incubated at 650C for 15 minutes, and then slowly cooled to room temperature. 1 ug of pCYB1 DNA was digested with 20 units of SalI and 20 units of XhoI in 30 ul of 1X SalI buffer, supplemented with 100 ug/ml of BSA at 370° C. for 120 minutes. 3 ul of agarose gel loading dye was added to the sample and the DNA fragments were separated by electrophoresis on a 1 % low melting agarose gel. The pCYB1 DNA fragment (6.8 Kb) was recovered from the low melting agarose gel by incubation at 65° C. for 10 minutes, 42° C. for 10 minutes, and the addition of 1 unit of β-agarase to the 100 ul volume of melted agarose gel slice at 42° C. for 60 minutes. Ligation of 0.5 μg pCYB1 DNA with 42 pmol of the linker cassette was carried out at 160° C. for 4 hours in 50 ul volume with the addition of 5 ul 10X T4 DNA ligase buffer and 3 ul T4 DNA Ligase. *E.coli* strain ER2504 was transformed by mixing 150 ul of competent cells with 15 ul of ligation sample on ice for 10 minutes, heating at 42° C. for 2 minutes, adding 1 ml of LB media (10 grams/liter tryptone, 5 grams/liter yeast extract, 10 grams/liter NaCl, 1 gram/liter Dextrose, 1 gram/liter MgCl$_2$ ×6H$_2$O, pH7.2 at 25C) and incubating at 37° C. for 60 minutes. The samples were plated onto LB plates, supplemented with 100 ug/ml ampicillin, and incubated overnight at 37° C. Transformants were cultured in LB medium, supplemented with 100 ug/ml ampicillin, for extraction of plasmid DNA using the Qiaprep250 kit (Qiagen, Studio City, Calif.) Positive clones were determined by restriction digest analysis: 1 ug of extracted DNA, 20 units SacI, 20 units PstI in a 30 ul of 1X NEB buffer 1 supplemented with 100 ug/ml ampicillin at 370C for 120 minutes. 3 ul of agarose gel loading dye was added to the samples and the DNA fragments were separated by electrophoresis on a 1% low melting agarose gel. The positive clones had a 1.5 Kb band corresponding to the digestion of the SacI site, which was introduced by the cassette, and the PsfI site downstream of the chitin-binding domain. One positive clone was designated pCYB165.

Insertion Of Linker Sequence Into pCYB166

The linker sequence which was added between the multiple cloning sites (MCS) and the N-terminus of the intein was excised from the pMYB1 29 vector (Example 15). The MCS/linker sequence 5'-CATA TGGCTAGCTCGCGAGT CGACCCCGGGGGGAGCTCCGAGCTCGAA-CAACAACAACAATAACAATAACAACAAC-CTCGGGATCGAGGGAAGGGGTACGCTCGAGGGG (intein)-3' (SEQ ID NO:133). See FIG. 38(B) 1 ug of pMYB1 29 DNA was digested with 20 units of SacI and 20 units of PstI in 30 ul of 1X NEB buffer 1, supplemented with 100 ug/ml of BSA at 370° C. for 120 minutes. 1 ug of pCYB165 DNA was digested with 20 units of SacI and 20 units of PstI in 30 ul of 1X NEB buffer 1, supplemented with 100 ug/ml of BSA at 37° C. for 120 minutes. 3 ul of agarose gel loading dye was added to each sample and the DNA fragments were separated by electrophoresis on a 1 % low melting agarose gel. Digested pMYB129 fragment DNA and pCYB165 vector DNA was recovered from the low melting agarose gel by incubation at 650° C. for 10 minutes, 42° C. for 10 minutes, and the addition of 1 unit of β-agarase to the 100 ul volume of melted agarose gel at 42° C. for 60 minutes. Ligation of 0.5 μg of digested pBYC5 vector DNA with 0.1 μg of pMAL-c2 fragment DNA was carried out at 16° C. for 4 hours in 40 ul volume with the addition of 4.0 ul 10X T4 DNA ligase buffer and 1.0 ul T4 DNA Ligase. *E.coli* strain ER2504 was transformed by mixing 150 ul of competent cells with 15 ul of ligation sample on ice for 10 minutes, heating at 42° C. for 2 minutes, adding 1 ml of LB media (10 grams/liter tryptone, 5 grams/liter yeast extract, 10 grams/liter NaCl, 1 gram/liter Dextrose, 1 gram/liter MgCl$_2$ ×6H$_2$O, pH7.2 at 25° C.) and incubating at 37° C. for 60 minutes. The samples were plated onto LB plates, supplemented with 100 ug/ml ampicillin, and incubated overnight at 37° C. Transformants were cultured in LB medium, supplemented with 100 ug/ml ampicillin, for extraction of plasmid DNA using the Qiaprep250 Kit (Qiagen, Studio City, Calif.) Positive clones were determined by restriction digest analysis: 1 ug of extracted DNA, 20 units SacI, 20 units PstI in a 30 ul of 1X NEB buffer 1 supplemented with 100 ug/ml of BSA at 37° C. for 120 minutes. 3 ul of agarose gel loading dye was added to the samples and the DNA fragments were separated by electrophoresis on a 1% low melting agarose gel. The positive clones had bands corresponding to the size of the fragment removed from the pMYB129 vector (1.5 Kb) and from the pCYB1 65 vector (5.3 Kb). One positive clone was designated pCYB166, see FIG. 38(B). Both the linker and the polylinker (MCS) regions in the pCYB constructs were sequenced.

These vectors will enable one to study the interactions of the target protein with other peptides, ligands or proteins. For example, use of these expression vectors may help to enhance current means of phage display (Example 22). These vectors may be used to construct and screen recombinant protein libraries. pCYB6 or its derivatives would allow expression of a target protein with a free N-terminus while pBYC1 66 would allow expression of a target protein with a free C-terminus. The added linker sequence should allow for better control of cleavage, thereby separating the target protein from the rest of the fusion more efficiently.

Fusion proteins expressed from such a library can be immobilized onto chitin matrix and positive clones can be selected by their biological functions or by its specific interactions with a desired molecule such as an antibody (see, e.g., Example 25).

EXAMPLE 24

Synthesis Of Cyclic Peptides Using A Modified CIVPS

This is a theoretical Example of how one might utilize protein splicing elements, (CIVPSs or inteins) to synthesize cyclic peptides either in vivo or in vitro. Cyclic peptides are important pharmacological agents and they are more stable than linear peptides, both within cells and when injected or ingested by higher organisms. Most peptides expressed in vivo are rapidly degraded which has forced researchers interested in looking for peptide ligands, inhibitors, agonist, antagonists or activators to either work with purified enzymes in vitro or to work in vivo with peptides or combinatorial peptide libraries expressed in the context of a larger protein, with all the potential unknown effects of the larger protein scaffold. Normally, cyclic peptides are synthesized by various microorganisms and isolated from these organisms or they are chemically synthesized de novo. The amino acid sequence of natural cyclic peptides is limited by their occurrence in nature. The available synthetic chemistry techniques also limit the production of cyclic peptides. It would be advantageous to combine the power of the potentially unlimited sequence diversity of genetically encoded cyclic peptides with the cell's synthetic machinery to produce cyclic peptides. Moreover, when these cyclic peptides are synthesized in vivo, they can be used to explore ligands or enzyme function in vivo. For example, individual or combinatorial cyclic peptide libraries can be used to screen in vivo for peptides which inhibit or activate an enzyme of interest. This has the advantage of being able to screen or select for a ligand, inhibitor or activator of a protein without having to have previously cloned or isolated the protein if an assay, screen or selection system is available for the activity or phenotype of the protein of interest.

Figure 37:
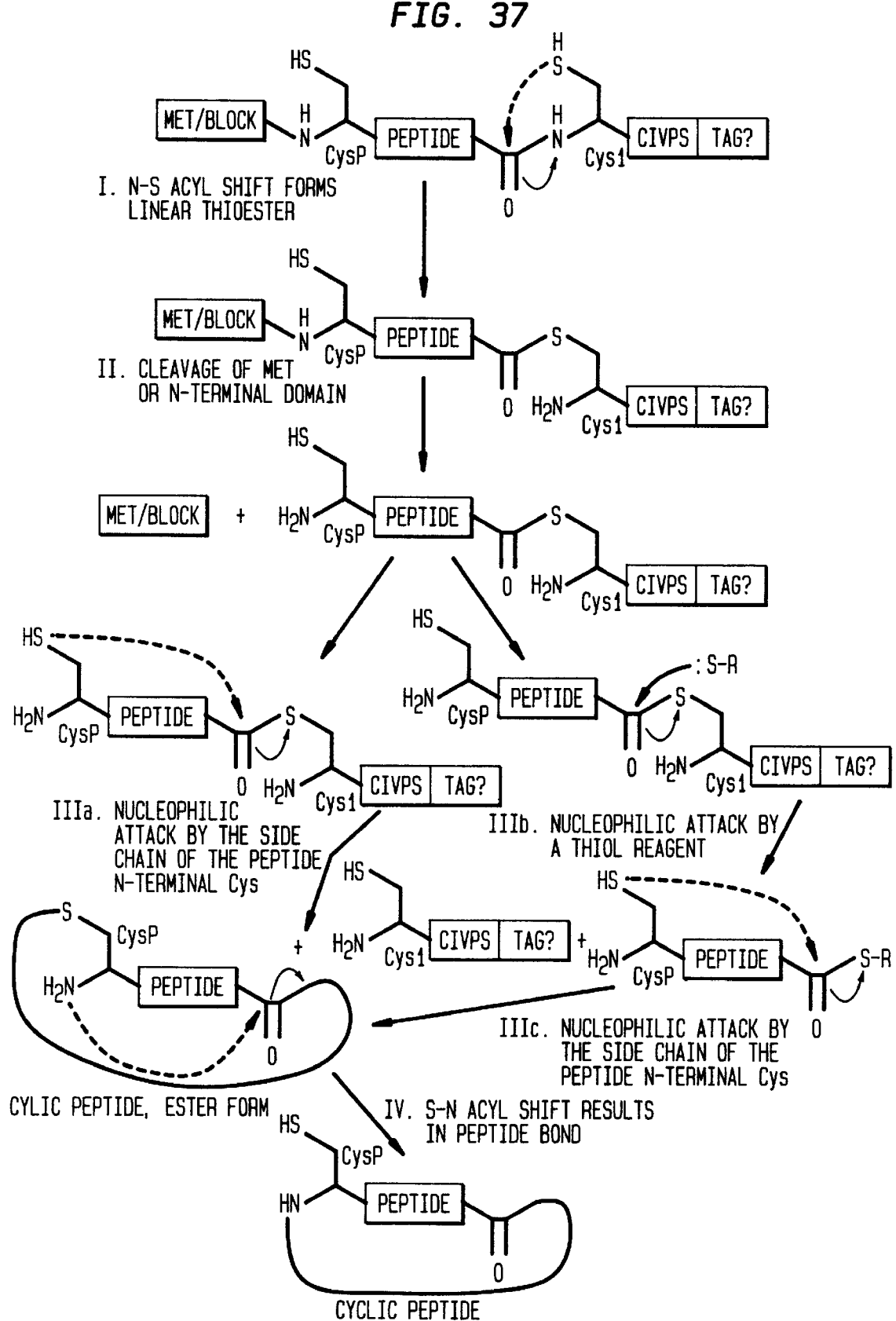
FIG. 37 describes potential pathways of CIVPS directed synthesis of cyclic peptides. Alternative pathways 111a and 111b rejoin at step IV.

In determining the mechanism of protein splicing (Chong et al., *J. Biol. Chem.* 271:22159–22168 (1996); Perler et al., *Proc. Natl. Acad. Sci. USA* 89:5577–5581 (1992); Shao et al., Biochemistry 35:3810–3815 (1996); Shao et al., *Biochemistry* 34:10844–10850 (1995); Xu et al., *EMBO J.* 13:5517–5522(1994); Xu and Perler, *EMBO J.* 15:5146–5153 (1996); Xu et al., *Cell* 75:1371–3177 (1993); Xu, *The NEB Transcript*, 8:1–5 (1997)), we have identified a step that can potentially be exploited for the development of a method of synthesizing cyclic peptides in vitro or in vivo. The first step in protein splicing is an acyl rearrangement of the CIVPS N-terminal amino acid (Cys1 in FIG. 37) to form an ester if the amino acid is a Ser or Thr or a thioester if the amino acid is a Cys (Reaction I, FIG. 37). Normally the equilibrium between the peptide bond conformation of a Ser, Thr or Cys vs. the ester/thioester form favors the peptide bond state. However, CIVPSs are enzymes that shift this equilibrium from the peptide bond conformation to the ester/thioester conformation as the first step in the protein splicing pathway (Xu et al., supra (1996), Chong et al., supra (1996); Shao et al., supra (1996) (Reaction I, FIG. 37). This ester/thioester is then cleaved by an intra-molecular nucleophilic attack on its adjacent carbonyl by the side chain hydroxyl or sulfhydryl of the Ser, Thr or Cys at the downstream splice junction (Xu et al, supra (1996), Chong et al. supra (1996)). We have previously demonstrated in the above Examples that CIVPSs can be mutated such that only the acyl rearrangement at the CIVPS N-terminus occurs. We have further demonstrated above that when Cys is present at the CIVPS (intein) N-terminus, the thioester can be cleaved by an inter-molecular reaction using simple nucleophiles such as hydroxylamine, DTT, $Hg(OAc)_2$, or free Cys (Chong et al., supra (1996); Shao et al., supra (1996); Xu and Perler supra (1996); Xu, supra (1997).

The strategy for using CIVPSs to synthesize cyclic peptides (FIG. 37) depends on the ability of the CIVPS to stabilize the thioester formed by an N-S acyl shift of the CIVPS N-terminal Cys (Cys 1 in FIG. 37), combined with the ability of the sulfhydryl group of Cys to mediate cleavage of this bond (Chong et al., supra (1996); Xu and Perler, supra (1996); Xu, supra(1997). If the downstream splice junction Cys and free Cys can mediate cleavage of the N-terminal splice junction, then a Cys (CysP in FIG. 37) at the N-terminus of a peptide, protein domain or small protein cloned in front of the CIVPS should also be able to cleave the N-terminal splice junction. Nucleophilic attack by the side chain of CysP at the N-terminus of the peptide on the carbonyl bond adjacent to the stabilized thioester of CIVPS Cys1, would result in cleavage of the N-terminal splice junction and production of a free CIVPS plus a cyclized peptide with the peptide N-terminal Cys (CysP) in the thioester conformation (Reaction IIIa, FIG. 37). The thioester in the cyclized peptide is no longer stabilized by the CIVPS and therefore spontaneously will rearrange to form a native peptide bond in the cyclic peptide (Reaction IV, FIG. 37). This reaction requires that the peptide N-terminal CysP be brought into proximity with the thioester at the CIVPS N-terminus, either because the peptide, domain or protein normally folds such that its N-terminus is near its C-terminus or by the normal movement of peptides in solution.

A Cys at the N-terminus of the peptide can be generated in numerous ways. If the peptide or protein to be cyclized is cloned directly after the initiating Met, the cell will naturally cleave off the initiating Met, leaving the Cys at the new N-terminus. Alternatively, the peptide N-terminal Cys (CysP) can be placed directly after any controllable cleavage signal, such as a protease site, a secretion signal sequence, etc. CysP becomes the N-terminus of the peptide to be cyclized upon digestion to remove the N-terminal region of the precursor (marked as 'Met/Block' in FIG. 37).

Control of in vivo cyclization would be limited to in vivo methods of cleavage at the N-terminus of the peptide. Cyclization in vitro allows more options. For example, one could use a protease/protease target site pair that doesn't naturally occur in the host cell for removal of the precursor N-terminal blocking sequence, either before or after purification of the precursor. Many IVPSs may have to be tested to find those that would have a catalytic pocket that would accept an N-terminal Cys as the nucleophile which would cleave the CIVPS generated thioester. Alternatively, the precursor can be purified using a chitin binding domain tag as described above or any other type of tag (marked 'Tag ?' in FIG. 37). After purification, the CIVPS/tag can be replaced by treatment with a thiol reagent such as DTT or aromatic thiols (Reaction IIIb, FIG. 37). This would still leave a thioester linkage at the C-terminus of the peptide to be cyclized, but would remove any interference from the CIVPS active-site. The cyclic peptide is then formed as described above, by the attack of the peptide N-terminal Cys (Reaction IIIc, FIG. 37). The N-terminal Cys of the peptide to be cyclized can be generated either before or after substitution of the CIVPS/tag by the thiol reagent. Another advantage of doing the reaction in vitro is that the presence of reducing reagents would reverse the dead end attack by internal Cys residues. The formation of a peptide bond after attack by the Cys side chain is limited to Cys residues at the N-termini of a protein or peptide, since internal Cys residues, which do not have a free amino group, cannot resolve the thioester via an acyl rearrangement (Reaction IV, FIG. 37). Thiol reagents in the reaction mixture would regenerate the C-terminal thioester after attack by an internal Cys resulting in fruitful attack by CysP (Reaction IIIb, FIG. 37) followed by the S-N acyl shift (Reaction IV, FIG. 37).

EXAMPLE 25

Screening Of Bacterial Or Phage Recombinant DNA Libraries On Chitin Membranes

The isolation of proteins expressed from genes with in a large recombinant DNA library can be accomplished by using antibodies that can detect the antigen produced by specific recombinants. Benton and Davis (*Science*, 196:180–182 (1977) and *Biochemistry*, 80: 1194–1198 (1982)) developed a method for screening up to 20, 000 recombinant λ plaques or bacterial colonies (containing a λgt11 vector) lifted on to a nitrocellulose membrane. Hannah and Meselson (*Gene*, 10:63–657 (1980)) developed a procedure to screen 10,000 bacterial colonies transferred to a nitrocellulose membrane followed by lysis and hybridization to specific DNA probes.

Isolation of proteins expressed from specific genes can be improved by construction of a recombinant DNA library expressing foreign proteins fused in frame to a N-terminus of an intein (Y) containing the small chitin binding domain (B) fused to a C-terminus of the intein. Substituting nitrocellulose with a chitin membrane or paper will increase the signal to noise ratio when screening bacterial or plaque lifts using antibodies against specific antigen-producing clones. The only proteins that will bind to the chitin membrane or paper during a plaque or bacterial colony lift are those antigens expressed in-frame and fused to the YB fusion protein. In contrast most proteins from the host will bind to nitrocellulose membranes. Any cross-reactivity of the antibody to the bacterial host and or phage host proteins will greatly decrease the signal to noise on a nitrocellulose membrane.

Alternative uses of chitin membranes or papers can be:

1. any type of detection system involving a chitin binding domain.
2. any purification protocol using the chitin binding domain.
3. any screening method using chitin binding fusions to capture certain proteins or ligands.

The following example protocol uses a recombinant vector expression vector producing a maltose binding protein from *E. coli* (M) fused to the N- terminus of the YB fusion. (MYB). After culture, *E. coli* cells ER2267 containing the vector expressing the MYB are mixed in a 1:500 ratio with the same pre cultured host cells that do not contain the expression vector. The mixture is titered to the right density on LB/AMP plates and grown overnight at 37° C.

Preparation Of The Chitin

Pre wet Whatman filter papers ( grade 2) were placed in plastic petri dishes and a 4 mm layer of 1% (w/v) chitosan in 5% (v/v) acetic acid in water is carefully poured on top of the Whatman filter paper. The petri dishes were placed under constant vacuum at 37° C. until the solution dries to a clear transparent layer over the filter paper. The papers were soaked three 5 minute washes with methanol ( 300 ml per 10 filters). Ten chitosan filter papers were placed in a sealed tray containing acetic anhydride (300 ml) and placed on a rotary platform shaker at room temperature for 20 hours. The regenerated chitin filter papers were washed in methanol followed by water and stored in 5% (v/v) methanol in water at 4° C.

Screening Of Bacterial Colonies

The following procedure is a modification of Maniatis et al., (*Molecular Cloning: A Laboratory Manual*, Second Edition, Cold Spring Harbor Press, Cold Spring Harbor, N.Y., 1989, pp. 12.2–12.44).

A replica plate of the bacteria was grown overnight at 37° C. A chitin paper was cut 0.5 cm less than the petri dish and soaked for 5 minutes in LB/AMP containing 1 mM IPTG. The Chitin paper was placed on to the replica plate and a pre wet nitrocellulose (diameter 0.25 cm wider than the chitin paper) was layered on top to keep the chitin paper from curling. The cells were induced at 37° C. for 2 hours. The chitin filter was marked with reference points and was gently lifted off the agar plate. The chitin filter paper was placed in a desiccator containing an open beaker of chloroform. The filter was stored in the chloroform atmosphere for 15 minutes at room temperature. Next, the chitin filter was soaked in 50 ml of 100 mM TrisHCl (pH 8.0), 150 mM NaCl, 5 mM $MgCl_2$, 50 µg/ml pancreatic DNAse I and 50 mg /ml lysozyme with gentle rotation on a rotary platform at room temperature for one hour. The turbid solution was removed and was replaced with 50 ml of the same enzyme/buffer solution and was mixed with gentle rotation for 18 hours at room temperature. The chitin filter paper was removed and soaked in 50 ml of Buffer D: 20 mM TrisHCl pH 7.5, 150 mM NaCl, 0.3 % (v/v) Tween 20, and 0.2 % (v/v) Triton X100 with gentle rotation at room temperature for 5 minutes. The wash was repeated two more times with fresh buffer D. The fourth wash contained the same buffer with NaCl concentration increased to 0.5 M. The chitin filter was soaked in Buffer D with 5% w/v dried milk for one hour at room temperature with gentle rotation. After two 5 minute washes containing 50 ml of Buffer D, the chitin filter was soaked in 10 ml of Buffer D containing a ½000 dilution of rabbit anti-MBP antiserum (NEB #800-30S) for 30 minutes at room temperature with gentle rotation. After two 5 minute washes containing 50 ml of Buffer D, the chitin filter was soaked in 10 ml of Buffer D containing a ½00 dilution of alkaline phosphatase-conjugated Goat affinity purified ant -rabbit IGG (Cappel # 5928) for 30 minutes at room temperature with gentle rotation. After two 5 minute washes containing 50 ml of Buffer D, the chitin paper was developed in 10 ml of 10 mM TrisHCl 9.5, 100 mM NaCl, 5 mM $MgCl_2$, 1.65 mg Bcip (Promega # s381c) and 3.3 mg NBT (Promega 3 s380c). The chitin paper was transferred to 200 ml water to stop development.

Screening Of Plaques

Immunological screening of expression libraries fused in frame to the N- terminus of the YB fusion (MYB) constructed in bacteriophage vectors would follow the above protocol with the elimination of the chloroform lysis and lysozyme/DNAse I treatment of the chitin filters.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. A modified protein comprising a target protein, or portion thereof, fused, either internally or terminally, to a controllable intervening protein sequence, or to an amino-terminal element or a carboxyl-terminal element of a controllable intervening protein sequence.

2. The modified protein of claim 1 wherein the controllable intervening protein sequence or element thereof comprises overlapping fragments.

3. The modified protein of claim 1 wherein the controllable intervening protein sequence or element thereof comprises fragments containing affinity tags.

4. The modified protein of claim 1 wherein the controllable intervening protein sequence or element thereof is fused to either the amino-terminus or the carboxyl-terminus of the target protein.

5. The modified protein of claim 1 wherein the controllable intervening protein sequence or element thereof and the target protein form a splice junction.

6. The modified protein of claim 5 wherein the amino acid residue at the carboxyl terminus of the splice junction comprises an amino acid residue having an hydroxyl or a sulfhydryl side chain.

7. The modified protein of claim 5 wherein the splice junction at the downstream end of the controllable intervening protein sequence or element thereof comprises an amino acid residue not having an hydroxyl or a sulfhydryl side chain at the amino terminus of the adjoining region of the target protein.

8. The modified protein of claim 5 wherein the splice junction at the upstream end of the controllable intervening protein sequence or element thereof comprises an amino acid residue having only an hydroxyl or a sulfhydryl side chain at the amino terminus of the controllable intervening protein sequence or element thereof.

9. The modified protein of claim 7 wherein the splice junction for cleavage at the upstream end of the controllable intervening protein sequence comprises a cysteine.

10. The modified protein of claim 6 wherein the splice junction at the downstream end of the controllable intervening protein sequence or element thereof comprises a His-Asn dipeptide at the carboxyl terminus of the controllable intervening protein sequence or element thereof and also comprises an amino acid residue having only an hydroxyl or a sulfhydryl side chain at the amino terminus of the adjoining region of the target protein.

11. The modified protein of claim 6 wherein the splice junction at the downstream end of the controllable intervening protein sequence or element thereof comprises an asparagine at the carboxyl terminus of the controllable inntervening protein sequence o element thereof and also comprises an amino acid residue having only an hydroxyl or a sulfhydryl side chain at the amino terminus of the adjoining region of the target protein.

12. The modified protein of claim 11 wherein the asparagine at the carboxyl terminus of the controllable intervening protein sequence or element thereof at the downstream splice junction is replaced by an amino acid lacking a carboxyl or an amino side chain.

13. The modified protein of claim 10 wherein the controllable intervening protein sequence is selected from the group consisting of CIVPS 1, CIVPS 2, CIVPS 3, and an intein endogenous to Saccharomyces.

14. The modified protein of claim 13 wherein the controllable intervening protein sequence is an intein endogenous to Saccharomyces cerevisiae.

15. The modified protein of claim 13 wherein the intein is inserted immediately before a serine, threonine or cysteine residue of the target protein.

16. The modified protein of claim 13 wherein CIVPS contains a serine, threonine or cysteine residue at its amino terminus.

17. The modified protein of claim 6 or claim 16, wherein at least one amino acid residue having an hydroxyl or a sulfhydryl side chain is modified.

18. The modified protein of claim 17 wherein the modification is an amino acid substitution.

19. The modified protein of claim 18 wherein the amino acid substitution replaces at least one of the amino acids of the controllable intervening protein sequence, or an amino acid at the amino terminus of a carboxyl-proximal element of a target protein, with a chemically derivatized amino acid in which the functionality of the side chain is masked by a removable chemical group.

20. The modified protein of claim 19 wherein the removable chemical group is chemically or photolytically removable.

21. The modified protein of claim 17 wherein the modification is a post-translational or co-translational chemical derivatization of the side chain.

22. The modified protein of claim 21 wherein the chemical derivatization of at least one of the amino acids of the controllable intervening protein sequence, or an amino acid at the amino terminus of a carboxyl-proximal element of a target protein, masks the functionality of the side chain with a removable chemical group.

23. The modified protein of claim 1 wherein the controllable intervening protein sequence or element thereof permits a process, conducted in cis or in trans, selected from the group of processes consisting of excision, cleavage, ligation, combined excision and ligation, combined cleavage and ligation, and cyclization under a condition suitable for said excision, cleavage, ligation, combined excision and ligation, combined cleavage and ligation, and cyclization.

24. The modified protein of claim 23 wherein said condition for excision, cleavage, ligation, combined excision and ligation, combined cleavage and ligation, and cyclization is selected from the group of conditions consisting of a change in temperature, an addition or a removal of a chemical reagent which facilitates or inhibits splicing or cleavage, a change in pH, an exposure to or an absence of light, dephosphorylation or deglycosylation of an amino acid residue, and contact with or removal of a peptide or a peptidomimetic capable of activating or blocking splicing or cleavage.

25. The modified protein of claim 23 wherein the controllable intervening protein sequence or element thereof comprises overlapping fragments and the controllable intervening protein sequence or element thereof permits excision or cleavage in trans.

26. The modified protein of claim 23 wherein the controllable intervening protein sequence or element thereof comprises fragments containing affinity tags and said controllable intervening protein sequence or element thereof permits excision or cleavage in trans.

27. The modified protein of claim 23 wherein the controllable intervening protein sequence or element thereof is fused to the amino-terminus or to the carboxyl-terminus of the target protein.

28. The modified protein of claim 23 wherein the controllable intervening protein sequence or element thereof and the target protein form a splice junction.

29. The modified protein of claim 28 wherein the amino acid residue at the carboxyl terminus of the splice junction comprises an amino acid residue having an hydroxyl or a sulfhydryl side chain, thus permitting splicing.

30. The modified protein of claim 28 wherein the splice junction at the downstream end of the controllable intervening protein sequence or element thereof comprises an amino acid residue not having an hydroxyl or a sulfhydryl side chain at the amino terminus of the adjoining region of the target protein, thus permitting cleavage.

31. The modified protein of claim 29 wherein the splice junction at the upstream end of the controllable intervening protein sequence or element thereof comprises an amino acid residue having only an hydroxyl or a sulfhydryl side chain at the amino terminus of the controllable intervening protein sequence or element thereof, thus permitting cleavage.

32. The modified protein of claim 30 wherein the splice junction for cleavage at the upstream end of the controllable intervening protein sequence comprises a cysteine, thus permitting target protein cyclization.

33. The modified protein of claim 29 wherein the splice junction at the downstream end of the controllable intervening protein sequence or element thereof comprises a His-Asn dipeptide at the carboxyl terminus of the controllable intervening protein sequence or element thereof and also comprises an amino acid residue having only an hydroxyl or a sulfhydryl side chain at the amino terminus of the adjoining region of the target protein.

34. The modified protein of claim 29 wherein the splice junction at the downstream end of the controllable intervening protein sequence or element thereof comprises an asparagine at the carboxyl terminus of the controllable intervening protein sequence or element thereof and also comprises an amino acid residue having only an hydroxyl or a sulfhydryl side chain at the amino terminus of the adjoining region of the target protein.

35. The modified protein of claim 37 wherein the asparagine at the carboxyl terminus of the controllable intervening protein sequence or element thereof at the downstream splice junction is replaced by an amino acid lacking a carboxyl or an amino side chain, thus permitting cleavage only at the amino terminus of the controllable intervening protein sequence.

36. The modified protein of claim 33 wherein the controllable intervening protein sequence is selected from the group consisting of CIVPS 1, CIVPS 2, CIVPS 3, and an intein endogenous to Saccharomyces.

37. The modified protein of claim 36 wherein the controllable intervening protein sequence is an intein endogenous to Saccharomyces cerevisiae.

38. The modified protein of claim 36 wherein the intein is inserted immediately before a serine, threonine or cysteine residue of the target protein.

39. The modified protein of claim 36 wherein CIVPS contains a serine, threonine or cysteine residue at its amino terminus.

40. The modified protein of claim 29 or claim 39, wherein at least one amino acid residue having an hydroxyl or a sulfhydryl side chain is modified such that cleavage is reduced.

41. The modified protein of claim 40 wherein the modification is an amino acid substitution.

42. The modified protein of claim 41 wherein the amino acid substitution replaces at least one of the amino acids of the controllable intervening protein sequence, or an amino acid at the amino terminus of a carboxyl-proximal element of a target protein, with a chemically derivatized amino acid in which the functionality of the side chain is masked by a removable chemical group.

43. The modified protein of claim 42 wherein the removable chemical group is chemically or photolytically removable.

44. The modified protein of claim 40 wherein the modification is a post-translational or co-translational chemical derivatization of the side chain.

45. The modified protein of claim 44 wherein the chemical derivatization of at least one of the amino acids of the controllable intervening protein sequence, or an amino acid at the amino terminus of a carboxyl-proximal element of a target protein, masks the functionality of the side chain with a removable chemical group.

46. A method of producing a modified protein comprising a target protein, or portion thereof, fused, either internally or terminally, to a controllable intervening protein sequence, or to an amino-terminal element or a carboxyl-terminal element of a controllable intervening protein sequence, the method comprising:
  (a) forming a DNA encoding a target protein having an in frame fusion of said controllable intervening protein sequence, or an amino-terminal element or a carboxyl-terminal element of said controllable intervening protein sequence; and,
  (b) transforming a host cell with the DNA encoding the modified protein and culturing the transformed host cell under conditions suitable for the expression of the modified protein.

47. The method of claim 46, wherein the DNA encoding the controllable intervening protein sequence is fused to the 5' end of the DNA encoding the target protein.

48. The method of claim 46, wherein the DNA encoding the controllable intervening protein sequence is fused to the 3' end of the DNA encoding the target protein.

49. The method of claim 46, wherein the controllable intervening sequence is endogenous to Saccharomyces.

50. The method of claim 49, wherein the controllable intervening sequence endogenous to Saccharomyces is fused to the target protein.

51. The method of claim 46 wherein the controllable intervening protein sequence or element thereof conducts a process, either in cis or in trans, selected from the group of processes consisting of excision, cleavage, ligation, combined excision and ligation, combined cleavage and ligation, and cyclization under a condition suitable for said excision, cleavage, ligation, combined excision and ligation, combined cleavage and ligation, and cyclization.

52. The method of claim 51 wherein said condition is selected from the group consisting of a change in temperature, an addition or a removal of a chemical reagent which facilitates or inhibits splicing or cleavage, a change in pH, an exposure to or an absence of to light, dephosphorylation or deglycosylation of an amino acid residue, and contact with or removal of a peptide or a peptidomimetic capable of activating or blocking splicing or cleavage.

53. The method of claim 46 wherein said condition comprises in vitro or in vivo contact with, or removal of, a peptide or a peptidomimetic capable of activating or blocking splicing or cleavage.

54. The method of claim 46 wherein the controllable intervening protein sequence or element thereof contains a serine, threonine or cysteine residue at its amino terminus.

55. The method of claim 46 wherein the controllable intervening protein sequence or element thereof contains an asparagine at its carboxyl terminus preceding a serine, threonine or cysteine of the target protein.

56. A method of producing a target protein comprising:
(a) producing a first modified protein wherein the amino-terminal portion of a controllable intervening protein sequence is fused to the carboxyl-terminus of the target protein;
(b) producing a second modified protein comprising a portion of the controllable intervening protein sequence; and,
(c) contacting the first and second modified proteins under a condition suitable for cleavage of the controllable intervening protein sequence in trans.

57. The method of claim 56 wherein said condition is selected from the group consisting of a change in temperature, an addition or a removal of a chemical reagent which facilitates or inhibits splicing or blocking of cleavage, a change in pH, an exposure to or an absence of light, dephosphorylation or deglycosylation of an amino acid residue, and contact with or removal of a peptide or a peptidomimetic capable of activating or blocking splicing or cleavage.

58. The method of claim 57 wherein said condition comprises in vitro or in vivo contact with or removal of a peptide or a peptidomimetic capable of activating or blocking splicing or cleavage.

59. The method of claim 56 wherein the first modified protein further comprises an affinity tag protein.

60. The method of claim 56 wherein the second modified protein further comprises an affinity tag protein.

61. A method of producing a target protein comprising:
(a) producing a first modified protein wherein the carboxyl-terminal portion of a controllable intervening protein sequence is fused to the amino terminus of the target protein;
(b) producing a second modified protein comprising a portion of the controllable intervening protein sequence; and,
(c) contacting the first and second modified proteins under a condition suitable for cleavage of the controllable intervening protein sequence in trans.

62. The method of claim 61 wherein said condition is selected from the group consisting of a change in temperature, an addition or a removal of a chemical reagent which facilitates or inhibits splicing or blocking of cleavage, a change in pH, an exposure to or an absence of light, dephosphorylation or deglycosylation of an amino acid residue, and contact with or removal of a peptide or a peptidomimetic capable of activating or blocking splicing or cleavage.

63. The method of claim 61 wherein said condition comprises in vitro or in vivo contact with or removal of a peptide or a peptidomimetic capable of activating or blocking splicing or cleavage.

64. The method of claim 61 wherein the first modified protein further comprises an affinity tag protein.

65. The method of claim 61 wherein the second modified protein further comprises an affinity tag protein.

66. A method for purification of a target protein comprising:
(a) forming a fusion protein comprising a controllable intervening protein sequence positioned between a target protein and a binding protein or portion thereof having affinity for a substrate;
(b) contacting the fusion protein with a substrate to which the binding protein or portion thereof binds;
(c) subjecting the substrate bound fusion protein to a condition suitable for the cleavage of the controllable intervening protein sequence or the cyclization of the target protein; and,
(d) recovering the target protein.

67. A method for purification of a target protein comprising:
(a) forming a fusion protein comprising a target protein fused to a controllable intervening protein sequence into which a binding protein or portion thereof is fused internally or terminally;
(b) contacting the fusion protein with a substrate to which the binding protein or portion thereof binds;
(c) subjecting the substrate bound fusion protein to a condition suitable for the cleavage of the controllable intervening protein sequence or the cyclization of the target protein; and,
(d) recovering the target protein.

68. The method of claim 66 or 67, wherein cleavage of the fusion protein also occurs at the carboxyl terminus of the controllable intervening protein sequence resulting in release of both the controllable intervening protein sequence and target protein.

69. The method of claim 68, wherein the controllable intervening protein sequence has also been modified to bind to the substrate to which the binding protein binds.

70. The method of claim 68, wherein the controllable intervening protein sequence has been modified to bind to a substrate other than the substrate to which the binding protein binds.

71. The method of claim 66 or 67, wherein the controllable intervening protein sequence is selected from the group consisting of CIVPS 1, 2, 3 or an intein endogenous to Saccharomyces.

72. The method of claim 66 or 67, wherein the substrate is contained within an affinity resin.

73. The method of claim 66 or 67 wherein said condition for cleavage of the controllable intervening protein sequence or the cyclization of the target protein is selected from the group consisting of a change in temperature, an addition or a removal of a chemical reagent which facilitates or inhibits splicing or cleavage, a change in pH, an exposure to or an absence of to light, dephosphorylation or deglycosylation of an amino acid residue, and contact with or removal of a peptide or a peptidomimetic capable of activating or blocking splicing or cleavage.

74. The method of claim 73 wherein the condition comprises in vitro or in vivo contact with, or the removal of, a peptide or a peptidomimetic capable of activating or blocking splicing or cleavage.

75. The method of claim 66 or 67 wherein the binding protein or portion thereof is selected from the group consisting of a sugar binding protein, a chitin binding protein, a receptor binding protein, an amino acid binding protein, a sulfate binding protein, a vitamin binding protein, a metal binding protein, a phosphate binding protein, a lectin binding protein and a nucleic acid binding protein.

76. The method of claim 75, wherein the sugar binding protein is maltose binding protein.

77. The method of claim 76, wherein the substrate is cross-linked amylose.

78. The method of claim 75, wherein the sugar binding protein is chitin binding protein.

79. The method of claim 75, wherein the chitin binding protein is endogenous to Bacillus circulans WL-12.

80. The method of claim 75, wherein the substrate is a chitin resin.

81. The method of claim 75, wherein the substrate is amylose attached to agarose beads.

82. A method for purification of a target protein comprising:
   (a) forming a fusion protein comprising a controllable intervening protein sequence and a target protein;
   (b) contacting the fusion protein with a substrate to which the controllable intervening protein sequence binds;
   (c) subjecting the substrate bound fusion protein to a condition suitable for the cleavage of the controllable intervening protein sequence or for the cyclization of the target protein, permitting separation of the target protein from the controllable intervening protein sequence; and,
   (d) recovering the target protein.

83. The method of claim 82 wherein said condition is selected from the group consisting of a change in temperature, an addition or a removal of a chemical reagent which facilitates or inhibits splicing or cleavage, a change in pH, an exposure to or an absence of light, dephosphorylation or deglycosylation of an amino acid residue, and contact with or removal of a peptide or a peptidomimetic capable of activating or blocking splicing or cleavage.

84. The method of claim 83 wherein said condition comprises in vitro or in vivo contact with, or the removal of, a peptide or a peptidomimetic capable of activating or blocking splicing or cleavage.

85. The method of claim 82 wherein the substrate is an antibody against the controllable intervening protein sequence.

86. A method for purification of a target protein comprising:
   (a) forming a fusion protein comprising a portion of a controllable intervening protein sequence inserted between a target protein and a binding protein or portion thereof having affinity for a substrate;
   (b) contacting the fusion protein with a substrate to which the binding protein or portion thereof binds;
   (c) contacting the substrate-bound fusion protein with a portion of the controllable intervening protein sequence;
   (d) subjecting the substrate-bound fusion protein and the portion of the controllable intervening protein sequence to a condition suitable for cleavage of the controllable intervening protein sequence in trans, thus permitting separation of the target protein from the controllable intervening protein sequence; and
   (e) recovering the target protein.

87. A method for purification of a target protein comprising:
   (a) forming a fusion protein comprising a target protein fused to a controllable intervening protein sequence into which a binding protein or portion thereof is fused internally or terminally;
   (b) contacting the fusion protein with a substrate to which the binding protein or portion thereof binds;
   (c) contacting the substrate-bound fusion protein with a portion of the controllable intervening protein sequence;
   (d) subjecting the substrate-bound fusion protein and the portion of the controllable intervening protein sequence to a condition suitable for cleavage of the controllable intervening protein sequence in trans, thus permitting separation of the target protein from the controllable intervening protein sequence; and
   (e) recovering the target protein.

88. The method of claim 86 or 87 wherein said condition is selected from the group consisting of a change in temperature, an addition or a removal of a chemical reagent which facilitates or inhibits splicing or cleavage, a change in pH, an exposure to or an absence of light, dephosphorylation or deglycosylation of an amino acid residue, and contact with or removal of a peptide or a peptidomimetic capable of activating or blocking splicing or cleavage.

89. The method of claim 88 wherein said condition comprises in vitro or in vivo contact with, or the removal of, a peptide or a peptidomimetic capable of activating or blocking splicing or cleavage.

90. The method of claim 86 or 87 wherein the portion of the controllable intervening protein sequence has an affinity tag.

91. A method for the purification of a target protein comprising:
   (a) forming a fusion protein comprising a portion of a controllable intervening protein sequence inserted between a target protein and a binding protein or portion thereof having affinity for a substrate;
   (b) contacting the fusion protein with a substrate to which the binding protein or portion thereof binds;
   (c) recovering the fusion protein of step (b);
   (d) contacting the recovered fusion protein of step (c) with a portion of the controllable intervening protein sequence;
   (e) subjecting the recovered fusion protein and the remaining portion of the controllable intervening protein sequence to a condition suitable for cleavage of the controllable intervening protein sequence in trans, thus permitting separation of the target protein from the binding protein or portion thereof; and
   (f) recovering the target protein.

92. A method for the purification of a target protein comprising:
   (a) forming a fusion protein comprising a target protein fused to a controllable intervening protein sequence into which a binding protein or portion thereof is fused internally or terminally;
   (b) contacting the fusion protein with a substrate to which the binding protein or portion thereof portion binds;
   (c) recovering the fusion protein of step (b);
   (d) contacting the recovered fusion protein of step (c) with a portion of the controllable intervening protein sequence;
   (e) subjecting the recovered fusion protein and a portion of the controllable intervening protein sequence to a condition suitable for cleavage of the controllable intervening protein sequence in trans, thus permitting separation of the target protein from the binding protein or portion thereof; and,
   (f) recovering the target protein.

93. The method of claim 91 or 92 wherein said condition is selected from the group consisting of a change in temperature, an addition or a removal of a chemical reagent which facilitates or inhibits splicing or cleavage, a change in pH, an exposure to or an absence of light, dephosphorylation or deglycosylation of an amino acid residue, and contact with or removal of a peptide or a peptidomimetic capable of activating or blocking splicing or cleavage.

94. The method of claim 93 wherein said condition comprises in vitro or in vivo contact with, or the removal of, a peptide or a peptidomimetic capable of activating or blocking splicing or cleavage.

95. The method of claim 91 or 92 wherein the portion of the controllable intervening protein sequence has an affinity tag.

96. A method for synthesizing a target protein comprising:
(a) cloning or synthesizing a DNA encoding a first portion of the target polypeptide;
(b) forming a genetic fusion of the 3'-terminus of the DNA encoding a first portion of the target polypeptide with the 5'-terminus of a second DNA encoding a controllable intervening protein sequence or element thereof to form a continuous open reading frame;
(c) transforming a suitable host cell with the fused DNA of step (b) and culturing the transformed host cell under conditions suitable for the expression of the encoded fusion polypeptide;
(d) isolating the fusion polypeptide from the host cell or its culture medium;
(e) contacting the fusion polypeptide of step (d) with a thiol compound to induce cleavage of the fusion polypeptide and to produce a thiol ester intermediate at the carboxyl terminus of the target polypeptide;
(f) contacting the thiol ester intermediate of step (e) with a second portion of the target polypeptide having an amino-terminal cysteine to form a peptide bond between the first and second portions of the target polypeptide; and
(g) recovering the target polypeptide.

97. A method for labeling a target protein comprising:
(a) cloning a DNA encoding a target polypeptide;
(b) forming a genetic fusion of the 3'-terminus of the DNA encoding the target polypeptide with the 5'-terminus of a second DNA encoding a controllable intervening protein sequence or element thereof to form a continuous open reading frame;
(c) transforming a suitable host cell with the fused DNA of step (b) and culturing the transformed host cell under conditions suitable for the expression of the encoded fusion polypeptide;
(d) isolating the fusion polypeptide from the host cell or its culture medium; and,
(e) contacting the fusion polypeptide of step (d) with a cysteine labeled at its sulfhydryl group or at its carboxyl group.

98. The method of claim 97 wherein the fusion polypeptide of step (d) is contacted with a thiol compound to induce cleavage of the fusion polypeptide, thus producing a thiol ester intermediate at the carboxyl terminus of the target polypeptide, and then contacting the thiol ester of step with a cysteine labeled at its sulfhydryl group or at its carboxyl group.

99. The method of claim 98 wherein the label of the cysteine is introduced following cleavage of the fusion polypeptide with a thiol compound of step (a).

100. The method of any of claims 97, 98, or 99 wherein the label is selected from the group consisting of a thiol containing nucleophile such as a peptide beginning with a cysteine, a fluorescent nucleophile compound, a radiolabeled compound, and a biotinylated nucleophile.

101. A method for binding and eluting a phage-displayed polypeptide from a target protein comprising:
(a) forming a fusion protein comprising a target protein, a controllable intervening protein sequence or an amino-terminal or a carboxyl-terminal portion of a controllable intervening protein sequence, and a polypeptide capable of binding specifically to a solid support;
(b) binding the fusion protein of step (a) to the solid support;
(c) contacting a phage-displayed polypeptide with the support-bound fusion protein of step (b) permitting binding of the phage-displayed polypeptide with the fusion protein;
(d) removing unbound phage-displayed polypeptide; and,
(e) eluting the bound phage-displayed polypeptide by inducing cleavage of the controllable intervening protein sequence.

102. The method of claim 101, wherein the phage-displayed polypeptide comprises a library of at least two sequence variations of the displayed polypeptides.

103. The method of claim 101, wherein the phage is filamentous.

* * * * *

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 2,
Line 55 replace "a", first occurrence, with -- an --

Column 3,
Line 17 delete "and", second occurrence
Line 27 after "from" insert -- one --
Line 65 replace "lie" with -- Ile --

Column 4,
Line 2 replace "βgalactosidase" with -- β-galactosidase --
Line 13 replace "l-Tlil" with -- I-TliI --
Line 14 replace "l -Pspl" with -- I-PspI --
Line 29 replace "BspEl" with -- BspEI --; and replace "Spel" with -- SpeI --
Line 34 replace "Xbal" with -- XbaI --; and replace "Sall" with -- SalI --
Line 50 replace "l -Pspl" with -- I-PspI --
Line 59 replace "l-Pspl" with -- I-PspI --
Line 65 replace "l-Pspl" with -- I-PspI --

Column 5,
Line 7 replace "doman" with -- domain --
Line 22 replace "CIVPS3=Pl-Pspl" with -- CIVPS3=PI-PspI --
Line 26 replace "anti-Pl-Pspl" with -- anti-PI-PspI --
Line 33 replace "Xhol-Knpl" with -- XhoI-KpnI --
Line 34 replace "BamHI-Stul" with -- BamHI-StuI --
Line 66 replace "Ml' and l'P" with -- MI' and I'P--; and replace " l'P and Ml' " with -- I'P and MI' --

Column 6,
Line 2 replace "l'-products" with -- I'-products --
Line 3 replace "Anti-Pi-Pspl" with -- Anti-PI-PspI --
Line 5 replace "l'P" with -- I'P --; and replace "Ml'" with -- MI' --
Line 10 replace "l-Ppl" with -- I-PspI --
Line 11 replace "Xmnl" with -- XmnI --
Line 12 replace "Ml', l'P" with -- MI', I'P --
Line 14 replace "l'P and Ml'" with -- I'P and MI' --; replace "MlP52" with -- MIP52 --; and replace "l-Pspl" with -- I-PspI --
Line 19 replace "l'P by Ml'22" with -- I'P by MI'22 --
Line 20 replace "Ml'22" with -- MI'22 --

UNITED STATES PATENT AND TRADEMARK OFFICE
CERTIFICATE OF CORRECTION

PATENT NO. : 5,834,247  
DATED : November 10, 1998  
INVENTOR(S) : Donald G. Comb et al.

Page 2 of 22

It is certified that error appears in the above-identified patent and that said Letters Patent is hereby corrected as shown below:

Column 6 (cont.),
Line 22 replace "Ml'22 and l'P" with -- MI'22 and I'P --
Lines 27 and 32 replace "Ml94" with -- MI94 --
Line 32 replace "(Ml)" with-- (MI) --
Line 33 relace "(l)" with -- (I) --
Line 43 replace "shows" with -- show --
Line 49 replace "Ml' l-249" with -- MI ' l-249 --
Line 50 replace "l' 250-537P" with -- I' 20-537P --; replace "Ml1-440" with -- MIl-440 --; and replace "l441-537P" with -- I441-537P --
Line 52 replace "(Ml441-537P)" with -- (MI441-537P) --
Line 53 replace "(Ml1-440His)" with -- (MIl-440His) --
Line 56 replace "Ml1-440" with -- MIl-440 --; and replace "l ' P" with -- I ' P --
Line 63 replace "Ml1-440" with -- MIl-440 --; and replace "1250-537P" with -- I250-537P --
Line 64 replace "l1-440" with -- Il-440 --; and "l250-537" with -- I250-537 --
Line 66 replace "Ml1-440" with -- MIl-440 --; and replace "l441-437P" with -- I441-437P --

Column 7,
Line 2 replace "Ml1-440" with -- MIl-440 --; and replace "Ml441-537P" with -- MI441-537P --
Line 7 replace "Ml1-440" with -- MIl-440 --; and replace "l441-537P" with -- I441-537P --
Line 8 replace "Ml1-440" with -- MIl-440 --; and replace "Ml441-537P" with -- MI441-537P --
Line 11 replace "M1-440" with -- MIl-440 --; replace "l441-537P" with -- I441-537P --; and replace "Ml441-537P" with -- MI441-537 --
Line 12 replace "l1-440" with -- Il-440 --; and replace "Ml155-537" with -- MI155-537 --
Line 16 replace "a" with -- an --
Line 17 replace "a", second occurrence, with -- an --

Column 8,
Line 5 replace "AMYB" with -- ΔMYB --
Line 17 replace "111a" with -- IIIa --
Line 18 replace "111b" with -- IIIb --
Line 25 replace "interesrt" with -- interest --
Line 30 replace "a" with -- an --

UNITED STATES PATENT AND TRADEMARK OFFICE
CERTIFICATE OF CORRECTION

PATENT NO.    : 5,834,247
DATED         : November 10, 1998
INVENTOR(S)   : Donald G. Comb et al.

It is certified that error appears in the above-identified patent and that said Letters Patent is hereby corrected as shown below:

Column 9,
Line 40 replace "370°" with -- 37° --
Line 63 replace "viva" with -- vivo -

Column 11,
Line 47 replace "Sl 982A" with -- Sl982A --

Column 12,
Line 1 replace "(1991))" with -- (1991) --
Line 17 replace "upstream        junction" with -- upstream junction --

Column 13,
Line 25 replace "$Hg^{2+)}$ 0" with -- $Hg^{2+}$).
Line 31 replace "l-Tli-ll" with -- I-Tli -II --; and replace "l-Tli-l" with -- I-Tli-I --
Line 32 replace "l-Pspl" with -- I-PspI --
Line 35 replace "IVPSI" with -- IVPSl --
Line 51 replace "l-Tli-l" with -- I-Tli -I --

Column 14,
Line 8 replace "example,)" with -- example, --
Line 47 replace "takes" with -- take --
Line 66 replace "an" with -- a --

Column 15,
Line 3 replace "lacz" with -- lacZ --
Lne 16 replace "BspEl" with -- BspEI --
Lines 17 and 21 replace "Spel" with -- SpeI --
Line 43 replace "primers O" with -- primers --

Column 18,
Line 4 replace "C-terninal" with -- C-terminal --
Lines 9 and 12 replace "transcleavage" with -- trans-cleavage --
Line 33 replace "and o" with -- and --

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 20,
Line 10 replace "endo_versions" with -- endo-versions --
Line 33 replace "4706-4706" with -- 4685-4706 --
Line 35 replace "IVPS2fragment" with -- IVPS2 fragment --
Line 50 replace "1 %" with -- 1% --

Column 21,
Line 4 replace "-700°C" with -- -70°C --
Line 25 replace "BamHl-Dral" with -- BamHI-DraI --
Line 29 replace "ladl$^q$" with -- lacI$^q$ --
Line 33 replace "Lacl$_q$" with --lacI$^q$ --
Line 39 replace "lacl$^q$" with -- lacI$^q$ --
Line 53 replace "example" with -- Example --

Column 22,
Line 1 replace "pAHOS" with -- pAHO5 --
Line 12 replace "$\mu$/ml" with -- $\mu$g/ml --
Line 56 replace "OD$_{600}$nm" with -- OD$_{600nm}$ --
Line 66 replace "ladZ" with -- lacZ --

Column 23,
Line 8 replace "l-Tli -l" with -- I-Tli I --
Line 20 replace "l-Pspl" with -- I-PspI --
Line 36 replace "Increasesin" with -- Increases in --
Line 41 replace "pVTl 42" with -- pVTl42 --
Line 47 replace "OD$_{600}$nm" with -- OD$_{600nm}$ --

Column 24,
Line 3 replace "OD$_{420}$nm" with -- OD$_{420nm}$ --; and replace "OD$_{550}$nm" with -- OD$_{550nm}$ --
Line 31 replace "followings" with -- follows --
Line 39 replace "100$\mu$/ml" with -- 100$\mu$g/ml --; and replace "OD$_{600}$nm" with
-- OD$_{600nm}$ --
Line 59 replace "l-Tli-l or l-Pspl" with -- I-Tli-I or I-PspI --
Line 65 replace "l-Tli-l" with -- I-Tli -I --

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 25,
Line 4 replace "l-PspI" with -- I-PspI --

Column 26,
Line 1 replace "133th" with -- 133$^{rd}$ --
Line 13 replace "compementary" with -- complementary --
Line 18 replace "133th" with -- 133$^{rd}$ --
Line 57 replace "100 µg/ml" with -- 100 ug/ml --
Line 64 replace "l-Tli-l, l-PspI" with -- I-Tli-I, I-PspI --

Column 27,
Line 5 replace "l-PspI" with -- I-PspI --
Line 9 replace "anti-l-Tli-l" with -- anti -I-Tli -I --
Lines 37 and 38 replace "BspEl" with -- BspEI --
Lines 39 and 40 replace "Spel" with -- SpeI --
Line 46 replace "BspEl" with -- BspEI --; and "Spel" with -- SpeI --
Line 48 replace "lacz1BspEl" with -- lacZl/BspEl --
Line 50 replace "lacZ2Spel" with -- lacZ2/SpeI --

Column 28,
Line 13 replace "Sall" with -- SalI --; and replace "Xbal" with -- XbaI --
Line 21 replace "Sall" with -- SalI --
Line 23 replace "Xbal" with -- XbaI --
Line 28 replace "Xbal" with -- XbaI --; and replace "Sal" with -- SalI --
Line 38 replace "an" with -- a --
Line 52 replace "Xmal" with -- XmaI --; and replace "PpuMl" with -- PpuMI --
Line 53 replace "Xmal" with -- XmaI --
Line 54 replace "pAll17" with -- pAII17 --; and replace "xmal" with -- XmaI --
Line 58 replace "Xmal" with -- XmaI --
Lines 58 and 60 and replace "PpuMl" with -- PpuMI --
Line 61 replace "Xmal" with -- XmaI --; and replace "PpuMl" with -- PpuMI --

UNITED STATES PATENT AND TRADEMARK OFFICE
CERTIFICATE OF CORRECTION

PATENT NO.   : 5,834,247
DATED         : November 10, 1998
INVENTOR(S)  : Donald G. Comb et al.

It is certified that error appears in the above-identified patent and that said Letters Patent is hereby corrected as shown below:

Column 29,
Line 8 replace "ClaI" with -- ClaI --; and replace "SspI" with -- SspI --
Line 9 replace "ClaI/EcoRV" with -- ClaI/EcoRV --
Line 13 replace "AgeI" with -- AgeI --
Line 20 replace "BsaI" with -- BsaI -
Line 23 replace "ClaI/SspI" with -- ClaI/SspI --
Line 26 replace "SalI" with -- SalI --
Line 28 replace "(BsaBI nt 3554-3563))" with -- (BsaBI nt 3554-3563) --
Line 30 replace "BstBl nt 5 3608-3613" with -- BstBI nt 3608-3613 --
Line 32 replace "PpuMI" with -- PpuMI --
Line 34 before "the resulting" delete "with"
Lines 42, 43 and 46 replace "NdeI" with -- NdeI --
Line 49 replace "XbaI/CaI" with -- XbaI/CaI --
Line 51 replace "ClaI/NdeI" with -- ClaI/NdeI --
Line 53 replace "NdeI/NsiI" with -- NdeI/NsiI --
Line 56 replace "NsiI/BamHI" with -- NsiI/BamHI --
Line 58 replace "BamHI/XbaI" with --BamHI/XbaI --
Line 61 replace "l-TliI" with -- I-TliI --

Column 30,
Line 5 replace "l-TliII" with -- I-TliII --; and replace "l-TliI" with -- I-TliI --
Line 12 replace "l-TliI" with -- I-TliI --
Lines 14 and 21 replace "l-TliI" with -- I-TliI --
Line 26 replace "PpuMI" with -- PpuMI --
Lines 30-31 replace "GAA<u>GC</u>AGCCTGTCACAGAGTCCTCTTTCACTCTATT"
with -- GAA<u>GC</u>ACGCCTGTCACAGAGTCCTCTTTCACTCTATT --
Line 37 replace "PpuMI" with -- PpuMI --
Line 38 replace "BsaBI" with -- BsaBI --
Line 45 replace "AgeI" with -- AgeI --; and replace "SmaI" with -- SmaI --
Line 48-49 replace
"AAGAAACGTTTGTTGTAGGACCATGTGTTAATTCTGCCGGACGGCTTTTAT
GCCACAATACCC" with --
AAGAAACGTTTGTTGTAGGACCATGTGTTA<u>ATT</u>CTGCCGGACGGCTTTTATG
CCACAATACCC --

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 31,
Line 3 replace "l-Tlil" with -- I-TliI --
Line 21 replace "Fokl" with -- FokI --
Line 53 replace "werre" with -- were --
Line 62 replace "l-Tlil" with -- I-TliI --

Column 32,
Line 12 replace "l-Tlil" with -- I-TliI --
Line 36 replace "l-lil" with -- I-TliI --
Line 51 replace "lacz" with -- lacZ --

Column 33,
Line 22 replace "BamHl" with -- BamHI --
Line 26 after "NO : 40)" insert -- 5'- GGTATTATGTGCATAGAGGAATCCA-3' (SEQ ID NO:41) (3428-3452) were used to generate CIVPS3/Thr and CIVPS3/Cys fragments (1614 bp), respectively. The PCR mixture contains Vent® DNA polymerase buffer, supplemented with 2mM magnesium sulfate, 400 $\mu$M of each dNTP, 100 $\mu$g/ml BSA, --
Line 50 replace "resspended" with -- resuspended --
Line 56 replace "bffer" with -- buffer --
Line 60 replace "microfge," with -- microfuge, --
Line 65 replace "Sited" with -- Site --

Column 34,
Line 4 replace "BamHI-Dral" with -- BamHI-DraI --
Line 5 "Smal" with -- SmaI --
Line 8 replace "lacl$^q$" with -- laqI$^q$ --
Line 25 replace "fsion" with -- fusion --
Line 39 replace "abot" with -- about --
Line 42 replace "pAHOS" with -- pAHO5 --
Line 58 replace "hors" with -- hours --
Line 61 replace "for", first occurrence, with -- four --
Line 67 replace "OD$_{600}$nm" with -- OD$_{600nm}$ --

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 35,
Line 7 replace "l-Pspl" with -- I-PspI --
Line 29 replace "ladZ" with -- lacZ --
Line 33 replace "l-Pspl" with -- I-PspI --
Line 39 replace "jnction" with -- junction --; replace "fuuion" with -- fusion --
Line 40 replace "jnction" with -- junction --
Line 50 replace "$OD_{600}nm$" with -- $OD_{600nm}$ --
Line 52 replace "00" with -- 100 --
Line 57 replace $650°$" with -- $65°$ --

Column 36,
Lines 2, 9 and 15 replace "l-Pspl" with -- I-PspI --
Line 11 replace "for" with -- four --
Line 19 replace "ßgalactosidase" with -- ß-galactosidase --
Lines 25, 31, 36, 37, 45 and 49 replace "l-Pspl" with -- I-PspI --

Column 37,
Line 28 replace "Perken" with -- Perkin --
Line 31 replace "PNEB" with -- pNEB --
Line 36, replace "Kpnl", both occurrences, with -- KpnI --
Line 41 replace "BamHl" with -- BamHI --
Line 52 replace "mixtre" with -- mixture --
Line 54 replace "bffer" with -- buffer --
Line 59 replace "EcoRI-Sall" with -- EcoRI-SalI --
Line 63 replace "Xmnl" with -- XmnI --

Column 38,
Line 14 replace "$MgCl-6H_sO$" with -- $MgCl_2-6H_2O$ --
Line 36 replace "$OD_{600}nm$" with -- $OD_{600nm}$ --
Line 37 replace "1.10" with -- 1.0 --
Line 53 replace "l-Pspl" with -- I-PspI --
Line 57 replace "anti-l-Pspl" with -- anti-I-PspI --

UNITED STATES PATENT AND TRADEMARK OFFICE
CERTIFICATE OF CORRECTION

PATENT NO.    : 5,834,247
DATED         : November 10, 1998
INVENTOR(S)   : Donald G. Comb et al.

It is certified that error appears in the above-identified patent and that said Letters Patent is hereby corrected as shown below:

Column 39,
Lines 1 and 3 replace "$OD_{600}nm$" with -- $OD_{600nm}$ --
Lines 19, 25, 26, 29, 32 and 47 replace "l-PspI" with -- I-PspI --

Column 40,
Line 4 replace "l-Pspl" with -- I-PspI --
Line 30 replace "Xhol" with -- XhoI --
Line 31 replace "Kpnl" with -- KpnI --
Lines 32 and 35 replace "Stul" with -- StuI --
Line 37 replace "$\mu$lat" with -- $\mu$l at --
Line 38 replace "an" with -- a --
Line 62 replace "Xhol" with --XhoI --
Lines 62 and 65 replace "Kpnl" with -- KpnI --

Column 41,
Line 6 replace "MIP521F/MIPS22R" with -- MIP521F/MIP522R --
Line 15 replace "Xhol" with -- XhoI --; and replace "Kpnl" with -- KpnI --
Line 17 replace "Stul" with -- StuI --
Lines 22-23 replace "$OD_{600}nm$" with -- $OD_{600nm}$ --
Line 35 replace "Xhol" with -- XhoI --; and replace "Kpnl" with -- KpnI --
Line 37 replace "Stul" with -- StuI --
Line 39 replace "Xhol-Kpnl" with -- XhoI-KpnI --
Lines 39, 41, 43, 45 and 60 replace "Stul" with -- StuI --
Line 61 replace "BamHl" with -- BamHI --

Column 42,
Lines 1 and 6 replace "Stul" with -- StuI --
Line 28 replace "anipicillin" with -- ampicillin --; replace "$OD_{600}nm$" with -- $OD_{600nm}$ --

Column 43,
Line 26 replace "$950^{\circ}C$" with -- $95^{\circ}C$ --
Line 33 delete the space after "GACAGT"
Line 34 replace "Stul" with -- StuI --
Lines 39 and 51 replace "Pstl" with -- PstI --

UNITED STATES PATENT AND TRADEMARK OFFICE
CERTIFICATE OF CORRECTION

PATENT NO.   : 5,834,247
DATED        : November 10, 1998
INVENTOR(S)  : Donald G. Comb et al.

It is certified that error appears in the above-identified patent and that said Letters Patent is hereby corrected as shown below:

Column 43 (cont.),
Line 51 replace "Stul" with -- StuI --
Lines 54 and 62 replace "Pstl/Stul" with -- PstI/StuI --
Line 65 replace "Pstl" with -- PstI --; and replace "Stul" with -- StuI --

Column 44,
Line 2 replace "$\mu$1" with -- $\mu$l --
Line 4 replace "Fusions" with -- Fusion --
Line 22 replace "Pstll" with -- PstI --
Line 23 replace "Stul" with -- StuI --
Line 27 replace "Pstl" with -- PstI --; and replace "Stul" with -- StuI --
Line 55 replace "Coornassie" with -- Coomassie --
Line 66 replace "110 mM" with -- 10 mM --

Column 45,
Line 22 replace "approxiamtely" with -- approximately --
Line 23 replace "(l=l-Pspl)" with -- (I=I-PspI) --
Line 27 replace "70 Da" with -- 70kDa --
Line 64 replace "Ndel/BamHI" with -- NdeI/BamHI --
Line 65 replace "BamHI/Ndel" with -- BamHI/NdeI --; and replace pAll" with -- pAII --

Column 46,
Line 6 replace "Ml'" with -- MI' --
Line 10 replace "Xbal/Bpu" with -- XbaI/Bpu --
Line 13 replace "11021/Xbal" with -- 1102I/XbaI --
Line 14 replace "pAll-17" with -- pAII-17 --
Line 16 replace "l ' P" with -- I ' P --
Line 23 replace "<u>GCGGCCGCT</u>CACGACGTTGTAAAACG" with -- <u>GCGGCCGCT</u>CACGACGTTGTAAAACG --
Line 28 replace "Ndel/Notl" with -- NdeI/NotI --
Line 29 replace "Notl/Ndel" with -- NotI/NdeI --
Line 30 replace "pl/M250" with -- pI/M250 --
Line 31 replace "pl/Ms50" with -- pI/M250 --
Line 33 replace "l ' P" with -- I ' P --
Line 37 replace "Ml' " with -- MI' --

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 46 (cont.),
Line 43 replace "200C" with -- $20°C$ --
Lines 53, 54 and 58 replace "l'P" with -- I'P --
Line 61 replace "ρg/ml" with -- $\mu$g/ml --

Column 47,
Line 1, 16 and 27 (both occurrences), replace "l ' P" with -- I ' P --
Line 47 replace "Ml'" with -- MI' --; and replace "l ' P" with -- I ' P --
Line 57 replace "6,500" with -- 6, 500 --
Line 65 replace "anti-PI-Pspl" with -- anti-PI-Pspl" with -- anti-PI-PspI --

Column 48,
Line 2 replace "Ml'" with -- MI' --
Line 5 replace "l ' P" with -- I ' P --
Lines 8, 9 and 13 replace "Ml'" with -- MI' --
Line 13 replace "l ' P" with -- I ' P --; replace " l ' " with -- I ' --
Line 17 replace "Ml ' " with -- MI ' --
Line 18 replace "anti - Pl-Pspl" with -- anti - PI - PspI --
Lines 19 and 28 replace "Ml ' " with -- MI ' --; replace " l ' P " with -- I ' P --
Line 29 replace "anti-Pl-Pspl" with -- anti-PI-PspI --
Line 30 replace "Ml ' " with -- MI ' --; and replace "l ' P" with -- I ' P --
Line 42 replace "surpa (1 989))" with -- supra (1989)) --; replace "surpa" with
-- supra --
Line 43 replace "anti-PI-Pspl" with -- anti-PI-PspI --
Line 45 replace "(Ml ' P*)" with -- (MI ' P*) --
Line 47 replace "l')" with -- I') --
Lines 48 and 50 replace "l-Psp" with -- I-Psp --
Line 50 replace "l-Pspl" with -- I-PspI --; replace "Pl-Pspl" with -- PI-PspI --
Line 51 replace "I-Pspl" with -- I-PspI --
Line 57 replace "Xmnl" with -- XmnI --; replace "l-Pspl" with -- I-PspI --
Line 59 replace "Ml', 1 ' P" with -- MI ' , 1 ' P --
Line 61 replace "Xmnl" with -- XmnI --
Line 62 replace "l-Pspl" with -- I-PspI --
Line 63 replace "Xmnl" with -- XmnI --
Line 67 replace "I-Pspl" with -- I-PspI --

UNITED STATES PATENT AND TRADEMARK OFFICE
CERTIFICATE OF CORRECTION

PATENT NO.    : 5,834,247
DATED         : November 10, 1998
INVENTOR(S)   : Donald G. Comb et al.

It is certified that error appears in the above-identified patent and that said Letters Patent is hereby corrected as shown below:

Column 49,
Line 5 replace "l - Psp" with -- I - Psp --
Line 12 replace "Ml ' and l ' P" with -- MI' and I ' P --
Line 23 replace "Ml ' 22" with -- MI ' 22 --
Line 25 replace "Ml ' " with -- MI ' --
Line 26 replace " l ' P" with -- I ' P --
Line 27 replace "pMl/L249" with -- pMI/L249 --
Line 28 replace "Ml'" with -- MI' --; replace "lle2" with -- Ile2 --
Line 31 replace "pMl/L249" with -- pMI/L249 --
Lines 40 and 43 replace "Xhol-Kpnl" with -- XhoI-KpnI --
Line 47 replace "pMl ' 22" with --pMI ' 22 --
Line 48 replace "Ml ' 22" with -- MI ' 22 --
Line 49 replace "Ml ' 22 AND l ' P" with -- MI ' 22 and I ' P --
Line 50 replace "l ' P " with -- I ' P --; replace "Ml ' 22" with -- MI ' 22 --
Line 51 replace "Ml ' " with -- MI ' --
Line 52 replace "pMl ' 22" with -- pMI ' 22 --

Column 50,
Line 5 replace "lle2Lys" with -- Ile2Lys --
Line 6 replace "Ml ' 22" with -- MI ' 22 --
Line 9 replace "l ' P" with -- I ' P --
Line 10 replace "Ml ' 22" with -- MI ' 22 --; replace " l' " with -- I ' --
Line 12 replace "l ' P" with -- I ' P --
Lines 22-23 replace "tran-scleaving" with -- trans-cleaving --
Line 35 replace " 1 ' P" with -- I ' P --
Line 36 replace "1 ' " with -- 1' --
Line 38 replace "Ml ' 22 plus l ' P" with -- MI ' 22 plus I ' P --
Line 55 replace "Xhol" with -- XhoI --; and replace "Kpnl" with -- Kpnl --
Line 56 replace "Stul" with -- StuI --
Line 59 replace "Xhol-Kpnl" with -- XhoI-KpnI --
Line 61 replace "BamHI-Stul" with -- BamHI-StuI --
Line 63 replace "Xhol and Kpnl" with -- Xhol and KpnI --
Line 65 replace "Xhol-Kpnl" with -- XhoI-KpnI --

UNITED STATES PATENT AND TRADEMARK OFFICE
CERTIFICATE OF CORRECTION

PATENT NO.       : 5,834,247
DATED            : November 10, 1998
INVENTOR(S)      : Donald G. Comb et al.

It is certified that error appears in the above-identified patent and that said Letters Patent is hereby corrected as shown below:

Column 51,
Line 2 replace "Ml" with -- MI --
Line 6 replace "CYS" with -- Cys --
Line 12 replace "Xhol" with -- XhoI --; replace "Kpnl" with -- KpnI --
Line 13 replace "an" with -- a --
Line 23 replace "Xhol-Kpnl" with -- Xhol-KpnI --
Line 29 replace "Ml" wih -- MI. --
Line 34 replace "Sphl" with -- SphI --
Line 41 replace "Stul" with -- StuI --
Line 42 replace "BamHI/Stul" with -- BamHI/StuI --
Line 46 replace "Stul" with -- StuI --
Lines 49 and 51 replace "Sphl" with -- SphI --
Line 52 replace "Ml" with -- MI --
Line 54 replace "BamHI-Sphl" with -- BamHI-SphI --
Lines 63 and 65 replace "Sphl" with -- SphI --

Column 52,
Line 2 replace "BamHI-Sphl" with -- BamHI-SphI --
Line 8 replace "Ml" with -- MI --
Lines 11 and 12 replace "Kpnl-Pstl" with -- KpnI-PstI --
Line 15 replace "Kpnl" with -- KpnI --; and replace "Pstl" with -- PstI --
Lines 16 and 17 replace "Kpnl-Pstl" with -- KpnI-PstI --
Line 25 replace "pM94" with -- pMI94 --; and "Ml" with -- MI --
Line 27 replace "pM147" with -- pMI47 --
Line 28, 31, and 34 replace "Ml94" with -- MI94 --
Line 44 replace "NaPO4" with -- NaPO$_4$ --
Line 48 replace "Ml94" with -- MI94 --
Line 52 replace "6 N H Cl" with -- 6 N HCl --

Column 53,
Line 1 replace "Ml" with -- MI --
Line 33 replace "Xhol" with -- XhoI --; replace "Stul" with -- StuI --
Line 41 after "Vent®" please insert -- DNA polymerase buffer, supplemented with 4mM Magnesium sulfate, --
Line 51 replace "100 $\mu$l" with -- 100 ul --; replace "Xhol with -- XhoI --
Line 55 replace "0.5 $\mu$g" with -- 0.5 ug --

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 53 (cont.),
Line 56 replace "Xhol" with -- XhoI --; and replace "Stul" with -- StuI --
Line 58 replace "0.5$\mu$g / 20$\mu$l" with -- 0.5ug/20ul --
Line 59 replace "Xhol-digested" with -- XhoI-digested --
Line 60 replace "XhoI-Stul" with -- XhoI-StuI --

Column 54,
Line 5 replace "100 $\mu$g/ml" with -- 100 ug/ml --; and replace "$OD_{600}$nm" with -- $OD_{600nm}$ --
Line 23 after "Wild-Type" please insert -- Yeast --
Line 29 replace "Xhol" with -- XhoI --
Line 30, replace "Pstl" with -- PstI --
Line 34 replace "melt" with -- melted --
Line 39 replace "150C" with -- 150° --
Line 55 replace "precipitated" with -- precipitate --
Line 58 delete "of" second occurrence Column 55,
Line 26 replace "Xhol" with -- XhoI --; replace "Pstl" with -- PstI --
Line 30 replace "melt" with -- melted --
Line 41 replace "Xhol" with -- XhoI --; replace "Kpnl" with -- KpnI --
Line 44 replace "melt" with -- melted --
Line 58 replace "Xhol-Kpnl" with -- XhoI-KpnI --

Column 56,
Lines 3 and 4 replace "Xhol-BamHI" with -- XhoI-BamHI --
Line 5 replace "BamHI-Agel" with -- BamHI-AgeI --
Line 9 replace "Xhol" with -- XhoI --
Line 12 replace "Xhol-BamHI" with -- XhoI-BamHI --
Line 14 replace "melt" with -- melted --
Line 22 replace "Agel" with -- AgeI --
Line 25 replace "melt" with -- melted --
Line 39 replace "BamHI-Agel" with -- BamHI-AgeI --
Line 60 replace "was" with -- were --

UNITED STATES PATENT AND TRADEMARK OFFICE
CERTIFICATE OF CORRECTION

PATENT NO.    : 5,834,247
DATED         : November 10, 1998
INVENTOR(S)   : Donald G. Comb et al.

It is certified that error appears in the above-identified patent and that said Letters Patent is hereby corrected as shown below:

Column 57,
Line 9 replace "a" with -- an --
Line 12 replace "ßmercapteothanol" with -- ß-mecapteothanol --
Line 45 replace "a", second occurrence, with -- at --
Line 48 replace "aspirator). The" with -- aspirator), the --
Line 67 after "created by" delete "a"

Column 58,
Lines 3 and 10 replace "stabiliser" with -- stabilizer --
Line 44 replace "as" with -- is --

Column 59,
Line 52 replace "Mll-440" with -- MIl-440 --
Line 55 replace "Ml'", both instances, with -- MI' --
Line 56 replace "Xhol" with -- XhoI --
Line 59 replace "Ml'" with -- MI' --
Line 63 replace "Xhol" with -- XhoI --
Line 66 replace "Xhol/BamHI" with -- XhoI/BamHI --
Line 67 replace "Ml'" with -- MI' --

Column 60,
Line 3 replace "Mll-440" with -- MIl-440 --; replace "Ml ' " with -- MI ' --
Lines 20, and 21 replace "Xhol" with -- XhoI --
Line 24 replace "pMl ' " with -- pMI ' --
Lines 26, 28 and 29 replace "Xhol/BamHl" with -- XhoI/BamHI --
Line 30 replace "Ml ' " with -- MI' --; replace "pMll-440" with -- MIl-440 --
Line 31 replace "Ml ' " with -- MI ' --
Line 32 replace "pMll-440" with -- Mil-440 --
Line 35 replace "laboratory" with -- Laboratory --
Line 40 replace "l ' P", both instances, with -- I ' P --
Lines 41 and 44 replace "Ndel" with --NdeI --
Line 47 replace "Ndel/BamHI" with -- NdeI/BamHI --
Line 49 replace "l ' P" with -- I ' P --
Line 55 replace "Ndel" with -- NdeI --
Line 56 replace "(5 ' GGGG" with -- (5 ' GGG<u>G</u> --
Line 60 replace "Ndel/BamHI" with -- NdeI/BamHI --

UNITED STATES PATENT AND TRADEMARK OFFICE
CERTIFICATE OF CORRECTION

PATENT NO.    : 5,834,247
DATED         : November 10, 1998
INVENTOR(S)   : Donald G. Comb et al.

It is certified that error appears in the above-identified patent and that said Letters Patent is hereby corrected as shown below:

Column 60 (cont.),
Line 63 replace "Ndel" with -- NdeI --
Line 64 replace "l ' P" with -- I ' P --
Line 66 replace "Ndel/BamHI" with -- NdeI/BamHI --
Line 67 replace "Ndel/" with -- NdeI/ --

Column 61,
Line 2 replace "Ndel/BamHI" with -- NdeI/BamHI --
Line 4 replace "l ' P" with -- I ' P --
Line 12 replace "Pstl" with -- PstI --; replace "Ndel" with -- NdeI --
Line 15 replace "Ndel" with -- NdeI --
Line 16 replace "Ndel/Pstl" with -- NdeI/PstI --
Line 18 replace "EcoRI/Pstl" with -- EcoRI/PstI --
Line 22 replace "Ndel" with -- NdeI --
Line 29 replace "Pstl" with -- PstI --
Line 34 replace "supra" with -- supra. --
Lines 35 and 44 repace "Mll-440" with -- MIl-440 --
Line 45 replace "Ml'" with -- MI' --
Lines 46 and 55 replace "pl441-537P" with -- pI441-537P --
Line 61 replace "Ml441-537P" with -- MI441-537P --
Line 62 replace "pl441-537P" with -- pI441-537P --

Column 62,
Line 7 replace "Ml441-537P" with -- MI441-537P --
Line 8 replace "pl441-537P" with -- pI441-537P --;replace "1441-537P" with
-- I441-537P --
Lines 10 and 12 replace "1441-537P" with -- I441-537P --
Line 15 replace "Mll4 440" with -- MIl-440 --
Line 19 replace "ll-440" with -- Il-440 --; replace "1250-537" with -- I250-537 --
Line 20 replace "l250-537P" with -- I250-537P --
Lines 25, 30, 43 and 47 replace "Ml1-440" with -- MIl-440 --
Line 47 replace "l441-537P" with -- I441-537P --
Line 49 replace "Ml1-440" with -- MIl-440 --
Lines 50, 52 and 55 replace "l441-537P" with -- I441-537P --
Lines 55 and 58 replace "Ml1-440" with -- MIl-440 --
Line 59 replace "441-537P" with -- I441-537P --

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 63,
Line 5, replace "Ml1-400" with -- MIl-440 --; and replace "l441-537P" with -- I441-537P --
Line 7, replace "l1-440" with -- Il-400 --; and replace "l441-537" with -- I441-537 --

Column 64,
Line 6, replace "Ll1-440His" with -- LIl-440His --
Line 8 "NdeI" with -- NdeI --; and replace "Kpnl" with -- KpnI --
Line 10 replace "Ll1-440" with -- LI1-440 --
Line 14 replace "Ll1-440His" with -- LIl-440His --
Line 15, replace "l1-440" with -- Il-440--
Line 16 replace "NO:823" with -- NO:83 --
Line 24 replace "Ml 1-440" with -- MIl-440 --
Line 25 replace "Ll1-440" with -- MIl-440 --; and replace "Afill" with -- AflII --
Line 27 after "encoding" insert -- 6 His residues, as shown below: --
Line 36 delete "(SEQ ID NO:83)"
Line 44 replace "10 $\mu M/\mu l$" with -- 10 pM/$\mu l$ --
Line 48 replace "Aflll" with -- AflII --
Lines 51, 53 and 54 replace "Aflll/BamHI" with -- AflII/BamHI --
Line 55 replace "Lll- 440" with -- LI1- 440 --; replace "Lll-440His" with
-- LIl-440His --
Line 57 replace "Lll-440" with -- LI1-440 --
Line 60 replace "Lll-440His" with -- LIl-440His --
Line 61 replace "Kpnl" with -- KpnI --
Line 64 replace "M' " with -- MI' --
Line 66 replace "Lll-440His" with --LIl-440His --
Line 67 replace "Kpnl" with -- KpnI --

Column 65,
Line 2 replace "Lll-440His" with -- LI1-440His --
Line 7 replace "Mil-440His" with -- MIl-440His --
Line 26 replace "1441-537P" with -- I441-537P --
Lines 28, 31 and 43, replace "Mil-440His" with -- MIl-440His --
Line 43 replace "1441-537P" with -- I441-537P --
Line 45 replace "11-440His" with -- MIl-440His --; replace "1441-537" with
-- I441-537 --

UNITED STATES PATENT AND TRADEMARK OFFICE
CERTIFICATE OF CORRECTION

PATENT NO.  : 5,834,247
DATED       : November 10, 1998
INVENTOR(S) : Donald G. Comb et al.

It is certified that error appears in the above-identified patent and that said Letters Patent is hereby corrected as shown below:

Column 66,
Line 13 after "such" insert -- as --
Line 35 replace "phes" with -- pheS --

Column 67,
Line 22 replace "V269L270" with -- ---V269L270 --; and replace C272G273." With -- C272G273---. --
Line 43 replace "thie" with -- the --
Line 50 replace "Sacl" with -- SacI --; replace "Sphl" with -- SphI --
Line 67 replace "Pstl" with -- PstI --

Column 68,
Lines 6 and 8 replace "Pstl/AflII" with -- PstI/AflIII --
Line 18 delete "(SEQ ID NO:88)"
Line 19 replace "Kpnl/SexAl" with -- KpnI/SexAI --
Lines 35 and 36 replace "Pstl" with --PstI --
Line 50 replace "Kpnl" with -- KpnI --

Column 69,
Line 2 replace "Kpnl" with -- KpnI --
Line 24 replace "Pstl" with -- PstI --
Line 25 replace "370º C" with -- 37º C --
Line 36 replace "Pstl" with -- PstI --
Line 43 replace "Kpnl" with -- KpnI --; and replace "SexAl" with -- SexAI --
Line 54 replace "Kpnl" with -- KpnI --

Column 70,
Line 10 replace "performied" with -- performed --
Line 26 replace "Dpnl" with -- DpnI --
Line 29 replace "place" with -- placed --
Line 32 replace "platted" with -- plated --

Column 71,
Line 26 delete "for"

UNITED STATES PATENT AND TRADEMARK OFFICE
CERTIFICATE OF CORRECTION

PATENT NO.    : 5,834,247
DATED         : November 10, 1998
INVENTOR(S)   : Donald G. Comb et al.

It is certified that error appears in the above-identified patent and that said Letters Patent is hereby corrected as shown below:

Column 72,
Line 48 replace "A*Methods*" with -- *Methods* --
Line 49 replace "3:S13614 S140" with -- 3:S136-S140 --

Column 74,
Line 52 replace "I-Pspl" with -- I-PspI --
Line 53 replace "l-Pspl" with -- I-PspI --
Line 56 replace "Sacl" with -- SacI --
Line 59 replace "Ndel" with -- NdeI --; replace "Sadl" with -- SacI --
Line 61 replace "Sac 1" with -- SacI --

Column 75,
Line 2 replace "4" with -- 4$\mu$l --
Line 29 replace "Pspl" with -- PspI --
Line 32 replace "30°" with -- 30°C --; and replace "OD600nm" with -- OD$_{600nm}$ --

Column 76,
Line 54 replace "H$_2$N-CysTyrlle" with -- H$_2$N-CysTyrIle --

Column 78,
Line 32 replace "Agel" with -- AgeI --
Line 52 replace "Xhol" with -- XhoI --
Line 53, replace "Pstl" with -- PstI --
Lines 53 and 54 ; replace "Xhol-Pstl" with -- XhoI-PstI --
Line 58 replace "Ndel" with -- NdeI --; and replace "Xhol" with -- XhoI --
Line 61 replace "placedthe" with -- placed the --
Line 64 replace "Agel" with -- AgeI --; and replace "Pstl" with -- PstI --
Line 66 replace "5'- GGTGGTACCGGTATTCTTAAAATTCTGAACGM" with
-- 5'-GGTGGTACCGGTATTCTTAAAATTCTGAACGAA --

Column 79,
Line 11 replace "Ndel" with -- NdeI --; and replace "Xhol" with -- XhoI --
Line 28 replace "Agel" with -- AgeI --; and replace "Pstl" with -- PstI --
Line 31 replace "Agel-Pstl" with -- AgeI-PstI --; and replace "pOYB" with -- pCYB --
Line 35 replace "Ndel" with -- NdeI --; and replace "Xhol" with -- XhoI --
Line 37 replace "Ndel-Xhol" with -- NdeI-XhoI --
Line 53 replace "was", second occurrence, with -- were --

UNITED STATES PATENT AND TRADEMARK OFFICE
CERTIFICATE OF CORRECTION

PATENT NO.    : 5,834,247
DATED         : November 10, 1998
INVENTOR(S)   : Donald G. Comb et al.

It is certified that error appears in the above-identified patent and that said Letters Patent is hereby corrected as shown below:

Column 80,
Line 2 replace "40°C." with -- 4°C. --
Line 50 replace "Agel" with -- AgeI --
Line 63 replace "5' -GGTGG- TGCTAGCACCT-" with
-- 5' -GGTGGTGCTAGCACCT- --

Column 81,
Line 7 replace "Nhel" with -- NheI --
Line 10 replace "Xhol" with -- XhoI --
Line 11 replace "Xhol" with -- XhoI --
Line 13 replace "Nhel" with -- NheI --; and replace "Aatll" with -- AatII --
Line 67 replace "Ml3" with -- M13 --

Column 82,
Line 34 replace "plasrnid" with -- plasmid --

Column 84,
Line 4 replace "Sacl" with -- SacI --
Line 9 replace "Agel" with -- AgeI --
Line 11 "Pstl" with -- PstI --
Line 34 "Ndel" with -- NdeI --; and replace "Sacl" with -- SacI --
Line 39 replace "Sacl" with -- SacI --
Line 40 replace "Ndel" with -- NdeI --
Line 45 replace "5'- GAGCTCGAACAACAACACCAaTAACAATAAC-" with
-- 5' -GAGCTCGAACAACAACAACAATAACAATAAC --
Lines 50 and 53, replace "Sacl" with -- SacI --

Column 85,
Lines 12, 25 and 36 replace "Sacl" with -- SacI --
Line 39 replace "650C" with -- 65°C --
Line 41 replace "Sall" with -- SalI --
Line 42 replace "Xhol" with -- XhoI --; replace "Sall" with -- SalI --
Line 43 replace "370°C." with -- 37°C. --
Line 52 replace "160°C." with -- 16°C. --
Line 67 replace "Sacl" with -- SacI --; replace "Pstl" with -- PstI --

UNITED STATES PATENT AND TRADEMARK OFFICE
CERTIFICATE OF CORRECTION

PATENT NO. : 5,834,247
DATED : November 10, 1998
INVENTOR(S) : Donald G. Comb et al.

It is certified that error appears in the above-identified patent and that said Letters Patent is hereby corrected as shown below:

Column 86,
Line 2 replace "370C" with -- 37°C --
Line 6 replace "Sacl" with -- SacI --
Line 7 replace "Psfl" with -- PstI --
Line 12 replace "pYMB1 29" with -- pYMB129 --
Line 17 replace "Sacl" with -- SacI --
Line 18 replace "Pstl" with -- PstI --
Line 19 replace "370°C." with -- 37°C. --
Line 20 replace "Sacl" with -- SacI --
Line 21 replace "Pstl" with -- PstI --
Line 27 replace "650° C." with -- 65° C. --
Line 46 replace "Sacl" with -- SacI --
Line 47 replace "Pstl" with -- PstI --

Column 88,
Line 15 replace "(1997)." With -- (1997)). --

Column 90,
Line 26 replace "TrisHCI" with -- TrisHCl --

Column 163,
Line 57 replace "o" with -- or --

Column 165,
Line 48 replace "37" with -- 34 --

Column 166,
Line 64 delete "to", second occurrence

UNITED STATES PATENT AND TRADEMARK OFFICE
CERTIFICATE OF CORRECTION

PATENT NO.    : 5,834,247
DATED         : November 10, 1998
INVENTOR(S)   : Donald G. Comb et al.

It is certified that error appears in the above-identified patent and that said Letters Patent is hereby corrected as shown below:

<u>Column 168,</u>
Line 51 delete "to"

<u>Column 169,</u>
Line 7 replace "75" with -- 76 --
Line 9 replace "75" with -- 76 --

<u>Column 170,</u>
Line 49 delete "portion", second occurrence

<u>Column 172,</u>
Line 10 after "step", insert -- (a) --
Line 20 replace "radiolableled" with -- radiolabeled --

Signed and Sealed this

Twenty-fifth Day of June, 2002

Attest:

JAMES E. ROGAN
*Attesting Officer*          *Director of the United States Patent and Trademark Office*

SEQUENCE LISTING ( 1 ) GENERAL INFORMATION:

( i i i ) NUMBER OF SEQUENCES: 155

( 2 ) INFORMATION FOR SEQ ID NO:1:

( i ) SEQUENCE CHARACTERISTICS:
( A ) LENGTH: 5837 base pairs
( B ) TYPE: nucleic acid
( C ) STRANDEDNESS: double
( D ) TOPOLOGY: Not Relevant ( x i ) SEQUENCE DESCRIPTION: SEQ ID NO:1:

| | | | | | | |
|---|---|---|---|---|---|---|
| GAATTCGCGA | TAAAATCTAT | TTTCTTCCTC | CATTTTTCAA | TTTCAAAAAC | GTAAGCATGA | 60 |
| GCCAAACCTC | TCGCCCTTTC | TCTGTCCTTC | CCGCTAACCC | TCTTGAAAAC | TCTCTCCAAA | 120 |
| GCATTTTTTG | ATGAAAGCTC | ACGCTCCTCT | ATGAGGGTCA | GTATATCTGC | AATGAGTTCG | 180 |
| TGAAGGGTTA | TTCTGTAGAA | CAACTCCATG | ATTTTCGATT | TGGATGGGGG | TTTAAAAATT | 240 |
| TGGCGGAACT | TTTATTTAAT | TTGAACTCCA | GTTTATATCT | GGTGGTATTT | ATGATACTGG | 300 |
| ACACTGATTA | CATAACAAAA | GATGGCAAGC | CTATAATCCG | AATTTTTAAG | AAAGAGAACG | 360 |
| GGGAGTTTAA | AATAGAACTT | GACCCTCATT | TTCAGCCCTA | TATATATGCT | CTTCTCAAAG | 420 |
| ATGACTCCGC | TATTGAGGAG | ATAAAGGCAA | TAAAGGGCGA | GAGACATGGA | AAAACTGTGA | 480 |
| GAGTGCTCGA | TGCAGTGAAA | GTCAGGAAAA | AATTTTTGGG | AAGGGAAGTT | GAAGTCTGGA | 540 |
| AGCTCATTTT | CGAGCATCCC | CAAGACGTTC | CAGCTATGCG | GGGCAAAATA | AGGGAACATC | 600 |
| CAGCTGTGGT | TGACATTTAC | GAATATGACA | TACCCTTTGC | CAAGCGTTAT | CTCATAGACA | 660 |
| AGGGCTTGAT | TCCCATGGAG | GGAGACGAGG | AGCTTAAGCT | CCTTGCCTTT | GATATTGAAA | 720 |
| CGTTTTATCA | TGAGGGAGAT | GAATTTGGAA | AGGGCGAGAT | AATAATGATT | AGTTATGCCG | 780 |
| ATGAAGAAGA | GGCCAGAGTA | ATCACATGGA | AAAATATCGA | TTTGCCGTAT | GTCGATGTTG | 840 |
| TGTCCAATGA | AAGAGAAATG | ATAAAGCGTT | TTGTTCAAGT | TGTTAAAGAA | AAAGACCCCG | 900 |
| ATGTGATAAT | AACTTACAAT | GGGGACAATT | TTGATTTGCC | GTATCTCATA | AAACGGGCAG | 960 |
| AAAAGCTGGG | AGTTCGGCTT | GTCTTAGGAA | GGGACAAAGA | ACATCCCGAA | CCCAAGATTC | 1020 |
| AGAGGATGGG | TGATAGTTTT | GCTGTGGAAA | TCAAGGGTAG | AATCCACTTT | GATCTTTTCC | 1080 |
| CAGTTGTGCG | AAGGACGATA | AACCTCCCAA | CGTATACGCT | TGAGGCAGTT | TATGAAGCAG | 1140 |
| TTTTAGGAAA | AACCAAAAGC | AAATTAGGAG | CAGAGGAAAT | TGCCGCTATA | TGGGAAACAG | 1200 |
| AAGAAAGCAT | GAAAAAACTA | GCCCAGTACT | CAATGGAAGA | TGCTAGGGCA | ACGTATGAGC | 1260 |
| TCGGGAAGGA | ATTCTTCCCC | ATGGAAGCTG | AGCTGGCAAA | GCTGATAGGT | CAAAGTGTAT | 1320 |
| GGGACGTCTC | GAGATCAAGC | ACCGGCAACC | TCGTGGAGTG | GTATCTTTTA | AGGGTGGCAT | 1380 |
| ACGCGAGGAA | TGAACTTGCA | CCGAACAAAC | CTGATGAGGA | AGAGTATAAA | CGGCGCTTAA | 1440 |
| GAACAACTTA | CCTGGGAGGA | TATGTAAAAG | AGCCAGAAAA | AGGTTTGTGG | GAAAATATCA | 1500 |
| TTTATTTGGA | TTTCCGCAGT | CTGTACCCTT | CAATAATAGT | TACTCACAAC | GTATCCCCAG | 1560 |
| ATACCCTTGA | AAAAGAGGGC | TGTAAGAATT | ACGATGTTGC | TCCGATAGTA | GGATATAGGT | 1620 |
| TCTGCAAGGA | CTTTCCGGGC | TTTATTCCCT | CCATACTCGG | GGACTTAATT | GCAATGAGGC | 1680 |
| AAGATATAAA | GAAGAAAATG | AAATCCACAA | TTGACCCGAT | CGAAAAGAAA | ATGCTCGATT | 1740 |
| ATAGGCAAAG | GGCTATTAAA | TTGCTTGCAA | ACAGCATCTT | ACCCAACGAG | TGGTTACCAA | 1800 |
| TAATTGAAAA | TGGAGAAATA | AAATTCGTGA | AAATTGGCGA | GTTTATAAAC | TCTTACATGG | 1860 |

```
AAAAACAGAA  GGAAAACGTT  AAAACAGTAG  AGAATACTGA  AGTTCTCGAA  GTAAACAACC  1920
TTTTTGCATT  CTCATTCAAC  AAAAAAATCA  AAGAAAGTGA  AGTCAAAAAA  GTCAAAGCCC  1980
TCATAAGACA  TAAGTATAAA  GGGAAAGCTT  ATGAGATTCA  GCTTAGCTCT  GGTAGAAAAA  2040
TTAACATAAC  TGCTGGCCAT  AGTCTGTTTA  CAGTTAGAAA  TGGAGAAATA  AAGGAAGTTT  2100
CTGGAGATGG  GATAAAAGAA  GGTGACCTTA  TTGTAGCACC  AAAGAAAATT  AAACTCAATG  2160
AAAAAGGGGT  AAGCATAAAC  ATTCCCGAGT  TAATCTCAGA  TCTTTCCGAG  GAAGAAACAG  2220
CCGACATTGT  GATGACGATT  TCAGCCAAGG  GCAGAAAGAA  CTTCTTTAAA  GGAATGCTGA  2280
GAACTTTAAG  GTGGATGTTT  GGAGAAGAAA  ATAGAAGGAT  AAGAACATTT  AATCGCTATT  2340
TGTTCCATCT  CGAAAAACTA  GGCCTTATCA  AACTACTGCC  CCGCGGATAT  GAAGTTACTG  2400
ACTGGGAGAG  ATTAAAGAAA  TATAAACAAC  TTTACGAGAA  GCTTGCTGGA  AGCGTTAAGT  2460
ACAACGGAAA  CAAGAGAGAG  TATTTAGTAA  TGTTCAACGA  GATCAAGGAT  TTTATATCTT  2520
ACTTCCCACA  AAAAGAGCTC  GAAGAATGGA  AAATTGGAAC  TCTCAATGGC  TTTAGAACGA  2580
ATTGTATTCT  CAAAGTCGAT  GAGGATTTTG  GGAAGCTCCT  AGGTTACTAT  GTTAGTGAGG  2640
GCTATGCAGG  TGCACAAAAA  AATAAAACTG  GTGGTATCAG  TTATTCGGTG  AAGCTTTACA  2700
ATGAGGACCC  TAATGTTCTT  GAGAGCATGA  AAAATGTTGC  AGAAAAATTC  TTTGGCAAGG  2760
TTAGAGTTGA  CAGAAATTGC  GTAAGTATAT  CAAAGAAGAT  GGCATACTTA  GTTATGAAAT  2820
GCCTCTGTGG  AGCATTAGCC  GAAAACAAGA  GAATTCCTTC  TGTTATACTC  ACCTCTCCCG  2880
AACCGGTACG  GTGGTCATTT  TTAGAGGCGT  ATTTTACAGG  CGATGGAGAT  ATACATCCAT  2940
CAAAAAGGTT  TAGGCTCTCA  ACAAAAAGCG  AGCTCCTTGC  AAATCAGCTT  GTGTTCTTGC  3000
TGAACTCTTT  GGGAATATCC  TCTGTAAAGA  TAGGCTTTGA  CAGTGGGGTC  TATAGAGTGT  3060
ATATAAATGA  AGACCTGCAA  TTTCCACAAA  CGTCTAGGGA  GAAAAACACA  TACTACTCTA  3120
ACTTAATTCC  CAAAGAGATC  CTTAGGGACG  TGTTTGGAAA  AGAGTTCCAA  AGAACATGA   3180
CGTTCAAGAA  ATTTAAAGAG  CTTGTTGACT  CTGGAAAACT  TAACAGGGAG  AAAGCCAAGC  3240
TCTTGGAGTT  CTTCATTAAT  GGAGATATTG  TCCTTGACAG  AGTCAAAAGT  GTTAAAGAAA  3300
AGGACTATGA  AGGGTATGTC  TATGACCTAA  GCGTTGAGGA  TAACGAGAAC  TTTCTTGTTG  3360
GTTTTGGTTT  GCTCTATGCT  CACAACAGCT  ATTACGGCTA  TATGGGGTAT  CCTAAGGCAA  3420
GATGGTACTC  GAAGGAATGT  GCTGAAAGCG  TTACCGCATG  GGGGAGACAC  TACATAGAGA  3480
TGACGATAAG  AGAAATAGAG  GAAAAGTTCG  GCTTTAAGGT  TCTTTATGCG  GACAGTGTCT  3540
CAGGAGAAAG  TGAGATCATA  ATAAGGCAAA  ACGGAAAGAT  TAGATTTGTG  AAAATAAAGG  3600
ATCTTTTCTC  TAAGGTGGAC  TACAGCATTG  GCGAAAAAGA  ATACTGCATT  CTCGAAGGTG  3660
TTGAAGCACT  AACTCTGGAC  GATGACGGAA  AGCTTGTCTG  GAAGCCCGTC  CCCTACGTGA  3720
TGAGGCACAG  AGCGAATAAA  AGAATGTTCC  GCATCTGGCT  GACCAACAGC  TGGTATATAG  3780
ATGTTACTGA  GGATCATTCT  CTCATAGGCT  ATCTAAACAC  GTCAAAAACG  AAAACTGCCA  3840
AAAAAATCGG  GGAAAGACTA  AAGGAAGTAA  AGCCTTTTGA  ATTAGGCAAA  GCAGTAAAAT  3900
CGCTCATATG  CCCAAATGCA  CCGTTAAAGG  ATGAGAATAC  CAAAACTAGC  GAAATAGCAG  3960
TAAAATTCTG  GGAGCTCGTA  GGATTGATTG  TAGGAGATGG  AAACTGGGGT  GGAGATTCTC  4020
GTTGGGCAGA  GTATTATCTT  GGACTTTCAA  CAGGCAAAGA  TGCAGAAGAG  ATAAAGCAAA  4080
AACTTCTGGA  ACCCCTAAAA  ACTTATGGAG  TAATCTCAAA  CTATTACCCA  AAAACGAGA   4140
AAGGGGACTT  CAACATCTTG  GCAAAGAGCC  TTGTAAAGTT  TATGAAAAGG  CACTTTAAGG  4200
ACGAAAAAGG  AAGACGAAAA  ATTCCAGAGT  TCATGTATGA  GCTTCCGGTT  ACTTACATAG  4260
```

| | | | | | |
|---|---|---|---|---|---|
| AGGCATTTCT | ACGAGGACTG | TTTTCAGCTG | ATGGTACTGT | AACTATCAGG | AAGGGAGTTC | 4320 |
| CAGAGATCAG | GCTAACAAAC | ATTGATGCTG | ACTTTCTAAG | GGAAGTAAGG | AAGCTTCTGT | 4380 |
| GGATTGTTGG | AATTTCAAAT | TCAATATTTG | CTGAGACTAC | TCCAAATCGC | TACAATGGTG | 4440 |
| TTTCTACTGG | AACCTACTCA | AAGCATCTAA | GGATCAAAAA | TAAGTGGCGT | TTTGCTGAAA | 4500 |
| GGATAGGCTT | TTTAATCGAG | AGAAAGCAGA | AGAGACTTTT | AGAACATTTA | AAATCAGCGA | 4560 |
| GGGTAAAAAG | GAATACCATA | GATTTTGGCT | TTGATCTTGT | GCATGTGAAA | AAAGTCGAAG | 4620 |
| AGATACCATA | CGAGGGTTAC | GTTTATGACA | TTGAAGTCGA | AGAGACGCAT | AGGTTCTTTG | 4680 |
| CAAACAACAT | CCTGGTACAC | AATACTGACG | GCTTTTATGC | CACAATACCC | GGGGAAAAGC | 4740 |
| CTGAACTCAT | TAAAAGAAA | GCCAAGGAAT | TCCTAAACTA | CATAAACTCC | AAACTTCCAG | 4800 |
| GTCTGCTTGA | GCTTGAGTAT | GAGGGCTTTT | ACTTGAGAGG | ATTCTTTGTT | ACAAAAAGC | 4860 |
| GCTATGCAGT | CATAGATGAA | GAGGGCAGGA | TAACAACAAG | GGGCTTGGAA | GTAGTAAGGA | 4920 |
| GAGATTGGAG | TGAGATAGCT | AAGGAGACTC | AGGCAAAGGT | TTTAGAGGCT | ATACTTAAAG | 4980 |
| AGGGAAGTGT | TGAAAAAGCT | GTAGAAGTTG | TTAGAGATGT | TGTAGAGAAA | ATAGCAAAAT | 5040 |
| ACAGGGTTCC | ACTTGAAAAG | CTTGTTATCC | ATGAGCAGAT | TACCAGGGAT | TTAAAGGACT | 5100 |
| ACAAAGCCAT | TGGCCCTCAT | GTCGCGATAG | CAAAAAGACT | TGCCGCAAGA | GGGATAAAAG | 5160 |
| TGAAACCGGG | CACAATAATA | AGCTATATCG | TTCTCAAAGG | GAGCGGAAAG | ATAAGCGATA | 5220 |
| GGGTAATTTT | ACTTACAGAA | TACGATCCTA | GAAAACACAA | GTACGATCCG | GACTACTACA | 5280 |
| TAGAAAACCA | AGTTTTGCCG | GCAGTACTTA | GGATACTCGA | AGCGTTTGGA | TACAGAAAGG | 5340 |
| AGGATTTAAG | GTATCAAAGC | TCAAAACAAA | CCGGCTTAGA | TGCATGGCTC | AAGAGGTAGC | 5400 |
| TCTGTTGCTT | TTTAGTCCAA | GTTTCTCCGC | GAGTCTCTCT | ATCTCTCTTT | TGTATTCTGC | 5460 |
| TATGTGGTTT | TCATTCACTA | TTAAGTAGTC | CGCCAAAGCC | ATAACGCTTC | CAATTCCAAA | 5520 |
| CTTGAGCTCT | TTCCAGTCTC | TGGCCTCAAA | TTCACTCCAT | GTTTTGGAT | CGTCGCTTCT | 5580 |
| CCCTCTTCTG | CTAAGCCTCT | CGAATCTTTT | TCTTGGCGAA | GAGTGTACAG | CTATGATGAT | 5640 |
| TATCTCTTCC | TCTGGAAACG | CATCTTAAA | CGTCTGAATT | TCATCTAGAG | ACCTCACTCC | 5700 |
| GTCGATTATA | ACTGCCTTGT | ACTTCTTTAG | TAGTTCTTTT | ACCTTTGGGA | TCGTTAATTT | 5760 |
| TGCCACGGCA | TTGTCCCCAA | GCTCCTGCCT | AAGCTGAATG | CTCACACTGT | TCATACCTTC | 5820 |
| GGGAGTTCTT | GGGATCC | | | | | 5837 |

( 2 ) INFORMATION FOR SEQ ID NO:2:

( i ) SEQUENCE CHARACTERISTICS:
        ( A ) LENGTH: 4707 base pairs
        ( B ) TYPE: nucleic acid
        ( C ) STRANDEDNESS: double
        ( D ) TOPOLOGY: Not Relevant ( i i i ) HYPOTHETICAL: NO ( i v ) ANTI-SENSE: NO ( v ) FRAGMENT TYPE: N-terminal ( i x ) FEATURE:
        ( A ) NAME/KEY: CDS
        ( B ) LOCATION: 363..4298

( x i ) SEQUENCE DESCRIPTION: SEQ ID NO:2:

| | | | | | |
|---|---|---|---|---|---|
| GGATCCCTCT | CTTTTTGGTA | ACCCCATACG | TCATTCCCTC | AACCAAAACT | TCAGCATCGT | 60 |
| TGCAGTGGTC | AGTGTGTCTG | TGGGAGATGA | AGAGGACGTC | GATTTTCTG | GGGTCTATCT | 120 |
| TGTATCTCCA | CATTCTAACT | AACGCTCCAG | GCCCAGGATC | AACGTAGATG | TTTTTGCTCG | 180 |

-continued

```
CCTTAATGAA GAAGCCACCA GTGGCTCTTG CCTGCGTTAT CGTGACGAAC CTTCCACCAC      240

CGCCACCGAG AAAAGTTATC TCTATCATCT CACACCTCCC CCATAACATC ACCTGCTCAA      300

TTTTTAAGCG TTCTTAAAGG CTTAAATACG TGAATTTAGC GTAAATTATT GAGGGATTAA      360
```

| | | | | | | | | | | | | | | | |
|---|---|---|---|---|---|---|---|---|---|---|---|---|---|---|---|
| GT ATG | ATA | CTT | GAC | GCT | GAC | TAC | ATC | ACC | GAG | GAT | GGG | AAG | CCG | ATT | 407 |
| Met | Ile | Leu | Asp | Ala | Asp | Tyr | Ile | Thr | Glu | Asp | Gly | Lys | Pro | Ile | |
| 1 | | | | 5 | | | | | 10 | | | | | 15 | |
| ATA | AGG | ATT | TTC | AAG | AAA | GAA | AAC | GGC | GAG | TTT | AAG | GTT | GAG | TAC GAC | 455 |
| Ile | Arg | Ile | Phe | Lys | Lys | Glu | Asn | Gly | Glu | Phe | Lys | Val | Glu | Tyr Asp | |
| | | | | 20 | | | | | 25 | | | | | 30 | |
| AGA | AAC | TTT | AGA | CCT | TAC | ATT | TAC | GCT | CTC | CTC | AAA | GAT | GAC | TCG CAG | 503 |
| Arg | Asn | Phe | Arg | Pro | Tyr | Ile | Tyr | Ala | Leu | Leu | Lys | Asp | Asp | Ser Gln | |
| | | | | 35 | | | | | 40 | | | | | 45 | |
| ATT | GAT | GAG | GTT | AGG | AAG | ATA | ACC | GCC | GAG | AGG | CAT | GGG | AAG | ATA GTG | 551 |
| Ile | Asp | Glu | Val | Arg | Lys | Ile | Thr | Ala | Glu | Arg | His | Gly | Lys | Ile Val | |
| | | | | 50 | | | | | 55 | | | | | 60 | |
| AGA | ATT | ATA | GAT | GCC | GAA | AAG | GTA | AGG | AAG | AAG | TTC | CTG | GGG | AGG CCG | 599 |
| Arg | Ile | Ile | Asp | Ala | Glu | Lys | Val | Arg | Lys | Lys | Phe | Leu | Gly | Arg Pro | |
| 65 | | | | | 70 | | | | | 75 | | | | | |
| ATT | GAG | GTA | TGG | AGG | CTG | TAC | TTT | GAA | CAC | CCT | CAG | GAC | GTT | CCC GCA | 647 |
| Ile | Glu | Val | Trp | Arg | Leu | Tyr | Phe | Glu | His | Pro | Gln | Asp | Val | Pro Ala | |
| 80 | | | | | 85 | | | | | 90 | | | | | 95 |
| ATA | AGG | GAT | AAG | ATA | AGA | GAG | CAT | TCC | GCA | GTT | ATT | GAC | ATC | TTT GAG | 695 |
| Ile | Arg | Asp | Lys | Ile | Arg | Glu | His | Ser | Ala | Val | Ile | Asp | Ile | Phe Glu | |
| | | | | 100 | | | | | 105 | | | | | 110 | |
| TAC | GAC | ATT | CCG | TTC | GCG | AAG | AGG | TAC | CTA | ATA | GAC | AAA | GGC | CTA ATT | 743 |
| Tyr | Asp | Ile | Pro | Phe | Ala | Lys | Arg | Tyr | Leu | Ile | Asp | Lys | Gly | Leu Ile | |
| | | | | 115 | | | | | 120 | | | | | 125 | |
| CCA | ATG | GAA | GGC | GAT | GAA | GAG | CTC | AAG | TTG | CTC | GCA | TTT | GAC | ATA GAA | 791 |
| Pro | Met | Glu | Gly | Asp | Glu | Glu | Leu | Lys | Leu | Leu | Ala | Phe | Asp | Ile Glu | |
| | | | | 130 | | | | | 135 | | | | | 140 | |
| ACC | CTC | TAT | CAC | GAA | GGG | GAG | GAG | TTC | GCG | AAG | GGG | CCC | ATT | ATA ATG | 839 |
| Thr | Leu | Tyr | His | Glu | Gly | Glu | Glu | Phe | Ala | Lys | Gly | Pro | Ile | Ile Met | |
| | | | | 145 | | | | | 150 | | | | | 155 | |
| ATA | AGC | TAT | GCT | GAT | GAG | GAA | GAA | GCC | AAA | GTC | ATA | ACG | TGG | AAA AAG | 887 |
| Ile | Ser | Tyr | Ala | Asp | Glu | Glu | Glu | Ala | Lys | Val | Ile | Thr | Trp | Lys Lys | |
| 160 | | | | | 165 | | | | | 170 | | | | | 175 |
| ATC | GAT | CTC | CCG | TAC | GTC | GAG | GTA | GTT | TCC | AGC | GAG | AGG | GAG | ATG ATA | 935 |
| Ile | Asp | Leu | Pro | Tyr | Val | Glu | Val | Val | Ser | Ser | Glu | Arg | Glu | Met Ile | |
| | | | | 180 | | | | | 185 | | | | | 190 | |
| AAG | CGG | TTC | CTC | AAG | GTG | ATA | AGG | GAG | AAA | GAT | CCC | GAT | GTT | ATA ATT | 983 |
| Lys | Arg | Phe | Leu | Lys | Val | Ile | Arg | Glu | Lys | Asp | Pro | Asp | Val | Ile Ile | |
| | | | | 195 | | | | | 200 | | | | | 205 | |
| ACC | TAC | AAC | GGC | GAT | TCT | TTC | GAC | CTT | CCC | TAT | CTA | GTT | AAG | AGG GCC | 1031 |
| Thr | Tyr | Asn | Gly | Asp | Ser | Phe | Asp | Leu | Pro | Tyr | Leu | Val | Lys | Arg Ala | |
| | | | | 210 | | | | | 215 | | | | | 220 | |
| GAA | AAG | CTC | GGG | ATA | AAG | CTA | CCC | CTG | GGA | AGG | GAC | GGT | AGT | GAG CCA | 1079 |
| Glu | Lys | Leu | Gly | Ile | Lys | Leu | Pro | Leu | Gly | Arg | Asp | Gly | Ser | Glu Pro | |
| | | | | 225 | | | | | 230 | | | | | 235 | |
| AAG | ATG | CAG | AGG | CTT | GGG | GAT | ATG | ACA | GCG | GTG | GAG | ATA | AAG | GGA AGG | 1127 |
| Lys | Met | Gln | Arg | Leu | Gly | Asp | Met | Thr | Ala | Val | Glu | Ile | Lys | Gly Arg | |
| 240 | | | | | 245 | | | | | 250 | | | | | 255 |
| ATA | CAC | TTT | GAC | CTC | TAC | CAC | GTG | ATT | AGG | AGA | ACG | ATA | AAC | CTC CCA | 1175 |
| Ile | His | Phe | Asp | Leu | Tyr | His | Val | Ile | Arg | Arg | Thr | Ile | Asn | Leu Pro | |
| | | | | 260 | | | | | 265 | | | | | 270 | |
| ACA | TAC | ACC | CTC | GAG | GCA | GTT | TAT | GAG | GCA | ATC | TTC | GGA | AAG | CCA AAG | 1223 |
| Thr | Tyr | Thr | Leu | Glu | Ala | Val | Tyr | Glu | Ala | Ile | Phe | Gly | Lys | Pro Lys | |
| | | | | 275 | | | | | 280 | | | | | 285 | |
| GAG | AAA | GTT | TAC | GCT | CAC | GAG | ATA | GCT | GAG | GCC | TGG | GAG | ACT | GGA AAG | 1271 |

-continued

```
            Glu  Lys  Val  Tyr  Ala  His  Glu  Ile  Ala  Glu  Ala  Trp  Glu  Thr  Gly  Lys
                 290                 295                 300

GGA  CTG  GAG  AGA  GTT  GCA  AAG  TAT  TCA  ATG  GAG  GAT  GCA  AAG  GTA  ACG         1319
Gly  Leu  Glu  Arg  Val  Ala  Lys  Tyr  Ser  Met  Glu  Asp  Ala  Lys  Val  Thr
     305                 310                 315

TAC  GAG  CTC  GGT  AGG  GAG  TTC  TTC  CCA  ATG  GAG  GCC  CAG  CTT  TCA  AGG         1367
Tyr  Glu  Leu  Gly  Arg  Glu  Phe  Phe  Pro  Met  Glu  Ala  Gln  Leu  Ser  Arg
320                 325                 330                 335

TTA  GTC  GGC  CAG  CCC  CTG  TGG  GAT  GTT  TCT  AGG  TCT  TCA  ACT  GGC  AAC         1415
Leu  Val  Gly  Gln  Pro  Leu  Trp  Asp  Val  Ser  Arg  Ser  Ser  Thr  Gly  Asn
                    340                 345                 350

TTG  GTG  GAG  TGG  TAC  CTC  CTC  AGG  AAG  GCC  TAC  GAG  AGG  AAT  GAA  TTG         1463
Leu  Val  Glu  Trp  Tyr  Leu  Leu  Arg  Lys  Ala  Tyr  Glu  Arg  Asn  Glu  Leu
               355                 360                 365

GCT  CCA  AAC  AAG  CCG  GAT  GAG  AGG  GAG  TAC  GAG  AGA  AGG  CTA  AGG  GAG         1511
Ala  Pro  Asn  Lys  Pro  Asp  Glu  Arg  Glu  Tyr  Glu  Arg  Arg  Leu  Arg  Glu
          370                 375                 380

AGC  TAC  GCT  GGG  GGA  TAC  GTT  AAG  GAG  CCG  GAG  AAA  GGG  CTC  TGG  GAG         1559
Ser  Tyr  Ala  Gly  Gly  Tyr  Val  Lys  Glu  Pro  Glu  Lys  Gly  Leu  Trp  Glu
     385                 390                 395

GGG  TTA  GTT  TCC  CTA  GAT  TTC  AGG  AGC  CTG  TAC  CCC  TCG  ATA  ATA  ATC         1607
Gly  Leu  Val  Ser  Leu  Asp  Phe  Arg  Ser  Leu  Tyr  Pro  Ser  Ile  Ile  Ile
400                 405                 410                 415

ACC  CAT  AAC  GTC  TCA  CCG  GAT  ACG  CTG  AAC  AGG  GAA  GGG  TGT  AGG  GAA         1655
Thr  His  Asn  Val  Ser  Pro  Asp  Thr  Leu  Asn  Arg  Glu  Gly  Cys  Arg  Glu
                    420                 425                 430

TAC  GAT  GTC  GCC  CCA  GAG  GTT  GGG  CAC  AAG  TTC  TGC  AAG  GAC  TTC  CCG         1703
Tyr  Asp  Val  Ala  Pro  Glu  Val  Gly  His  Lys  Phe  Cys  Lys  Asp  Phe  Pro
               435                 440                 445

GGG  TTT  ATC  CCC  AGC  CTG  CTC  AAG  AGG  TTA  TTG  GAT  GAA  AGG  CAA  GAA         1751
Gly  Phe  Ile  Pro  Ser  Leu  Leu  Lys  Arg  Leu  Leu  Asp  Glu  Arg  Gln  Glu
          450                 455                 460

ATA  AAA  AGG  AAG  ATG  AAA  GCT  TCT  AAA  GAC  CCA  ATC  GAG  AAG  AAG  ATG         1799
Ile  Lys  Arg  Lys  Met  Lys  Ala  Ser  Lys  Asp  Pro  Ile  Glu  Lys  Lys  Met
     465                 470                 475

CTT  GAT  TAC  AGG  CAA  CGG  GCA  ATC  AAA  ATC  CTG  GCA  AAC  AGC  ATT  TTA         1847
Leu  Asp  Tyr  Arg  Gln  Arg  Ala  Ile  Lys  Ile  Leu  Ala  Asn  Ser  Ile  Leu
480                 485                 490                 495

CCG  GAA  GAA  TGG  GTT  CCA  CTA  ATT  AAA  AAC  GGT  AAA  GTT  AAG  ATA  TTC         1895
Pro  Glu  Glu  Trp  Val  Pro  Leu  Ile  Lys  Asn  Gly  Lys  Val  Lys  Ile  Phe
                    500                 505                 510

CGC  ATT  GGG  GAC  TTC  GTT  GAT  GGA  CTT  ATG  AAG  GCG  AAC  CAA  GGA  AAA         1943
Arg  Ile  Gly  Asp  Phe  Val  Asp  Gly  Leu  Met  Lys  Ala  Asn  Gln  Gly  Lys
               515                 520                 525

GTG  AAG  AAA  ACG  GGG  GAT  ACA  GAA  GTT  TTA  GAA  GTT  GCA  GGA  ATT  CAT         1991
Val  Lys  Lys  Thr  Gly  Asp  Thr  Glu  Val  Leu  Glu  Val  Ala  Gly  Ile  His
          530                 535                 540

GCG  TTT  TCC  TTT  GAC  AGG  AAG  TCC  AAG  AAG  GCC  CGT  GTA  ATG  GCA  GTG         2039
Ala  Phe  Ser  Phe  Asp  Arg  Lys  Ser  Lys  Lys  Ala  Arg  Val  Met  Ala  Val
     545                 550                 555

AAA  GCC  GTG  ATA  AGA  CAC  CGT  TAT  TCC  GGA  AAT  GTT  TAT  AGA  ATA  GTC         2087
Lys  Ala  Val  Ile  Arg  His  Arg  Tyr  Ser  Gly  Asn  Val  Tyr  Arg  Ile  Val
560                 565                 570                 575

TTA  AAC  TCT  GGT  AGA  AAA  ATA  ACA  ATA  ACA  GAA  GGG  CAT  AGC  CTA  TTT         2135
Leu  Asn  Ser  Gly  Arg  Lys  Ile  Thr  Ile  Thr  Glu  Gly  His  Ser  Leu  Phe
                    580                 585                 590

GTC  TAT  AGG  AAC  GGG  GAT  CTC  GTT  GAG  GCA  ACT  GGG  GAG  GAT  GTC  AAA         2183
Val  Tyr  Arg  Asn  Gly  Asp  Leu  Val  Glu  Ala  Thr  Gly  Glu  Asp  Val  Lys
               595                 600                 605

ATT  GGG  GAT  CTT  CTT  GCA  GTT  CCA  AGA  TCA  GTA  AAC  CTA  CCA  GAG  AAA         2231
```

| | | | | | | | | | | | | | | | |
|---|---|---|---|---|---|---|---|---|---|---|---|---|---|---|---|
| Ile | Gly | Asp | Leu | Leu | Ala | Val | Pro | Arg | Ser | Val | Asn | Leu | Pro | Glu | Lys |
| | | 610 | | | | 615 | | | | | | 620 | | | |

| AGG | GAA | CGC | TTG | AAT | ATT | GTT | GAA | CTT | CTT | CTG | AAT | CTC | TCA | CCG | GAA | 2279 |
| Arg | Glu | Arg | Leu | Asn | Ile | Val | Glu | Leu | Leu | Leu | Asn | Leu | Ser | Pro | Glu | |
| | 625 | | | | | 630 | | | | | 635 | | | | | |

| GAG | ACA | GAA | GAT | ATA | ATA | CTT | ACG | ATT | CCA | GTT | AAA | GGC | AGA | AAG | AAC | 2327 |
| Glu | Thr | Glu | Asp | Ile | Ile | Leu | Thr | Ile | Pro | Val | Lys | Gly | Arg | Lys | Asn | |
| 640 | | | | | 645 | | | | | 650 | | | | | 655 | |

| TTC | TTC | AAG | GGA | ATG | TTG | AGA | ACA | TTA | CGT | TGG | ATT | TTT | GGT | GAG | GAA | 2375 |
| Phe | Phe | Lys | Gly | Met | Leu | Arg | Thr | Leu | Arg | Trp | Ile | Phe | Gly | Glu | Glu | |
| | | | | 660 | | | | | 665 | | | | | 670 | | |

| AAG | AGA | GTA | AGG | ACA | GCG | AGC | CGC | TAT | CTA | AGA | CAC | CTT | GAA | AAT | CTC | 2423 |
| Lys | Arg | Val | Arg | Thr | Ala | Ser | Arg | Tyr | Leu | Arg | His | Leu | Glu | Asn | Leu | |
| | | | 675 | | | | | 680 | | | | | 685 | | | |

| GGA | TAC | ATA | AGG | TTG | AGG | AAA | ATT | GGA | TAC | GAC | ATC | ATT | GAT | AAG | GAG | 2471 |
| Gly | Tyr | Ile | Arg | Leu | Arg | Lys | Ile | Gly | Tyr | Asp | Ile | Ile | Asp | Lys | Glu | |
| | | 690 | | | | 695 | | | | | 700 | | | | | |

| GGG | CTT | GAG | AAA | TAT | AGA | ACG | TTG | TAC | GAG | AAA | CTT | GTT | GAT | GTT | GTC | 2519 |
| Gly | Leu | Glu | Lys | Tyr | Arg | Thr | Leu | Tyr | Glu | Lys | Leu | Val | Asp | Val | Val | |
| | 705 | | | | | 710 | | | | | 715 | | | | | |

| CGC | TAT | AAT | GGC | AAC | AAG | AGA | GAG | TAT | TTA | GTT | GAA | TTT | AAT | GCT | GTC | 2567 |
| Arg | Tyr | Asn | Gly | Asn | Lys | Arg | Glu | Tyr | Leu | Val | Glu | Phe | Asn | Ala | Val | |
| 720 | | | | | 725 | | | | | 730 | | | | | 735 | |

| CGG | GAC | GTT | ATC | TCA | CTA | ATG | CCA | GAG | GAA | GAA | CTG | AAG | GAA | TGG | CGT | 2615 |
| Arg | Asp | Val | Ile | Ser | Leu | Met | Pro | Glu | Glu | Glu | Leu | Lys | Glu | Trp | Arg | |
| | | | | 740 | | | | | 745 | | | | | | 750 | |

| ATT | GGA | ACT | AGA | AAT | GGA | TTC | AGA | ATG | GGT | ACG | TTC | GTA | GAT | ATT | GAT | 2663 |
| Ile | Gly | Thr | Arg | Asn | Gly | Phe | Arg | Met | Gly | Thr | Phe | Val | Asp | Ile | Asp | |
| | | | 755 | | | | | 760 | | | | | 765 | | | |

| GAA | GAT | TTT | GCC | AAG | CTT | CTT | GGC | TAC | TAT | GTG | AGC | GAG | GGA | AGT | GCG | 2711 |
| Glu | Asp | Phe | Ala | Lys | Leu | Leu | Gly | Tyr | Tyr | Val | Ser | Glu | Gly | Ser | Ala | |
| | | 770 | | | | | 775 | | | | | 780 | | | | |

| AGG | AAG | TGG | AAG | AAT | CAA | ACT | GGA | GGT | TGG | AGT | TAC | ACT | GTG | AGA | TTG | 2759 |
| Arg | Lys | Trp | Lys | Asn | Gln | Thr | Gly | Gly | Trp | Ser | Tyr | Thr | Val | Arg | Leu | |
| | 785 | | | | | 790 | | | | | 795 | | | | | |

| TAC | AAC | GAG | AAC | GAT | GAA | GTT | CTT | GAC | GAC | ATG | GAA | CAC | TTA | GCC | AAG | 2807 |
| Tyr | Asn | Glu | Asn | Asp | Glu | Val | Leu | Asp | Asp | Met | Glu | His | Leu | Ala | Lys | |
| 800 | | | | | 805 | | | | | 810 | | | | | 815 | |

| AAG | TTT | TTT | GGG | AAA | GTC | AAA | CGT | GGA | AAG | AAC | TAT | GTT | GAG | ATA | CCA | 2855 |
| Lys | Phe | Phe | Gly | Lys | Val | Lys | Arg | Gly | Lys | Asn | Tyr | Val | Glu | Ile | Pro | |
| | | | | 820 | | | | | 825 | | | | | 830 | | |

| AAG | AAA | ATG | GCT | TAT | ATC | ATC | TTT | GAG | AGC | CTT | TGT | GGG | ACT | TTG | GCA | 2903 |
| Lys | Lys | Met | Ala | Tyr | Ile | Ile | Phe | Glu | Ser | Leu | Cys | Gly | Thr | Leu | Ala | |
| | | | 835 | | | | | 840 | | | | | 845 | | | |

| GAA | AAC | AAA | AGG | GTT | CCT | GAG | GTA | ATC | TTT | ACC | TCA | TCA | AAG | GGC | GTT | 2951 |
| Glu | Asn | Lys | Arg | Val | Pro | Glu | Val | Ile | Phe | Thr | Ser | Ser | Lys | Gly | Val | |
| | | 850 | | | | | 855 | | | | | 860 | | | | |

| AGA | TGG | GCC | TTC | CTT | GAG | GGT | TAT | TTC | ATC | GGC | GAT | GGC | GAT | GTT | CAC | 2999 |
| Arg | Trp | Ala | Phe | Leu | Glu | Gly | Tyr | Phe | Ile | Gly | Asp | Gly | Asp | Val | His | |
| | 865 | | | | | 870 | | | | | 875 | | | | | |

| CCA | AGC | AAG | AGG | GTT | CGC | CTA | TCA | ACG | AAG | AGC | GAG | CTT | TTA | GTA | AAT | 3047 |
| Pro | Ser | Lys | Arg | Val | Arg | Leu | Ser | Thr | Lys | Ser | Glu | Leu | Leu | Val | Asn | |
| 880 | | | | | 885 | | | | | 890 | | | | | 895 | |

| GGC | CTT | GTT | CTC | CTA | CTT | AAC | TCC | CTT | GGA | GTA | TCT | GCC | ATT | AAG | CTT | 3095 |
| Gly | Leu | Val | Leu | Leu | Leu | Asn | Ser | Leu | Gly | Val | Ser | Ala | Ile | Lys | Leu | |
| | | | | 900 | | | | | 905 | | | | | 910 | | |

| GGA | TAC | GAT | AGC | GGA | GTC | TAC | AGG | GTT | TAT | GTA | AAC | GAG | GAA | CTT | AAG | 3143 |
| Gly | Tyr | Asp | Ser | Gly | Val | Tyr | Arg | Val | Tyr | Val | Asn | Glu | Glu | Leu | Lys | |
| | | | 915 | | | | | 920 | | | | | 925 | | | |

| TTT | ACG | GAA | TAC | AGA | AAG | AAA | AAG | AAT | GTA | TAT | CAC | TCT | CAC | ATT | GTT | 3191 |

| | | | | | | | | | | | | | | | | |
|---|---|---|---|---|---|---|---|---|---|---|---|---|---|---|---|---|
| Phe | Thr | Glu | Tyr | Arg | Lys | Lys | Lys | Asn | Val | Tyr | His | Ser | His | Ile | Val | |
| | | 930 | | | | 935 | | | | | 940 | | | | | |

| CCA | AAG | GAT | ATT | CTC | AAA | GAA | ACT | TTT | GGT | AAG | GTC | TTC | CAG | AAA | AAT | 3239 |
|---|---|---|---|---|---|---|---|---|---|---|---|---|---|---|---|---|
| Pro | Lys | Asp | Ile | Leu | Lys | Glu | Thr | Phe | Gly | Lys | Val | Phe | Gln | Lys | Asn | |
| 945 | | | | | 950 | | | | | 955 | | | | | | |

| ATA | AGT | TAC | AAG | AAA | TTT | AGA | GAG | CTT | GTA | GAA | AAT | GGA | AAA | CTT | GAC | 3287 |
|---|---|---|---|---|---|---|---|---|---|---|---|---|---|---|---|---|
| Ile | Ser | Tyr | Lys | Lys | Phe | Arg | Glu | Leu | Val | Glu | Asn | Gly | Lys | Leu | Asp | |
| 960 | | | | | 965 | | | | | 970 | | | | | 975 | |

| AGG | GAG | AAA | GCC | AAA | CGC | ATT | GAG | TGG | TTA | CTT | AAC | GGA | GAT | ATA | GTC | 3335 |
|---|---|---|---|---|---|---|---|---|---|---|---|---|---|---|---|---|
| Arg | Glu | Lys | Ala | Lys | Arg | Ile | Glu | Trp | Leu | Leu | Asn | Gly | Asp | Ile | Val | |
| | | | | 980 | | | | | 985 | | | | | 990 | | |

| CTA | GAT | AGA | GTC | GTA | GAG | ATT | AAG | AGA | GAG | TAC | TAT | GAT | GGT | TAC | GTT | 3383 |
|---|---|---|---|---|---|---|---|---|---|---|---|---|---|---|---|---|
| Leu | Asp | Arg | Val | Val | Glu | Ile | Lys | Arg | Glu | Tyr | Tyr | Asp | Gly | Tyr | Val | |
| | | | 995 | | | | | 1000 | | | | | 1005 | | | |

| TAC | GAT | CTA | AGT | GTC | GAT | GAA | GAT | GAG | AAT | TTC | CTT | GCT | GGC | TTT | GGA | 3431 |
|---|---|---|---|---|---|---|---|---|---|---|---|---|---|---|---|---|
| Tyr | Asp | Leu | Ser | Val | Asp | Glu | Asp | Glu | Asn | Phe | Leu | Ala | Gly | Phe | Gly | |
| | | | 1010 | | | | | 1015 | | | | | 1020 | | | |

| TTC | CTC | TAT | GCA | CAT | AAT | AGC | TAT | TAT | GGG | TAT | TAT | GGG | TAC | GCA | AAA | 3479 |
|---|---|---|---|---|---|---|---|---|---|---|---|---|---|---|---|---|
| Phe | Leu | Tyr | Ala | His | Asn | Ser | Tyr | Tyr | Gly | Tyr | Tyr | Gly | Tyr | Ala | Lys | |
| | | | | 1025 | | | | | 1030 | | | | | 1035 | | |

| GCC | CGT | TGG | TAC | TGT | AAG | GAG | TGC | GCA | GAG | AGC | GTT | ACG | GCC | TGG | GGG | 3527 |
|---|---|---|---|---|---|---|---|---|---|---|---|---|---|---|---|---|
| Ala | Arg | Trp | Tyr | Cys | Lys | Glu | Cys | Ala | Glu | Ser | Val | Thr | Ala | Trp | Gly | |
| 1040 | | | | | 1045 | | | | | 1050 | | | | | 1055 | |

| AGG | GAA | TAT | ATA | GAG | TTC | GTA | AGG | AAG | GAA | CTG | GAG | GAA | AAG | TTC | GGG | 3575 |
|---|---|---|---|---|---|---|---|---|---|---|---|---|---|---|---|---|
| Arg | Glu | Tyr | Ile | Glu | Phe | Val | Arg | Lys | Glu | Leu | Glu | Glu | Lys | Phe | Gly | |
| | | | | 1060 | | | | | 1065 | | | | | 1070 | | |

| TTC | AAA | GTC | TTA | TAC | ATA | GAC | ACA | GAT | GGA | CTC | TAC | GCC | ACA | ATT | CCT | 3623 |
|---|---|---|---|---|---|---|---|---|---|---|---|---|---|---|---|---|
| Phe | Lys | Val | Leu | Tyr | Ile | Asp | Thr | Asp | Gly | Leu | Tyr | Ala | Thr | Ile | Pro | |
| | | | 1075 | | | | | 1080 | | | | | 1085 | | | |

| GGG | GCA | AAA | CCC | GAG | GAG | ATA | AAG | AAG | AAA | GCC | CTA | GAG | TTC | GTA | GAT | 3671 |
|---|---|---|---|---|---|---|---|---|---|---|---|---|---|---|---|---|
| Gly | Ala | Lys | Pro | Glu | Glu | Ile | Lys | Lys | Lys | Ala | Leu | Glu | Phe | Val | Asp | |
| | | 1090 | | | | | 1095 | | | | | 1100 | | | | |

| TAT | ATA | AAC | GCC | AAG | CTC | CCA | GGG | CTG | TTG | GAG | CTT | GAG | TAC | GAG | GGC | 3719 |
|---|---|---|---|---|---|---|---|---|---|---|---|---|---|---|---|---|
| Tyr | Ile | Asn | Ala | Lys | Leu | Pro | Gly | Leu | Leu | Glu | Leu | Glu | Tyr | Glu | Gly | |
| | | | 1105 | | | | | 1110 | | | | | 1115 | | | |

| TTC | TAC | GTG | AGA | GGG | TTC | TTC | GTG | ACG | AAG | AAG | AAG | TAT | GCG | TTG | ATA | 3767 |
|---|---|---|---|---|---|---|---|---|---|---|---|---|---|---|---|---|
| Phe | Tyr | Val | Arg | Gly | Phe | Phe | Val | Thr | Lys | Lys | Lys | Tyr | Ala | Leu | Ile | |
| 1120 | | | | | 1125 | | | | | 1130 | | | | | 1135 | |

| GAT | GAG | GAA | GGG | AAG | ATA | ATC | ACT | AGG | GGG | CTT | GAA | ATA | GTC | AGG | AGG | 3815 |
|---|---|---|---|---|---|---|---|---|---|---|---|---|---|---|---|---|
| Asp | Glu | Glu | Gly | Lys | Ile | Ile | Thr | Arg | Gly | Leu | Glu | Ile | Val | Arg | Arg | |
| | | | | 1140 | | | | | 1145 | | | | | 1150 | | |

| GAC | TGG | AGC | GAA | ATA | GCC | AAA | GAA | ACC | CAA | GCA | AAA | GTC | CTA | GAG | GCT | 3863 |
|---|---|---|---|---|---|---|---|---|---|---|---|---|---|---|---|---|
| Asp | Trp | Ser | Glu | Ile | Ala | Lys | Glu | Thr | Gln | Ala | Lys | Val | Leu | Glu | Ala | |
| | | | | 1155 | | | | | 1160 | | | | | 1165 | | |

| ATC | CTA | AAG | CAT | GGC | AAC | GTT | GAG | GAG | GCA | GTA | AAG | ATA | GTT | AAG | GAG | 3911 |
|---|---|---|---|---|---|---|---|---|---|---|---|---|---|---|---|---|
| Ile | Leu | Lys | His | Gly | Asn | Val | Glu | Glu | Ala | Val | Lys | Ile | Val | Lys | Glu | |
| | | | 1170 | | | | | 1175 | | | | | 1180 | | | |

| GTA | ACT | GAA | AAG | CTG | AGC | AAG | TAC | GAA | ATA | CCT | CCA | GAA | AAG | CTA | GTT | 3959 |
|---|---|---|---|---|---|---|---|---|---|---|---|---|---|---|---|---|
| Val | Thr | Glu | Lys | Leu | Ser | Lys | Tyr | Glu | Ile | Pro | Pro | Glu | Lys | Leu | Val | |
| | | 1185 | | | | | 1190 | | | | | 1195 | | | | |

| ATT | TAC | GAG | CAG | ATC | ACG | AGG | CCC | CTT | CAC | GAG | TAC | AAG | GCT | ATA | GGT | 4007 |
|---|---|---|---|---|---|---|---|---|---|---|---|---|---|---|---|---|
| Ile | Tyr | Glu | Gln | Ile | Thr | Arg | Pro | Leu | His | Glu | Tyr | Lys | Ala | Ile | Gly | |
| 1200 | | | | | 1205 | | | | | 1210 | | | | | 1215 | |

| CCG | CAC | GTT | GCC | GTG | GCA | AAA | AGG | TTA | GCC | GCT | AGA | GGA | GTA | AAG | GTG | 4055 |
|---|---|---|---|---|---|---|---|---|---|---|---|---|---|---|---|---|
| Pro | His | Val | Ala | Val | Ala | Lys | Arg | Leu | Ala | Ala | Arg | Gly | Val | Lys | Val | |
| | | | | 1220 | | | | | 1225 | | | | | 1230 | | |

| AGG | CCT | GGC | ATG | GTG | ATA | GGG | TAC | ATA | GTG | CTG | AGG | GGA | GAC | GGG | CCA | 4103 |
|---|---|---|---|---|---|---|---|---|---|---|---|---|---|---|---|---|
| Arg | Pro | Gly | Met | Val | Ile | Gly | Tyr | Ile | Val | Leu | Arg | Gly | Asp | Gly | Pro | |
| | | | 1235 | | | | | 1240 | | | | | 1245 | | | |

| ATA | AGC | AAG | AGG | GCT | ATC | CTT | GCA | GAG | GAG | TTC | GAT | CTC | AGG | AAG | CAT | 4151 |

| | | | | | | | | | | | | | | | |
|---|---|---|---|---|---|---|---|---|---|---|---|---|---|---|---|
| Ile | Ser | Lys | Arg | Ala | Ile | Leu | Ala | Glu | Glu | Phe | Asp | Leu | Arg | Lys | His |
| | | 1250 | | | | | 1255 | | | | 1260 | | | | |

```
AAG TAT GAC GCT GAG TAT TAC ATA GAA AAT CAG GTT TTA CCT GCC GTT        4199
Lys Tyr Asp Ala Glu Tyr Tyr Ile Glu Asn Gln Val Leu Pro Ala Val
    1265                    1270                1275

CTT AGA ATA TTA GAG GCC TTT GGG TAC AGG AAA GAA GAC CTC AGG TGG        4247
Leu Arg Ile Leu Glu Ala Phe Gly Tyr Arg Lys Glu Asp Leu Arg Trp
1280                1285                1290                1295

CAG AAG ACT AAA CAG ACA GGT CTT ACG GCA TGG CTT AAC ATC AAG AAG        4295
Gln Lys Thr Lys Gln Thr Gly Leu Thr Ala Trp Leu Asn Ile Lys Lys
                1300                1305                1310

AAG TAATGTTTAT GTACTCGTAA TGCGAGTATT AAGTGGGTGA TGAGATGGCA             4348
Lys

GTATTGAGCA TAAGGATTCC GGATGATCTA AAAGAGAAGA TGAAGGAGTT TGACATAAAC      4408

TGGAGTGAGG AGATCAGGAA GTTCATAAAA GAGAGGATAG AGTATGAGGA AAGGAAGAGA      4468

ACCCTTGAGA AAGCTCTAGA ACTTCTAAAG AATACTCCAG GATCAGTCGA GAGAGGATTT      4528

TCAGCAAGGG CAGTGAGGGA GGATCGTGAT AGTCATTGAT GCATCAATCC TAGCTAAAAT      4588

AATTCTAAAA GAAGAGGGCT GGGAACAGAT AACTCTTACA CCGAGCACGA TAACTTTGGA      4648

CTATGCTTTT GTTGAATGTA CAAACGCAAT ATGGAAGGCT GTCAGGCGGA ACAGGATCC       4707
```

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
AGTGTCTCCG GAGAAAGTGA GAT                                               23
```

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
AGTATTGTGT ACCAGGATGT TG                                                22
```

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
AGCATTTTAC CGGAAGAATG GGTT                                              24
```

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GCTATTATGT GCATAGAGGA ATCCA 25

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

AGGGTCGACA GATTTGATCC AGCG 24

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

GAGAACTTTG TTCGTACCTG 20

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

GGTATTATTT CTTCTAAAGC A 21

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

GTTGTTTGTT GGTTTTACCA 20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

ATGGCAAATG CTGTATGGAT 20

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:12:

AGTGTCTCCG GAGAAAGTGA GAT 23

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATTGTGTACT AGTATGTTGT TTGCAA        26

( 2 ) INFORMATION FOR SEQ ID NO:14:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GCCTCCGGAG ACACTATCGC CAAAATCACC GCCGTAA        37

( 2 ) INFORMATION FOR SEQ ID NO:15:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GCCACTAGTA CACAATACGC CGAACGATCG CCAGTTCT        38

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CCTTCTAGAC CGGTGCAGTA TGAAGG        26

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GCCGTCGACC CTAGTGTCTC AGGAGAAAGT GAGATC        36

( 2 ) INFORMATION FOR SEQ ID NO:18:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GCCTCTAGAA TTGTGTACCA GGATGTTGTT TGC        33

( 2 ) INFORMATION FOR SEQ ID NO:19:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

GCAAAGAACC GGTGCGTCTC TTC  23

( 2 ) INFORMATION FOR SEQ ID NO:20:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

AGCAACAGAG TTACCTCTTG  20

( 2 ) INFORMATION FOR SEQ ID NO:21:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

CAGTTTCCAG CTCCTACAAT GAGACCTACG AGC  33

( 2 ) INFORMATION FOR SEQ ID NO:22:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

GTAGTGTCGA CCCCATGCGG  20

( 2 ) INFORMATION FOR SEQ ID NO:23:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

CGTTTTGCCT GATTATTATC TCACTTTC  28

( 2 ) INFORMATION FOR SEQ ID NO:24:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

GTCCACCTTC GAAAAAAGAT CC  22

( 2 ) INFORMATION FOR SEQ ID NO:25:

( i ) SEQUENCE CHARACTERISTICS:

(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:25:

CCGCATAAAG GACCTTAAAG C                                              21

(2) INFORMATION FOR SEQ ID NO:26:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:26:

GAGGAAGAGA TCATCATCAT AGC                                            23

(2) INFORMATION FOR SEQ ID NO:27:

(i) SEQUENCE CHARACTERISTICS:
(A) LENGTH: 40 base pairs
(B) TYPE: nucleic acid
(C) STRANDEDNESS: double
(D) TOPOLOGY: linear (xi) SEQUENCE DESCRIPTION: SEQ ID NO:27:

GTCCTTCGTG CGGACAGTGT CTCAGGAGAA AGTGAGATAA                           40

(2) INFORMATION FOR SEQ ID NO:28:

(i) SEQUENCE CHARACTERISTICS:
(A) LENGTH: 40 base pairs
(B) TYPE: nucleic acid
(C) STRANDEDNESS: double
(D) TOPOLOGY: linear (xi) SEQUENCE DESCRIPTION: SEQ ID NO:28:

GTCCTTTATG CGGACTAGGT CTCAGGAGAA AGTGAGATAA                           40

(2) INFORMATION FOR SEQ ID NO:29:

(i) SEQUENCE CHARACTERISTICS:
(A) LENGTH: 61 base pairs
(B) TYPE: nucleic acid
(C) STRANDEDNESS: double
(D) TOPOLOGY: linear (xi) SEQUENCE DESCRIPTION: SEQ ID NO:29:

CCGGTTCTTT GCAAACAACA TCCTGGTACA CAATTAAGAC GGCTTTTATG CCACAATACC     60
C                                                                    61

(2) INFORMATION FOR SEQ ID NO:30:

(i) SEQUENCE CHARACTERISTICS:
(A) LENGTH: 22 amino acids
(B) TYPE: amino acid
(C) STRANDEDNESS: unknown
(D) TOPOLOGY: unknown (xi) SEQUENCE DESCRIPTION: SEQ ID NO:30:

Ile Lys Ile Leu Ala Asn Ser Ile Leu Pro Glu Glu Trp Val Pro Leu
 1               5                  10                  15
Ile Lys Asn Gly Lys Val
            20

( 2 ) INFORMATION FOR SEQ ID NO:31:

( i ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:31:

```
Ile Lys Leu Leu Ala Asn Ser Ile Leu Pro Asn Glu Trp Leu Pro
 1               5                  10                  15

Ile Ile Glu Asn Gly Glu Ile
                20
```

( 2 ) INFORMATION FOR SEQ ID NO:32:

( i ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:32:

```
Lys Val Leu Tyr Ala Asp Ser Val Ser Gly Glu Ser Glu Ile Ile Ile
 1               5                  10                  15

Arg Gln Asn Gly Lys Ile
                20
```

( 2 ) INFORMATION FOR SEQ ID NO:33:

( i ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:33:

```
Ala Ile Leu Tyr Val Gly Cys Gly Ala Lys Gly Thr Asn Val Leu Met
 1               5                  10                  15

Ala Asp Gly Ser Ile Glu
                20
```

( 2 ) INFORMATION FOR SEQ ID NO:34:

( i ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:34:

```
Lys Val Val Lys Asn Lys Cys Leu Ala Glu Gly Thr Arg Ile Arg Asp
 1               5                  10                  15

Pro Val Thr Gly Thr Thr
                20
```

( 2 ) INFORMATION FOR SEQ ID NO:35:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:35:

```
Glu Asx Gly Lys Ala Gly Phe Gly Phe Leu Tyr Ala His Asn Ser Tyr
```

```
        1               5                   10                  15
    Tyr Gly Tyr Tyr Gly Tyr Ala
                    20
```

( 2 ) INFORMATION FOR SEQ ID NO:36:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:36:

```
    Glu Asn Phe Leu Val Gly Phe Gly Leu Leu Tyr Ala His Asn Ser Tyr
    1               5                   10                  15
    Tyr Gly Tyr Met Gly Tyr Pro
                    20
```

( 2 ) INFORMATION FOR SEQ ID NO:37:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:37:

```
    Glu Thr His Arg Phe Phe Ala Asn Asn Ile Leu Val His Asn Thr Asp
    1               5                   10                  15
    Gly Phe Tyr Ala Thr Ile Pro
                    20
```

( 2 ) INFORMATION FOR SEQ ID NO:38:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:38:

```
    Asp His Gln Phe Leu Leu Ala Asn Gln Val Val Val His Asn Cys Gly
    1               5                   10                  15
    Glu Arg Gly Asn Glu Met Ala
                    20
```

( 2 ) INFORMATION FOR SEQ ID NO:39:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:39:

```
    Glu Leu His Thr Leu Val Ala Glu Gly Val Val Val His Asn Cys Ser
    1               5                   10                  15
    Pro Pro Phe Lys Gln Ala Glu
                    20
```

( 2 ) INFORMATION FOR SEQ ID NO:40:

( i ) SEQUENCE CHARACTERISTICS:
        ( A ) LENGTH: 25 base pairs
        ( B ) TYPE: nucleic acid
        ( C ) STRANDEDNESS: single ( D ) TOPOLOGY: linear ( x i ) SEQUENCE DESCRIPTION: SEQ ID NO:40:

GCAATTATGT GCATAGAGGA ATCCA 25

( 2 ) INFORMATION FOR SEQ ID NO:41:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GGTATTATGT GCATAGAGGA ATCCA 25

( 2 ) INFORMATION FOR SEQ ID NO:42:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

ATTATGTGCA TAGAGGAATC CAAAG 25

( 2 ) INFORMATION FOR SEQ ID NO:43:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

GGTACCCGTC GTGCTAGCAT TTACCGGAA GAATGGGTAC CA 42

( 2 ) INFORMATION FOR SEQ ID NO:44:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

CCCGCTATTA TGTGCATAGA GGGATCC 27

( 2 ) INFORMATION FOR SEQ ID NO:45:

( i ) SEQUENCE CHARACTERISTICS:
        ( A ) LENGTH: 4 amino acids
        ( B ) TYPE: amino acid
        ( C ) STRANDEDNESS: unknown
        ( D ) TOPOLOGY: unknown ( i x ) FEATURE:
        ( A ) NAME/KEY: peptide
        ( B ) LOCATION: 1
        ( D ) OTHER INFORMATION: /note= "Xaa at position 1 = (Ala/Val)"

( i x ) FEATURE:
        ( A ) NAME/KEY: peptide
        ( B ) LOCATION: 4
        ( D ) OTHER INFORMATION: /note= "Xaa at position 4 =
            ( S e r / C y s / T h r )"

( x i ) SEQUENCE DESCRIPTION: SEQ ID NO:45:

Xaa His Asn Xaa
1                                                                                          4

( 2 ) INFORMATION FOR SEQ ID NO:46:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

GATCCCTCTA TGCACATAAT TCAGGCCTC                                                            29

( 2 ) INFORMATION FOR SEQ ID NO:47:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

AATTGAGGCC TGAATTATGT GCATAGAGG                                                            29

( 2 ) INFORMATION FOR SEQ ID NO:48:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GCTCGAGGCT AGCATTTTAC CGGAAGAATG GGTAC                                                     35

( 2 ) INFORMATION FOR SEQ ID NO:49:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

CCATTCTTCC GGTAAAATGC TAGCCTCGAG CGTAC                                                     35

( 2 ) INFORMATION FOR SEQ ID NO:50:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GATCCCTCTA TAAGCATAAT TCAGG                                                                25

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

CCTGAATTAT GCTTATAGAG G                                                                    21

( 2 ) INFORMATION FOR SEQ ID NO:52:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GATCCCTCTA TGCACTGAAT TCAGG    25

( 2 ) INFORMATION FOR SEQ ID NO:53:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CCTGAATTCA GTGCATAGAG G    21

( 2 ) INFORMATION FOR SEQ ID NO:54:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GTCAGGCCTC TCAGACAGTA CAGCTCGTAC AT    32

( 2 ) INFORMATION FOR SEQ ID NO:55:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

AGGCCT    6

( 2 ) INFORMATION FOR SEQ ID NO:56:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

CCCCTGCAGT TAAAAGTAAT TGCTTTCCAA ATAAG    35

( 2 ) INFORMATION FOR SEQ ID NO:57:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

CTGCAG    6

( 2 ) INFORMATION FOR SEQ ID NO:58:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:58:

GGAATTCCAT ATGAAAATCG AAGAAGGT                                                              2 8

( 2 ) INFORMATION FOR SEQ ID NO:59:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:59:

CGGGATCCCG TTATAGTGAG ATAACGTCCC G                                                     3

( 2 ) INFORMATION FOR SEQ ID NO:60:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:60:

GGAATTCCAT ATGCCAGAGG AAGAACTG                                                                2

( 2 ) INFORMATION FOR SEQ ID NO:61:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:61:

ATAGTTTAGC GGCCGCTCAC GACGTTGTAA AACG                                          3 4

( 2 ) INFORMATION FOR SEQ ID NO:62:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:62:

TCGAGGCTAG CAAATTACCG GAAGAATGGG TAC                                            3 3

( 2 ) INFORMATION FOR SEQ ID NO:63:

( i ) SEQUENCE CHARACTERISTICS:
        ( A ) LENGTH: 25 base pairs
        ( B ) TYPE: nucleic acid ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:63:

CCATTCTTCC GGTAATTTGC TAGCC 25

( 2 ) INFORMATION FOR SEQ ID NO:64:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:64:

TCGAGGCTTG CATTTTACCG GAAGAATGGG TAC 33

( 2 ) INFORMATION FOR SEQ ID NO:65:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:65:

CCATTCTTCC GGTAAAATGC AAGCC 25

( 2 ) INFORMATION FOR SEQ ID NO:66:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:66:

GATCCCTCTA TAAGCATAAT ATTGGCATGC AGTA 34

( 2 ) INFORMATION FOR SEQ ID NO:67:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:67:

TACTGCATGC CAATATTATG CTTATAGAGG 30

( 2 ) INFORMATION FOR SEQ ID NO:68:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:68:

GATCCCTCTA TGCACATAAT TAAGGCATG 29

( 2 ) INFORMATION FOR SEQ ID NO:69:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:69:

CCTTAATTAT GTGCATAGAG G 21

( 2 ) INFORMATION FOR SEQ ID NO:70:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:70:

GCGCTCGAGG GGTGCTTTGC CAAGGGTACC AAT 33

( 2 ) INFORMATION FOR SEQ ID NO:71:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:71:

CCTCCGCAAT TATGGACGAC AACCTGGT 28

( 2 ) INFORMATION FOR SEQ ID NO:72:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:72:

GAATGCGGAA TTCAGGCCTC CGCA 24

( 2 ) INFORMATION FOR SEQ ID NO:73:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: unknown ( i i ) MOLECULE TYPE: Other Nucleic Acid ( x i ) SEQUENCE DESCRIPTION: SEQ ID NO:73:

ATGGACGACA ACCTGGGATC CAAGCAAAAA CTGATGATC 39

( 2 ) INFORMATION FOR SEQ ID NO:74:

( i ) SEQUENCE CHARACTERISTICS:
          ( A ) LENGTH: 35 base pairs
          ( B ) TYPE: nucleic acid
          ( C ) STRANDEDNESS: single
          ( D ) TOPOLOGY: unknown ( i i ) MOLECULE TYPE: Other Nucleic Acid ( x i ) SEQUENCE DESCRIPTION: SEQ ID NO:74:

GATCCCAGGT TGTCGTCCAT GCATGCGGAG GCCTG    35

( 2 ) INFORMATION FOR SEQ ID NO:75:

( i ) SEQUENCE CHARACTERISTICS:
          ( A ) LENGTH: 35 base pairs
          ( B ) TYPE: nucleic acid
          ( C ) STRANDEDNESS: single
          ( D ) TOPOLOGY: unknown ( i i ) MOLECULE TYPE: Other Nucleic Acid ( x i ) SEQUENCE DESCRIPTION: SEQ ID NO:75:

AATTCAGGCC TCCGCATGCA TGGACGACAA CCTGG    35

( 2 ) INFORMATION FOR SEQ ID NO:76:

( i ) SEQUENCE CHARACTERISTICS:
          ( A ) LENGTH: 36 base pairs
          ( B ) TYPE: nucleic acid
          ( C ) STRANDEDNESS: single
          ( D ) TOPOLOGY: unknown ( i i ) MOLECULE TYPE: Other Nucleic Acid ( x i ) SEQUENCE DESCRIPTION: SEQ ID NO:76:

GATCCCAGGT TGTCGTCCAT GCATGCGGTG GCCTGA    36

( 2 ) INFORMATION FOR SEQ ID NO:77:

( i ) SEQUENCE CHARACTERISTICS:
          ( A ) LENGTH: 36 base pairs
          ( B ) TYPE: nucleic acid
          ( C ) STRANDEDNESS: single
          ( D ) TOPOLOGY: unknown ( i i ) MOLECULE TYPE: Other Nucleic Acid ( x i ) SEQUENCE DESCRIPTION: SEQ ID NO:77:

CCGGTCAGGC CTCCGCATGC ATGGACGACA ACCTGG    36

( 2 ) INFORMATION FOR SEQ ID NO:78:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: Genomic DNA ( x i ) SEQUENCE DESCRIPTION: SEQ ID NO:78:

GGTCGTCAGA CTGTCGATGA AGCC    24

( 2 ) INFORMATION FOR SEQ ID NO:79:

( i ) SEQUENCE CHARACTERISTICS:
          ( A ) LENGTH: 31 base pairs
          ( B ) TYPE: nucleic acid ( C ) STRANDEDNESS: single
( D ) TOPOLOGY: linear ( x i ) SEQUENCE DESCRIPTION: SEQ ID NO:79:

ATTGGATCCT TATCTGTATT CCGTAAACTT A           31

( 2 ) INFORMATION FOR SEQ ID NO:80:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:80:

GAACATATGA AGAAAAAGAA TGTATATCAC TCTC           34

( 2 ) INFORMATION FOR SEQ ID NO:81:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:81:

GGGGGATCCA AAGCCAGCAA GGAAATTCTC           30

( 2 ) INFORMATION FOR SEQ ID NO:82:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: Genomic DNA ( i x ) FEATURE:
    ( A ) NAME/KEY: Coding Sequence
    ( B ) LOCATION: 1...21
    ( D ) OTHER INFORMATION:

( x i ) SEQUENCE DESCRIPTION: SEQ ID NO:82:

CTT AAG TTT ACG GAA TAC AGA TAAGGATCC           30
Leu Lys Phe Thr Glu Tyr Arg
 1               5

( 2 ) INFORMATION FOR SEQ ID NO:83:

( i ) SEQUENCE CHARACTERISTICS:
    ( A ) LENGTH: 42 base pairs
    ( B ) TYPE: nucleic acid
    ( C ) STRANDEDNESS: double
    ( D ) TOPOLOGY: linear ( i i ) MOLECULE TYPE: Genomic DNA ( i x ) FEATURE:
    ( A ) NAME/KEY: Coding Sequence
    ( B ) LOCATION: 6...38
    ( D ) OTHER INFORMATION:

( x i ) SEQUENCE DESCRIPTION: SEQ ID NO:83:

TTAAG TTT ACG GAA TAC AGA CAC CAC CAC CAC CAC CAC TAAG           42
      Phe Thr Glu Tyr Arg His His His His His His
       1           5                   10

( 2 ) INFORMATION FOR SEQ ID NO:84:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:84:

```
TTAAGTTTAC GGAATACAGA CACCACCACC ACCACCACTA AG                42
```

( 2 ) INFORMATION FOR SEQ ID NO:85:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:85:

```
CTAGCTTAGT GGTGGTGGTG GTGGTGTCTG TATTCCGTAA AC                42
```

( 2 ) INFORMATION FOR SEQ ID NO:86:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:86:

```
GTACCGAGCT CATGTCACAT CTCGCAGAAC TGGTTGCCAG T                 41
```

( 2 ) INFORMATION FOR SEQ ID NO:87:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:87:

```
ACATGCATGC TTATTTAAAC TGTTTGAGGA AACGCAGATC                   40
```

( 2 ) INFORMATION FOR SEQ ID NO:88:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:88:

```
Ala Glu Val Asp Val Met Gly Lys Asn Gly Lys Trp Leu Glu Val Leu
 1               5                  10                  15
Gly Cys Phe Ala Lys Gly Thr Asn Val Leu Asn Gln Val Val His
            20                  25                  30
```

```
Asn  Cys  Gly  Met  Val  His  Pro  Asn  Val
         35                      40
```

( 2 ) INFORMATION FOR SEQ ID NO:89:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:89:

```
GAAGTGGACG  TCATGGGTAA  AAACGGTAAA  TGGCTGGAAG  TGCTGGGC                48
```

( 2 ) INFORMATION FOR SEQ ID NO:90:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:90:

```
TAATTGCGGG  ATGGTGCATC  CGAA                                            24
```

( 2 ) INFORMATION FOR SEQ ID NO:91:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:91:

```
CACGTTCGGA  TGCACCATCC  CGCAATTATG  GACGACAACC  TGG                     43
```

( 2 ) INFORMATION FOR SEQ ID NO:92:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:92:

```
TTTAAAACAT  TGGTACCCTT  GGCAAAGCAG  CCCAGCACTT  CCAGCC                  46
```

( 2 ) INFORMATION FOR SEQ ID NO:93:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:93:

```
ATTTACCGTT  TTTACCCATG  ACGTCCACTT  CTGCA                               35
```

( 2 ) INFORMATION FOR SEQ ID NO:94:

( i ) SEQUENCE CHARACTERISTICS:
   ( A ) LENGTH: 29 base pairs
   ( B ) TYPE: nucleic acid
   ( C ) STRANDEDNESS: single
   ( D ) TOPOLOGY: linear ( i i ) MOLECULE TYPE: Genomic DNA ( x i ) SEQUENCE DESCRIPTION: SEQ ID NO:94:

GGAATTCTGC TTTGCCAAGG GTACCAATG        29

( 2 ) INFORMATION FOR SEQ ID NO:95:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: Genomic DNA ( x i ) SEQUENCE DESCRIPTION: SEQ ID NO:95:

ATTGGTTCTG CAGATTATGG ACGACAACCT GGTTGGC        37

( 2 ) INFORMATION FOR SEQ ID NO:96:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: Genomic DNA ( x i ) SEQUENCE DESCRIPTION: SEQ ID NO:96:

CTCTGGTTTC GGCTTCGGGA TGGGG        25

( 2 ) INFORMATION FOR SEQ ID NO:97:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: Genomic DNA ( x i ) SEQUENCE DESCRIPTION: SEQ ID NO:97:

CCCCATCCCG AAGCCGAAAC CAGAG        25

( 2 ) INFORMATION FOR SEQ ID NO:98:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: Genomic DNA ( x i ) SEQUENCE DESCRIPTION: SEQ ID NO:98:

GGCTGGAAGT GCTGGGCGCG TTTGCCAAGG GTACCAATGT TTTAA        45

( 2 ) INFORMATION FOR SEQ ID NO:99:

( i ) SEQUENCE CHARACTERISTICS:
      ( A ) LENGTH: 35 base pairs
      ( B ) TYPE: nucleic acid
      ( C ) STRANDEDNESS: single (D) TOPOLOGY: linear (i i) MOLECULE TYPE: Genomic DNA (x i) SEQUENCE DESCRIPTION: SEQ ID NO:99:

GGTACCCTTG GCAAACGCGC CCAGCACTTC CAGCC 35

(2) INFORMATION FOR SEQ ID NO:100:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: Genomic DNA (x i) SEQUENCE DESCRIPTION: SEQ ID NO:100:

GGTTGTCGTC CATGCGTGCG GGATGGTGC 29

(2) INFORMATION FOR SEQ ID NO:101:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: Genomic DNA (x i) SEQUENCE DESCRIPTION: SEQ ID NO:101:

GCACCATCCC GCACGCATGG ACGACAACC 29

(2) INFORMATION FOR SEQ ID NO:102:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: Genomic DNA (x i) SEQUENCE DESCRIPTION: SEQ ID NO:102:

TATGACGACA AATCCTGGTG TATCCGCTTG GCAGGTC 37

(2) INFORMATION FOR SEQ ID NO:103:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (i i) MOLECULE TYPE: Genomic DNA (x i) SEQUENCE DESCRIPTION: SEQ ID NO:103:

ATAAGCTGTG TTGACCTGCC AAGCGGATAC ACCAGGATTT GTCGTCA 47

(2) INFORMATION FOR SEQ ID NO:104:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: Genomic DNA (x i) SEQUENCE DESCRIPTION: SEQ ID NO:104:

AACACAGCTT ATACTGCGGG ACAATTGGTC ACATATAACG GC 42

( 2 ) INFORMATION FOR SEQ ID NO:105:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:105:

TTTATACGTC TTGCCGTTAT ATGTGACCAA TTGTCCCGCA GT 42

( 2 ) INFORMATION FOR SEQ ID NO:106:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:106:

AAGACGTATA AATGTTTGCA GCCCCACACC TCCTTGGCAG GA 42

( 2 ) INFORMATION FOR SEQ ID NO:107:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:107:

GGATGGTTCC CATCCTGCCA AGGAGGTGTG GGGCTGCAAA CA 42

( 2 ) INFORMATION FOR SEQ ID NO:108:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:108:

TGGGAACCAT CCAACGTTCC TGCCTTGTGG CAGCTTCAAT CGAGCT 46

( 2 ) INFORMATION FOR SEQ ID NO:109:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:109:

CGATTGAAGC TGCCACAAGG CAGGAACGTT 30

( 2 ) INFORMATION FOR SEQ ID NO:110:

( i ) SEQUENCE CHARACTERISTICS:
    ( A ) LENGTH: 8 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:110:

Cys Tyr Phe Asn Cys Pro Arg Gly
1               5

( 2 ) INFORMATION FOR SEQ ID NO:111:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:111:

Cys Tyr Phe Gly Asn Cys Pro Arg Gly
1               5

( 2 ) INFORMATION FOR SEQ ID NO:112:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:112:

Cys Tyr Ile Gln Asn Cys Pro Leu Gly
1               5

( 2 ) INFORMATION FOR SEQ ID NO:113:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:113:

Cys Gly Met Glu Leu Asp Asp Leu Pro Lys Lys Arg Leu Arg Lys
1               5                   10                  15

( 2 ) INFORMATION FOR SEQ ID NO:114:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:114:

Met Glu Leu Asp Asp Leu Pro Lys Lys Arg Leu Arg Lys Cys
1               5                   10

( 2 ) INFORMATION FOR SEQ ID NO:115:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO:115:

GATCCCAGGT TGTCGTCCAT GCATGCGGAG GCCTG　　　35

( 2 ) INFORMATION FOR SEQ ID NO:116:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:116:

AATTCAGGCC TCCGCATGCA TGGACGACAA CCTGG　　　35

( 2 ) INFORMATION FOR SEQ ID NO:117:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:117:

GGTGGTACCG GTATTCTTAA AATTCTGAAC GAAATAGCA　　　39

( 2 ) INFORMATION FOR SEQ ID NO:118:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:118:

GGTGGTCTGC AGTCATAGAC CAGTTACCTC ATGAAAATCA CC　　　42

( 2 ) INFORMATION FOR SEQ ID NO:119:

( i ) SEQUENCE CHARACTERISTICS:
    ( A ) LENGTH: 57 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:119:

GGTGGTCATA TGAAAATCGA AGAAGGTAAA CTGACAAATC CTGGTGTATC CGCTTGG　　　57

( 2 ) INFORMATION FOR SEQ ID NO:120:

( i ) SEQUENCE CHARACTERISTICS:
    ( A ) LENGTH: 53 base pairs
    ( B ) TYPE: nucleic acid
    ( C ) STRANDEDNESS: single ( D ) TOPOLOGY: linear ( i i ) MOLECULE TYPE: Genomic DNA ( x i ) SEQUENCE DESCRIPTION: SEQ ID NO:120:

GTGGTCTCGA GACCGTTGTT ACCGTTGTTT TGAAGCTGCC ACAAGGCAGG AAC 53

( 2 ) INFORMATION FOR SEQ ID NO:121:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:121:

GATCCCAGGT TGTTGTACAC AACTGTGGTG GCCTGA 36

( 2 ) INFORMATION FOR SEQ ID NO:122:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:122:

CCGGTCAGGC CACCACAGTT GTGACAACAA CCTGG 35

( 2 ) INFORMATION FOR SEQ ID NO:123:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:123:

GGTGGTGCTA GCACCTTCAA TGGTGAGATG AAACTT 36

( 2 ) INFORMATION FOR SEQ ID NO:124:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:124:

GTTGTTGCTA GCGGTGGTGA CGTCGGTGGA GATGTTTTGC TTAACGTT 48

( 2 ) INFORMATION FOR SEQ ID NO:125:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:125:

CTAGCAACAA CGGTAACGGC CGTAACGGTG GCAACAACGG TGGCAACAAC GACGT 55

(2) INFORMATION FOR SEQ ID NO:126:

(i) SEQUENCE CHARACTERISTICS:
  (A) LENGTH: 47 base pairs
  (B) TYPE: nucleic acid
  (C) STRANDEDNESS: single
  (D) TOPOLOGY: linear (ii) MOLECULE TYPE: Genomic DNA (xi) SEQUENCE DESCRIPTION: SEQ ID NO:126:

CGTTGTTGCC ACCGTTGTTG CCACCGTTAC GGCCGTTACC GTTGTTG 47

(2) INFORMATION FOR SEQ ID NO:127:

(i) SEQUENCE CHARACTERISTICS:
  (A) LENGTH: 19 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:127:

Ala Ser Asn Asn Gly Asn Gly Arg Asn Gly Gly Asn Asn Gly Gly Asn
1               5                   10                  15

Asn Asp Val (2) INFORMATION FOR SEQ ID NO:128:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (ii) MOLECULE TYPE: Genomic DNA (xi) SEQUENCE DESCRIPTION: SEQ ID NO:128:

CCGGTTCCGG GAGCTCGTAA CTGCA 25

(2) INFORMATION FOR SEQ ID NO:129:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ii) MOLECULE TYPE: Genomic DNA (xi) SEQUENCE DESCRIPTION: SEQ ID NO:129:

GTTACGAGCT CCCGGAA 17

(2) INFORMATION FOR SEQ ID NO:130:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: Genomic DNA (xi) SEQUENCE DESCRIPTION: SEQ ID NO:130:

TCGACCCCGG GGGGAGCTCC C 21

( 2 ) INFORMATION FOR SEQ ID NO:131:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:131:

```
TCGAGGGAGC TCCCCCCGGG G                                                  21
```

( 2 ) INFORMATION FOR SEQ ID NO:132:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:132:

```
GAGCTCGAAC AACAACAACA ATAACAATAA CAACAACCTC GGGATCGAGG GAAGGATTTC        60
AGAATTCGGA TCCTCTAGAG TCGACCTGCA GGCAAGCTTG                              100
```

( 2 ) INFORMATION FOR SEQ ID NO:133:

( i ) SEQUENCE CHARACTERISTICS:
        ( A ) LENGTH: 109 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:133:

```
CATATGGCTA GCTCGCGAGT CGACCCCGGG GGGAGCTCCG AGCTCGAACA ACAACAACAA        60
TAACAATAAC AACAACCTCG GGATCGAGGG AAGGGGTACG CTCGAGGGG                    109
```

( 2 ) INFORMATION FOR SEQ ID NO:134:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:134:

```
His Asn Phe Ile Lys His Arg Leu Pro Gly His Arg
 1               5                  10
```

( 2 ) INFORMATION FOR SEQ ID NO:135:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:135:

```
Phe His Lys His Ser Pro Arg Ser Pro Ile Phe Ile
```

1                    5                         1 0

( 2 ) INFORMATION FOR SEQ ID NO:136:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:136:

His  Tyr  Thr  Arg  Phe  His  Thr  His  Pro  Lys  Pro  Leu
1                    5                         1 0

( 2 ) INFORMATION FOR SEQ ID NO:137:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:137:

Met  Pro  Arg  Trp  His  His  His  Thr  Pro  Pro  Ala  Tyr
1                    5                         1 0

( 2 ) INFORMATION FOR SEQ ID NO:138:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:138:

Trp  His  Lys  His  Tyr  Pro  Phe  Lys  Ile  Pro  Thr  Gln
1                    5                         1 0

( 2 ) INFORMATION FOR SEQ ID NO:139:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:139:

Ala  Ala  Lys  Tyr  His  His  His  Arg  Trp  Pro  Leu  Phe
1                    5                         1 0

( 2 ) INFORMATION FOR SEQ ID NO:140:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:140:

His  Val  His  Arg  His  His  Val  Arg  Pro  His  Val  His

```
               1               5                    1 0
```

( 2 ) INFORMATION FOR SEQ ID NO:141:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:141:

```
Ala  Lys  Leu  Pro  Trp  His  His  His  His  Gly  Arg  Pro
 1                   5                        1 0
```

( 2 ) INFORMATION FOR SEQ ID NO:142:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:142:

```
Lys  Trp  Phe  His  Pro  Pro  Arg  Trp  His  Phe  Pro  Tyr
 1                   5                        1 0
```

( 2 ) INFORMATION FOR SEQ ID NO:143:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:143:

```
Tyr  His  Lys  His  Arg  Pro  Tyr  Tyr  Ala  Thr  Gln  Met
 1                   5                        1 0
```

( 2 ) INFORMATION FOR SEQ ID NO:144:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:144:

```
Lys  His  Leu  Gln  His  Tyr  Pro  Arg  Val  Lys  Val  Ala
 1                   5                        1 0
```

( 2 ) INFORMATION FOR SEQ ID NO:145:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:145:

```
Phe  His  Lys  Leu  Pro  Pro  Arg  Tyr  Thr  Pro  Thr  Val
```

```
                  1                    5                          1 0
```

( 2 ) INFORMATION FOR SEQ ID NO:146:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:146:

```
Ile  Glu  Tyr  Val  Pro  Ser  Leu  Ala  Pro  Leu  Ser  Pro
 1                    5                          1 0
```

( 2 ) INFORMATION FOR SEQ ID NO:147:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:147:

```
Phe  His  Lys  Met  Pro  Asn  Leu  Lys  Pro  Ser  Lys  His
 1                    5                          1 0
```

( 2 ) INFORMATION FOR SEQ ID NO:148:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:148:

```
Tyr  His  Trp  Lys  Pro  Lys  Asp  Val  Ser  Arg  Met  Pro
 1                    5                          1 0
```

( 2 ) INFORMATION FOR SEQ ID NO:149:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:149:

```
Lys  His  Arg  Leu  Pro  Thr  Pro  Pro  Pro  Ser  Pro  Ala
 1                    5                          1 0
```

( 2 ) INFORMATION FOR SEQ ID NO:150:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:150:

```
Met  Leu  Lys  Leu  Asp  Tyr  Ser  Val  Leu  Ser  Tyr  Gly
```

(2) INFORMATION FOR SEQ ID NO:151:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:151:

His Phe Lys His Asn Arg Gln Pro Tyr His Leu Pro
1               5                   10

(2) INFORMATION FOR SEQ ID NO:152:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:152:

Trp His Lys Gln Trp Ser Gln Met Pro Ser Lys Leu
1               5                   10

(2) INFORMATION FOR SEQ ID NO:153:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:153:

Asp Tyr Ala Ser Thr Phe Thr Ala Val Asp Ala Asn
1               5                   10

(2) INFORMATION FOR SEQ ID NO:154:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:154:

His Pro His Met Ser Pro Ser Thr Leu Ala Ala Gly
1               5                   10

(2) INFORMATION FOR SEQ ID NO:155:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:155:

Ala Trp Asp Cys Pro Met Leu Ser Cys Thr Ser Trp
1               5                   10